US011365252B2

(12) United States Patent
Luetkens et al.

(10) Patent No.: US 11,365,252 B2
(45) Date of Patent: Jun. 21, 2022

(54) CD229 CAR T CELLS AND METHODS OF USE THEREOF

(71) Applicant: UNIVERSITY OF UTAH RESEARCH FOUNDATION, Salt Lake City, UT (US)

(72) Inventors: Tim Luetkens, Salt Lake City, UT (US); Djordje Atanackovic, Salt Lake City, UT (US); Sabarinath Venniyil Radhakrishnan, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 246 days.

(21) Appl. No.: 16/319,386

(22) PCT Filed: Jul. 19, 2017

(86) PCT No.: PCT/US2017/042840
§ 371 (c)(1),
(2) Date: Jan. 21, 2019

(87) PCT Pub. No.: WO2018/017708
PCT Pub. Date: Jan. 25, 2018

(65) Prior Publication Data
US 2019/0330338 A1 Oct. 31, 2019

Related U.S. Application Data

(60) Provisional application No. 62/413,776, filed on Oct. 27, 2016, provisional application No. 62/364,527, filed on Jul. 20, 2016.

(51) Int. Cl.
| | |
|---|---|
| C07K 16/28 | (2006.01) |
| A61P 35/00 | (2006.01) |
| A61K 35/17 | (2015.01) |
| A61K 38/17 | (2006.01) |
| A61K 39/395 | (2006.01) |
| A61K 45/06 | (2006.01) |
| C07K 14/725 | (2006.01) |
| C07K 14/705 | (2006.01) |
| C12N 5/0783 | (2010.01) |
| G01N 33/574 | (2006.01) |

(52) U.S. Cl.
CPC .......... *C07K 16/2803* (2013.01); *A61K 35/17* (2013.01); *A61K 38/177* (2013.01); *A61K 38/1774* (2013.01); *A61K 39/3955* (2013.01); *A61K 45/06* (2013.01); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *G01N 33/57407* (2013.01); *C07K 2317/33* (2013.01); *C07K 2317/52* (2013.01); *C07K 2317/53* (2013.01); *C07K 2317/55* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2319/02* (2013.01); *C07K 2319/03* (2013.01); *C07K 2319/30* (2013.01); *C07K 2319/33* (2013.01); *C07K 2319/42* (2013.01); *C12N 2510/00* (2013.01)

(58) Field of Classification Search
CPC .............. C12N 2510/00; C12N 5/0636; C07K 2319/33; C07K 2319/03; C07K 2317/622; C07K 16/2803
USPC ........................................... 424/133.1, 136.1
See application file for complete search history.

(56) References Cited

U.S. PATENT DOCUMENTS

| | | | |
|---|---|---|---|
| 3,929,992 | A | 12/1975 | Sehgal et al. |
| 4,816,397 | A | 3/1989 | Boss et al. |
| 4,816,567 | A | 3/1989 | Cabilly et al. |
| 5,225,539 | A | 7/1993 | Winter |
| 5,665,772 | A | 9/1997 | Cottens et al. |
| 6,004,973 | A | 12/1999 | Guitard et al. |
| 6,015,815 | A | 1/2000 | Mollison |
| 6,111,090 | A | 8/2000 | Gorman et al. |
| 7,025,962 | B1 | 4/2006 | Gorman et al. |
| 7,091,213 | B2 | 8/2006 | Metcalf, III et al. |
| 7,132,255 | B2 | 11/2006 | Blumberg |
| 7,618,632 | B2 | 11/2009 | Collins et al. |

(Continued)

FOREIGN PATENT DOCUMENTS

| | | | |
|---|---|---|---|
| EP | 0090505 | B1 | 8/1990 |
| EP | 0125023 | B1 | 6/1991 |

(Continued)

OTHER PUBLICATIONS

Olson et al. (Clinical Immunology 204 (2019) 69-73).*
Radhakrishnan et al. (Nat Commun. 2020; 11: 798. Published online Feb. 7, 2020).*
Luetkens et al. (JNCCN Journal of the National Comprehensive Cancer Network, (Jul. 2020) vol. 18, No. 7.5, pp. 920. Abstract No. YIA20-003. Meeting Info: National Compehensive Cancer Network Annual Conference, NCCN 2020. Orlando, FL, United States. Mar. 19, 2020-Mar. 22, 2020).*

(Continued)

*Primary Examiner* — Lynn A Bristol
(74) *Attorney, Agent, or Firm* — Ballard Spahr LLP

(57) ABSTRACT

Disclosed are chimeric antigen receptor (CAR) polypeptides comprising a CD229 antigen binding domain, a transmembrane domain, and an intracellular signaling domain. Disclosed are nucleic acid sequences capable of encoding a CAR polypeptide comprising a CD229 antigen binding domain, a transmembrane domain, and an intracellular signaling domain. Also disclosed are vectors and cells comprising one or both of the CAR polypeptides and nucleic acid sequences capable of encoding CAR polypeptides. Also disclosed are methods of treating.

20 Claims, 27 Drawing Sheets

Specification includes a Sequence Listing.

(56) References Cited

U.S. PATENT DOCUMENTS

| | | |
|---|---|---|
| 7,727,950 B2 | 6/2010 | Armstrong et al. |
| 7,812,135 B2 | 10/2010 | Smith et al. |
| 7,943,743 B2 | 5/2011 | Korman et al. |
| 8,008,449 B2 | 8/2011 | Korman et al. |
| 8,124,084 B2 | 2/2012 | Lefrancois et al. |
| 8,354,509 B2 | 1/2013 | Carven et al. |
| 8,388,967 B2 | 3/2013 | Smith et al. |
| 8,586,023 B2 | 11/2013 | Shiku et al. |
| 8,591,881 B2 | 11/2013 | Palese et al. |
| 8,591,886 B2 | 11/2013 | Ponath et al. |
| 8,609,089 B2 | 12/2013 | Langermann et al. |
| RE44,768 E | 2/2014 | Skotnicki et al. |
| 2003/0152913 A1 | 8/2003 | Hua et al. |
| 2004/0047858 A1 | 3/2004 | Blumberg et al. |
| 2009/0082299 A1 | 3/2009 | Felber et al. |
| 2010/0028330 A1 | 2/2010 | Collins et al. |
| 2010/0166768 A1 | 7/2010 | Sleeman et al. |
| 2010/0178684 A1 | 7/2010 | Woo et al. |
| 2010/0247521 A1 | 9/2010 | Jones et al. |
| 2011/0027286 A1 | 2/2011 | Thurston et al. |
| 2012/0039906 A1 | 2/2012 | Olive |
| 2012/0114649 A1 | 5/2012 | Langermann et al. |
| 2012/0122185 A1 | 5/2012 | Palese et al. |
| 2012/0141413 A1 | 6/2012 | Pavlakis et al. |
| 2012/0177598 A1 | 7/2012 | Lefrancois et al. |
| 2013/0156774 A1 | 6/2013 | Kuchroo et al. |
| 2014/0271618 A1 | 9/2014 | Markel et al. |
| 2014/0271677 A1 | 9/2014 | Palese et al. |
| 2016/0046724 A1 | 2/2016 | Brogdon et al. |

FOREIGN PATENT DOCUMENTS

| | | |
|---|---|---|
| EP | 0519596 A1 | 12/1992 |
| EP | 0120694 B1 | 7/1993 |
| EP | 0194276 B1 | 8/1993 |
| EP | 0239400 B1 | 8/1994 |
| EP | 1866339 B1 | 12/2007 |
| EP | 2381623 A1 | 10/2011 |
| EP | 1947183 B1 | 7/2013 |
| WO | WO-1986/001533 A1 | 3/1986 |
| WO | WO-1994/009010 A1 | 4/1994 |
| WO | WO-1995/014023 A1 | 5/1995 |
| WO | WO-1995/016691 A1 | 6/1995 |
| WO | WO-1996/041807 A1 | 12/1996 |
| WO | WO-1998/002441 A2 | 1/1998 |
| WO | WO-1999/015530 A1 | 4/1999 |
| WO | WO-1999/020758 A1 | 4/1999 |
| WO | WO-1999/040196 A1 | 8/1999 |
| WO | WO-1999/052552 A1 | 10/1999 |
| WO | WO-2901/003720 A2 | 1/2001 |
| WO | WO-2001/014387 A1 | 3/2001 |
| WO | WO-2005/055808 A2 | 6/2005 |
| WO | WO-2005/115451 A2 | 12/2005 |
| WO | WO-2006/083289 A2 | 8/2006 |
| WO | WO-2006/121168 A1 | 11/2006 |
| WO | WO-2006/122806 A2 | 11/2006 |
| WO | WO-2007/005874 A2 | 1/2007 |
| WO | WO-2007/044729 A2 | 4/2007 |
| WO | WO-2009/101611 A1 | 8/2009 |
| WO | WO-2009/104019 A1 | 8/2009 |
| WO | WO-2009/114335 A2 | 9/2009 |
| WO | WO-2010/003118 A1 | 1/2010 |
| WO | WO-2010/019570 A2 | 2/2010 |
| WO | WO-2010/027827 A2 | 3/2010 |
| WO | WO-2010/051043 A1 | 5/2010 |
| WO | WO-2010/077634 A1 | 7/2010 |
| WO | WO-2010/114484 A1 | 10/2010 |
| WO | WO-2010/125571 A1 | 11/2010 |
| WO | WO-2011/006342 A1 | 1/2011 |
| WO | WO-2011/028683 A1 | 3/2011 |
| WO | WO-2011/051726 A2 | 5/2011 |
| WO | WO-2011/090754 A1 | 7/2011 |
| WO | WO-2012/006552 A1 | 1/2012 |
| WO | WO-2012/007926 A1 | 1/2012 |
| WO | WO-2012/079000 A1 | 6/2012 |
| WO | WO-2013/006490 A2 | 1/2013 |
| WO | WO-2013/023184 A1 | 2/2013 |
| WO | WO-2013/039954 A1 | 3/2013 |
| WO | WO-2013/054331 A1 | 4/2013 |
| WO | WO-2013/082366 A1 | 6/2013 |
| WO | WO-2014/022332 A1 | 2/2014 |
| WO | WO-2014/059251 A1 | 4/2014 |
| WO | WO-2014/110591 A1 | 7/2014 |
| WO | WO-2014/153270 A1 | 9/2014 |
| WO | WO-2015/079417 A1 | 6/2015 |

OTHER PUBLICATIONS

Luetkens et al. (Bone Marrow Transplantation, (2019) vol. 53, pp. 118-119. Abstract No. O140. Meeting Info: 44th Annual Meeting of the European Society for Blood and Marrow Transplantation. Lisbon, Portugal. Mar. 18, 2018-Mar. 21, 2018).*

Radhakrishnan et al. (Blood, (Dec. 7, 2017) vol. 130, No. Suppl. 1, p. 3142. Meeting Info.: 59th Annual Meeting of the American-Society-of-Hematology (ASH). Atlanta, GA, USA. Dec. 9-12, 2017).*

Radhakrishnan et al. (Blood, (Dec. 2017) vol. 130, Supp. Supplement 1. Abstract No. 3142. Meeting Info: 59th Annual Meeting of the American Society of Hematology, ASH 2017. Atlanta, GA, United States. Dec. 9, 2017-Dec. 12, 2017).*

U.S. Appl. No. 62/413,776, filed Oct. 29, 2017, Tim Luetkens (Univ. of Utah Res. Found.).

PCT, PCT/US2017/042840 (WO 2018/017708), Jul. 19, 2017 (Jan. 25, 2018), Tim Luetkens (Univ. of Utah Res. Found.).

Agata, Y. et al., Expression of the PD-1 Antigen on the Surface of Stimulated Mouse T and B Lymphocytes. Int Immunol. 1996; 8(5):765-75.

Alemany, R. et al., Replicative Adenoviruses for Cancer Therapy. Nat Biotechnol. 2000; 18(7):723-7.

Atanackovic, D. et al., Surface Molecule CD229 as a Novel Target for the Diagnosis and Treatment of Multiple Myeloma. Haematologica. 2011; 96(10):1512-20.

Bierer, B.E. et al., Cyclosporin A and FK506: Molecular Mechanisms of Immunosuppression and Probes for Transplantation Biology. Curr Opin Immunol. 1993; 5(5):763-73.

Blank, C. et al., Interaction of PD-L1 on Tumor Cells with PD-1 on Tumor-Specific T Cells as a Mechanism of Immune Evasion: Implications for Tumor Immunotherapy. Cancer Immunol Immunother. 2005; 54(4):307-14.

Brummelkamp, T.R. et al., A System for Stable Expression of Short Interfering RNAs in Mammalian Cells. Science. 2002; 296(5567):550-3.

Carter, L. et al., PD-1 :PD-L Inhibitory Pathway Affects Both CD4+ and CD8+ T Cells and is Overcome by IL-2. Eur J Immunol. 2002; 32(3):634-43.

Casulo, C. et al., A Phase I Study of PRO131921, a Novel Anti-CD20 Monoclonal Antibody in Patients with relapsed/Refractory CD20+ Indolent NHL: Correlation Between Clinical Responses and AUC Pharmacokinetics. Clin Immunol. 2014; 154(1):37-46 (19 pages).

Chaidos, A. et al., Clinical Drug Resistance Linked to Interconvertible Phenotypic and functional States of Tumor-Propagating Cells in Multiple Myeloma. Blood. 2013; 121(2):318-28.

Cheson, B.D. et al., Report of an International Workshop to Standardize Workshop to Standardize Response Criteria for Non-Hodgkin's Lymphomas. NCI Sponsors International Working Group. J Clin Oncol. 1999; 17(4):1244-53.

Cheson, B.D. et al., Revised Response Criteria for Malignant Lymphoma. J Clin Oncol. 2007; 25(5):579-86.

Chresta, C.M. et al., AZD8055 is a Potent, Selective, and Orally Bioavailable ATP-Competitive Mammalian Target of Rapamycin Kinase Inhibitor with in Vitro and in Vivo Antitumor Activity. Cancer Res. 2010; 70(1):288-98.

Chu, J. et al., CS1-Specific Chimeric Antigen Receptor (CAR)-Engineered Natural Killer Cells Enhance In Vitro and In Vivo Antitumor Activity Against Human Multiple Myeloma. Leukemia. 2014; 28(4):917-27 (25 pages).

(56) References Cited

OTHER PUBLICATIONS

Chu, J. et al., Genetic Modification of T Cells Redirected Toward CSI Enhances Eradication of Myeloma Cells. Clin Cancer res. 2014; 20(15):3989-4000.

Dong, H. and Chen, L., B7-H1 Pathway and Its Role in the Evasion of Tumor Immunity. J Mol Med (Berl). 2003; 81(5):281-7.

Engel, P. et al., The SAP and SLAM Families in Immune Responses and X-Linked Lymphoproliferative Disease. Nat Rev Immunol. 2003;3(10):813-21.

Forero-Torres, A. et al., Results of Phase 1 Study of AME-133v (LY2469298), an Fc-Engineered Humanized Monoclonal Anti-CD20 Antibody, in Fc?RIIIa-Genotyped Patients with Previously Treated Follicular Lymphoma. Clin Cancer Res. 2012; 18(5):1395-403.

Freeman, G.J. et al., Engagement of the PD-1 Immunoinhibitory Receptor by a Novel B7 Family Member Leads to Negative Regulation of Lymphocyte Activation. J Exp Med. 2000; 192(7):1027-34.

García-Martínez, J.M. et al., Ku-0063794 is a Specific Inhibitor of the Mammalian Target of Rapamycin (mTOR). Biochem J. 2009; 421(1):29-42.

Garfall, A.L. et al., Chimeric Antigen Receptor T Cells Against CD19for Multiple Myeloma. N Engl J Med. 2015; 373(11):1040-7.

GenBank Direct Submission DE805786.1 (Dec. 9, 2013) Retrieved from: <https://www.ncbi.nlm.nih.gov/nucgss/DE805786.1> Nucleotides 179-96 (1 page).

GenBank Direct Submission HF427422.1 (Oct. 25, 2012) Retrieved from: <https://www.ncbi.nlm.nih.gov/nucgss/HF427422.1> Nucleotides 347-84 (1 page).

Goldenberg, D.M. et al., Veltuzumab (Humanized Anti-CD20 Monoclonal Antibody): Characterization, Current Clinical Results, and Future Prospects. Leuk Lymphoma. 2010; 51(5):747-55.

Grupp, S.A. et al., Chimeric Antigen Receptor-Modified T Cells for Acute Lymphoid Leukemia. N Engl J Med. 2013; 368(16):1509-18.

Henderson, D.J. et al., Comparison of the Effects of FK-506, Cyclosporin A and Rapamycin on IL-2 Production. Immunology. 1991; 73(3):316-21.

Huang, Y.-H. et al., CEACAM1 Regulates TIM-3-Mediated Tolerance and Exhaustion. Nature. 2015; 517(7534):386-90 (43 pages).

Kappos, L. et al., Ocrelizumab in Relapsing-Remitting Multiple Sclerosis: a Phase 2, randomised, Placebo-Controled, Multicentre Trial. Lancet. 2011; 378(9805):1779-87 (13 pages).

Knight, S.D., Discovery of GSK2126458, a Highly Potent Inhibitor of PI3K and the Mammalian Target of Rapamycin. ACS Med Chem Lett. 2010; 1(1):39-43.

Köhler, G. and Milstein, C., Continuous Cultures of Fused Cells Secreting Antibody of Predefined Specificity. Nature. 1975;256:495-7.

Konishi, J. et al., B7-H1 Expression on Non-Small Cell Lung cancer Cells and Its Relationship with Tumor-Infiltrating Lymphocytes and Their PD-1 Expression. Clin Cancer Res. 2004; 10(15):5094-100.

Latchman, Y. et al., PD-L2 is a Second Ligand for PD-1 and Inhibits T Cell Activation. Nat Immunol. 2001; 2(3):261-8.

Lim, S.H. et al.,Anti-CD20 Monoclonal Antibodies: Historical and Future Perspectives. Haematologica. 2010; 95(1):135-43.

Liu, J. et al., Calcineurin is a Common Target of cyclophilin-Cyclosporin A and FKBP-FK506 complexes. Cell. 1991; 66(4):807-15.

Lonial, S. et al., Elotuzumab Therapy for Relapsed or Refractory Multiple Myeloma. N Engl J Med. 2015; 373(7):621-32.

Mahindra, A. et al., Latest Advances and Current Challenges in the Treatment of Multiple Myeloma. Nat Rev Clin Oncol. 2012; 9(3):135-43.

Mamonkin, M. et al., A T-Cell-Directed Chimeric Antigen Receptor for the Selective Treatment of T-Cell Malignancies. Blood. 2015; 126(8):983-92 (17 pages).

Markel, G. et al., CD66a Interactions Between Human Melanoma and NK Cells: a Novel Class I MHC-Independent Inhibitory Mechanism of Cytotoxicity. J Immunol. 2002; 168(6):2803-10.

Markel, G. et al., Dynamic Expression of Protective CEACAM1 on Melanoma Cells During Specific Immune Attack. Immunology. 2009; 126(2):186-200.

Markel, G. et al., Inhibition of Human Tumor-Infiltrating Lymphocyte Effector Functions by the Homophilic Carcinoembryonic Cell Adhesion Molecule 1 Interactions. J Immunol. 2006; 177(9):6062-71.

Markel, G. et al., Systemic Dysregulation of CEACAM1 in Melanoma Patients. Cancer Immunol Immunother. 2010; 59(2):215-30.

McAlpine, J.B. et al., Revised NMR Assignments for Rapamycin. J Antibiotics. 1991; 44(6):688-90.

Miyagishi, M. and Taira, K., U6 Promoter-Driven siRNAs with Four Uridine 3' Overhangs Efficiently Suppress Targeted Gene Expression in Mammalian Cells. Nat BiotechnoL 2002; 20(5):497-500.

Monney, L. et al., Th1-Specific Cell Surface Protein Tim-3 Regulates Macrophage Activation and Severity of an Autoimmune Disease. Nature. 2002; 415(6871):536-41.

Morrison, S.L. et al., Chimeric Human Antibody Molecules: Mouse Antigen-Binding Domains with Human Constant Region Domains. Proc Natl Acad Sci USA. 1984; 81(21):6851-5.

National Cancer Institute, Surveillance, Epidemiology, and End Results Program: Cancer Stat Facts: Myeloma. Retrieved from the Internet: <https://seer.cancer.gov/statfacts/html/mulmy.html> (2018) (2 pages).

Ngiow, S.F. et al., Anti-TIM3 Antibody Promotes T Cell IFN-γ-Mediated Antitumor Immunity and Suppresses Established Tumors. Cancer Res. 2011; 71(10):3540-51 (13 pages).

Novak, A.J. et al., Expression of BCMA, TACI, and BAFF-R in Multiple Myeloma: a Mechanism for Growth and Survival. Blood. 2004; 103(2):689-94.

Ortenberg, R. et al., Novel Immunotherapy for Malignant Melanoma with a Monoclonal Antibody that Blocks CEACAM1 Homophilic Interactions. Mol Cancer Ther. 2012; 11(6):1300-10.

Porter, D.L. et al., Chimeric Antigen Receptor-Modified T Cells in Chronic Lymphoid Leukemia. N Engl J Med. 2011; 365(8):725-33 (12 pages).

Pyonteck, S.M. et al., CSF-1R Inhibition Alters Macrophage Polarization and Blocks Glioma Progression. Nat Med. 2013; 19(10):1264-72 (23 pages).

Queen, C. et al., A Humanized Antibody that Binds to the Interleukin 2 Receptor. Proc Natl Acad Sci USA. 1989; 86(24):10029-33.

Robak, T. et al., New Anti-CD20 Monoclonal Antibodies for the Treatment of B-Cell Lymphoid Malignancies. BioDrugs. 2011; 25(1):13-25.

Robak, T., GA-101, a Third-Generation, Humanized and Glyco-Engineered Anti-CD20 mAB for the Treatment of B-Cell Lymphoid Malignancies. Curr Opin Investig Drugs. 2009; 10(6):588-96.

Sadelain, M. et al., The Basic Principles of Chimeric Antigen Receptor (CAR) Design. Cancer Discov. 2013; 3(4):388-98.

Schofield, D.J. et al., Application of Phage Display to High Throughput Antibody Generation and Characterization. Gen Biol. 2007; 8(11):R254 (18 pages).

Stephan, S.B. et al., Biopolymer Implants Enhance the Efficacy of Adoptive T-Cell Therapy. Nat Biotechnol. 2015; 33(1):97-101 (18 pages).

Stern, N. et al., Carcinoembryonic Antigen (CEA) Inhibits NK Killing via Interaction with CEA-Related Cell Adhesion Molecule 1. J Immunol. 2005; 174(11):6692-701.

Tiscornia G., Development of Lentiviral Vectors Expressing siRNA, Chapter 3, in Gene Transfer: Delivery and Expression of DNA and RNA (eds. Friedmann and Rossi). Cold Spring Harbor Laboratory Press, Cold Spring Harbor, N.Y., USA (2007) pp. 23-34.

Van Duyne, G.D. et al., Atomic Structure of the Rapamycin Human Immunophilin FKBP-12 Complex. J Am Chem Soc. 1991; 113(19):7433-4.

Venkatesan, A.M., et al., Bis(morpholino-1,3,5-triazine) Derivatives: Potent Adenosine 5'-triphosphate Competitive Phosphatidylinositol-3-Kinase/Mammalian Target of Rapamycin Inhibitors: Discovery of Compound 26 (PKI-587), a Highly Efficacious Dual Inhibitor. J Med Chem. 2010; 53(6):2636-45.

(56) References Cited

OTHER PUBLICATIONS

Yousef, S. et al., CD229 is Expressed on the Surface of Plasma Cells Carrying an Aberrant Phenotype and Chemotherapy-Resistant Precursor Cells in Multiple Myeloma. Hum Vaccin Immunother. 2015; 11(7):1606-11.

Yu, K. et al., Biochemical, Cellular, and In vivo Activity of Novel ATP-Competitive and Selective Inhibitors of the Mammalian Target of Rapamycin. Cancer Res. 69(15):6232-40.

Zamarin, D. and Palese, P., Oncolytic Newcastle Disease Virus for Cancer Therapy: Old Challenges and New Directions. Future Microbiol. 2012; 7(3):347-67 (37 pages).

Zhang, C. et al., Amyloid-Like Aggregates of the Yeast Prion Protein Ure2 Enter Vertebrate Cells by Specific Endocytotic Pathways and Induce Apoptosis. PLoS One. 2010; 5(9):e12529 (12 pages).

International Search Report and Written Opinion dated Nov. 21, 2017 by the International Searching Authority for Patent Application No. PCT/US2017/042840, which was filed on Jul. 19, 2017 and published as WO 2018/017708 on Jan. 25, 2018 (Inventor—Luetkens et al.; Applicant—University of Utah Research Foundation; (15 pages).

International Preliminary Reporton Patentability dated Jan. 22, 2019 by the International Searching Authority for Patent Application No. PCT/US2017/042840, which was filed on Jul. 19, 2017 and published as WO 2018/017708 on Jan. 25, 2018 (Inventor—Luetkens et al.; Applicant—University of Utah Research Foundation; (10 pages).

\* cited by examiner

CD229 CAR T CELLS AND METHODS OF USE THEREOF

CROSS-REFERENCE TO RELATED PATENT APPLICATIONS

This application claims the benefit of priority under 35 U.S.C. § 371 of International Application No. PCT/US2017/042840 filed on Jul. 19, 2017, which claims priority to U.S. Provisional Application No. 62/364,527, filed on Jul. 20, 2016, and U.S. Provisional Application No. 62/413,776, filed Oct. 27, 2016. The content of these earlier filed applications are hereby incorporated by reference in its entirety.

Please add the following new paragraph on page 1 directly beneath the Cross-Reference to Related Patent Applications paragraph added above:

REFERENCE TO SEQUENCE LISTING

The Sequence Listing submitted Jan. 21, 2019 as a text file named "21101_0335U3_Sequence_Listing.txt," created on Jan. 17, 2019, and having a size of 196,955 bytes is hereby incorporated by reference pursuant to 37 C.F.R. § 1.52(e)(5).

BACKGROUND

Multiple myeloma (MM) is an incurable plasma cell malignancy with significant morbidity and mortality. While proteasome inhibitors and immunomodulatory agents have improved rate and depth of responses, most patients will eventually relapse. Accordingly, there is an urgent medical need for more effective therapeutic strategies capable of eradicating minimal residual disease. Chimeric antigen receptors (CARs) combine an antibody domain directed against a surface antigen with signaling domains that induce T cell activation. CD229, a member of the SLAM (signaling lymphocyte activation molecule) family of proteins, is strongly expressed on both MM cell lines and primary MM cells, including chemotherapy-resistant CD19-138-pre-plasma cells. CD229 is physiologically expressed on T and B lymphocytes and natural killer (NK) cells but absent from myeloid cells, hematopoietic stem cells, and nonhematopoietic cells. Thus, a CD229-specific CAR T cell can be used to target MM cells.

BRIEF SUMMARY

Disclosed are chimeric antigen receptor (CAR) polypeptides comprising a CD229 antigen binding domain, a transmembrane domain, and an intracellular signaling domain.

Disclosed are nucleic acid sequences capable of encoding a CAR polypeptide comprising a CD229 antigen binding domain, a transmembrane domain, and an intracellular signaling domain.

Disclosed are antibodies or fragments thereof that bind to human CD229, wherein said antibody comprises a variable heavy chain comprising a sequence having at least 90% identity to a sequence set forth in SEQ ID NOs:16, 17, 18, 19, 20, 21, 22, 23, 24, 25, 26, 27, 28, 29, or 30; a variable light chain comprising a sequence having at least 90% identity to a sequence set forth in SEQ ID NOs:31, 32, 33, 34, 35, 36, 37, 38, 39, 40, 41, 42, 43, 44, or 45; or both.

Disclosed are nucleic acid sequences comprising a variable heavy chain comprising a sequence having at least 90% identity to a sequence set forth in SEQ ID NOs: 134, 135, 136, 137, 138, 139, 140, 141, 142, 143, 144, 145, 146, 147, or 148; a variable light chain comprising a sequence having at least 90% identity a sequence set forth in SEQ ID NOs:149, 150, 151, 152, 153, 154, 155, 156, 157, 158, 159, 160, 161, 162, or 163; or both.

Disclosed are methods of treating multiple myeloma comprising administering an effective amount of a T cell genetically modified to express a CAR polypeptide comprising a CD229 antigen binding domain, a transmembrane domain, and an intracellular signaling domain.

Disclosed are methods of detecting CD229 on a cell comprising administering a composition comprising an antibody or fragment thereof comprising a variable heavy chain comprising a sequence having at least 90% identity to a sequence set forth in SEQ ID NOs: 16, 17, 18, 19, 20, 21, 22, 23, 24, 25, 26, 27, 28, 29, or 30; a variable light chain comprising a sequence having at least 90% identity to a sequence set forth in SEQ ID NOs:31, 32, 33, 34, 35, 36, 37, 38, 39, 40, 41, 42, 43, 44, or 45; or both to a sample and detecting the binding of the antibody or fragment thereof to CD229.

Disclosed are methods of killing CD229 positive cells comprising administering an effective amount of a T cell genetically modified to express a CAR polypeptide comprising a CD229 antigen binding domain, a transmembrane domain, and an intracellular signaling domain.

Disclosed are methods of activating a T cell expressing a CAR polypeptide comprising a CD229 antigen binding domain, a transmembrane domain, and an intracellular signaling domain comprising culturing the T cell with a cell expressing CD229 and detecting the presence or absence of IFN-γ after culturing, wherein the presence of IFN-γ indicates the activation of the T cell.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 2A, 2B, 2C, 2D, 2E, and 2F show the generation and screening of fully human monoclonal antibodies and CARs against CD229. (A) Schema demonstrating the principle of antibody phage display. After incubation of the phage library with immobilized CD229, bound phages are eluted and amplified in E. coli. Enriched phage undergo repeated selections to provide a pool of CD229-specific antibodies for the generation of CAR constructs. (B) Analysis of monoclonal binders expressed as soluble scFv constructs in BL21 cells by time-resolved fluorescence assay. (C) Schematic representation of the three screening formats used for antibody binding assays. (D) Schematic representation of the CAR screening assay determining CAR surface expression and antigen binding. (E) Results of CAR surface expression and antigen binding by flow cytometry of human 293 cells expressing each of 23 CAR constructs as determined by flow cytometry. (F) Comparison of binding of 23 unique clones to CD229 in three antibody formats. (Bottom) Binding of anti-CD229 scFvs expressed in E. coli determined by time resolved florescence (TRF) assay. (Middle) Binding of anti-CD229 scFv-Fc antibodies expressed in 293F cells determined by TRF assay. (Top) Binding of anti-CD229 CARs expressed in 293T cells shown as mean fluorescence intensity (MFI) by flow cytometry.

Figure 3A:
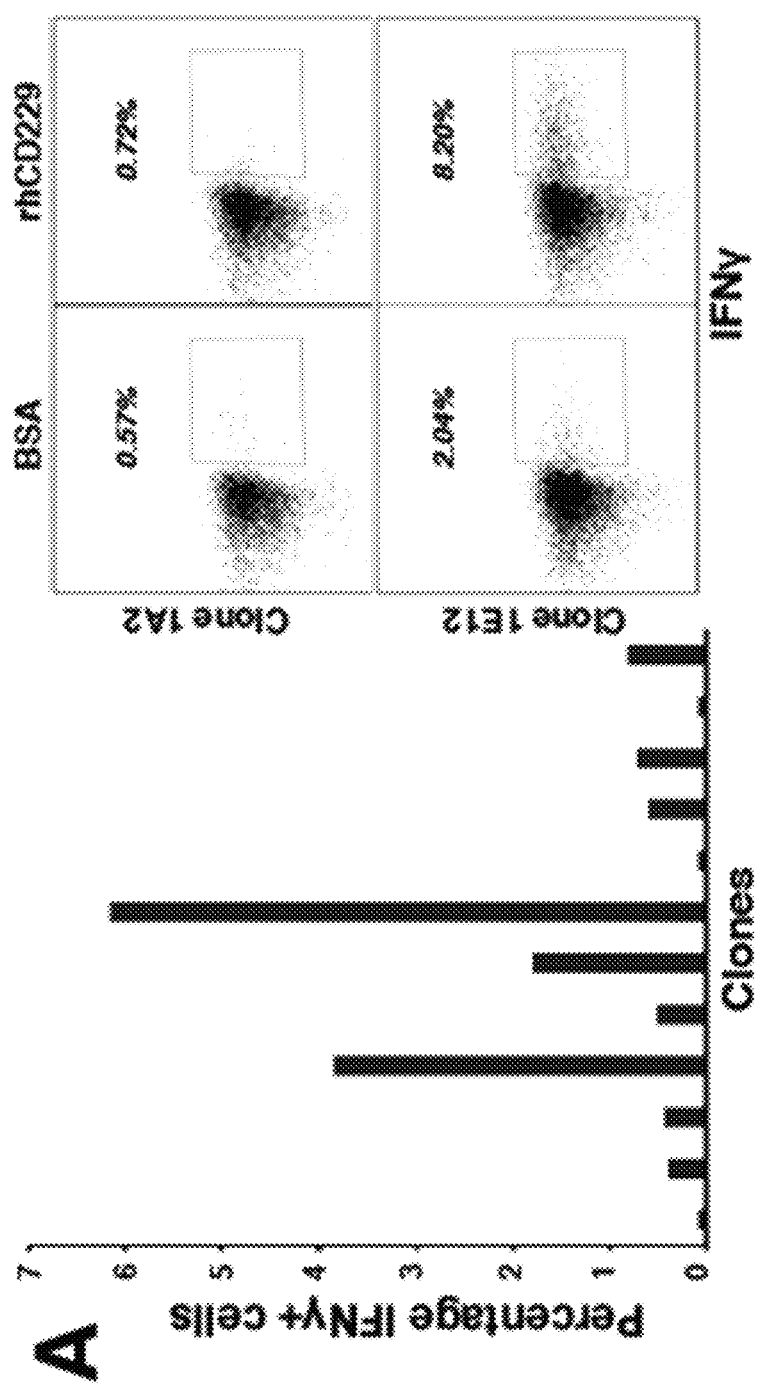
Figure 3B:
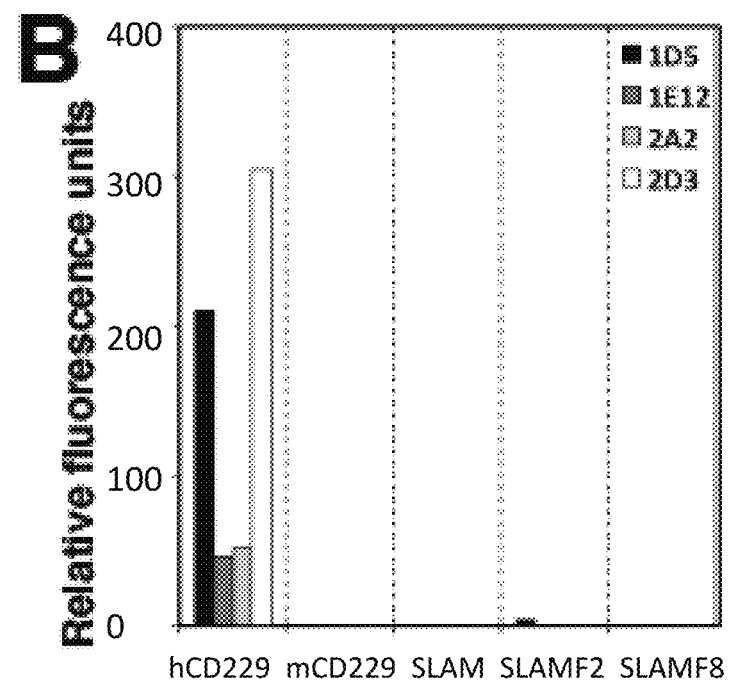
Figure 3C:
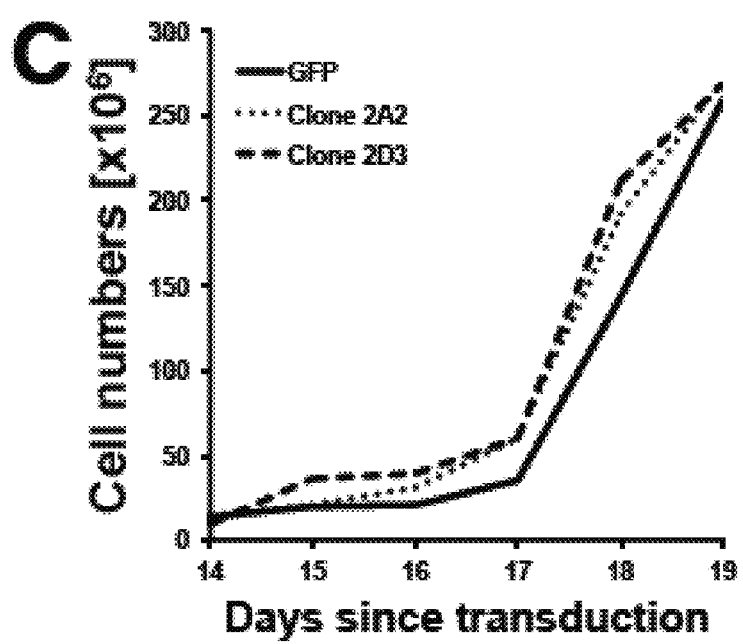

FIGS. 3A, 3B, and 3C show the activation and cross-reactivity of anti-CD229 CAR T cells. (A) Intracellular interferon gamma (IFNγ) staining of primary human T cells expressing each of 12 CAR constructs as determined by flow cytometry. Example dot plots are shown for non-reactive clone 1A2 and reactive clone 1E12. Both clones showed no significant reactivity towards immobilized BSA. A relatively low percentage of IFNγ-positive cells was expected as this assay was performed with freshly transduced CAR T cells which had not been enriched for CAR expression and only showed an average transduction rate of 20%. (B) Preliminary crossreactivity analysis of 4 randomly elected clones against human CD229 (hCD229), murine CD229 (mCD229) and four other SLAM family receptors. (C) Expansion curves of primary human T cells after lentiviral transduction of constructs expressing each of two anti-CD229 CARs or GFP alone.

Figures 4A, 4B:
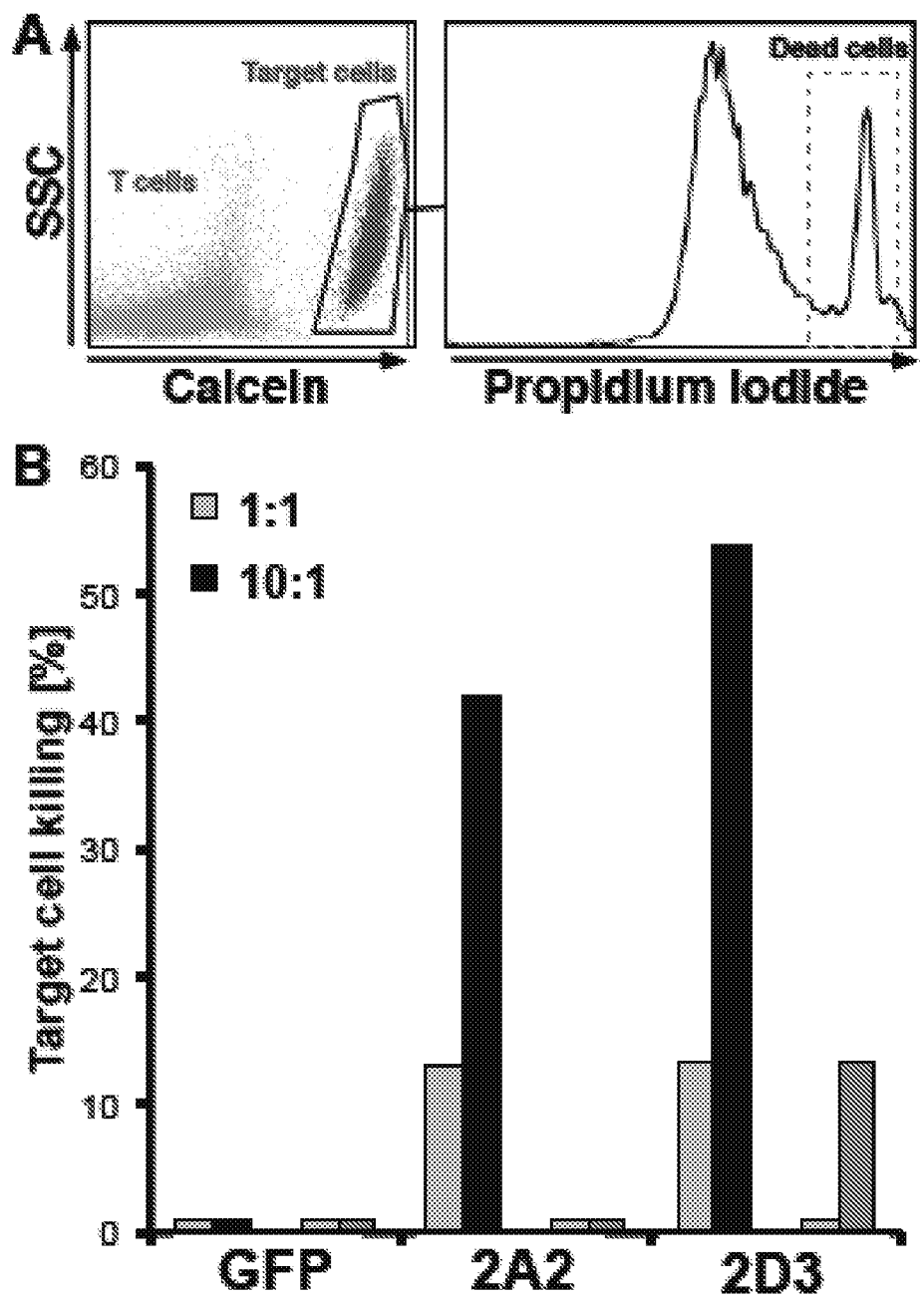
Figures 5A, 5B:
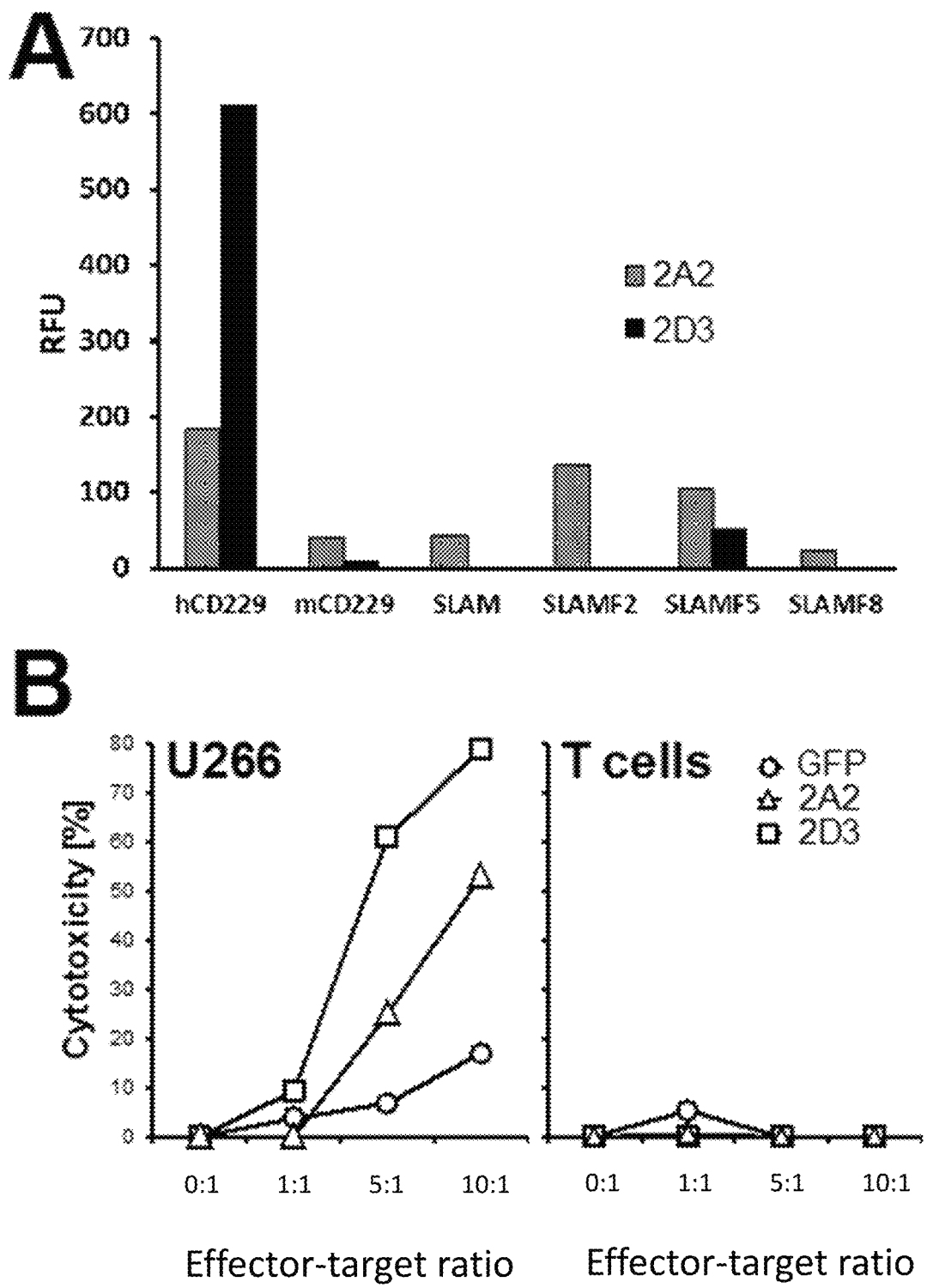
Figure 5C:
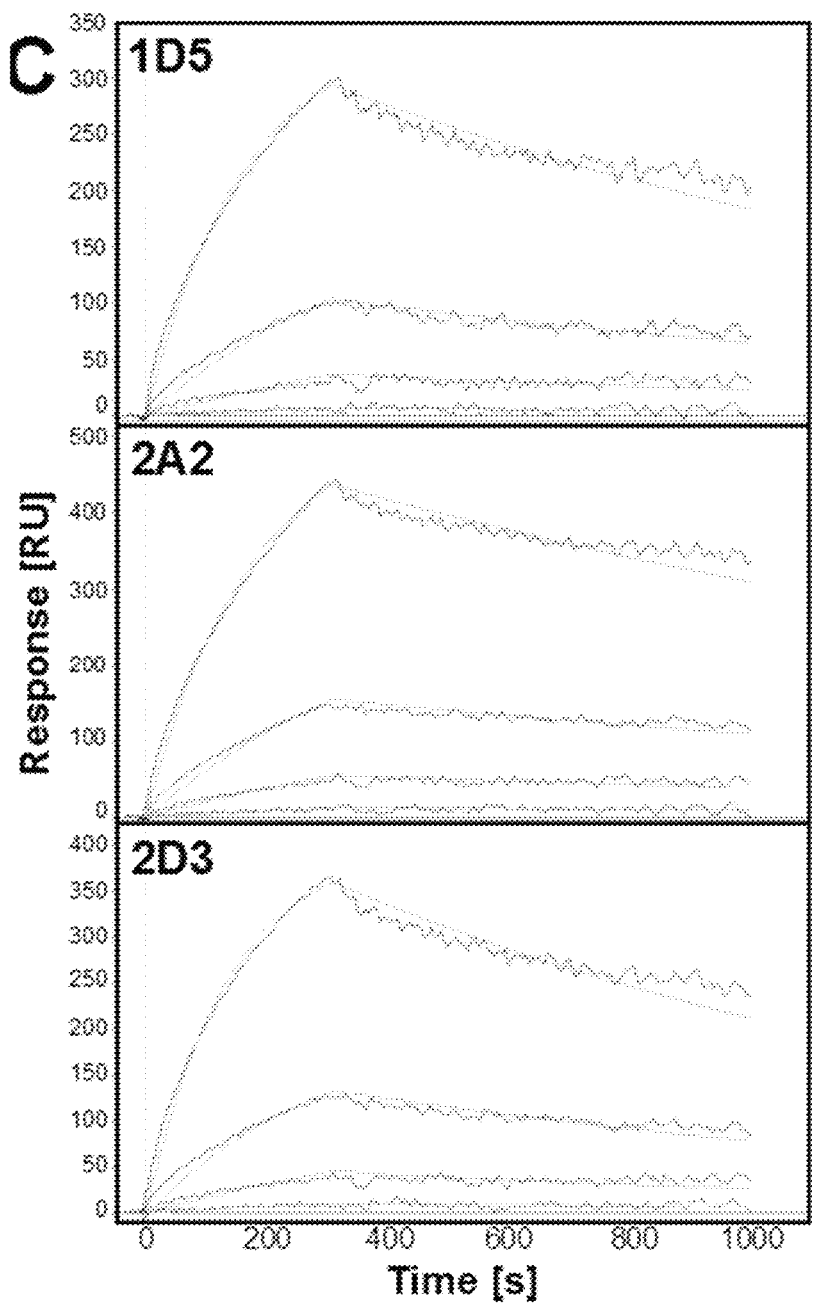
Figures 5D, 5E:
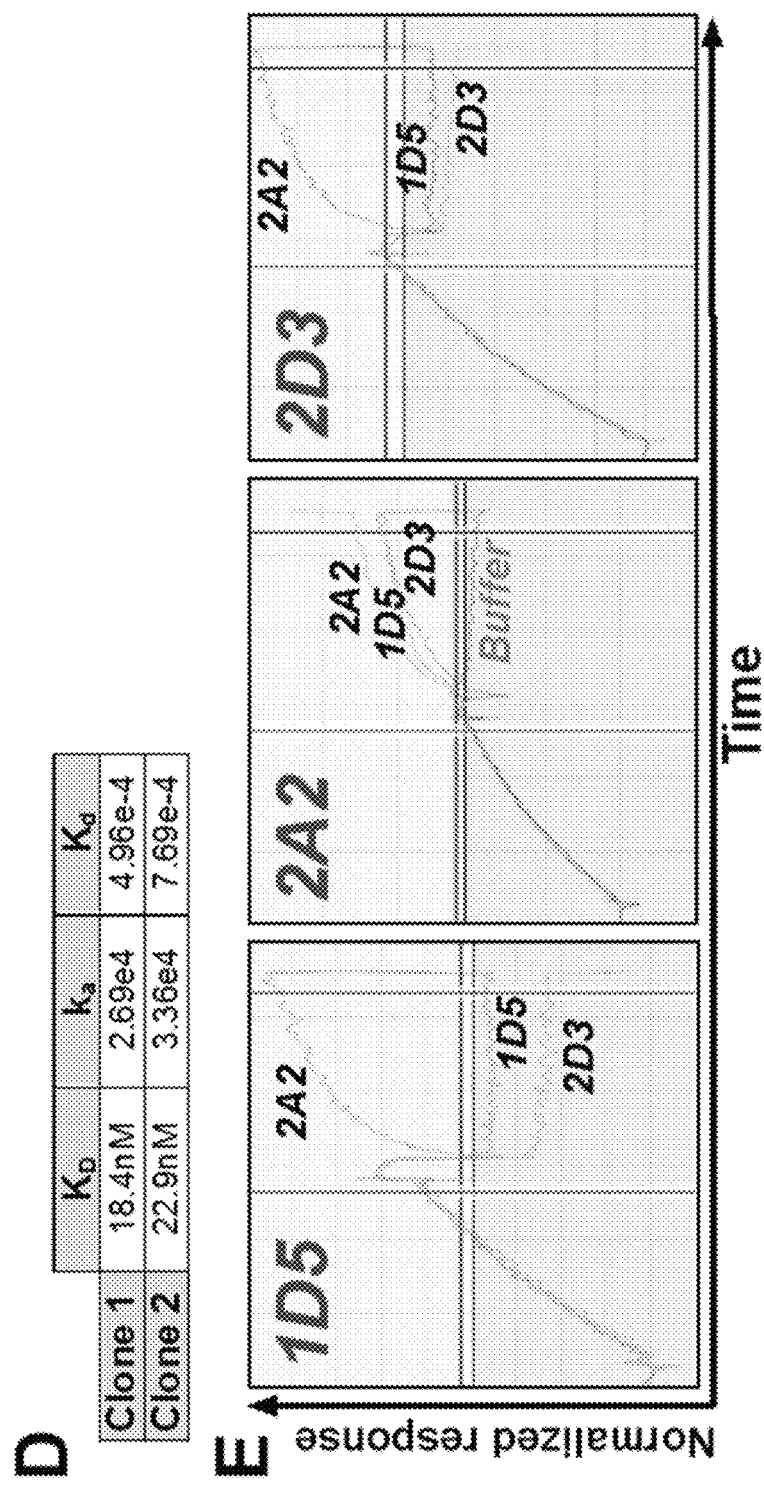

FIGS. 4A and 4B show the cytoxicity of anti-CD229 CAR T cells against CD229-expressing target cells. (A) Gating schema of the flow cytometry-based cytotoxicity assay used to determine activity of anti-CD229 CAR constructs. (B) T cells expressing two different anti-CD229 CAR clones (2A2 and 2D3) or GFP were incubated with K562 cells expressing CD229 (set of bars on the left of each group) or autologous untreated T cells (set of bars on the right of each group). Target cells were stained with Calcein-AM prior to the cytotoxicity assay. GFP sorted anti-CD229 CAR T cells were incubated with target cells at effector-target ratios of 0:1, 1:1, and 10:1 for 4 hours at 37° C. Target cell killing was assessed by flow cytometry. T cell clones expressing anti-CD229 CAR showed strong cytotoxic activity against K562-CD229 cells but only limited toxicity against autologous T cells.

FIGS. 5A, 5B, 5C, 5D, and 5E show the binding, cross-reactivity, and selectivity of anti CD229 CAR T cells. (A) Cross-reactivity screening of 2 anti-CD229 antibody clones expressed as scFv-Fc constructs in mammalian cells by TRF assay using recombinant SLAM family members. 2A2 shows some cross-reactivity while 2D3 is specific to human CD229 only. (B) Cytotoxic activity of primary human T cells expressing CAR constructs based on two antibodies or GFP alone against CD229 positive myeloma cell line U266 and healthy autologous T cells as determined by flow cytometry. Anti-CD229 CARs specifically kill myeloma cells but not healthy T cells co-expressing CD229. (C) Sensorgrams of 3 anti-CD229 antibodies expressed as scFv-Fc in mammalian cells using high-throughput surface plasmon resonance (SPR) and resulting (D) equilibrium and rate constants demonstrating slow on- and off-rates for all 3 clones. (E) Competition SPR using immobilized CD229 and sequential injections of the primary antibodies followed by individual injection of antibodies to determine their ability to compete for the epitope recognized by the primary antibody. 1D5 and 2D3 occupy the same epitope space while 2A2 binds to a distinct epitope. Due to the lack of self-competition, 2A2 most likely binds to an epitope occurring twice in recombinant CD229, a tandem Ig domain-containing protein.

FIGS. 6A-6G show the expression of CD229 in MM. (A) Schematic representation of clonotypic hierarchy and interconversion of myeloma plasma cells (PC), the CD138low PC population, and chemotherapy-resistant Pre-PC. (B) (Top panel) Gating scheme to identify chemotherapy resistant CD19-138-plasma cells. Initial gates include CD19-2-3-14-16-235a-(left), followed by gating for CD200+3 19+ (Middle) and then differentiated into CD38+ plasma cells that are CD138-positive and -negative, respectively. (Bottom panel) Expression of CD229 in four patients with MM. Histogram represents CD38+CD138high (far right), histogram CD38+CD138low (middle) and histogram fluorescence minus one (FMO) control (far left). (C) In a clonogenic growth assay, clonal MM clusters were counted 7-10 days after culture initiation using MM cell line MOLP-8 (left) or KMS-12-BM (right). Bars indicate standard error of mean values derived from three separate experiments. Numbers of colonies produced by MM cells transfected with CD229 siRNA or scrambled control siRNA were compared to those of cultures with untreated cells. Asterisks indicate statistically significant differences ($*P<0.05$). (D) CD229 mRNA expression was analyzed in healthy tissues by qRT-PCR and normalized to the tissue's respective expression of housekeeping gene GAPDH. (E) Expression of 4 targets suggested for the treatment of MM on CD34+ hematopoietic progenitor cells in the bone marrow of 3 MM patients. Expression was determined by flow cytometry. Red represents an isotype control, blue staining with the target-specific antibody. (F) Expression of CAR targets on peripheral blood lymphocyte subsets obtained from a healthy donor. Expression was determined by flow cytometry. (G) Expression of CAR targets on B lineage cells from the bone marrow of a MM patient with >10% bone marrow plasma cell infiltration. Gating on B cell subsets was performed as previously described. Expression of CAR targets on CD19-CD38+CD138+MM plasma cells from 3 patients with >10% bone marrow plasma cell infiltration as well as human MM cell lines U266 and RPMI8226 was determined by flow cytometry.

FIGS. 7A-7L show the generation and screening of fully human monoclonal antibodies and CARs against CD229. (A) Schema demonstrating the principle of antibody phage display. After incubation of the phage library with immobilized CD229, bound phages are eluted and amplified in *E. coli*. Enriched phage undergo repeated selections to provide a pool of CD229-specific antibodies for the generation of CAR constructs. (B) Analysis of monoclonal binders expressed as soluble scFv constructs in BL21 cells by time-resolved fluorescence assay. (C) Schematic representation of the three screening formats used for antibody binding assays. (D) Schematic representation of the CAR screening assay determining CAR surface expression and antigen binding. (E) Results of CAR surface expression and antigen binding by flow cytometry of human 293 cells expressing each of 23 CAR constructs as determined by flow cytometry. (F) Comparison of binding of 23 unique clones to CD229 in three antibody formats. (Bottom) Binding of anti-CD229 scFvs expressed in *E. coli* determined by time resolved florescence (TRF) assay. (Middle) Binding of anti-CD229 scFv-Fc antibodies expressed in 293F cells determined by TRF assay. (Top) Binding of anti-CD229 CARs expressed in 293T cells shown as mean fluorescence intensity (MFI) by flow cytometry. (G) Representative sensorgrams of two CD229-specific antibodies, as determined by surface plasmon resonance. (H) Cross-reactivity analysis of 16 CD229 antibodies against all known SLAM family receptors as well as murine CD229, and anti-human Fc as determined by surface plasmon resonance. (I) Expression of CD229 as determined by flow cytometry staining using anti-CD229 scFv clone 2D3 (Panel E, lower left) on untransfected 293 cells or 293 cells transfected with a CD229 expression construct. (J) Expression of CD229 as determined by flow cytometry staining with 2D3 on healthy lymphocyte subsets, T cells activated with CD3/CD28 beads and stimulated with IL-2, as well as MM cell line U266. Far left areas represent isotype control staining, black lines and far right areas represent 2D3 staining. Bottom panels show CD19-CD38+CD138+MM plasma cells from 3 patients with >10% MM plasma cell infiltration. (K) Computational model of the structure of CD229. The bottom left of the four main regions indicates C2-type 2 domain deleted in isoform 3. (L) RT-PCR of CD229 isoforms in lymphocyte subsets and MM cell line U266.

FIGS. 8A-8H show the manufacturing and efficacy of CD229 CAR T cells. (A) Primary human T cells were isolated and activated using CD3/CD28 beads and stimulated every 2 days by addition of 40 U/ml of IL-2. T cells were transduced with lentiviral supernatants encoding a CD19-specific CAR based on scFv clone FMC63 or our CD229-specific CAR based on scFv clone 2D3 on days 2 and 3 and kept at a concentration of $0.4 \times 10^6$ cells/ml until day 12. PD-1 expression on these cells was determined multiple times throughout CAR T cells manufacturing by flow cytometry. (B) CAR T cell expansion during manufacturing. (C) CAR T cell phenotype was evaluated multiple times throughout manufacturing for both CAR T cell populations by flow cytometry. (D) K562 cells transduced with a GFP control construct or a CD229 expression construct were sorted for reporter expression and incubated for 4 h with CD229 CAR T cells. Cytotoxicity was determined by flow cytometry. (E) Human MM cell lines U266 and RPMI8226 were transduced with luciferase and incubated overnight with T cells transduced with GFP or our CD229 CAR construct. Luminescence was determined the next morning after addition of luciferin and cytotoxicity was calculated as the fraction of luminescence signal of untreated target cells. Note: different effector-target ratios were used for the two cell lines. Reduced efficacy compared to panel F of the CAR T cells used for this experiment may be the result of prolonged expansion for more than 3 weeks. (F) CD19 and CD229 CAR T cells were incubated overnight with U266 cells transduced with a luciferase construct at very low effector-target ratios. Cytotoxicity was determined as described above. (G) Healthy lymphocytes subsets were purified and stained with calcein AM, and T cells activated for multiple days with CD3/CD28 beads and repeatedly stimulated with IL-2 were incubated for 4 h with CD229 CAR T cells. Cytotoxicity was determined by flow cytometry. (H) NSG mice were injected with $5 \times 10^6$ U266 cells expressing luciferase on day 0. $5 \times 10^6$ CAR T cells or PBS were injected on day 7 and bioluminescence was determined on day 6, day 13, and day 24.

Figure 9:
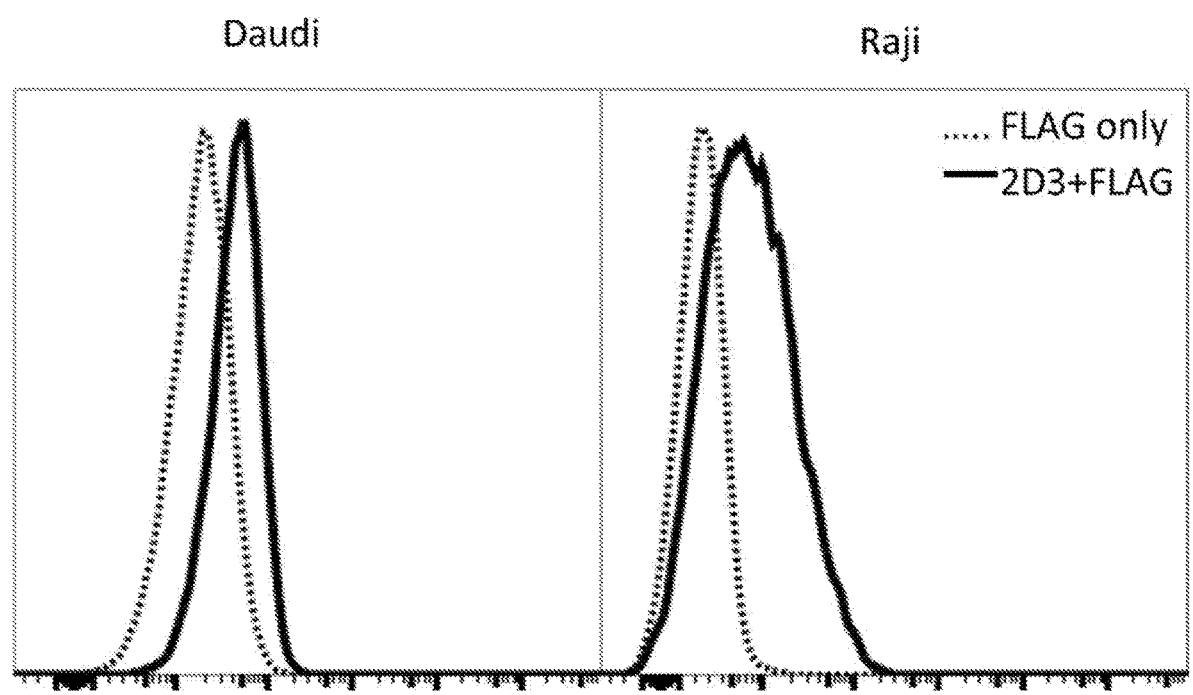

FIG. 9 shows the presence of CD229 as recognized by clone 2D3 on two Burkitt's lymphoma cell lines.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. If a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a CD229 antigen binding domain" includes a plurality of such binding domains, reference to "the CD229 antigen binding domain" is a reference to one or more CD229 antigen binding domains and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range¬from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

A "single-chain variable fragment (scFv)" means a protein comprising the variable regions of the heavy and light chains of an antibody. A scFv can be a fusion protein comprising a variable heavy chain, a linker, and a variable light chain.

A "fragment antigen-binding fragment (Fab)" is a region of an antibody that binds to antigen. An Fab comprises constant and variable regions from both heavy and light chains.

A "CDR" or complementarity determining region is a region of hypervariability interspersed within regions that are more conserved, termed "framework regions" (FR).

The term "monoclonal antibody" (monoclonal antibody) refers to an antibody, or population of like antibodies, obtained from a population of substantially homogeneous antibodies, and is not to be construed as requiring production of the antibody by any particular method, including but not limited to, monoclonal antibodies can be made by the hybridoma method first described by Kohler and Milstein (Nature, 256: 495-497, 1975), or by recombinant DNA methods.

The term "chimeric antibody" (or "chimeric immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al. (1984), infra; Morrison et al., Proc. Natl. Acad. Sci. U.S.A. 81:6851).

The term "humanized antibody" refers to forms of antibodies that contain sequences from non-human (eg, murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody can comprise all or substantially all of at least one, and in one aspect two, variable domains, in which all or substantially all of the hypervariable loops correspond to those of a non-human immunoglobulin and all or substantially all of the FR regions are those of a human immunoglobulin sequence. The humanized antibody optionally also can comprise at least a portion of an immunoglobulin constant region (Fc), or that of a human immunoglobulin (see, e.g., Cabilly et al., U.S. Pat. No. 4,816,567; Cabilly et al., European Patent No. 0,125, 023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1; Queen et al. (1989) Proc. Natl. Acad. Sci. USA, Vol 86:10029-10033).

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

B. Chimeric Antigen Receptor (CAR) Polypeptide

Disclosed are chimeric antigen receptor (CAR) polypeptides comprising a CD229 antigen binding domain, a transmembrane domain, and an intracellular signaling domain.

The CD229 antigen binding domain, transmembrane domain, and intracellular signaling domain can be any of those described herein and any combination of those described herein.

In some instances, any of the disclosed CAR polypeptides can further comprise a tag sequence. In some instances, the tag sequence can be located between the CD229 antigen binding domain and the transmembrane domain or between the CD229 antigen binding domain and a hinge region. In some instances, the tag sequence can be a hemagglutinin tag, histidine tag, glutathione-S-transferase tag, or fluorescent tag. For example, the tag can be any sequence capable of aiding in the purification of the CAR polypeptide or capable of detecting the CAR polypeptide.

1. CD229 Antigen Binding Domain

In some instances, the CD229 antigen binding domain can be an antibody fragment or an antigen-binding fragment that specifically binds to CD229. In some instances, the CD229 antigen binding domain can be any recombinant or engineered protein domain capable of binding CD229.

In some instances, the CD229 antigen binding domain can be a Fab or a single-chain variable fragment (scFv) of an antibody that specifically binds CD229. In some instances, the scFv, comprising both the heavy chain variable region and the light chain variable region, can comprise the N-terminal region of the heavy chain variable region linked to the C-terminal region of the light chain variable region. In some instances, the scFv comprises the C-terminal region of the heavy chain variable region linked to the N-terminal region of the light chain variable region.

In some instances, the CD229 antigen binding domain comprises an amino acid sequence set forth in SEQ ID NO: 1, 2, 3, 4, 5, 6, 7, 8, 9, 10, 11, 12, 13, 14, or 15. In some instances, the CD229 antigen binding domain can comprise a heavy chain variable region, a light chain variable region, and a linker that links the heavy chain variable region to the light chain variable region. For example, SEQ ID NOs:1-15 comprise the heavy chain variable region, linker, and light chain variable region (see Table 1). In some instances, the linker can be directly involved in the binding of CD229 to the CD229 antigen binding domain. In some instances, the linker can be indirectly involved in the binding of CD229 to the CD229 antigen binding domain.

TABLE 1

CD229 antigen binding domains. Variable heavy chain (bold), linker (underlined), and variable light chain

| SEQ ID NO: 1 | QITLKESGPTLVKPTQTLTLTCTFSGFSLSTSGVGVGWI RQPPGKALEWLALIYWNDDKRYSPSLKSRLTIAKDTSKN QVVLTMTNMDPVDATYYCARMGWNDPHMVDYWGQGTLVT VSSLEGGGGSGGGGSGGGASDIQMTQSPSSLSASVGDRV TITCRASQSIGSSLHWYQQKPGKAPKFLIYDASSLESGV PSRFSGSGSGTEFTLTISSLQPDDFATYYCQQYNSYPLT FGGGTKLEIKR |
|---|---|
| SEQ ID NO: 2 | QMQLVESGAEVKKPGSSVKVSCKASGGTFSSYAISWVRQ APGQGLEWMGGIIPIFGTANYAQKFQGRVTITADKSTST AYMELSSLRSEDTAVYYCAADMELRDYYYGMDVWGQGTL VTVSSLEGGGGSGGGGSGGGASQSGLTQPRSVSGSPGQS VTISCTGTSSDVGGYNYVSWYQQHPGKAPKLMIYDVSKR PSGVPDRFSGSKSGNTASLTVSGLQAEDEADYYCSSYAG SNTFVFGSGTKLTVLG |
| SEQ ID NO: 3 | QVQLLESGGGVAQPGRSLKLSCAASGFTFSSYGMHWVRQ APGEGLEWVAVISYDGSNKYYADSVKGRFTISRDNSKNT LYLQMNSLRAEDTAVYYCAKDTCTNGVCYPDYWGQGTLV TVSSLEGGGGSGGGGSGGGASDIVMTQSPATLSVSPGER ATLSCRASQSVGSSLAWYQQKPGQAPRLLIYGGSVRATG IPARFSGSGSGTEFTLTISSLQSEDFAAYYCQQYNSYPL TFGGGTKLEIKR |
| SEQ ID NO: 4 | EVQLVQSGAEVKKPGASVKVSCKASGYTFTSYGISWVRQ APGQGLEWMGWISAYNGNTNYAQKLQGRVTMTTDTSTST AYMELRSLRSDDTTVYYCARSPSTVVTPFSDYWGQGTLV TVSSLEGGGGSGGGGSGGGASNFMLTQPHSVSESPGKTV TISCTGSSGSIASNYVQWYQQRPGSSPTTVIYEDNQRPS GVPDRFSGSIDSSSNSASLTISGLKTEDEADYYCQSYDG SNPVVFGGGTQLTVLG |
| SEQ ID NO: 5 | EVQLVESGGGLVQPGRSLRLSCAASGFTFDDYAMHWVRQ APGKGLEWVSGISWNSGSIGYADSVKGRFTISRDNAKNS LYLQMNSLRAEDTALYYCAKRHGGTNAFDIWGQGTMVTV SSLEGGGGSGGGGSGGGASDIQMTQSPSSLSASVGDRVT ITCRASQSISSYLNWYQQKPGKAPKLLIYAASSLQSGVP SRFSGSGSGTDFTLTISSLQPEDFATYYCQQSYSTLYTF GQGTKLEIKR |
| SEQ ID NO: 6 | QITLKESGPTLVKPTETLTLTCTFSGFSLNTGGVSVGWV RQTPGKALEWLALIYWNDDKRYSPSLKSRLTITKDTSKN QVVLTMTNMDTVDTATYYCAHSAAGVDYWGQGTLVTVSS LEGGGGSGGGGSGGGASDIQMTQSPSSLSASVGDRVTIT CQASQDISNYLNWYQQKPGKAPKLLIYDASNLETGVPSR FSGSGSGTDFTFTISSLQPEDIATYYCQQYDNLPITFGP GTKVDIKR |
| SEQ ID NO: 7 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARGWNYELDYWGQGTLVTVSS LEGGGGSGGGGSGGGASNFMLTQPHSVSGSPGKTVTISC TRSSGYIASNYVQWYQQRPGSAPTTVIYEDNQRPSGVPD RFSGSIDSSSNSASLTISGLKTEDEADYYCQSYDSSNQG VFGGGTKLTVLV |
| SEQ ID NO: 8 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDWGQGTLVTVSSL EGGGGSGGGGSGGGASNFMLTQPHSVSGSPGKTVTISCT RSSGYIASNYVQWYQQRPGSSPTTLIYDDDQRPSGVPDR FSGSIDRSSNSASLTISGLKTEDEGDYYCQSYDSSLVIF GGGTKVTVLG |
| SEQ ID NO: 9 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAHISSSGGTEVQDYWGQGTL VTVSSLEGGGGSGGGGSGGGASDIQMTQSPSSLSASVGD RVTITCRASQSIGSSLHWYQQKPGKAPKFLIYDASSLES GVPSRFSGSGSGTEFTLTISSLQPDDCATYYCQQYNSYP LTFGGGTKLEIKR |
| SEQ ID NO: 10 | QMQLVQSGAEVKKPGSSVKVSCKASGGTFSSYAISWVRQ APGQGLEWMGGIIPIFGTANYAQKFQGRVTITADKSTST AYMELSSLRSDDTAVYYCARDELWATNYYYMDVWGKGTL VTVSSLEGGGGSGGGGSGGGASQSALTQPRSVSGSPGQS |

TABLE 1-continued

CD229 antigen binding domains. Variable heavy chain (bold), linker (underlined), and variable light chain

|  | |
|---|---|
| | VTISCTGTSSDVGSYNYVSWYQQSPGKAPKLMIYDVSNR PSGVSNRFSGSKSGNTASLTISGLQSEDEADYYCTSYGS YDIPVIFGGGTKLTVLG |
| SEQ ID NO: 11 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDYWGRGTLVTVSP <u>LEGGGGSGGGGSGGGAS</u>NFMLTQPHSVSGSPGKAVTISC TRSSGNIARSFVQWYQQRPGSAPTAVIYEDNRRPSGVPD RFSGSFDSSSNSASLTISGLKTEDEADYYCQSYDSSNHV VFGGGTKVTVLG |
| SEQ ID NO: 12 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDYWGQGTLVTVSS <u>LEGGGGSGGGGSGGGAS</u>NFMLTQPHSVSGSPGKTVTISC TRSSGYIASNYVQWYQQRPGSSPTTLIYDDDQRPSGVPD RFSGSIDRSSNSASLTISGLKTEDEGDYYCQSYDSTTEV FGTGTKLTVLG |
| SEQ ID NO: 13 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAQAKPYSSDFDIWGQGTMVT VSS<u>LEGGGGSGGGGSGGGAS</u>NFMLTQPHSVSESPGKTVT ISCTGSSSGIASNYVQWYQQRPGSSPTTVIYEDNQRPSG VPDRFSGSIDSSSNSASLTISGLKTEDEADYYCQSYDSS NQGVFGGGTQLTVLG |
| SEQ ID NO: 14 | QVQLVESGGGLVQPGRSLRLSCAASGFTFDDYAMHWVRQ APGKGLEWVSGISWNSGSIGYADSAKGRFTISRDNSKNT LYLQMNSLRAEDTAVYYCAKRGNSNSFDYWGQGTLVTVS SLE<u>GGGGSGGGGSGGGAS</u>DIQMTQSPSSVSASVGDRVTI TCRASQSISSYLNWYQQKPGKAPKLLIYAASSLQSGVPS RFSGSGSGTDFTLTISSLQPEDFATYYCQQSYSTPWTFG QGTKLEIKR |
| SEQ ID NO: 15 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAQAKPYSSDFDIWGQGTMVT VSS<u>LEGGGGSGGGGSGGGAS</u>DIQMTQSPSSLSASVGDRV TISCQASQDISNYLNWYQQKPGKAPKLLIYAASSLQSGV PSRFSGSGSGTDFTLTISSLQPEDFATYYCLQDYNYPWT FGQGTKVEIKR |

In some instances, the CD229 antigen binding domain comprises a variable heavy chain comprising a sequence having at least 90% identity to a sequence set forth in SEQ ID NOs: 16, 17, 18, 19, 20, 21, 22, 23, 24, 25, 26, 27, 28, 29, or 30 (See Table 2). In some instances, the CD229 antigen binding domain comprises a variable heavy chain comprising a sequence having at least 90, 91, 92, 93, 94, 95, 96, 97, 98, 99, or 100% identity to a sequence set forth in SEQ ID NOs:16, 17, 18, 19, 20, 21, 22, 23, 24, 25, 26, 27, 28, 29, or 30.

TABLE 2

Variable Heavy Chains

| | |
|---|---|
| SEQ ID NO: 16 | QITLKESGPTLVKPTQTLTLTCTFSGFSLSTSGVGVGWI RQPPGKALEWLALIYWNDDKRYSPSLKSRLTIAKDTSKN QVVLTMTNMDPVDTATYYCARMGWNDPHMVDYWGQGTLV TVSS |
| SEQ ID NO: 17 | QMQLVESGAEVKKPGSSVKVSCKASGGTFSSYAISWVRQ APGQGLEWMGGIIPIFGTANYAQKFQGRVTITADKSTST AYMELSSLRSEDTAVYYCAADMELRDYYYGMDVWGQGTL VTVSS |
| SEQ ID NO: 18 | QVQLLESGGGVAPGRSLKLSCAASGFTFSSYGMHWVRQ APGEGLEWVAVISYDGSNKYYADSVKGRFTISRDNSKNT LYLQMNSLRAEDTAVYYCAKDTCTNGVCYPDYWGQGTLV TVSS |
| SEQ ID NO: 19 | EVQLVQSGAEVKKPGASVKVSCKASGYTFTSYGISWVRQ APGQGLEWMGWISAYNGNTNYAQKLQGRVTMTTDTSTST AYMELRSLRSDDTTVYYCARSPSTVVTPFSDYWGQGTLV TVSS |
| SEQ ID NO: 20 | EVQLVESGGGLVQPGRSLRLSCAASGFTFDDYAMHWVRQ APGKGLEWVSGISWNSGSIGYADSVKGRFTISRDNAKNS LYLQMNSLRAEDTALYYCAKRHGGTNAFDIWGQGTMVTV SS |
| SEQ ID NO: 21 | QITLKESGPTLVKPTETLTLTCTFSGFSLNTGGVSVGWV RQTPGKALEWLALIYWNDDKRYSPSLKSRLTITKDTSKN QVVLTMTNMDTVDATYYCAHSAAGVDYWGQGTLVTVSS |
| SEQ ID NO: 22 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARGWNYELDYWGQGTLVTVSS |
| SEQ ID NO: 23 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDYWGQGTLVTVSS |
| SEQ ID NO: 24 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAHISSSGGTEWQDYWGQGT LVTVSS |
| SEQ ID NO: 25 | QMQLVQSGAEVKKPGSSVKVCKASGGTFSSYAISWVRQA PGQGLEWMGGIIPIFGTANYAQKFQGRVTITADKSTSTA YMELSSLRSDDTAVYYCARDELWATNYYYMDVWGKGTLV TVSS |
| SEQ ID NO: 26 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDYWGRGTLVTVSP |
| SEQ ID NO: 27 | QVQLVESGAEVKKPGASVKVSCKASGYTFTAYYIHWLRQ APGQDLEWMGWIDPNSGGTNYAQKFQGRVTMTRDTSIST AYMELSRLRSDDTAVYYCARDWNYELDYWGQGTLVTVSS |
| SEQ ID NO: 28 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAQAKPYSSDFDIWGQGTMVT VSS |
| SEQ ID NO: 29 | QVQLVESGGGLVQPGRSLRLSCAASGFTFDDYAMHWVRQ APGKGLEWVSGISWNSGSIGYADSAKGRFTISRDNSKNT LYLQMNSLRAEDTAVYYCAKRGNSNSFDYWGQGTLVTVS S |
| SEQ ID NO: 30 | QITLKESGPTLVKPTQTLTLTCTFSGFSLSTSGVGVGWI RQPPGKALEWLALIYWNDDKRYSPSLKSRLTITKDTSKN QVVLTMTNMDPVDTATYYCAQAKPYSSDFDIWGQGTMVT VSS |

In some instances, the CD229 antigen binding domain comprises a variable light chain comprising a sequence having at least 90% identity a sequence set forth in SEQ ID NOs:31, 32, 33, 34, 35, 36, 37, 38, 39, 40, 41, 42, 43, 44, or 45 (see Table 3). In some instances, the CD229 antigen binding domain comprises a variable light chain comprising a sequence having at least 90, 91, 92, 93, 94, 95, 96, 97, 98, 99, or 100% identity to a sequence set forth in SEQ ID NOs:31, 32, 33, 34, 35, 36, 37, 38, 39, 40, 41, 42, 43, 44, or 45.

TABLE 3

Variable Light Chains.

SEQ ID NO: 31 DIQMTQSPSSLSASVGDRVTITCRASQSIGSSLHWYQQKPGKAPKFLIYDASSLE
SGVPSRFSGSGSGTEFTLTISSLQPDDFATYYCQQYNSYPLTFGGGTKLEIKR

SEQ ID NO: 32 QSGLTQPRSVSGSPGQSVTISCTGTSSDVGGYNYVSWYQQHPGKAPKLMIYDV
SKRPSGVPDRFSGSKSGNTASLTVSGLQAEDEADYYCSSYAGSNTFVFGSGTK
LTVLG

SEQ ID NO: 33 DIVMTQSPATLSVSPGERATLSCRASQSVGSSLAWYQQKPGQAPRLLIYGGSV
RATGIPARFSGSGSGTEFTLTISSLQSEDFAAYYCQQYNSYPLTFGGGTKLEIKR

SEQ ID NO: 34 NFMLTQPHSVSESPGKTVTISCTGSSGSIASNYVQWYQQRPGSSPTTVIYEDNQ
RPSGVPDRFSGSIDSSSNSASLTISGLKTEDEADYYCQSYDGSNPVVFGGGTQL
TVLG

SEQ ID NO: 35 DIQMTQSPSSLSASVGDRVTITCRASQSISSYLNWYQQKPGKAPKLLIYAASSL
QSGVPSRFSGSGSGTDFTLTISSLQPEDFATYYCQQSYSTLYTFGQGTKLEIKR

SEQ ID NO: 36 DIQMTQSPSSLSASVGDRVTITCQASQDISNYLNWYQQKPGKAPKWYDASNL
ETGVPSRFSGSGSGTDFTFTISSLQPEDIATYYCQQYDNLPITFGPGTKVDIKR

SEQ ID NO: 37 NFMLTQPHSVSGSPGKTVTISCTRSSGYIASNYVQWYQQRPGSAPTTVIYEDNQ
RPSGVPDRFSGSIDSSSNSASLTISGLKTEDEADYYCQSYDSSNQGVFGGGTKL
TVLV

SEQ ID NO: 38 NFMLTQPHSVSGSPGKTVTISCTRSSGYIASNYVQWYQQRPGSSPTTLIYDDDQ
RPSGVPDRFSGSIDRSSNSASLTISGLKTEDEGDYYCQSYDSSLVIFGGGTKVTV
LG

SEQ ID NO: 39 DIQMTQSPSSLSASVGDRVTITCRASQSIGSSLHWYQQKPGKAPKFLIYDASSLE
SGVPSRFSGSGSGTEFTLTISSLQPDDCATYYCQQYNSYPLTFGGGTKLEIKR

SEQ ID NO: 40 QSALTQPRSVSGSPGQSVTISCTGTSSDVGSYNYVSWYQQSPGKAPKLMIYDV
SNRPSGVSNRFSGSKSGNTASLTISGLQSEDEADYYCTSYGSYDIPVIFGGGTKL
TVLG

SEQ ID NO: 41 NFMLTQPHSVSGSPGKAVTISCTRSSGNIARSFVQWYQQRPGSAPTAVIYEDNR
RPSGVPDRFSGSFDSSSNSASLTISGLKTEDEADYYCQSYDSSNHVVFGGGTKV
TVLG

SEQ ID NO: 42 NFMLTQPHSVSGSPGKTVTISCTRSSGYIASNYVQWYQQRPGSSPTTLIYDDDQ
RPSGVPDRFSGSIDRSSNSASLTISGLKTEDEGDYYCQSYDSTTEVFGTGTKLTV
LG

SEQ ID NO: 43 NFMLTQPHSVSESPGKTVTISCTGSSGSIASNYVQWYQQRPGSSPTTVIYEDNQ
RPSGVPDRFSGSIDSSSNSASLTISGLKTEDEADYYCQSYDSSNQGVFGGGTQL
TVLG

SEQ ID NO: 44 DIQMTQSPSSVSASVGDRVTITCRASQSISSYLNWYQQKPGKAPKLLIYAASSL
QSGVPSRFSGSGSGTDFTLTISSLQPEDFATYYCQQSYSTPWTFGQGTKLEIKR

SEQ ID NO: 45 DIQMTQSPSSLSASVGDRVTISCQASQDISNYLNWYQQKPGKAPKLLIYAASSL
QSGVPSRFSGSGSGTDFTLTISSLQPEDFATYYCLQDYNYPWTFGQGTKVEIKR

In some instances, the CD229 antigen binding domain comprises a heavy chain immunoglobulin variable region comprising a complementarity determining region 1 (CDR1) comprising the sequence of SEQ ID NO:46, 49, 52, 57, 60, 63, 66, 69, 71, 74, 77, 80, 83 or 86; a CDR2 comprising the sequence of SEQ ID NO:47, 50, 53, 55, 58, 61, 64, 67, 70, 72, 75, 78, 81, 84, or 87; and a CDR3 comprising the sequence of SEQ ID NO:48, 51, 54, 56, 59, 62, 65, 68, 71, 73, 76, 79, 82, 85, or 88.

TABLE 4

CDRs present in the heavy chain

| CDRs present in the heavy chain of SEQ ID NOs: | CDR1 | CDR2 | CDR3 |
| --- | --- | --- | --- |
| SEQ ID NO: 1 | GFSLSTSGVG (SEQ ID NO: 46) | IYWNDDK (SEQ ID NO: 47) | ARMGWNDPHMVDY (SEQ ID NO: 48) |
| SEQ ID NO: 2 | GGTFSSYA (SEQ ID NO: 49) | IIPIFGTA (SEQ ID NO: 50) | AADMELRDYYYGMDV (SEQ ID NO: 51) |
| SEQ ID NO: 3 | GFTFSSYG (SEQ ID NO: 52) | ISYDGSNK (SEQ ID NO: 53) | AKDTCTNGVCYPDY (SEQ ID NO: 54) |

TABLE 4-continued

CDRs present in the heavy chain

| CDRs present in the heavy chain of SEQ ID NOs: | CDR1 | CDR2 | CDR3 |
|---|---|---|---|
| SEQ ID NO: 4 | . . . | ISAYNGNT (SEQ ID NO: 55) | ARSPSTVVTPFSDY (SEQ ID NO: 56) |
| SEQ ID NO: 5 | GFTFDDYA (SEQ ID NO: 57) | ISWNSGSI (SEQ ID NO: 58) | AKRHGGTNAFDI (SEQ ID NO: 59) |
| SEQ ID NO: 6 | GFSLNTGGVS (SEQ ID NO: 60) | IYWNDDK (SEQ ID NO: 61) | AHSAAGVDY (SEQ ID NO: 62) |
| SEQ ID NO: 7 | GYTFTAYY (SEQ ID NO: 63) | IDPNSGGT (SEQ ID NO: 64) | ARGWNYELDY (SEQ ID NO: 65) |
| SEQ ID NO: 8 | GYTFTAYY (SEQ ID NO: 66) | IDPNSGGT (SEQ ID NO: 67) | ARDWNYELDY (SEQ ID NO: 68) |
| SEQ ID NO: 9 | GFSLSTSGVG (SEQ ID NO: 69) | IYWNDDK (SEQ ID NO: 70) | AHISSSGGTEVQDY (SEQ ID NO: 71) |
| SEQ ID NO: 10 | GGTFSSYA (SEQ ID NO: 71) | IIPIFGTA (SEQ ID NO: 72) | ARDELWATNYYYMDV (SEQ ID NO: 73) |
| SEQ ID NO: 11 | GYTFTAYY (SEQ ID NO: 74) | IDPNSGGT (SEQ ID NO: 75) | ARDWNYELDY (SEQ ID NO: 76) |
| SEQ ID NO: 12 | GYTFTAYY (SEQ ID NO: 77) | IDPNSGGT (SEQ ID NO: 78) | ARDWNYELDY (SEQ ID NO: 79) |
| SEQ ID NO: 13 | GFSLSTSGVG (SEQ ID NO: 80) | IYWNDDK (SEQ ID NO: 81) | AQAKPYSSDFDI (SEQ ID NO: 82) |
| SEQ ID NO: 14 | GFTFDDYA (SEQ ID NO: 83) | ISWNSGSI (SEQ ID NO: 84) | AKRGNSNSFDY (SEQ ID NO: 85) |
| SEQ ID NO: 15 | GFSLSTSGVG (SEQ ID NO: 86) | IYWNDDK (SEQ ID NO: 87) | AQAKPYSSDFDI (SEQ ID NO: 88) |

In some instances, the CD229 antigen binding domain comprises a light chain immunoglobulin variable region comprising a CDR1 comprising the sequence of SEQ ID NO:89, 91, 93, 95, 97, 99, 101, 103, 105, 107, 109, 111, 113, 115, or 117; a CDR2 comprising the sequence of DAS, DVS, GGS, EDN, DDD, or AAS; and a CDR3 comprising the sequence of SEQ ID NO:90, 92, 94, 96, 98, 100, 102, 104, 106, 108, 110, 112, 114, 116, or 118.

TABLE 5

CDRs present in the light chain

| CDRs present in the light chain of SEQ ID NOs: | CDR1 | CDR2 | CDR3 |
|---|---|---|---|
| SEQ ID NO: 1 | QSIGSS (SEQ ID NO: 89) | DAS | QQYNSYPLT (SEQ ID NO: 90) |
| SEQ ID NO: 2 | SSDVGGYNY (SEQ ID NO: 91) | DVS | SSYAGSNTFV (SEQ ID NO: 92) |
| SEQ ID NO: 3 | QSVGSS (SEQ ID NO: 93) | GGS | QQYNSYPLT (SEQ ID NO: 94) |
| SEQ ID NO: 4 | SGSIASNY (SEQ ID NO: 95) | EDN | QSYDGSNPVV (SEQ ID NO: 96) |
| SEQ ID NO: 5 | QSISY (SEQ ID NO: 97) | AAS | QQSYSTLYT (SEQ ID NO: 98) |
| SEQ ID NO: 6 | QDISNY (SEQ ID NO: 99) | DAS | QQYDNLPIT (SEQ ID NO: 100) |
| SEQ ID NO: 7 | SGYIASNY (SEQ ID NO: 101) | EDN | QSYDSSNQGV (SEQ ID NO: 102) |

TABLE 5-continued

CDRs present in the light chain

| CDRs present in the light chain of SEQ ID NOs: | CDR1 | CDR2 | CDR3 |
| --- | --- | --- | --- |
| SEQ ID NO: 8 | SGYIASNY (SEQ ID NO: 103) | DDD | QSYDSSLVI (SEQ ID NO: 104) |
| SEQ ID NO: 9 | QSIGSS (SEQ ID NO: 105) | DAS | QQYNSYPLT (SEQ ID NO: 106) |
| SEQ ID NO: 10 | SSDVGSYNY (SEQ ID NO: 107) | DVS | TSYGSYDIPVI (SEQ ID NO: 108) |
| SEQ ID NO: 11 | SGNIARSF (SEQ ID NO: 109) | EDN | QSYDSSNHVV (SEQ ID NO: 110) |
| SEQ ID NO: 12 | SGYIASNY (SEQ ID NO: 111) | DDD | QSYDSTTEV (SEQ ID NO: 112) |
| SEQ ID NO: 13 | SGSIASNY (SEQ ID NO: 113) | EDN | QSYDSSNQGV (SEQ ID NO: 114) |
| SEQ ID NO: 14 | QSISSY (SEQ ID NO: 115) | AAS | QQSYSTPWT (SEQ ID NO: 116) |
| SEQ ID NO: 15 | QDISNY (SEQ ID NO: 117) | AAS | LQDYNYPWT (SEQ ID NO: 118) |

In some instances, the CD229 antigen binding domain comprises a heavy chain immunoglobulin variable region comprising a complementarity determining region 1 (CDR1) comprising the sequence of SEQ ID NO:46, 49, 52, 57, 60, 63, 66, 69, 71, 74, 77, 80, 83 or 86; a CDR2 comprising the sequence of SEQ ID NO:47, 50, 53, 55, 58, 61, 64, 67, 70, 72, 75, 78, 81, 84, or 87; and a CDR3 comprising the sequence of SEQ ID NO:48, 51, 54, 56, 59, 62, 65, 68, 71, 73, 76, 79, 82, 85, or 88 and a light chain immunoglobulin variable region comprising a CDR1 comprising the sequence of SEQ ID NO:89, 91, 93, 95, 97, 99, 101, 103, 105, 107, 109, 111, 113, 115, or 117; a CDR2 comprising the sequence of DAS, DVS, GGS, EDN, DDD, or AAS; and a CDR3 comprising the sequence of SEQ ID NO:90, 92, 94, 96, 98, 100, 102, 104, 106, 108, 110, 112, 114, 116, or 118.

2. Transmembrane Domain

In some instances, the transmembrane domain comprises an immunoglobulin Fc domain. In some instances, the immunoglobulin Fc domain can be an immunoglobulin G Fc domain.

In some instances, the transmembrane domain comprises a CD8α domain, CD3ζ, FcεR1γ, CD4, CD7, CD28, OX40, or H2-Kb.

In some instances, the transmembrane domain can be located between the CD229 antigen binding domain and the intracellular signaling domain.

3. Intracellular Signaling Domain

In some instances, the intracellular signaling domain comprises a co-stimulatory signaling region. In some instances, the co-stimulatory signaling region can comprise the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In some instances, the intracellular signaling domain can be a T cell signaling domain. For example, the intracellular signaling domain can comprise a CD3ζ signaling domain. In some instances, CD3ζ signaling domain is the intracellular domain of CD3ζ.

In some instances, the intracellular signaling domain comprises a CD3ζ signaling domain and a co-stimulatory signaling region, wherein the co-stimulatory signaling region comprises the cytoplasmic domain of CD28, 4-1BB, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

4. Hinge Region

Any of the disclosed CAR polypeptides can further comprise a hinge region. For example, disclosed are CAR polypeptides comprising a CD229 antigen binding domain, a transmembrane domain, and an intracellular signaling domain and further comprising a hinge region.

In some instances, the hinge region can be located between the CD229 antigen binding domain and the transmembrane domain.

In some instances, the hinge region allows for the CD229 antigen binding domain to bind to the antigen. For example, the hinge region can increase the distance of the binding domain to the cell surface and provide flexibility.

C. CAR Nucleic Acid Sequence

Disclosed are nucleic acid sequences capable of encoding any of the disclosed CAR polypeptides. For example, disclosed are nucleic acid sequences capable of encoding a CAR polypeptide comprising a CD229 antigen binding domain, a transmembrane domain, and an intracellular signaling domain.

1. CD229 Antigen Binding Domain

In some instances, the nucleic acid sequence that encodes the CD229 antigen binding domain comprises the sequence of SEQ ID NO: 119, 120, 121, 122, 123, 124, 125, 126, 127, 128, 129, 130, 131, 132, or 133.

TABLE 6

Nucleic acid sequences encoding CD229 antigen binding domains. Variable heavy chain (bold), linker (underlined), and variable light chain.

| | |
|---|---|
| SEQ ID NO: 119 | CAGATCACCTTGAAGGAGTCTGGTCCTACGCTGGTGAAACCCACACA GACCCTCACGCTGACCTGCACCTTCTCTGGGTTCTCACTCAGCACTA GTGGAGTGGGTGTGGGCTGGATCCGTCAGCCCCAGGAAAGGCCCT GGAGTGGCTTGCACTCATTTATTGGAATGATGATAAGCGCTACAGCC CATCTCTGAAGAGCAGGCTCACCATCGCCAAGGACACCTCCAAAAAC CAGGTGGTCCTTACAATGACCAACATGGACCCTGTGGACACAGCCAC GTATTACTGTGCACGGATGGGCTGGAACGATCCTCATATGGTTGACT ACTGGGGCCAGGGCACCCTGGTCACCGTCTCCTCA<u>CTCGAGGGTGGA GGCGGTTCAGGCGGAGGTGGCTCTGGCGGTGGCGCTAGC</u>GACATCCAGA TGACCCAGTCTCCATCCTCCCTGTCTGCGTCTGTAGGAGACAGAGTCACC ATCACTTGCCGGGCAAGTCAGAGCATTGGCAGCTCTTTACATTGGTATCA GCAGAAACCAGGGAAAGCCCCTAAGTTCCTGATCTATGATGCCTCCAGTT TGGAAAGTGGGGTCCCATCAAGGTTCAGCGGCAGTGGATCTGGGACAGA ATTCACTCTCACCATCAGCAGCCTGCAGCCTGATGATTTTGCAACTTATTA CTGCCAACAGTATAATAGTTACCCGCTCACTTTCGGCGGAGGGACCAAGC TGGAGATCAAACGT |
| SEQ ID NO: 120 | CAGATGCAGCTGGTGGAGTCTGGGGCTGAGGTGAAGAAGCCTGGGT CCTCGGTGAAGGTCTCCTGCAAGGCTTCTGGAGGCACCTTCAGCAGC TATGCTATCAGCTGGGTGCGACAGGCCCCTGGACAAGGGCTTGAGT GGATGGGAGGGATCATCCCTATCTTTGGTACAGCAAACTACGCACAG AAGTTCCAGGGCAGAGTCACGATTACCGCGGACAAATCCACGAGCAC AGCCTACATGGAGCTGAGCAGCCTGAGATCTGAGGACACGGCCGTG TATTACTGTGCGGCCGATATGGAACTACGGGACTACTACTACGGTAT GGACGTCTGGGGCCAAGGAACCCTGGTCACCGTCTCCTCA<u>CTCGAGG GTGGAGGCGGTTCAGGCGGAGGTGGCTCTGGCGGTGGCGCTAGC</u>CAGTC TGGGCTGACTCAGCCTCGCTCAGTGTCCGGGTCTCCTGGACAGTCAGTCA CCATCTCCTGCACTGGAACCAGCAGTGATGTTGGTGGTTATAACTATGTC TCCTGGTACCAACAGCACCCAGGCAAAGCCCCCAAACTCATGATTTATGA TGTCAGTAAGCGGCCCTCAGGGGTCCCTGATCGCTTCTCTGGCTCCAAGT CTGGCAACACGGCCTCCCTGACCGTCTCTGGGCTCCAGGCTGAGGATGAG GCTGATTATTACTGCAGCTCCTATGCAGGCAGCAATACTTTTGTCTTCGGA TCTGGGACCAAGCTGACCGTCCTAGGT |
| SEQ ID NO: 121 | CAGGTGCAGCTGTTGGAGTCTGGGGGAGGCGTGGCCCAGCCTGGGA GGTCCCTGAAACTCTCCTGTGCAGCCTCTGGATTCACCTTCAGTAGC TATGGCATGCACTGGGTCCGCCAGGCTCAGGCGAGGGGCTGGAGT GGGTGGCAGTTATATCATATGATGGAAGTAATAAATACTATGCAGAC TCCGTGAAGGGCCGATTCACCATCTCCAGAGACAATTCCAAGAACAC GCTGTATCTGCAAATGAACAGTCTGAGAGCCGAGGACACGGCTGTAT ATTACTGTGCAAAAGATACTTGTACTAATGGTGTATGCTACCCTGAC TACTGGGGCCAGGGCACCCTGGTCACCGTCTCCTCA<u>CTCGAGGGTGG AGGCGGTTCAGGCGGAGGTGGCTCTGGCGGTGGCGCTAGC</u>GATATTGTG ATGACGCAGTCTCCAGCCACCCTGTCTGTGTCTCCAGGGGAAAGAGCCAC CCTCTCCTGCAGGGCCAGCCAGAGTGTTGGCAGCAGCTTAGCCTGGTACC AGCAGAAACCTGGCCAGGCTCCCAGGCTCCTCATCTATGGTGGATCCGTC AGGGCCACTGGTATCCCAGCCAGGTTCAGTGGCAGTGGGTCTGGGACAG AGTTCACTCTCACCATCAGCAGCCTGCAGTCTGAAGATTTTGCAGCTTATT ACTGTCAGCAGTATAATAGTTACCCGCTCACTTTCGGCGGAGGGACCAAG CTGGAGATCAAACGT |
| SEQ ID NO: 122 | GAAGTGCAGCTGGTGCAGTCTGGAGCTGAGGTGAAGAAGCCTGGGG CCTCAGTGAAGGTCTCCTGCAAGGCTTCTGGTTACACCTTTACCAGC TATGGTATCAGCTGGGTGCGACAGGCCCCTGGACAAGGGCTTGAGT GGATGGGATGGATCAGCGCTTACAATGGTAACAAACTATGCACAG AAGCTCCAGGGCAGAGTCACCATGACCACAGACACATCCACGAGCAC AGCCTACATGGAGCTGAGGAGCCTGAGATCTGACGACACGACCGTG TATTACTGTGCGAGATCGCCTAGTACGGTGGTAACCCCATTCAGCGA CTACTGGGGCCAGGGCACCCTGGTCACCGTCTCCTCA<u>CTCGAGGGTG GAGGCGGTTCAGGCGGAGGTGGCTCTGGCGGTGGCGCTAGC</u>CAATTTTATG CTGACTCAGCCCCACTCTGTGTCGGAGTCTCCGGGGAAGACGGTAACCAT CTCCTGCACCGGCAGCAGTGGCAGCATTGCCAGCAACTATGTGCAGTGGT ACCAGCAGCGCCCGGGCAGTTCCCCCACCACTGTGATCTATGAGGATAAC CAAAGACCCTCTGGGGTCCCTGATCGGTTCTCTGGCTCCATCGACAGCTC CTCCAACTCTGCCTCCCTCACCATCTCTGGACTGAAGACTGAGGACGAGG CTGACTACTACTGTCAGTCTTATGATGGCAGCAACCCTGTGGTTTTCGGC GGAGGGACCCAGCTCACCGTTTTAGGT |
| SEQ ID NO: 123 | GAGGTGCAGCTGGTGGAGTCTGGGGGAGGCTTGGTACAGCCTGGCA GGTCCCTGAGACTCTCCTGTGCAGCCTCTGGATTCACCTTTGATGAT TATGCCATGCACTGGGTCCGGCAAGCTCCAGGGAAGGGCCTGGAGT GGGTCTCAGGTATTAGTTGGAATAGTGGTAGCATAGGCTATGCGGAC TCTGTGAAGGGCCGATTCACCATCTCCAGAGACAACGCCAAGAACTC CCTGTATCTGCAAATGAACAGTCTGAGAGCTGAGGACACGGCCTTGT ATTACTGTGCAAAACGGCATGGAGGGACCAATGCTTTTGATATCTGG GGCCAAGGGACAATGGTCACCGTCTCTTCA<u>CTCGAGGGTGGAGGCGGT TCAGGCGGAGGTGGCTCTGGCGGTGGCGCTAGC</u>GACATCCAGATGACCC

TABLE 6-continued

Nucleic acid sequences encoding CD229 antigen binding domains. Variable heavy chain (bold), linker (underlined), and variable light chain.

| | |
|---|---|
| | AGTCTCCATCCTCCCTGTCTGCATCTGTAGGAGACAGAGTCACCATCACT<br>TGCCGGGCAAGTCAGAGCATTAGCAGCTATTTAAATTGGTATCAGCAGAA<br>ACCAGGGAAAGCCCCTAAGCTCCTGATCTATGCTGCATCCAGTTTGCAAA<br>GTGGGGTCCCATCAAGGTTCAGTGGCAGTGGATCTGGGACAGATTTCACT<br>CTCACCATCAGCAGTCTGCAACCTGAAGATTTTGCAACTTACTACTGTCA<br>ACAGAGTTACAGTACCCTTTACACTTTTGGCCAGGGGACCAAGCTGGAGA<br>TCAAACGT |
| SEQ ID NO: 124 | CAGATCACCTTGAAGGAGTCTGGACCTACGCTGGTGAAACCCACAGA<br>AACCCTCACGCTGACCTGCACCTTCTCTGGGTTCTCACTCAACACTG<br>GTGGAGTGAGTGTGGGCTGGGTCCGTCAGACCCCAGGAAAGGCCCT<br>GGAGTGGCTTGCACTCATTTATTGGAATGATGATAAGCGCTACAGCC<br>CATCTCTGAAGAGCAGGCTCACCATCACCAAGGACACCTCCAAAAAC<br>CAGGTGGTCCTTACAATGACCAACATGGACACTGTGGACACGGCCAC<br>ATATTACTGTGCACACAGCGCGGCTGGAGTTGACTACTGGGGCCAGG<br>GAACCCTGGTCACCGTCTCTTCA<u>CTCGAGGGTGGAGGCGGTTCAGGCG<br>GAGGTGGCTCTGGCGGTGGCGCTAGC</u>GACATCCAGATGACCCAGTCTCCA<br>TCCTCCCTGTCTGCATCTGTAGGAGACAGAGTCACCATCACTTGCCAGGC<br>GAGTCAGGACATTAGCAACTATTTAAATTGGTATCAGCAGAAACCAGGG<br>AAAGCCCCTAAGCTCCTGATCTACGATGCATCCAATTTGGAAACAGGGGT<br>CCCATCAAGGTTCAGTGGAAGTGGATCTGGGACAGATTTTACTTTCACCA<br>TCAGCAGCCTGCAGCCTGAAGATATTGCAACATATTACTGTCAACAGTAT<br>GATAATCTCCCCATCACTTTCGGCCCTGGGACCAAAGTGGATATCAAACG<br>T |
| SEQ ID NO: 125 | CAGGTGCAGCTGGTGGAGTCTGGGGCTGAGGTGAAGAAGCCTGGGG<br>CCTCAGTGAAGGTCTCCTGCAAGGCTTCTGGATACACTTTTACCGCC<br>TACTATATACACTGGCTGCGACAGGCCCCTGGACAAGACCTTGAGTG<br>GATGGGATGGATCGACCCTAACAGTGGTGGCACAAACTATGCACAGA<br>AATTTCAGGGCAGGGTCACCATGACCAGGGACACGTCCATCAGCACA<br>GCCTACATGGAGCTGAGCAGGCTGAGATCTGACGACACGGCCGTGT<br>ATTACTGTGCGAGAGGCTGGAATTACGAACTTGACTACTGGGGCCAG<br>GGCACCCTGGTCACCGTCTCCTCA<u>CTCGAGGGTGGAGGCGGTTCAGGC<br>GGAGGTGGCTCTGGCGGTGGCGCTAGC</u>AATTTTATGCTGACTCAGCCCCA<br>CTCTGTGTCGGGGTCTCCGGGGAAGACGGTGACCATCTCCTGCACCCGCA<br>GCAGTGGCTACATTGCCAGCAACTATGTACAGTGGTACCAGCAGCGCCCG<br>GGCAGTGCCCCCACCACTGTGATCTATGAGGATAACCAAAGACCCTCTGG<br>GGTCCCTGATCGGTTCTCTGGCTCCATCGACAGCTCCTCCAACTCTGCCTC<br>CCTCACCATCTCTGGACTGAAGACTGAGGACGAGGCTGACTACTACTGTC<br>AGTCTTATGATAGCAGCAATCAAGGGGTGTTCGGCGGAGGGACCAAGCT<br>GACCGTCCTAGTG |
| SEQ ID NO: 126 | CAGGTGCAGCTGGTGGAGTCTGGGGCTGAGGTGAAGAAGCCTGGGG<br>CCTCAGTGAAGGTCTCCTGCAAGGCTTCTGGATACACTTTTACCGCC<br>TACTATATACACTGGCTGCGACAGGCCCCTGGACAAGACCTTGAGTG<br>GATGGGATGGATCGACCCTAACAGTGGTGGCACAAACTATGCACAGA<br>AATTTCAGGGCAGGGTCACCATGACCAGGGACACGTCCATCAGCACA<br>GCCTACATGGAGCTGAGCAGGCTGAGATCTGACGACACAGCCGTGT<br>ATTACTGTGCGAGAGACTGGAATTACGAACTTGACTACTGGGGCCAG<br>GGCACCCTGGTCACCGTCTCCTCA<u>CTCGAGGGTGGAGGCGGTTCAGGC<br>GGAGGTGGCTCTGGCGGTGGCGCTAGC</u>AATTTTATGCTGACTCAGCCCCA<br>CTCTGTGTCGGGGTCTCCGGGGAAGACGGTGACCATCTCCTGCACCCGCA<br>GCAGTGGCTACATTGCCAGCAACTATGTACAGTGGTACCAGCAGCGCCCG<br>GGCAGTTCCCCCACCACTCTGATATATGACGATAACAAAGACCCTCTGG<br>GGTCCCTGATCGGTTCTCTGGCTCCATCGACAGATCCTCCAATTCTGCCTC<br>CCTCACCATCTCTGGGCTGAAGACTGAGGACGAGGGTGACTACTACTGTC<br>AGTCTTATGATAGCAGCCTTGTGATATTCGGCGGGGGGACCAAGGTCACC<br>GTCCTAGGT |
| SEQ ID NO: 127 | CAGATCACCTTGAAGGAGTCGGGTCCTACGCTGGTGAAACCCACACA<br>GACCCTCACGCTGACCTGCACCTTCTCTGGGTTCTCACTCAGCACTA<br>GTGGAGTGGGTGTGGGCTGGATCCGTCAGCCCCAGGAAAGGCCCT<br>GGAGTGGCTTGCACTCATTTATTGGAATGATGATAAGCGCTACAGCC<br>CATCTCTGAAGAGCAGGCTCACCATCACCAAGGACACCTCCAAAAAC<br>CAGGTGGTCCTTACAATGACCAACATGGACCCTGTGGACACAGCCAC<br>ATATTACTGTGCACACATTTCCAGTAGTGGTGGTACCGAAGTACAAG<br>ACTACTGGGGCCAGGGAACCCTGGTCACCGTCTCCTCA<u>CTCGAGGGT<br>GGAGGCGGTTCAGGCGGAGGTGGCTCTGGCGGTGGCGCTAGC</u>GACATCC<br>AGATGACCCAGTCTCCATCCTCCCTGTCTGCGTCTGTAGGAGACAGAGTC<br>ACCATCACTTGCCGGGCAAGTCAGAGCATTGGCAGCTCTTTACATTGGTA<br>TCAGCAGAAACCAGGGAAAGCCCCTAAGTTCCTGATCTATGATGCCTCCA<br>GTTTGGAAAGTGGGGTCCCATCAAGGTTCAGCGGCAGTGGATCTGGGAC<br>AGAATTCACTCTCACCATCAGCAGCCTGCAGCCTGATGATTGTGCAACTT<br>ATTACTGCCAACAGTATAATAGTTACCCGCTCACTTTCGGCGGAGGGACC<br>AAGCTGGAGATCAAACGT |

TABLE 6-continued

Nucleic acid sequences encoding CD229 antigen binding domains. Variable heavy chain (bold), linker (underlined), and variable light chain.

SEQ ID NO: 128
**CAAATGCAGCTGGTGCAGTCTGGGGCTGAGGTGAAGAAGCCTGGGT
CCTCGGTGAAGGTCTCCTGTAAGGCTTCTGGAGGCACCTTCAGCAGC
TATGCTATCAGCTGGGTGCGACAGGCCCCTGGACAAGGGCTTGAGT
GGATGGGAGGGATCATCCCTATCTTTGGTACAGCAAACTACGCACAG
AAGTTCCAGGGCAGAGTCACGATTACCGCGGACAAATCCACGAGCAC
AGCCTACATGGAGCTGAGCAGCCTGAGATCTGACGACACGGCCGTG
TATTACTGTGCGAGAGATGAACTCTGGGCTACAAACTACTACTACAT
GGACGTCTGGGGCAAAGGAACCCTGGTCACCGTCTCCTCA**CTCGAGG
GTGGAGGCGGTTCAGGCGGAGGTGGCTCTGGCGGTGGCGCTAGCCAGTC
TGCGCTGACTCAGCCTCGCTCAGTGTCCGGGTCTCCTGGACAGTCAGTCA
CCATCCTGCACTGGAACCAGCAGTGATGTTGGTAGTTATAACTATGTC
TCCTGGTACCAACAGAGCCCAGGCAAAGCCCCCAAACTCATGATTTATGA
TGTCAGTAATCGGCCCTCAGGGGTTTCTAATCGCTTCTCTGGCTCCAAGTC
TGGCAACACGGCCTCCCTGACCATCTCTGGGCTCCAGTCTGAGGACGAGG
CTGATTATTATTGCACCTCATATGGAAGCTACGACATACCTGTGATTTTCG
GCGGAGGGACCAAGCTGACCGTCCTAGGT

SEQ ID NO: 129
**CAGGTGCAGCTGGTGGAGTCTGGGGCTGAGGTGAAGAAGCCTGGGG
CCTCAGTGAAGGTCTCCTGCAAGGCTTCTGGATACACTTTTACCGCC
TACTATATACACTGGCTGCGACAGGCCCCTGGACAAGACCTTGAGTG
GATGGGATGGATCGACCCTAACAGTGGTGGCACAAACTATGCACAGA
AATTTCAGGGCAGGGTCACCATGACCAGGGACACGTCCATCAGCACA
GCCTACATGGAGCTGAGCAGGCTGAGATCTGACGACACGGCCGTGT
ATTACTGTGCGAGAGACTGGAATTACGAACTTGACTACTGGGGCCGG
GGCACCCTGGTCACCGTCTCCCA**CTCGAGGGTGGAGGCGGTTCAGGC
GGAGGTGGCTCTGGCGGTGGCGCTAGCAATTTTATGCTGACTCAGCCCCA
CTCTGTGTCGGGGTCTCCGGGGAAGGCGGTGACCATCTCCTGCACCCGCA
GCAGTGGCAACATTGCCAGGAGTTTTGTGCAGTGGTACCAACAGCGCCCG
GGCAGTGCCCCCACCGCTGTGATCTATGAGGATAACCGAAGACCCTCTGG
GGTCCCTGATCGCTTCTCTGGCTCCTTCGACAGCTCCTCCAATTCTGCCTC
CCTCACCATCTCTGGCCTGAAGACTGAGGACGAGGCTGACTACTACTGTC
AGTCTTATGATAGCAGCAATCATGTGGTATTCGGCGGAGGGACCAAGGTC
ACCGTCCTAGGT

SEQ ID NO: 130
**CAGGTGCAGCTGGTGGAGTCTGGGGCTGAGGTGAAGAAGCCTGGGG
CCTCAGTGAAGGTCTCCTGCAAGGCTTCTGGATACACTTTTACCGCC
TACTATATACACTGGCTGCGACAGGCCCCTGGACAAGACCTTGAGTG
GATGGGATGGATCGACCCTAACAGTGGTGGCACAAACTATGCACAGA
AATTTCAGGGCAGGGTCACCATGACCAGGGACACGTCCATCAGCACA
GCCTACATGGAGCTGAGCAGGCTGAGATCTGACGACACGGCCGTGT
ATTACTGTGCGAGAGACTGGAATTACGAGCTTGACTACTGGGGCCAG
GGCACCCTGGTCACCGTCTCCTCA**CTCGAGGGTGGAGGCGGTTCAGGC
GGAGGTGGCTCTGGCGGTGGCGCTAGCAATTTTATGCTGACTCAGCCCCA
CTCTGTGTCGGGGTCTCCGGGGAAGACGGTGACCATCTCCTGCACCCGCA
GCAGTGGCTACATTGCCAGCAACTATGTACAGTGGTACCAGCAGCGCCCG
GGCAGTTCCCCCACCACTCTGATATATGACGATGACCAAAGACCCTCTGG
GGTCCCTGATCGGTTCTCTGGCTCCATCGACAGATCCTCCAATTCTGCCTC
CCTCACCATCTCTGGGCTGAAGACTGAGGACGAGGGTGACTACTACTGTC
AGTCTTATGATAGCACCACGGAAGTCTTCGGAACTGGGACCAAGCTGACC
GTCCTAGGT

SEQ ID NO: 131
**CAGATCACCTTGAAGGAGTCTGGTCCTACGCTGGTGAAACCCACACA
GACCCTCACGCTGACCTGCACCTTCTCTGGGTTCTCACTCAGCACTA
GTGGAGTGGGTGTGGGCTGGATCCGTCAGCCCCCAGGAAAGGCCCT
GGAGTGGCTTGCACTCATTTATTGGAATGATGATAAGCGCTACAGCC
CATCTCTGAAGAGCAGGCTCACCATCACCAAGGACACCTCCAAAAAC
CAGGTGGTCCTTACAATGACCAACATGGACCCTGTGGACACAGCCAC
ATATTACTGTGCCCAGGCAAAACCGTATAGCAGCGATTTTGATATCT
GGGGCCAAGGGACAATGGTCACCGTCTCTTCA**CTCGAGGGTGGAGGC
GGTTCAGGCGGAGGTGGCTCTGGCGGTGGCGCTAGCAATTTTATGCTGAC
TCAGCCCCACTCTGTGTCGGAGTCTCCGGGGAAGACGGTAACCATCTCCT
GCACCGGCAGCAGTGGCAGCATTGCCAGCAACTATGTGCAGTGGTACCA
GCAGCGCCCGGGCAGTTCCCCCACCACTGTGATCTATGAGGATAACCAAA
GACCCTCTGGGGTCCCTGATCGGTTCTCTGGCTCCATCGACAGCTCCTCTA
ACTCTGCCTCCCTCACCATCTCTGGACTGAAGACTGAGGACGAGGCTGAC
TACTACTGTCAGTCTTATGATAGCAGCAATCAGGGGTATTCGGCGGCGG
GACCCAGCTCACCGTCCTAGGT

SEQ ID NO: 132
**CAGGTGCAGCTGGTGGAGTCTGGGGGAGGCTTGGTACAGCCTGGCA
GGTCCCTGAGACTCTCCTGTGCAGCCTCTGGATTCACCTTTGATGAT
TATGCCATGCACTGGGTCCGGCAAGCTCCAGGGAAGGGCCTGGAGT
GGGTCTCAGGTATTAGTTGGAATAGTGGTAGCATAGGCTATGCGGAC
TCCGCGAAGGGCCGGTTCACCATCTCCAGAGACAATTCCAAGAACAC
GCTGTATCTGCAAATGAACAGCCTGAGAGCCGAGGACACGGCCGTCT
ATTACTGTGCGAAAGGGGAACTCCAACTCTTTTGACTACTGGGGC
CAGGGAACCCTGGTCACCGTCTCCTCA**CTCGAGGGTGGAGGCGGTTCA

TABLE 6-continued

Nucleic acid sequences encoding CD229 antigen binding domains. Variable heavy chain (bold), linker (underlined), and variable light chain.

| | |
|---|---|
| | GGCGGAGGTGGCTCTGGCGGTGGCGCTAGCGACATCCAGATGACCCAGT<br>CTCCATCTTCCGTGTCTGCATCTGTAGGAGACAGAGTCACCATCACTTGC<br>CGGGCAAGTCAGAGCATTAGCAGCTATTTAAATTGGTATCAGCAGAAAC<br>CAGGGAAAGCCCCTAAGCTCCTGATCTATGCTGCATCCAGTTTGCAAAGT<br>GGGGTCCCATCAAGGTTCAGTGGCAGTGGATCTGGGACAGATTTCACTCT<br>CACCATCAGCAGTCTGCAACCTGAAGATTTTGCAACTTACTACTGTCAAC<br>AGAGTTACAGTACCCCCTGGACGTTCGGCCAAGGGACCAAGCTGGAGAT<br>CAAACGT |
| SEQ ID NO: 133 | CAGATCACCTTGAAGGAGTCTGGTCCTACGCTGGTGAAACCCACACA<br>GACCCTCACGCTGACCTGCACCTTCTCTGGGTTCTCACTCAGCACTA<br>GTGGAGTGGGTGTGGGCTGGATCCGTCAGCCCCAGGAAAGGCCCT<br>GGAGTGGCTTGCACTCATTTACTGGAATGATGATAAGCGCTACAGCC<br>CATCTCTGAAGAGCAGGCTCACCATCACCAAGGACACCTCCAAAAAC<br>CAGGTGGTCCTTACAATGACCAACATGGACCCTGTGGACACAGCCAC<br>ATATTACTGTGCCCAGGCAAAACCGTATAGCAGCGATTTTGATATCT<br>GGGGCCAAGGGACAATGGTCACCGTCTCTTCA<u>CTCGAGGGTGGAGGC<br>GGTTCAGGCGGAGGTGGCTCTGGCGGTGGCGCTAGC</u>GACATCCAGATGA<br>CCCAGTCTCCATCCTCCCTGTCTGCATCTGTAGGAGACAGAGTCACCATC<br>TCTTGCCAGGCGAGTCAGGACATTAGTAACTATTTAAATTGGTATCAGCA<br>GAAACCAGGGAAAGCCCCTAAGCTCCTGATCTATGCTGCATCCAGTTTGC<br>AAAGTGGGGTCCCATCAAGGTTCAGTGGCAGTGGATCTGGGACAGATTTC<br>ACTCTCACCATCAGCAGTCTGCAACCTGAAGATTTTGCAACTTATTACTGT<br>CTACAAGATTACAATTACCCGTGGACGTTCGGCCAGGGGACCAAGGTGG<br>AAATCAAACGT |

In some instances, nucleic acid sequence encoding the CD229 antigen binding domain comprises a variable heavy chain comprising a sequence having at least 90% identity to a sequence set forth in SEQ ID NOs:134, 135, 136, 137, 138, 139, 140, 141, 142, 143, 144, 145, 146, 147, or 148 (See Table 7). In some instances, the CD229 antigen binding domain comprises a variable heavy chain comprising a sequence having at least 90, 91, 92, 93, 94, 95, 96, 97, 98, 99, or 100% identity to a sequence set forth in SEQ ID NOs:134, 135, 136, 137, 138, 139, 140, 141, 142, 143, 144, 145, 146, 147, or 148.

TABLE 7

| Nucleic Acid Sequences Encoding Variable Heavy Chains | |
|---|---|
| SEQ ID NO: 134 | CAGATCACCTTGAAGGAGTCTGGTCCTACGCTGGTGAAACCCACACAGAC<br>CCTCACGCTGACCTGCACCTTCTCTGGGTTCTCACTCAGCACTAGTGGAGT<br>GGGTGTGGGCTGGATCCGTCAGCCCCAGGAAAGGCCCTGGAGTGGCTTG<br>CACTCATTTATTGGAATGATGATAAGCGCTACAGCCCATCTCTGAAGAGC<br>AGGCTCACCATCGCCAAGGACACCTCCAAAAACCAGGTGGTCCTTACAAT<br>GACCAACATGGACCCTGTGGACACAGCCACGTATTACTGTGCACGGATGG<br>GCTGGAACGATCCTCATATGGTTGACTACTGGGGCCAGGGCACCCTGGTC<br>ACCGTCTCCTCA |
| SEQ ID NO: 135 | CAGATGCAGCTGGTGGAGTCTGGGGCTGAGGTGAAGAAGCCTGGGTCCTC<br>GGTGAAGGTCTCCTGCAAGGCTTCTGGAGGCACCTTCAGCAGCTATGCTAT<br>CAGCTGGGTGCGACAGGCCCCTGGACAAGGGCTTGAGTGGATGGGAGGG<br>ATCATCCCTATCTTTGGTACAGCAAACTACGCACAGAAGTTCCAGGGCAG<br>AGTCACGATTACCGCGGACAAATCCACGAGCACAGCCTACATGGAGCTGA<br>GCAGCCTGAGATCTGAGGACACGGCCGTGTATTACTGTGCGGCCGATATG<br>GAACTACGGGACTACTACTACGGTATGGACGTCTGGGGCCAAGGAACCCT<br>GGTCACCGTCTCCTCA |
| SEQ ID NO: 136 | CAGGTGCAGCTGTTGGAGTCTGGGGGAGGCGTGGCCCAGCCTGGGAGGTC<br>CCTGAAACTCTCCTGTGCAGCCTCTGGATTCACCTTCAGTAGCTATGGCAT<br>GCACTGGGTCCGCCAGGCTCCAGGCAGGGGCTGGAGTGGGTGGCAGTTA<br>TATCATATGATGGAAGTAATAAATACTATGCAGACTCCGTGAAGGGCCGA<br>TTCACCATCTCCAGAGACAATTCCAAGAACACGCTGTATCTGCAAATGAA<br>CAGTCTGAGAGCCGAGGACACGGCTGTATATTACTGTGCAAAAGATACTT<br>GTACTAATGGTGTATGCTACCCTGACTACTGGGGCCAGGGCACCCTGGTC<br>ACCGTCTCCTCA |
| SEQ ID NO: 137 | GAAGTGCAGCTGGTGCAGTCTGGAGCTGAGGTGAAGAAGCCTGGGGCCTC<br>AGTGAAGGTCTCCTGCAAGGCTTCTGGTTACACCTTTACCAGCTATGGTAT<br>CAGCTGGGTGCGACAGGCCCCTGGACAAGGGCTTGAGTGGATGGGATGGA<br>TCAGCGCTTACAATGGTAACACAAACTATGCACAGAAGCTCCAGGGCAGA<br>GTCACCATGACCACAGACACATCCACGAGCACAGCCTACATGGAGCTGAG<br>GAGCCTGAGATCTGACGACACGACCGTGTATTACTGTGCGAGATCGCCTA<br>GTACGGTGGTAACCCCATTCAGCGACTACTGGGGCCAGGGCACCCTGGTC<br>ACCGTCTCCTCA |

TABLE 7-continued

Nucleic Acid Sequences Encoding Variable Heavy Chains

SEQ ID NO: 138  GAGGTGCAGCTGGTGGAGTCTGGGGGAGGCTTGGTACAGCCTGGCAGGTC
CCTGAGACTCTCCTGTGCAGCCTCTGGATTCACCTTTGATGATTATGCCAT
GCACTGGGTCCGGCAAGCTCCAGGGAAGGGCCTGGAGTGGGTCTCAGGTA
TTAGTTGGAATAGTGGTAGCATAGGCTATGCGGACTCTGTGAAGGGCCGA
TTCACCATCTCCAGAGACAACGCCAAGAACTCCCTGTATCTGCAAATGAA
CAGTCTGAGAGCTGAGGACACGGCCTTGTATTACTGTGCAAAACGGCATG
GAGGGACCAATGCTTTTGATATCTGGGGCCAAGGGACAATGGTCACCGTC
TCTTCA

SEQ ID NO: 139  CAGATCACCTTGAAGGAGTCTGGACCTACGCTGGTGAAACCCACAGAAAC
CCTCACGCTGACCTGCACCTTCTCTGGGTTCTCACTCAACACTGGTGGAGT
GAGTGTGGGCTGGGTCCGTCAGACCCCAGGAAAGGCCCTGGAGTGGCTTG
CACTCATTTATTGGAATGATGATAAGCGCTACAGCCCATCTCTGAAGAGC
AGGCTCACCATCACCAAGGACACCTCCAAAAACCAGGTGGTCCTTACAAT
GACCAACATGGACACTGTGGACACGGCCACATATTACTGTGCACACACGCG
CGGCTGGAGTTGACTACTGGGGCCAGGGAACCCTGGTCACCGTCTCTTCA

SEQ ID NO: 140  CAGGTGCAGCTGGTGGAGTCTGGGGCTGAGGTGAAGAAGCCTGGGGCCTC
AGTGAAGGTCTCCTGCAAGGCTTCTGGATACACTTTTACCGCCTACTATAT
ACACTGGCTGCGACAGGCCCCTGGACAAGACCTTGAGTGGATGGGATGGA
TCGACCCTAACAGTGGTGGCACAAACTATGCACAGAAATTTCAGGGCAGG
GTCACCATGACCAGGGACACGTCCATCAGCACAGCCTACATGGAGCTGAG
CAGGCTGAGATCTGACGACACGGCCGTGTATTACTGTGCGAGAGGCTGGA
ATTACGAACTTGACTACTGGGGCCAGGGCACCCTGGTCACCGTCTCCTCA

SEQ ID NO: 141  CAGGTGCAGCTGGTGGAGTCTGGGGCTGAGGTGAAGAAGCCTGGGGCCTC
AGTGAAGGTCTCCTGCAAGGCTTCTGGATACACTTTTACCGCCTACTATAT
ACACTGGCTGCGACAGGCCCCTGGACAAGACCTTGAGTGGATGGGATGGA
TCGACCCTAACAGTGGTGGCACAAACTATGCACAGAAATTTCAGGGCAGG
GTCACCATGACCAGGGACACGTCCATCAGCACAGCCTACATGGAGCTGAG
CAGGCTGAGATCTGACGACACGGCCGTGTATTACTGTGCGAGAGACTGGA
ATTACGAACTTGACTACTGGGGCCAGGGCACCCTGGTCACCGTCTCCTCA

SEQ ID NO: 142  CAGATCACCTTGAAGGAGTCGGTCCTACGCTGGTGAAACCCACACAGAC
CCTCACGCTGACCTGCACCTTCTCTGGGTTCTCACTCAGCACTAGTGGAGT
GGGTGTGGGCTGGATCCGTCAGCCCCCAGGAAAGGCCCTGGAGTGGCTTG
CACTCATTTATTGGAATGATGATAAGCGCTACAGCCCATCTCTGAAGAGC
AGGCTCACCATCACCAAGGACACCTCCAAAAACCAGGTGGTCCTTACAAT
GACCAACATGGACCCTGTGGACACAGCCACATATTACTGTGCACACATTT
CCAGTAGTGGTGGTACCGAAGTACAAGACTACTGGGGCCAGGGAACCCTG
GTCACCGTCTCCTCA

SEQ ID NO: 143  CAAATGCAGCTGGTGCAGTCTGGGGCTGAGGTGAAGAAGCCTGGGTCCTC
GGTGAAGGTCTCCTGTAAGGCTTCTGGAGGCACCTTCAGCAGCTATGCTAT
CAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACAAATCCACGAGCACAGCCTACATGGAGCTGA
GCAGCCTGAGATCTGACGACACGGCCGTGTATTACTGTGCGAGAGATGAA
CTCTGGGCTACAAACTACTACTACATGGACGTCTGGGGCAAAGGAACCCT
GGTCACCGTCTCCTCA

SEQ ID NO: 144  CAGGTGCAGCTGGTGGAGTCTGGGGCTGAGGTGAAGAAGCCTGGGGCCTC
AGTGAAGGTCTCCTGCAAGGCTTCTGGATACACTTTTACCGCCTACTATAT
ACACTGGCTGCGACAGGCCCCTGGACAAGACCTTGAGTGGATGGGATGGA
TCGACCCTAACAGTGGTGGCACAAACTATGCACAGAAATTTCAGGGCAGG
GTCACCATGACCAGGGACACGTCCATCAGCACAGCCTACATGGAGCTGAG
CAGGCTGAGATCTGACGACACGGCCGTGTATTACTGTGCGAGAGACTGGA
ATTACGAACTTGACTACTGGGGCCGGGGCACCCTGGTCACCGTCTCCCCA

SEQ ID NO: 145  CAGGTGCAGCTGGTGGAGTCTGGGGCTGAGGTGAAGAAGCCTGGGGCCTC
AGTGAAGGTCTCCTGCAAGGCTTCTGGATACACTTTTACCGCCTACTATAT
ACACTGGCTGCGACAGGCCCCTGGACAAGACCTTGAGTGGATGGGATGGA
TCGACCCTAACAGTGGTGGCACAAACTATGCACAGAAATTTCAGGGCAGG
GTCACCATGACCAGGGACACGTCCATCAGCACAGCCTACATGGAGCTGAG
CAGGCTGAGATCTGACGACACGGCCGTGTATTACTGTGCGAGAGACTGGA
ATTACGAGCTTGACTACTGGGGCCAGGGCACCCTGGTCACCGTCTCCTCA

SEQ ID NO: 146  CAGATCACCTTGAAGGAGTCTGGTCCTACGCTGGTGAAACCCACACAGAC
CCTCACGCTGACCTGCACCTTCTCTGGGTTCTCACTCAGCACTAGTGGAGT
GGGTGTGGGCTGGATCCGTCAGCCCCCAGGAAAGGCCCTGGAGTGGCTTG
CACTCATTTATTGGAATGATGATAAGCGCTACAGCCCATCTCTGAAGAGC
AGGCTCACCATCACCAAGGACACCTCCAAAAACCAGGTGGTCCTTACAAT
GACCAACATGGACCCTGTGGACACAGCCACATATTACTGTGCCCAGGCAA
AACCGTATAGCAGCGATTTTGATATCTGGGGCCAAGGGACAATGGTCACC
GTCTCTTCA

SEQ ID NO: 147  CAGGTGCAGCTGGTGGAGTCTGGGGGAGGCTTGGTACAGCCTGGCAGGTC
CCTGAGACTCTCCTGTGCAGCCTCTGGATTCACCTTTGATGATTATGCCAT

TABLE 7-continued

Nucleic Acid Sequences Encoding Variable Heavy Chains

```
               GCACTGGGTCCGGCAAGCTCCAGGGAAGGGCCTGGAGTGGGTCTCAGGTA
               TTAGTTGGAATAGTGGTAGCATAGGCTATGCGGACTCCGCGAAGGGCCGG
               TTCACCATCTCCAGAGACAATTCCAAGAACACGCTGTATCTGCAAATGAA
               CAGCCTGAGAGCCGAGGACACGGCCGTCTATTACTGTGCGAAAAGGGGGA
               ACTCCAACTCTTTTGACTACTGGGGCCAGGGAACCCTGGTCACCGTCTCCT
               CA

SEQ ID NO: 148 CAGATCACCTTGAAGGAGTCTGGTCCTACGCTGGTGAAACCCACACAGAC
               CCTCACGCTGACCTGCACCTTCTCTGGGTTCTCACTCAGCACTAGTGGAGT
               GGGTGTGGGCTGGATCCGTCAGCCCCCAGGAAAGGCCCTGGAGTGGCTTG
               CACTCATTTACTGGAATGATAAGCGCTACAGCCCATCTCTGAAGAGC
               AGGCTCACCATCACCAAGGACACCTCCAAAAACCAGGTGGTCCTTACAAT
               GACCAACATGGACCCTGTGGACACAGCCACATATTACTGTGCCCAGGCAA
               AACCGTATAGCAGCGATTTTGATATCTGGGGCCAAGGGACAATGGTCACC
               GTCTCTTCA
```

In some instances, the CD229 antigen binding domain comprises a variable light chain comprising a sequence having at least 90% identity a sequence set forth in SEQ ID NOs:149, 150, 151, 152, 153, 154, 155, 156, 157, 158, 159, 160, 161, 162, or 163 (see Table 8). In some instances, the CD229 antigen binding domain comprises a variable light chain comprising a sequence having at least 90, 91, 92, 93, 94, 95, 96, 97, 98, 99, or 100% identity to a sequence set forth in SEQ ID NOs:149, 150, 151, 152, 153, 154, 155, 156, 157, 158, 159, 160, 161, 162, or 163.

TABLE 8

Nucleic Acid Sequences Encoding Variable Light Chains.

```
SEQ ID NO: 149 GACATCCAGATGACCCAGTCTCCATCCTCCCTGTCTGCGTCTGTAGGAGAC
               AGAGTCACCATCACTTGCCGGGCAAGTCAGAGCATTGGCAGCTCTTTACA
               TTGGTATCAGCAGAAACCAGGGAAAGCCCCTAAGTTCCTGATCTATGATG
               CCTCCAGTTTGGAAAGTGGGGTCCCATCAAGGTTCAGCGGCAGTGGATCT
               GGGACAGAATTCACTCTCACCATCAGCAGCCTGCAGCCTGATGATTTTGCA
               ACTTATTACTGCCAACAGTATAATAGTTACCCGCTCACTTTCGGCGGAGGG
               ACCAAGCTGGAGATCAAACGT

SEQ ID NO: 150 CAGTCTGGGCTGACTCAGCCTCGCTCAGTGTCCGGGTCTCCTGGACAGTCA
               GTCACCATCTCCTGCACTGGAACCAGCAGTGATGTTGGTGGTTATAACTAT
               GTCTCCTGGTACCAACAGCACCCAGGCAAAGCCCCCAAACTCATGATTTA
               TGATGTCAGTAAGCGGCCCTCAGGGGTCCCTGATCGCTTCTCTGGCTCCAA
               GTCTGGCAACACGGCCTCCCTGACCGTCTCTGGGCTCCAGGCTGAGGATG
               AGGCTGATTATTACTGCAGCTCCTATGCAGGCAGCAATACTTTTGTCTTCG
               GATCTGGGACCAAGCTGACCGTCCTAGGT

SEQ ID NO: 151 GATATTGTGATGACGCAGTCTCCAGCCACCCTGTCTGTGTCTCCAGGGGAA
               AGAGCCACCCTCTCCTGCAGGGCCAGCCAGAGTGTTGGCAGCAGCTTAGC
               CTGGTACCAGCAGAAACCTGGCCAGGCTCCCAGGCTCCTCATCTATGGTG
               GATCCGTCAGGGCCACTGGTATCCCAGCCAGGTTCAGTGGCAGTGGGTCT
               GGGACAGAGTTCACTCTCACCATCAGCAGCCTGCAGTCTGAAGATTTTGC
               AGCTTATTACTGTCAGCAGTATAATAGTTACCCGCTCACTTTCGGCGGAGG
               GACCAAGCTGGAGATCAAACGT

SEQ ID NO: 152 AATTTTATGCTGACTCAGCCCCACTCTGTGTCGGAGTCTCCGGGGAAGACG
               GTAACCATCTCCTGCACCGGCAGCAGTGGCAGCATTGCCAGCAACTATGT
               GCAGTGGTACCAGCAGCGCCCGGGCAGTTCCCCCACCACTGTGATCTATG
               AGGATAACCAAAGACCCTCTGGGGTCCCTGATCGGTTCTCTGGCTCCATCG
               ACAGCTCCTCCAACTCTGCCTCCCTCACCATCTCTGGACTGAAGACTGAGG
               ACGAGGCTGACTACTACTGTCAGTCTTATGATGGCAGCAACCCTGTGGTTT
               TCGGCGGAGGGACCCAGCTCACCGTTTTAGGT

SEQ ID NO: 153 GACATCCAGATGACCCAGTCTCCATCCTCCCTGTCTGCATCTGTAGGAGAC
               AGAGTCACCATCACTTGCCGGGCAAGTCAGAGCATTAGCAGCTATTTAAA
               TTGGTATCAGCAGAAACCAGGGAAAGCCCCTAAGCTCCTGATCTATGCTG
               CATCCAGTTTGCAAAGTGGGGTCCCATCAAGGTTCAGTGGCAGTGGATCT
               GGGACAGATTTCACTCTCACCATCAGCAGTCTGCAACCTGAAGATTTTGCA
               ACTTACTACTGTCAACAGAGTTACAGTACCCTTTACACTTTTGGCCAGGGG
               ACCAAGCTGGAGATCAAACGT

SEQ ID NO: 154 GACATCCAGATGACCCAGTCTCCATCCTCCCTGTCTGCATCTGTAGGAGAC
               AGAGTCACCATCACTTGCCAGGCGAGTCAGGACATTAGCAACTATTTAAA
               TTGGTATCAGCAGAAACCAGGGAAAGCCCCTAAGCTCCTGATCTACGATG
               CATCCAATTTGGAAACAGGGGTCCCATCAAGGTTCAGTGGAAGTGGATCT
               GGGACAGATTTTACTTTCACCATCAGCAGCCTGCAGCCTGAAGATATTGCA
               ACATATTACTGTCAACAGTATGATAATCTCCCCATCACTTTCGGCCCTGGG
               ACCAAAGTGGATATCAAACGT
```

TABLE 8-continued

Nucleic Acid Sequences Encoding Variable Light Chains.

SEQ ID NO: 155 AATTTTATGCTGACTCAGCCCCACTCTGTGTCGGGGTCTCCGGGGAAGACG
GTGACCATCTCCTGCACCCGCAGCAGTGGCTACATTGCCAGCAACTATGTA
CAGTGGTACCAGCAGCGCCCGGGCAGTGCCCCCACCACTGTGATCTATGA
GGATAACCAAAGACCCTCTGGGGTCCCTGATCGGTTCTCTGGCTCCATCGA
CAGCTCCTCCAACTCTGCCTCCCTCACCATCTCTGGACTGAAGACTGAGGA
CGAGGCTGACTACTACTGTCAGTCTTATGATAGCAGCAATCAAGGGGTGT
TCGGCGGAGGGACCAAGCTGACCGTCCTAGTG

SEQ ID NO: 156 AATTTTATGCTGACTCAGCCCCACTCTGTGTCGGGGTCTCCGGGGAAGACG
GTGACCATCTCCTGCACCCGCAGCAGTGGCTACATTGCCAGCAACTATGTA
CAGTGGTACCAGCAGCGCCCGGGCAGTTCCCCCACCACTCTGATATATGA
CGATGACCAAAGACCCTCTGGGGTCCCTGATCGGTTCTCTGGCTCCATCGA
CAGATCCTCCAATTCTGCCTCCCTCACCATCTCTGGGCTGAAGACTGAGGA
CGAGGGTGACTACTACTGTCAGTCTTATGATAGCAGCCTTGTGATATTCGG
CGGGGGGACCAAGGTCACCGTCCTAGGT

SEQ ID NO: 157 GACATCCAGATGACCCAGTCTCCATCCTCCCTGTCTGCGTCTGTAGGAGAC
AGAGTCACCATCACTTGCCGGGCAAGTCAGAGCATTGGCAGCTCTTTACA
TTGGTATCAGCAGAAACCAGGGAAAGCCCCTAAGTTCCTGATCTATGATG
CCTCCAGTTTGGAAAGTGGGGTCCCATCAAGGTTCAGCGGCAGTGGATCT
GGGACAGAATTCACTCTCACCATCAGCAGCCTGCAGCCTGATGATTGTGC
AACTTATTACTGCCAACAGTATAATAGTTACCCGCTCACTTTCGGCGGAGG
GACCAAGCTGGAGATCAAACGT

SEQ ID NO: 158 CAGTCTGCGCTGACTCAGCCTCGCTCAGTGTCCGGGTCTCCTGGACAGTCA
GTCACCATCTCCTGCACTGGAACCAGCAGTGATGTTGGTAGTTATAACTAT
GTCTCCTGGTACCAACAGAGCCCAGGCAAAGCCCCCAAACTCATGATTTA
TGATGTCAGTAATCGGCCCTCAGGGGTTTCTAATCGCTTCTCTGGCTCCAA
GTCTGGCAACACGGCCTCCCTGACCATCTCTGGGCTCCAGTCTGAGGACG
AGGCTGATTATTATTGCACCTCATATGGAAGCTACGACATACCTGTGATTT
TCGGCGGAGGGACCAAGCTGACCGTCCTAGGT

SEQ ID NO: 159 AATTTTATGCTGACTCAGCCCCACTCTGTGTCGGGGTCTCCGGGGAAGGCG
GTGACCATCTCCTGCACCCGCAGCAGTGGCAACATTGCCAGGAGTTTTGTG
CAGTGGTACCAACAGCGCCCGGGCAGTGCCCCCACCGCTGTGATCTATGA
GGATAACCGAAGACCCTCTGGGGTCCCTGATCGCTTCTCTGGCTCCTTCGA
CAGCTCCTCCAATTCTGCCTCCCTCACCATCTCTGGCCTGAAGACTGAGGA
CGAGGCTGACTACTACTGTCAGTCTTATGATAGCAGCAATCATGTGGTATT
CGGCGGAGGGACCAAGGTCACCGTCCTAGGT

SEQ ID NO: 160 AATTTTATGCTGACTCAGCCCCACTCTGTGTCGGGGTCTCCGGGGAAGACG
GTGACCATCTCCTGCACCCGCAGCAGTGGCTACATTGCCAGCAACTATGTA
CAGTGGTACCAGCAGCGCCCGGGCAGTTCCCCCACCACTCTGATATATGA
CGATGACCAAAGACCCTCTGGGGTCCCTGATCGGTTCTCTGGCTCCATCGA
CAGATCCTCCAATTCTGCCTCCCTCACCATCTCTGGGCTGAAGACTGAGGA
CGAGGGTGACTACTACTGTCAGTCTTATGATAGCACCACGGAAGTCTTCG
GAACTGGGACCAAGCTGACCGTCCTAGGT

SEQ ID NO: 161 AATTTTATGCTGACTCAGCCCCACTCTGTGTCGGAGTCTCCGGGGAAGACG
GTAACCATCTCCTGCACCGGCAGCAGTGGCAGCATTGCCAGCAACTATGT
GCAGTGGTACCAGCAGCGCCCGGGCAGTTCCCCCACCACTGTGATCTATG
AGGATAACCAAAGACCCTCTGGGGTCCCTGATCGGTTCTCTGGCTCCATCG
ACAGCTCCTCTAACTCTGCCTCCCTCACCATCTCTGGACTGAAGACTGAGG
ACGAGGCTGACTACTACTGTCAGTCTTATGATAGCAGCAATCAGGGGGTA
TTCGGCGGCGGGACCCAGCTCACCGTCCTAGGT

SEQ ID NO: 162 GACATCCAGATGACCCAGTCTCCATCTTCCGTGTCTGCATCTGTAGGAGAC
AGAGTCACCATCACTTGCCGGGCAAGTCAGAGCATTAGCAGCTATTTAAA
TTGGTATCAGCAGAAACCAGGGAAAGCCCCTAAGCTCCTGATCTATGCTG
CATCCAGTTTGCAAAGTGGGGTCCCATCAAGGTTCAGTGGCAGTGGATCT
GGGACAGATTTCACTCTCACCATCAGCAGTCTGCAACCTGAAGATTTTGCA
ACTTACTACTGTCAACAGAGTTACAGTACCCCCTGGACGTTCGGCCAAGG
GACCAAGCTGGAGATCAAACGT

SEQ ID NO: 163 GACATCCAGATGACCCAGTCTCCATCCTCCCTGTCTGCATCTGTAGGAGAC
AGAGTCACCATCTCTTGCCAGGCGAGTCAGGACATTAGTAACTATTTAAAT
TGGTATCAGCAGAAACCAGGGAAAGCCCCTAAGCTCCTGATCTATGCTGC
ATCCAGTTTGCAAAGTGGGGTCCCATCAAGGTTCAGTGGCAGTGGATCTG
GGACAGATTTCACTCTCACCATCAGCAGTCTGCAACCTGAAGATTTTGCAA
CTTATTACTGTCTACAAGATTACAATTACCCGTGGACGTTCGGCCAGGGGA
CCAAGGTGGAAATCAAACGT

In some instances, the nucleic acid sequence that encodes the CD229 antigen binding domain comprises a heavy chain immunoglobulin variable region comprising a CDR1 comprising the sequence of SEQ ID NO:164, 167, 170, 173, 176, 179, 182, 185, 188, 191, 194, 197, 200, 203, or 206; a CDR2 comprising the sequence of SEQ ID NO:165, 168, 171, 174, 177, 180, 183, 186, 189, 192, 195, 198, 201, 204, or 207; and a CDR3 comprising the sequence of SEQ ID NO:166, 169, 172, 175, 178, 181, 184, 187, 190, 193, 196, 199, 202, 205, or 208.

TABLE 9

CDRs present in the heavy chain

| CDRs present in the heavy chain of SEQ ID NOs: | CDR1 | CDR2 | CDR3 |
|---|---|---|---|
| SEQ ID NO: 119 | gggttctcactcagcactagtggag tgggt (SEQ ID NO: 164) | atttattggaatgatgataa g (SEQ ID NO: 165) | gcacggatgggctggaacgatcct catatggttgactac (SEQ ID NO: 166) |
| SEQ ID NO: 120 | ggaggcaccttcagcagctatgct (SEQ ID NO: 167) | atcatccctatctttggtac agca (SEQ ID NO: 168) | gcggccgatatggaactacgggac tactactacggtatggacgtc (SEQ ID NO: 169) |
| SEQ ID NO: 121 | ggattcaccttcagtagctatggc (SEQ ID NO: 170) | atatcatatgatggaagta ataaa (SEQ ID NO: 171) | gcaaaagatacttgtactaatggtgt atgctaccctgactac (SEQ ID NO: 172) |
| SEQ ID NO: 122 | ggttacacctttaccagctatggt (SEQ ID NO: 173) | atcagcgcttacaatggta acaca (SEQ ID NO: 174) | gcgagatcgcctagtacggtggtaa ccccattcagcgactac (SEQ ID NO: 175) |
| SEQ ID NO: 123 | ggattcacctttgatgattatgcc (SEQ ID NO: 176) | attagttggaatagtggta gcata (SEQ ID NO: 177) | gcaaaacggcatggagggaccaat gcttttgatatc (SEQ ID NO: 178) |
| SEQ ID NO: 124 | gggttctcactcaacactggtggagtg agt (SEQ ID NO: 179) | atttattggaatgatgataa g (SEQ ID NO: 180) | gcacacagcgcggctggagttgac tac (SEQ ID NO: 181) |
| SEQ ID NO: 125 | ggatacacttttaccgcctactat (SEQ ID NO: 182) | atcgaccctaacagtggt ggcaca (SEQ ID NO: 183) | gcgagaggctggaattacgaacttg actac (SEQ ID NO: 184) |
| SEQ ID NO: 126 | ggatacacttttaccgcctactat (SEQ ID NO: 185) | atcgaccctaacagtggt ggcaca (SEQ ID NO: 186) | gcgagagactggaattacgaacttg actac (SEQ ID NO: 187) |
| SEQ ID NO: 127 | gggttctcactcagcactagtggagtg ggt (SEQ ID NO: 188) | atttattggaatgatgataa g (SEQ ID NO: 189) | gcacacatttccagtagtggtggtac cgaagtacaagactac (SEQ ID NO: 190) |
| SEQ ID NO: 128 | ggaggcaccttcagcagctatgct (SEQ ID NO: 191) | atcatccctatctttggtac agca (SEQ ID NO: 192) | gcgagagatgaactctgggctacaa actactactacatggacgtc (SEQ ID NO: 193) |
| SEQ ID NO: 129 | ggatacacttttaccgcctactat (SEQ ID NO: 194) | atcgaccctaacagtggt ggcaca (SEQ ID NO: 195) | gcgagagactggaattacgaacttg actac (SEQ ID NO: 196) |
| SEQ ID NO: 130 | ggatacacttttaccgcctactat (SEQ ID NO: 197) | atcgaccctaacagtggt ggcaca (SEQ ID NO: 198) | gcgagagactggaattacgagcttg actac (SEQ ID NO: 199) |
| SEQ ID NO: 131 | gggttctcactcagcactagtggagtg ggt (SEQ ID NO: 200) | atttattggaatgatgataa g (SEQ ID NO: 201) | gcccaggcaaaaccgtatagcagc gattttgatatc (SEQ ID NO: 202) |
| SEQ ID NO: 132 | ggattcacctttgatgattatgcc (SEQ ID NO: 203) | attagttggaatagtggta gcata (SEQ ID NO: 204) | gcgaaaaggggggaactccaactctt ttgactac (SEQ ID NO: 205) |
| SEQ ID NO: 133 | gggttctcactcagcactagtggagtg ggt (SEQ ID NO: 206) | atttactggaatgatgata ag (SEQ ID NO: 207) | gcccaggcaaaaccgtatagcagc gattttgatatc (SEQ ID NO: 208) |

In some instances, the nucleic acid sequence that encodes the CD229 antigen binding domain comprises a light chain immunoglobulin variable region comprising a CDR1 comprising the sequence of SEQ ID NO:209, 211, 213, 215, 217, 219, 221, 223, 225, 227, 229, 231, 233, 235, or 237; a CDR2 comprising the sequence of gatgcctcc, gatgtcagt, ggtggatcc, gaggataac, gctgcatcc, gatgcatcc, gaggataac, gacgatgac, gatgcctcc, gatgtcagt, gaggataac, gacgatgac, gaggataac, gctgcatcc, or gctgcatcc; and a CDR3 comprising the sequence of SEQ ID NO: 210, 212, 214, 216, 218, 220, 222, 224, 226, 228, 230, 232, 234, 236, or 238.

TABLE 10

CDRs present in the light chain

| CDRs present in the light chain of SEQ ID NOs: | CDR1 | CDR2 | CDR3 |
|---|---|---|---|
| SEQ ID NO: 119 | cagagcattggcagctct (SEQ ID NO: 209) | gatgcctcc | caacagtataatagttacccgctcact (SEQ ID NO: 210) |
| SEQ ID NO: 120 | agcagtgatgttggtggttataactat (SEQ ID NO: 211) | gatgtcagt | agctcctatgcaggcagcaatactttt gtc (SEQ ID NO: 212) |
| SEQ ID NO: 121 | cagagtgttggcagcagc (SEQ ID NO: 213) | ggtggatcc | cagcagtataatagttacccgctcact (SEQ ID NO: 214) |
| SEQ ID NO: 122 | agtggcagcattgccagcaactat (SEQ ID NO: 215) | gaggataac | cagtcttatgatggcagcaaccctgt ggtt (SEQ ID NO: 216) |
| SEQ ID NO: 123 | cagagcattagcagctat (SEQ ID NO: 217) | gctgcatcc | caacagagttacagtaccctnacact (SEQ ID NO: 218) |
| SEQ ID NO: 124 | caggacattagcaactat (SEQ ID NO: 219) | gatgcatcc | caacagtatgataatctccccatcact (SEQ ID NO: 220) |
| SEQ ID NO: 125 | agtggctacattgccagcaactat (SEQ ID NO: 221) | gaggataac | cagtcttatgatagcagcaatcaagg ggtg (SEQ ID NO: 222) |
| SEQ ID NO: 126 | agtggctacattgccagcaactat (SEQ ID NO: 223) | gacgatgac | cagtcttatgatagcagccttgtgata (SEQ ID NO: 224) |
| SEQ ID NO: 127 | cagagcattggcagctct (SEQ ID NO: 225) | gatgcctcc | caacagtataatagttacccgctcact (SEQ ID NO: 226) |
| SEQ ID NO: 128 | agcagtgatgttggtagttataactat (SEQ ID NO: 227) | gatgtcagt | acctcatatggaagctacgacatac ctgtgatt (SEQ ID NO: 228) |
| SEQ ID NO: 129 | agtggcaacattgccaggagtttt (SEQ ID NO: 229) | gaggataac | cagtcttatgatagcagcaatcatgt ggta (SEQ ID NO: 230) |
| SEQ ID NO: 130 | agtggctacattgccagcaactat (SEQ ID NO: 231) | gacgatgac | cagtcttatgatagcaccacggaagt c (SEQ ID NO: 232) |
| SEQ ID NO: 131 | agtggcagcattgccagcaactat (SEQ ID NO: 233) | gaggataac | cagtcttatgatagcagcaatcagg gggta (SEQ ID NO: 234) |
| SEQ ID NO: 132 | cagagcattagcagctat (SEQ ID NO: 235) | gctgcatcc | caacagagttacagtaccccctgga cg (SEQ ID NO: 236) |
| SEQ ID NO: 133 | caggacattagtaactat (SEQ ID NO: 237) | gctgcatcc | ctacaagattacaattacccgtggac g (SEQ ID NO: 238) |

In some instances, the nucleic acid sequence that encodes the CD229 antigen binding domain comprises a heavy chain immunoglobulin variable region comprising a CDR1 comprising the sequence of SEQ ID NO:164, 167, 170, 173, 176, 179, 182, 185, 188, 191, 194, 197, 200, 203, or 206; a CDR2 comprising the sequence of SEQ ID NO:165, 168, 171, 174, 177, 180, 183, 186, 189, 192, 195, 198, 201, 204, or 207; and a CDR3 comprising the sequence of SEQ ID NO:166, 169, 172, 175, 178, 181, 184, 187, 190, 193, 196, 199, 202, 205, or 208; and a light chain immunoglobulin variable region comprising a CDR1 comprising the sequence of SEQ ID NO:209, 211, 213, 215, 217, 219, 221, 223, 225, 227, 229, 231, 233, 235, or 237; a CDR2 comprising the sequence gatgcctcc, gatgtcagt, ggtggatcc, gaggataac, gctgcatcc, gatgcatcc, gaggataac, gacgatgac, gatgcctcc, gatgtcagt, gaggataac, gacgatgac, gaggataac, gctgcatcc, or gctgcatcc; and a CDR3 comprising the sequence of SEQ ID NO: 210, 212, 214, 216, 218, 220, 222, 224, 226, 228, 230, 232, 234, 236, or 238.

2. Transmembrane Domain

In some instances, the transmembrane domain comprises a nucleic acid sequence that encodes an immunoglobulin Fc domain. In some instances, the immunoglobulin Fc domain can be an immunoglobulin G Fc domain.

In some instances, the transmembrane domain comprises a nucleic acid sequence that encodes a CD8α domain, CD3ζ, FcεR1γ, CD4, CD7, CD28, OX40, or H2-Kb.

In some instances, the transmembrane domain can be located between the CD229 antigen binding domain and the intracellular signaling domain.

3. Intracellular Domain

In some instances, the intracellular signaling domain comprises a nucleic acid that encodes a co-stimulatory signaling region. In some instances, the co-stimulatory signaling region can comprise the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In some instances, the intracellular signaling domain can be a nucleic acid sequence encoding a T cell signaling domain. For example, the intracellular signaling domain can comprise a nucleic acid sequence that encodes a CD3ζ signaling domain. In some instances, CD3ζ signaling domain is the intracellular domain of CD3ζ.

In some instances, the intracellular signaling domain comprises a nucleic acid sequence encoding a CD3ζ signaling domain and a co-stimulatory signaling region, wherein the co-stimulatory signaling region comprises the cytoplasmic domain of CD28, 4-1BB, CD27, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

D. Vectors

Disclosed are vectors comprising the nucleic acid sequence of the disclosed CAR nucleic acid sequences. In some instances, the vector can be selected from the group consisting of a DNA, a RNA, a plasmid, and a viral vector. In some instances, the vector can comprise a promoter.

E. Cells

Disclosed are cells comprising any of the disclosed CAR polypeptides, CAR nucleic acids, or disclosed vectors. These cells can be considered genetically modified.

In some instances, the cell can be a T cell. For example, T cell can be a CD8+ T cell. In some instances, the can be a human cell.

Thus, disclosed are T cells expressing one of the CAR polypeptides disclosed herein.

F. Antibodies

Disclosed are antibodies or fragments thereof that bind to human CD229, wherein said antibody comprises a variable heavy chain comprising a sequence having at least 90% identity to one of the variable heavy chain amino acid sequences provided in Table 1 or Table 2. Disclosed are antibodies or fragments thereof that bind to human CD229, wherein said antibody comprises a variable heavy chain comprising a sequence having at least 90% identity to a sequence set forth in SEQ ID NOs:16, 17, 18, 19, 20, 21, 22, 23, 24, 25, 26, 27, 28, 29, or 30.

Disclosed are antibodies or fragments thereof that bind to human CD229, wherein said antibody comprises a variable heavy chain comprising SEQ ID NO:16, 17, 18, 19, 20, 21, 22, 23, 24, 25, 26, 27, 28, 29, or 30.

Disclosed are antibodies or fragments thereof that bind to human CD229, wherein said antibody comprises a variable light chain comprising a sequence having at least 90% identity to one of the variable heavy chain amino acid sequences provided in Table 1 or Table 3. Disclosed are antibodies or fragments thereof that bind to human CD229, wherein said antibody comprises a variable light chain comprising a sequence having at least 90% identity to a sequence set forth in SEQ ID NOs:31, 32, 33, 34, 35, 36, 37, 38, 39, 40, 41, 42, 43, 44, or 45.

Disclosed are antibodies or fragments thereof that bind to human CD229, wherein said antibody comprises a variable light chain comprising SEQ ID NO:31, 32, 33, 34, 35, 36, 37, 38, 39, 40, 41, 42, 43, 44, or 45.

Disclosed are antibodies or fragments thereof that bind to human CD229, wherein said antibody comprises a variable heavy chain comprising a sequence having at least 90% identity to a sequence set forth in SEQ ID NOs:16, 17, 18, 19, 20, 21, 22, 23, 24, 25, 26, 27, 28, 29, or 30 and a variable light chain comprising a sequence having at least 90% identity to a sequence set forth in SEQ ID NOs:31, 32, 33, 34, 35, 36, 37, 38, 39, 40, 41, 42, 43, 44, or 45. Disclosed are antibodies or fragments thereof that bind to human CD229, wherein said antibody comprises a variable heavy chain comprising a sequence set forth in SEQ ID NOs:16, 17, 18, 19, 20, 21, 22, 23, 24, 25, 26, 27, 28, 29, or 30 and a variable light chain comprising a sequence set forth in SEQ ID NOs:31, 32, 33, 34, 35, 36, 37, 38, 39, 40, 41, 42, 43, 44, or 45.

In some instances, the antibody or fragment thereof comprises a CD229 antigen binding domain, wherein the CD229 antigen binding domain comprises a heavy chain immunoglobulin variable region comprising a CDR1 comprising the sequence of SEQ ID NO:46, 49, 52, 57, 60, 63, 66, 69, 71, 74, 77, 80, 83 or 86; a CDR2 comprising the sequence of SEQ ID NO:47, 50, 53, 55, 58, 61, 64, 67, 70, 72, 75, 78, 81, 84, or 87; and a CDR3 comprising the sequence of SEQ ID NO:48, 51, 54, 56, 59, 62, 65, 68, 71, 73, 76, 79, 82, 85, or 88.

In some instances, the antibody or fragment thereof comprises a CD229 antigen binding domain, wherein the CD229 antigen binding domain comprises a light chain immunoglobulin variable region comprising a CDR1 comprising the sequence of SEQ ID NO:89, 91, 93, 95, 97, 99, 101, 103, 105, 107, 109, 111, 113, 115, or 117; a CDR2 comprising the sequence of DAS, DVS, GGS, EDN, DDD, or AAS; and a CDR3 comprising the sequence of SEQ ID NO:90, 92, 94, 96, 98, 100, 102, 104, 106, 108, 110, 112, 114, 116, or 118.

In some instances, the disclosed antibodies or fragments thereof further comprise a tag sequence.

Disclosed are nucleic acid sequences that encode the disclosed antibodies or fragments thereof. For example, disclosed are nucleic acid sequences comprising a variable heavy chain comprising a sequence having at least 90% identity to a sequence set forth in SEQ ID NOs: 134, 135, 136, 137, 138, 139, 140, 141, 142, 143, 144, 145, 146, 147, or 148. Disclosed are nucleic acid sequences that encode the disclosed antibodies or fragments thereof. For example, disclosed are nucleic acid sequences comprising a variable heavy chain comprising a sequence set forth in SEQ ID NOs:134, 135, 136, 137, 138, 139, 140, 141, 142, 143, 144, 145, 146, 147, or 148. Also disclosed are nucleic acid sequences comprising a variable light chain comprising a sequence having at least 90% identity to a sequence set forth in SEQ ID NOs:149, 150, 151, 152, 153, 154, 155, 156, 157, 158, 159, 160, 161, 162, or 163. Also disclosed are nucleic acid sequences comprising a variable light chain comprising a sequence set forth in SEQ ID NO:149, 150, 151, 152, 153, 154, 155, 156, 157, 158, 159, 160, 161, 162, or 163.

Disclosed are nucleic acid sequences comprising a variable heavy chain comprising a sequence having at least 90% identity to a sequence set forth in SEQ ID NOs: 134, 135, 136, 137, 138, 139, 140, 141, 142, 143, 144, 145, 146, 147, or 148; and a variable light chain comprising a sequence having at least 90% identity a sequence set forth in SEQ ID NOs:149, 150, 151, 152, 153, 154, 155, 156, 157, 158, 159, 160, 161, 162, or 163. Disclosed are nucleic acid sequences comprising a variable heavy chain comprising a sequence set forth in SEQ ID NO: 134, 135, 136, 137, 138, 139, 140, 141, 142, 143, 144, 145, 146, 147, or 148; and a variable light chain comprising a sequence set forth in SEQ ID NO:149, 150, 151, 152, 153, 154, 155, 156, 157, 158, 159, 160, 161, 162, or 163.

Disclosed are nucleic acid sequences capable of encoding a single chain variable fragment comprising a variable heavy chain comprising a sequence having at least 90% identity a sequence set forth in SEQ ID NOs:16, 17, 18, 19, 20, 21, 22, 23, 24, 25, 26, 27, 28, 29, or 30.

Disclosed are nucleic acid sequences capable of encoding a single chain variable fragment comprising a variable light chain comprising a sequence having at least 90% identity a sequence set forth in SEQ ID NOs:31, 32, 33, 34, 35, 36, 37, 38, 39, 40, 41, 42, 43, 44, or 45.

Disclosed are nucleic acid sequences capable of encoding a single chain variable fragment comprising a variable heavy chain comprising a sequence having at least 90% identity a sequence set forth in SEQ ID NOs:16, 17, 18, 19, 20, 21, 22, 23, 24, 25, 26, 27, 28, 29, or 30; and a variable light chain comprising a sequence having at least 90% identity a sequence set forth in SEQ ID NOs:31, 32, 33, 34, 35, 36, 37, 38, 39, 40, 41, 42, 43, 44, or 45.

In some instances, the disclosed antibodies or fragments thereof can be bispecific. For example, the antibody or fragment thereof can comprise a first Fab region comprising the heavy and light chain of one of SEQ ID NOs: 1-15 and a second Fab region comprising the heavy and light chain of one of SEQ ID NOs: 1-15, wherein the first and second Fab regions are different.

In some instances, the bispecific antibodies can be trifunctional.

In some instances, the disclosed antibodies or fragments thereof can be mouse, human, humanized, chimeric, or a combination thereof.

In some instances, the disclosed antibodies or fragments thereof are monoclonal.

G. Phage Display Library

Disclosed are phage display libraries comprising immunoglobulin genes. In some instances, the library displays scFv domains comprising both heavy and light chain variables. In some instances, the library displays antibodies.

H. Methods of Treating

1. Multiple Myeloma

Disclosed are methods of treating multiple myeloma comprising administering an effective amount of a T cell genetically modified to express one or more of the disclosed CAR polypeptides to a subject in need thereof. For example, disclosed are methods of treating multiple myeloma comprising administering an effective amount of a T cell genetically modified to express a CAR polypeptide comprising a CD229 antigen binding domain, a hinge and transmembrane domain, and an intracellular signaling domain.

Disclosed are methods of treating multiple myeloma comprising administering an effective amount of at least one of the disclosed vectors to a subject in need thereof. For example, disclosed are methods of treating multiple myeloma comprising administering an effective amount of a vector comprising the nucleic acid sequence capable of encoding a disclosed CAR polypeptide to a subject in need thereof. In some instances, the vectors can comprise targeting moieties. In some instances, the targeting moieties target T cells.

Disclosed are methods of treating multiple myeloma comprising administering an effective amount of a composition comprising one or more of the disclosed antibodies or fragments thereof. For example, disclosed are methods of treating multiple myeloma comprising administering an effective amount of a composition comprising an antibody or fragment thereof comprising a variable heavy chain comprising a sequence having at least 90% identity to a sequence set forth in SEQ ID NOs:16, 17, 18, 19, 20, 21, 22, 23, 24, 25, 26, 27, 28, 29, or 30; a variable light chain comprising a sequence having at least 90% identity to a sequence set forth in SEQ ID NOs:31, 32, 33, 34, 35, 36, 37, 38, 39, 40, 41, 42, 43, 44, or 45; or both.

In some instances, the disclosed methods of treating multiple myeloma further comprise administering a therapeutic agent. In some instances, the therapeutic agent can be, but is not limited to, conventional chemotherapy including but not limited to alkylating agents, antimetabolites, antimicrotubule agents, topoisomerase inhibitors, and cytotoxic antibiotics; high-dose chemotherapy including but not limited to high-dose Melphalan chemotherapy with or without stem cell transplant; proteasome inhibitors such as, but not limited to, bortezomib, ixazomib, and carfilzomib; immunomodulatory agents (IMiDS) such as, but not limited to, thalidomide, lenalidomide, and pomalidomide; histone deacetylase (HDAC) inhibitors such as, but not limited to panobinostat; monoclonal antibodies such as, but not limited to, daratumumab or elotuzumab; bispecific antibodies; and immune checkpoint inhibitors such as, but not limited to, ipilimumab, nivolumab, and pembrolizumab.

2. Lymphoma

Disclosed are methods of treating lymphoma comprising administering an effective amount of a T cell genetically modified to express one or more of the disclosed CAR polypeptides to a subject in need thereof. For example, disclosed are methods of treating lymphoma comprising administering an effective amount of a T cell genetically modified to express a CAR polypeptide comprising a CD229 antigen binding domain, a transmembrane domain, and an intracellular signaling domain.

Disclosed are methods of treating lymphoma comprising administering an effective amount of at least one of the disclosed vectors to a subject in need thereof. For example, disclosed are methods of treating lymphoma comprising administering an effective amount of a vector comprising the nucleic acid sequence capable of encoding a disclosed CAR polypeptide to a subject in need thereof. In some instances, the vectors can comprise targeting moieties. In some instances, the targeting moieties target T cells.

Disclosed are methods of treating lymphoma comprising administering an effective amount of a composition comprising one or more of the disclosed antibodies or fragments thereof. For example, disclosed are methods of treating lymphoma comprising administering an effective amount of a composition comprising an antibody or fragment thereof comprising a variable heavy chain comprising a sequence having at least 90% identity to a sequence set forth in SEQ ID NOs:16, 17, 18, 19, 20, 21, 22, 23, 24, 25, 26, 27, 28, 29, or 30; a variable light chain comprising a sequence having at least 90% identity to a sequence set forth in SEQ ID NOs:31, 32, 33, 34, 35, 36, 37, 38, 39, 40, 41, 42, 43, 44, or 45; or both.

In some instances, the disclosed methods of treating lymphoma further comprise administering a therapeutic agent. In some instances, the therapeutic agent can be, but is not limited to, conventional chemotherapy, vaccines, monoclonal antibodies, T cell immunotherapies, and other immunomodulatory agents.

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In one embodiment, a first CAR-expressing cell described herein, e.g., a BCMA CAR-expressing cell described herein, may be used in combination with a second CAR-expressing cell. In one embodiment, the second CAR-expressing cell expresses a CAR comprising a different anti-BMCA binding domain, e.g., an anti-BCMA binding domain described herein that differs from the anti-BCMA binding domain in the CAR expressed by the first CAR-expressing cell. In one embodiment, the second CAR-expressing cell expresses a CAR comprising an antigen-binding domain that targets an antigen other than BCMA (e.g., CD19, CD20, CS-1, kappa light chain, CD139, Lewis Y antigen, or CD38). In one embodiment, a first CAR-expressing cell described herein, e.g., a BCMA CAR-expressing cell described herein, is used in combination with a second CAR-expressing cell comprising a CD19 CAR. In one embodiment, a BCMA CAR-expressing cell described herein is used in combination with a CD19 CAR-expressing cell to treat a BCMA-associated cancer described herein, e.g., multiple myeloma. In some embodiments, the multiple myeloma is CD19-negative, e.g., having a vast majority (e.g., at least 98%, 99%, 99.5%, 99.9%, or 99.95%) of the neoplastic plasma cells with a CD19-negative phenotype, e.g., as detected flow cytometry, RT-PCR, or both flow cytometry and RT-PCR. As shown in Example 17 herein, a CD19 CAR can be effective even against a CD19-negative multiple myeloma. While not wishing to be bound by theory, the CD19 CAR may act on a small but important CD19-positive population of neoplastic cells, by targeting a cell that expresses levels of CD19 that fall below the detection threshold of the assays described herein, or by targeting a non-neoplastic cell that supports the neoplastic cells. In embodiments, a CD19 CAR can remove B cells, e.g., B regulatory B cells.

For example, in one embodiment, the first CAR-expressing cell described herein, e.g., a BCMA CAR-expressing cell, and the second CAR-expressing cell described herein, e.g., a CD19 CAR-expressing cell, are prepared in the same composition and are administered simultaneously. In another embodiment, the first CAR-expressing cell described herein, e.g., a BCMA CAR-expressing cell, and the second CAR-expressing cell described herein, e.g., a CD19 CAR-expressing cell, are prepared in separate compositions, and the separate compositions are administered simultaneously or sequentially. When the BCMA CAR-expressing cell and the second CAR-expressing cell are prepared in separate compositions, the BCMA CAR-expressing cell can be administered first, and the second CAR-expressing cell can be administered second, or the order of administration can be reversed.

In one embodiment, a CD19 CAR is a CD19 CAR, e.g., a humanized CD19 CAR, described in WO2014/153270, filed Mar. 15, 2014 (which is incorporated by reference herein in its entirety) or a sequence at least 95%, e.g., 95-99%, identical thereto. In some embodiments, the CD19 CAR construct is a CAR19 construct provided in PCT publication WO2012/079000 (which is incorporated by reference herein in its entirety) or a sequence at least 95%, e.g., 95-99%, identical thereto. In one embodiment, the anti- CD19 binding domain is a scFv described in WO2012/079000, or a sequence at least 95%, e.g., 95-99%, identical thereto.

In embodiments, a first CAR-expressing cell is administered to a subject, and a second CAR-expressing cell is administered to the subject. In embodiments, the first CAR-expressing cell comprises a CAR (e.g., BCMA or CD19 CAR) comprising a CD27 costimulatory domain and a CD3zeta (mutant or wild type) primary signaling domain. In embodiments, the second CAR-expressing cell comprises a CAR (e.g., BCMA CAR) comprising a 4-1BB costimulatory domain and a CD3zeta (mutant or wild type) primary signaling domain. Without wishing to be bound by theory, in embodiments, the first CAR-expressing cell can be less toxic than the second CAR-expressing cell and be used to debulk a tumor.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositomomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; *vinca* alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine@, Nordopan®, Uracil nitrogen Mustard®, Uracillost®, Uracilmostaza®, Uramustin@, Uramustine®), chlormethine (Mustargen®), cyclophosphamide (Cytoxan®, Neosar®, Clafen@, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel@, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU@), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU@); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan@, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E, 18R, 19R,21R,23 S,24E, 26E,28Z,30 S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9]hexatriaconta-16,24,26, 28-tetraen-12-yl]propyl]-2-methoxycyclohexyl dimethylphosphinate, also known as AP23573 and MK8669, and described in PCT Publication No. WO 03/0643 83); everolimus (Afinitor® or RAD001); rapamycin (AY22989, Sirolimus®); simapimod (CAS 164301-51-3); emsirolimus, (5-{2,4-Bis[(3 S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N2-[1,4-dioxo-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 383), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1 S)-2-[(2R)-2-methyl-2-oxiranyl]-2-oxo-1-(phenylmethyl) ethyl]-L-serinamide (ONX-0912).

In embodiments, a CAR-expressing cell described herein is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgVH) gene. In other embodiments, the subject does not comprise a leukemic cell comprising a mutation in the immunoglobulin heavy-chain variable-region (IgVH) gene. In embodiments, the fludarabine is administered at a dosage of about 10-50 mg/m2 (e.g., about 10-15, 15-20, 20-25, 25-30, 30-35, 35-40, 40-45, or 45-50 mg/m2), e.g., intravenously. In embodiments, the cyclophosphamide is administered at a dosage of about 200-300 mg/m2 (e.g., about 200-225, 225-250, 250-275, or 275-300 mg/m2), e.g., intravenously. In embodiments, the rituximab is administered at a dosage of about 400-600 mg/m2 (e.g., 400-450, 450-500, 500-550, or 550-600 mg/m2), e.g., intravenously.

In embodiments, a CAR-expressing cell described herein is administered to a subject in combination with bendamustine and rituximab. In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgVH) gene. In other embodiments, the subject does not comprise a leukemic cell comprising a mutation in the immunoglobulin heavy-chain variable-region (IgVH) gene. In embodiments, the bendamustine is administered at a dosage of about 70-110 mg/m2 (e.g., 70-80, 80-90, 90-100, or 100-110 mg/m2), e.g., intravenously. In embodiments, the rituximab is administered at a dosage of about 400-600 mg/m2 (e.g., 400-450, 450-500, 500-550, or 550-600 mg/m2), e.g., intravenously.

In embodiments, a CAR-expressing cell described herein is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously.

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/m2 (e.g., about 300-325, 325-350, 350-375, 375-400, 400-425, or 425-450 mg/m2), e.g., intravenously. In embodiments, bendamustine is administered at a dosage of about 75-125 mg/m2 (e.g., 75-100 or 100-125 mg/m2, e.g., about 90 mg/m2), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1(2010): 135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s53111bl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 mg/m2 to 750 mg/m2, e.g., about 150-175 mg/m2, 175-200 mg/m2, 200-225 mg/m2, 225-250 mg/m2, 250-300 mg/m2, 300-325 mg/m2, 325-350 mg/m2, 350-375 mg/m2, 375-400 mg/m2, 400-425 mg/m2, 425-450 mg/m2, 450-475 mg/m2, 475-500 mg/m2, 500-525 mg/m2, 525-550 mg/m2, 550-575 mg/m2, 575-600 mg/m2, 600-625 mg/m2, 625-650 mg/m2, 650-675 mg/m2, or 675-700 mg/m2, where m2 indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1K human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/125326 1bl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378(2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or R05072759) is a humanized and glyco-engineered anti-CD20 monoclonal antibody. See, e.g., Robak. Curr. Opin. Investig. Drugs. 10.6(2009):588-96; Clinical Trial Identifier Numbers: NCT01995669, NCT01889797, NCT02229422, and NCT01414205; and www.accessdatafda.gov/drugsatfda_docs/label/2013/125486s0001b1.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1(2011): 13-25; and Forero-Torres et al. Clin Cancer Res. 18.5(2012): 1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1(2011):13-25; and Casulo et al. Clin Immunol. 154.1(2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-0 15 is smaller than monoclonal antibodies, but retains Fc-mediated effector functions. See, e.g., Robak et al. BioDrugs 25.1(2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

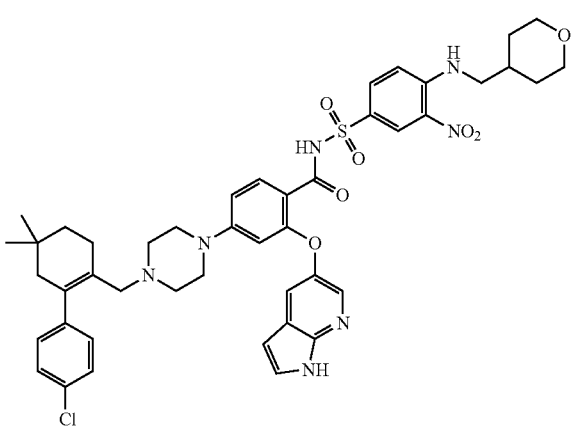 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

Without being bound by theory, it is believed that in some cancers, B cells (e.g., B regulatory cells) can suppress T cells. Further, it is believed that a combination of oxiplatin and the B cell depleting agent may reduce tumor size and/or eliminate tumors in a subject. In some embodiments, a CAR-expressing cell described herein (e.g., BCMA CAR) is administered in combination with a B cell depleting agent (e.g., a CD19 CAR-expressing cell, a CD20 CAR-expressing cell, rituximab, ocrelizumab, epratuzumab, or belimumab) and oxiplatin. In embodiments, the cancer cell can be CD19 negative or CD19 positive; or BCMA negative or BMCA positive. In embodiments, a CAR-expressing cell described herein (e.g., BCMA CAR) is administered in combination with a B cell depleting agent and oxiplatin to treat a cancer, e.g., a cancer described herein, e.g., solid cancer, e.g., prostate cancer, pancreatic cancer, or lung cancer.

In embodiments, a CAR-expressing cell described herein (e.g., BCMA CAR) may deplete B cells (e.g., B cells having a plasma cell-like phenotype, e.g., that express BCMA, CD19, and/or CD20) in a subject. In embodiments, the B cell can be CD19 negative or CD19 positive; or BCMA negative or BMCA positive. In some embodiments, a CAR-expressing cell described herein (e.g., BCMA CAR) is administered in combination with oxiplatin. In embodiments, a CAR-expressing cell described herein is administered in combination with oxiplatin is used to treat a cancer, e.g., solid cancer, e.g., prostate cancer, pancreatic cancer, or lung cancer. In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesùs, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmuco sally, orally, intranasally, or via pulmonary administration.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse. In one embodiment, a CAR expressing cell described herein is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to aphersis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as multiple myeloma, ALL or CLL). In an embodiment, the subject has CLL. In embodiments, the subject has multiple myeloma. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d]pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102. In one embodiment, the kinase inhibitor is a DGK inhibitor, e.g., a DGK inhibitor described herein, such as, e.g., DGKinh1 (D5919) or DGKinh2 (D5794).

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

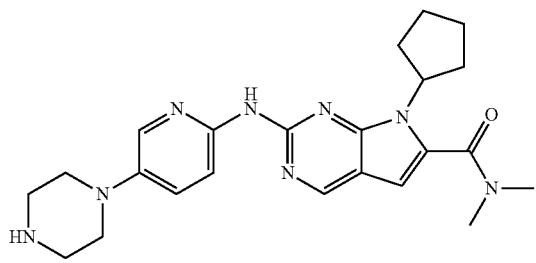 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

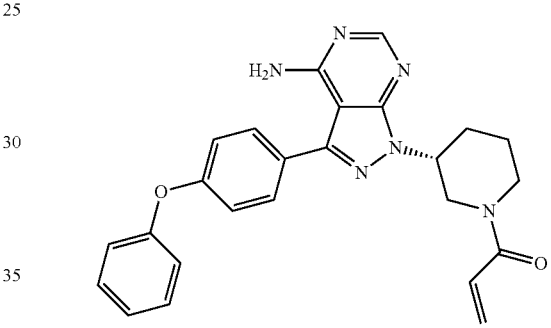

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered. In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at 55th ASH Annual Meeting and Exposition, New Orleans, La.

7-10 December Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

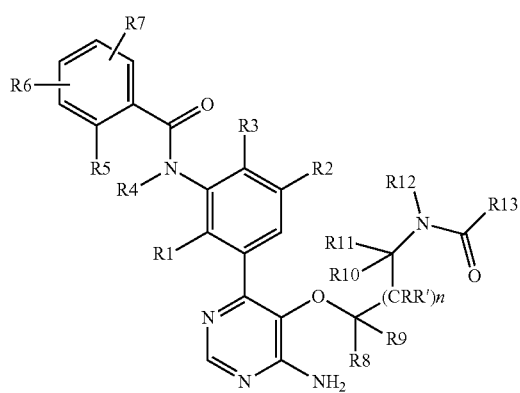

wherein,
R1 is hydrogen, C1-C6 alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —CH2-, —CH2-CH2-, —CH═CH—, —CH═CH—CH2-; —CH2-CH═CH—; or —CH2-CH2-CH2-;
R6 and R7 stand independently from each other for H, C1-C6 alkyl optionally substituted by hydroxyl, C3-C6 cycloalkyl optionally substituted by halogen or hydroxy, or halogen;
R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;
R12 is hydrogen or C1-C6 alkyl optionally substituted by halogen or C1-C6 alkoxy;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;
n is 0 or 1; and
R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2- fluorobenzamide; N-(3-(6-Amino-5-(((2 S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2 S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1 (2H)-one; N-(3-(5-(((2 S,4 S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2 S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1 (2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3 S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2 S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R,23 S,24E,26E,28Z,3 0S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 383), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

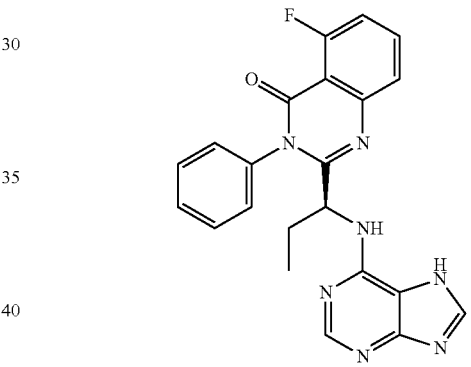

Duvelisib (also called IPI-145; Infinity Pharmaceuticals and Abbvie) is a small molecule that blocks PI3K-δ,γ. The structure of duvelisib (8-Chloro-2-phenyl-3-[(1 S)-1-(9H-purin-6-ylamino)ethyl]-1(2H)-isoquinolinone) is shown below.

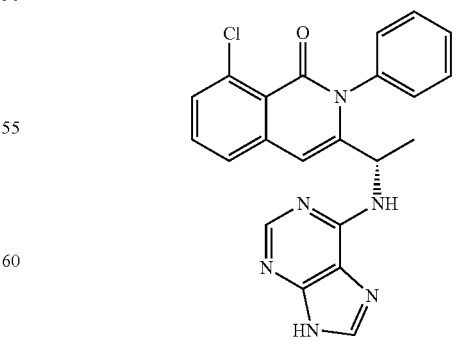

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgVH) gene. In other embodiments, the subject does not comprise a leukemic cell comprising a mutation in the immunoglobulin heavy-chain variable-region (IgVH) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m2 (e.g., 350-375, 375-400, 400-425, 425-450, 450-475, or 475-500 mg/m2), e.g., intravenously.

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-N2-[2-isopropoxy-5-methyl-4-(4-piperidinyl)phenyl]-N4-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-N2-{4-[4-(dimethylamino)-1-piperidinyl]-2-methoxyphenyl}-N4-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7, 8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl] phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, a CAR expressing cell described herein is administered to a subject in combination with a biphosphonate, e.g., Pamidronate (Aredia®); Zoledronic acid or Zoledronate (Zometa®, Zomera®, Aclasta®, or Reclast®); Alendronate (Fosamax®); Risedronate (Actonel®); Ibandronate (Boniva®); Clondronate (Bonefos®); Etidronate (Didronel®); Tiludronate (Skelid®); Pamidronate (Aredia®); Neridronate (Nerixia®); Strontiun ranelate (Protelos®, or Protos®); and Teriparatide (Forteo®).

In one embodiment, a CAR expressing cell described herein is administered to a subject in combination with a corticosteroid, e.g., dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

In one embodiment, a CAR expressing cell described herein is administered to a subject in combination with an immunomodulator, e.g., Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics.

In one embodiment, a CAR expressing cell described herein is administered to a subject in combination with a proteasome inhibitor, e.g., Bortezomib (Velcade®); Ixazomib citrate (MLN9708, CAS 1201902-80-8); Danoprevir (RG7227, CAS 850876-88-9); Ixazomib (MLN2238, CAS 1072833-77-2); and (S)—N-[(phenylmethoxy)carbonyl]-L-leucyl-N-(1-formyl-3-methylbutyl)-L-Leucinamide (MG-132, CAS 133407-82-6).

In one embodiment, a CAR expressing cell described herein is administered to a subject in combination with a vascular endothelial growth factor (VEGF) receptor, e.g., Bevacizumab (Avastin®), axitinib (Inlyta®); Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF 1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3 aa,5 3,6ac)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

In one embodiment, a CAR expressing cell described herein is administered to a subject in combination with a CD20 antibody or a conjugate thereof, e.g., Rituximab (Riuxan® and MabThera®); and Tositumomab (Bexxar®); and Ofatumumab (Arzerra®), Ibritumomab tiuxetan (Zevalin®); and Tositumomab, In one embodiment, a CAR expressing cell described herein is administered to a subject in combination with an anticonvulsant, e.g., Anticonvulsants (antiepileptic or antiseizure drugs): aldehydes, e.g., paraldehyde; aromatic allylic alcohols, e.g., stiripentol (Diacomit®); barbiturates, e.g., phenobarbital (Luminal®), methylphenobarbital (Mebaral®), barbexaclone (Maliasin®), benzodiazepines, e.g., clobazam (Onfi®), clonazepam (Klonopin®), clorazepate (Tranxene® and Novo-Clopate®), diazepam (Valium®, Lembrol®, Diastat®), midazolam (Versed®), lorazepam (Ativan® and Orfidal®), nitrazepam (Alodorm®, Arem®, Insoma®), temazepam (Restoril®, Normison®), nimetzepam (Erimin®), bromides, e.g., potassium bromide; carbamates, e.g., felbamate (Felbatol®); carboxamides, e.g., carbamazepine (Tegretol®, Equetro®), oxcarbazepine (Trileptal®, Oxcarb®), eslicarbazepine acetate (Aptiom®); fatty acids, e.g., valproates (valproic acid, sodium valproate, divalproex sodium), vigabatrin (Sabril®), progabide (Gabren®), tiagabine (Gabitril®); fructose derivatives, e.g., topiramate (Topamax®); GABA analogs, e.g., gabapentin (Neurontin®), pregabalin (Lyrica®); hydantoins, e.g., ethotoin (Peganone®), phenytoin (Dilantin®), mephenytoin (Mesantoin®), fosphenytoin (Cerebyx®, Prodilantin®); oxazolidinediones, e.g., paramethadione (Paradione®), trimethadione (Tridione®); propionates, e.g., beclamide (Choracon®, Hibicon®, Posedrine®); pyrimidinediones, e.g., primidone (Mysoline®); pyrrolidines, e.g., brivaracetam, levetiracetam, seletracetam (Keppra®); succinimides, e.g., ethosuximide (Zarontin®), phensuximide (Milontin®), mesuximide (Celontin®, Petinutin®); sulfonamides, e.g., acetazolamide (Diamox®), sultiame (Ospolot®), methazolamide (Neptazane®), zonisamide (Zonegran®); triazines, e.g., lamotrigine (Lamictal®); ureas, e.g., pheneturide, phenacemide (Phenurone®); valproylamides (amide derivaties of valproate), e.g., valpromide (Depamide®), valnoctamide; AMPA receptor antagonist, e.g., perampanel (Fycompa®).

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

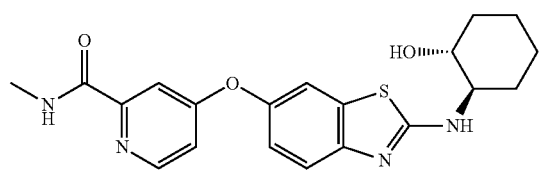 [SMILES: CNC(=O)c1cc(Oc2ccc3nc(N[C@@H]4CCCC[C@H]4O)sc3c2)ccn1]

In embodiments, a CAR-expressing cell described herein is administered to a subject in combination with a CD19 CART cell (e.g., CTL019, e.g., as described in WO2012/079000, incorporated herein by reference). In embodiments, the subject has acute myeloid leukemia (AML), e.g., a CD19 positive AML or a CD19 negative AML. In embodiments, the subject has a CD19+ lymphoma, e.g., a CD19+Non-Hodgkin's Lymphoma (NHL), a CD19+FL, or a CD19+ DLBCL. In embodiments, the subject has a relapsed or refractory CD19+ lymphoma. In embodiments, a lymphodepleting chemotherapy is administered to the subject prior to, concurrently with, or after administration (e.g., infusion) of CD19 CART cells. In an example, the lymphodepleting chemotherapy is administered to the subject prior to administration of CD19 CART cells. For example, the lymphodepleting chemotherapy ends 1-4 days (e.g., 1, 2, 3, or 4 days) prior to CD19 CART cell infusion. In embodiments, multiple doses of CD19 CART cells are administered, e.g., as described herein. For example, a single dose comprises about 5×108 CD19 CART cells. In embodiments, a lymphodepleting chemotherapy is administered to the subject prior to, concurrently with, or after administration (e.g., infusion) of a CAR-expressing cell described herein, e.g., a non-CD19 CAR-expressing cell. In embodiments, a CD19 CART is administered to the subject prior to, concurrently with, or after administration (e.g., infusion) of a non-CD19 CAR-expressing cell, e.g., a non-CD19 CAR-expressing cell described herein.

In some embodiments, a CAR-expressing cell described herein is administered to a subject in combination with a CD19 CAR-expressing cell, e.g., CTL019, e.g., as described in WO2012/079000, incorporated herein by reference, for treatment of a disease associated with the expression of BCMA, e.g., a cancer described herein. Without being bound by theory, it is believed that administering a CD19 CAR-expressing cell in combination with a CAR-expressing cell improves the efficacy of a CAR-expressing cell described herein by targeting early lineage cancer cells, e.g., cancer stem cells, modulating the immune response, depleting regulatory B cells, and/or improving the tumor microenvironment. For example, a CD19 CAR-expressing cell targets cancer cells that express early lineage markers, e.g., cancer stem cells and CD19-expressing cells, while the CAR-expressing cell described herein targets cancer cells that express later lineage markers, e.g., BCMA. This preconditioning approach can improve the efficacy of the CAR-expressing cell described herein. In such embodiments, the CD19 CAR-expressing cell is administered prior to, concurrently with, or after administration (e.g., infusion) of a CAR-expressing cell described herein.

In embodiments, a CAR-expressing cell described herein also expresses a CAR targeting CD19, e.g., a CD19 CAR. In an embodiment, the cell expressing a CAR described herein and a CD19 CAR is administered to a subject for treatment of a cancer described herein, e.g., AML. In an embodiment, the configurations of one or both of the CAR molecules comprise a primary intracellular signaling domain and a costimulatory signaling domain. In another embodiment, the configurations of one or both of the CAR molecules comprise a primary intracellular signaling domain and two or more, e.g., 2, 3, 4, or 5 or more, costimulatory signaling domains. In such embodiments, the CAR molecule described herein and the CD19 CAR may have the same or a different primary intracellular signaling domain, the same or different costimulatory signaling domains, or the same number or a different number of costimulatory signaling domains. Alternatively, the CAR described herein and the CD19 CAR are configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antibody fragment. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In one embodiment, the subject can be administered an agent which enhances the activity of a CAR-expressing cell. For example, in one embodiment, the agent can be an agent which inhibits an inhibitory molecule, e.g., the agent is a checkpoint inhibitor. Inhibitory molecules, e.g., Programmed Death 1 (PD1), can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In embodiments, a CAR-expressing cell described herein is administered in combination with an inhibitor of an inhibitory molecule, e.g., in combination with a checkpoint inhibitor, e.g., in combination with an inhibitor of PD1 and/or PD-L1. In embodiments, a CAR-expressing cell described herein is administered in combination with an inhibitor of PD1. In embodiments, a CAR-expressing cell described herein is administered in combination with an inhibitor of PD-L1.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in Gene Transfer: Delivery and Expression of DNA and RNA (eds. Friedmann and Rossi). Cold Spring Harbor Laboratory Press, Cold Spring Harbor, N.Y., USA, 2007; Brummelkamp T R, et al. (2002) Science 296: 550-553; Miyagishi M, et al. (2002) Nat. Biotechnol. 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. FIGS. 41A-41E depicts examples of vectors for expressing a component, e.g., all of the components, of the CAR with a dsRNA molecule that inhibits expression of the molecule that modulates or regulates, e.g., inhibits, T-cell function.

dsRNA molecules can be useful for inhibiting expression of a molecule that modulates or regulates, e.g., inhibits, T-cell function, wherein the molecule that modulates or regulates, e.g., inhibits, T-cell function is PD-1.

In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to LAG3. In embodiments, the agent that enhances the activity of a CAR-expressing cell, e.g., inhibitor of an inhibitory molecule, is administered in combination with an allogeneic CAR, e.g., an allogeneic CAR described herein (e.g., described in the Allogeneic CAR section herein).

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+T helper 1 and CD8+T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 or BCMA CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI: 10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. J Immunol. 2002 Mar. 15; 168(6): 2803-10; Markel et al. J Immunol. 2006 Nov. 1; 177(9): 6062-71; Markel et al. Immunology. 2009 February; 126(2): 186-200; Markel et al. Cancer Immunol Immunother. 2010 February; 59(2):215-30; Ortenberg et al. Mol Cancer Ther. 2012 June; 11(6):1300-10; Stern et al. J Immunol. 2005 Jun. 1; 174(11):6692-701; Zheng et al. PLoS One. 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) Nature doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 or BCMA CAR described herein. For example, BMS-986016 (Bristol-Myers Squib) is a monoclonal antibody that targets LAW. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell or NK cell that does not express an anti-BCMA CAR.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CAR-expressing cell therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-cancer activity. In a preferred embodiment, the cytokine administered after administration of CAR-expressing cells is IL-7.

Combination with a Low, Immune Enhancing, Dose of an mTOR Inhibitor

Methods described herein use low, immune enhancing, doses of mTOR inhibitors, e.g., allosteric mTOR inhibitors, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CAR-expressing cells, in the subject. Methods for measuring mTOR inhibition, dosages, treatment regimens, and suitable pharmaceutical compositions are described in U.S. Patent Application No. 2015/01240036, hereby incorporated by reference.

In an embodiment, administration of a low, immune enhancing, dose of an mTOR inhibitor results in one or more of the following: i) a decrease in the number of PD-1 positive immune effector cells; ii) an increase in the number of PD-1 negative immune effector cells; iii) an increase in the ratio of PD-1 negative immune effector cells/PD-1 positive immune effector cells; iv) an increase in the number of naive T cells; v) an increase in the expression of one or more of the following markers: CD62Lhigh, CD127high, CD27+, and BCL2, e.g., on memory T cells, e.g., memory T cell precursors; vi) a decrease in the expression of KLRG1, e.g., on memory T cells, e.g., memory T cell precursors; or vii) an increase in the number of memory T cell precursors, e.g., cells with any one or combination of the following characteristics: increased CD62Lhigh increased CD127high increased CD27+, decreased KLRG1, and increased BCL2;

and wherein any of the foregoing, e.g., i), ii), iii), iv), v), vi), or vii), occurs e.g., at least transiently, e.g., as compared to a non-treated subject.

In another embodiment, administration of a low, immune enhancing, dose of an mTOR inhibitor results in increased or prolonged proliferation or persistence of CAR-expressing cells, e.g., in culture or in a subject, e.g., as compared to non-treated CAR-expressing cells or a non-treated subject. In embodiments, increased proliferation or persistence is associated with in an increase in the number of CAR-expressing cells. Methods for measuring increased or prolonged proliferation are described in Examples 15 and 16. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume. Methods for measuring increased killing of cancer cells are described herein, e.g., in Examples 2, 5-6, 8, and 13. In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof. In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, at least 70 but no more than 90%, at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, at least 60 but no more than 80%, at least 5 but no more than 70%, at least 10 but no more than 70%, at least 15, but no more than 70%, at least 20 but no more than 70%, at least 30 but no more than 70%, at least 40 but no more than 70%, at least 50 but no more than 70%, at least 5 but no more than 60%, at least 10 but no more than 60%, at least 15, but no more than 60%, at least 20 but no more than 60%, at least 30 but no more than 60%, at least 40 but no more than 60%, at least 5 but no more than 50%, at least 10 but no more than 50%, at least 15, but no more than 50%, at least 20 but no more than 50%, at least 30 but no more than 50%, at least 40 but no more than 50%, at least 5 but no more than 40%, at least 10 but no more than 40%, at least 15, but no more than 40%, at least 20 but no more than 40%, at least 30 but no more than 40%, at least 35 but no more than 40%, at least 5 but no more than 30%, at least 10 but no more than 30%, at least 15, but no more than 30%, at least 20 but no more than 30%, or at least 25 but no more than 30%.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof. In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

The extent of mTOR inhibition can be conveyed as, or corresponds to, the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by various methods, such as measuring P70 S6 kinase activity by the Boulay assay, as described in U.S. Patent Application No. 2015/01240036, hereby incorporated by reference, or as described in U.S. Pat. No. 7,727,950, hereby incorporated by reference; measuring the level of phosphorylated S6 by western blot; or evaluating a change in the ratio of PD1 negative immune effector cells to PD1 positive immune effector cells.

As used herein, the term "mTOR inhibitor" refers to a compound or ligand, or a pharmaceutically acceptable salt thereof, which inhibits the mTOR kinase in a cell. In an embodiment, an mTOR inhibitor is an allosteric inhibitor. Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity. In an embodiment, an mTOR inhibitor is a catalytic inhibitor.

Rapamycin is a known macrolide antibiotic produced by *Streptomyces hygroscopicus* having the structure shown in Formula A.

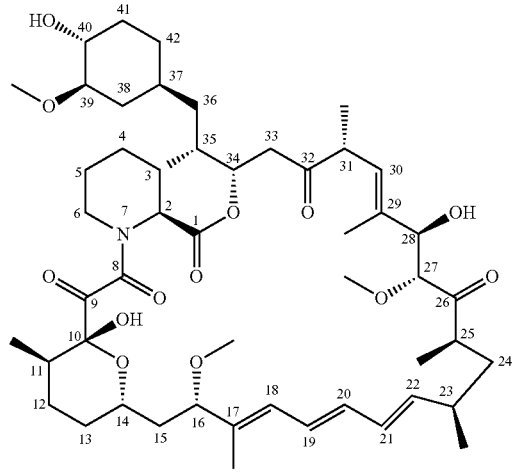

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, 0-substituted analogs in which the hydroxyl group on the cyclohexyl ring of rapamycin is replaced by OR1 in which R1 is hydroxyalkyl, hydroxyalkoxyalkyl, acylaminoalkyl, or aminoalkyl; e.g. RAD001, also known as everolimus, as described in U.S. Pat. No. 5,665,772 and WO94/09010, the contents of each are incorporated by reference.

Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807, the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S, 15R, 16E, 18R, 19R, 21R,23 S,24E,26E,28E,30S,32S,35R)-1,18-dihydroxy-12-{(1R)-2-[(1 S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone, as described in U.S. Pat. No. 5,665,772 and WO94/09010, the contents of each are incorporated by reference.

Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form (the synthesis of BEZ235 is described in WO2006/122806); CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3 d]pyrimidin-7-yl]-2-methoxy-phenyl}-methanol; 3-[2,4-bis[(3 5)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO 10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); and (E)-N-(8-(6-amino-5-(trifluoromethyl)

pyridin-3-yl)-1-(6-(2-cyanopropan-2-yl)pyridin-3-yl)-3-methyl-1H-imidazo[4,5-c]quinolin-2(3H)-ylidene) cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTOR inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Methods and Biomarkers for Evaluating CAR-Effectiveness or Sample Suitability

In another aspect, the invention features a method of evaluating or monitoring the effectiveness of a CAR-expressing cell therapy (e.g., a BCMACAR therapy), in a subject (e.g., a subject having a cancer, e.g., a hematological cancer), or the suitability of a sample (e.g., an apheresis sample) for a CAR therapy (e.g., a BCMACAR therapy). The method includes acquiring a value of effectiveness to the CAR therapy, or sample suitability, wherein said value is indicative of the effectiveness or suitability of the CAR-expressing cell therapy.

In embodiments, the value of effectiveness to the CAR therapy, or sample suitability, comprises a measure of one, two, three, four, five, six or more (all) of the following: (i) the level or activity of one, two, three, or more (e.g., all) of resting TEFF cells, resting TREG cells, younger T cells (e.g., younger CD4 or CD8 cells, or gamma/delta T cells), or early memory T cells, or a combination thereof, in a sample (e.g., an apheresis sample or a manufactured CAR-expressing cell product sample); (ii) the level or activity of one, two, three, or more (e.g., all) of activated TEFF cells, activated TREG cells, older T cells (e.g., older CD4 or CD8 cells), or late memory T cells, or a combination thereof, in a sample (e.g., an apheresis sample or a manufactured CAR-expressing cell product sample); (iii) the level or activity of an immune cell exhaustion marker, e.g., one, two or more immune checkpoint inhibitors (e.g., PD-1, PD-L1, TIM-3 and/or LAG-3) in a sample (e.g., an apheresis sample or a manufactured CAR-expressing cell product sample). In one embodiment, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3; (iv) the level or activity of CD27 and/or CD45RO− (e.g., CD27+CD45RO−) immune effector cells, e.g., in a CD4+ or a CD8+ T cell population, in a sample (e.g., an apheresis sample or a manufactured CAR-expressing cell product sample); (v) the level or activity of one, two, three, four, five, ten, twenty or more of the biomarkers chosen from CCL20, IL-17a and/or IL-6, PD-1, PD-L1, LAG-3, TIM-3, CD57, CD27, CD122, CD62L, KLRG1; (vi) a cytokine level or activity (e.g., quality of cytokine reportoire) in a CAR-expressing cell product sample, e.g., BCMA-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (e.g., a population) of CAR-expressing immune effector cells, e.g., a plurality (e.g., a population) of T cells or NK cells, or a combination thereof. In one embodiment, the CAR-expressing cell therapy is a BCMACAR therapy.

In some embodiments of any of the methods disclosed herein, the measure of one or more of (i)-(vii) is obtained from an apheresis sample acquired from the subject. The apheresis sample can be evaluated prior to infusion or re-infusion.

In some embodiments of any of the methods disclosed herein, the measure of one or more of (i)-(vii) is obtained from a manufactured CAR-expressing cell product sample, e.g., BCMACAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of (i)-(vii) evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of (i)-(vii).

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc02lovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULTIE1, and EIF1AY.

In some embodiments of any of the methods disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods disclosed herein, a complete responder has, or is identified as having, a greater percentage of CD27+CD45RO− immune effector cells, e.g., in the CD8+ population, compared to a reference value, e.g., a non-responder number of CD27+CD45RO− immune effector cells.

In some embodiments of any of the methods disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods disclosed herein, a complete responder has, or is identified as having, a greater percentage of one, two, three, or more (e.g., all) of resting TEFF cells, resting TREG cells, younger T cells (e.g., younger CD4 or CD8 cells, or gamma/delta T cells), or early memory T cells, or a combination thereof, compared to a reference value, e.g., a non-responder number of resting TEFF cells, resting TREG cells, younger T cells (e.g., younger CD4 or CD8 cells), or early memory T cells.

In some embodiments of any of the methods disclosed herein, a non-responder has, or is identified as having, a greater percentage of one, two, three, or more (e.g., all) of activated TEFF cells, activated TREG cells, older T cells (e.g., older CD4 or CD8 cells), or late memory T cells, or a combination thereof, compared to a reference value, e.g., a responder number of activated TEFF cells, activated TREG cells, older T cells (e.g., older CD4 or CD8 cells), or late memory T cells.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In one embodiment, a non-responder has, or is identified as having, a greater percentage of PD-1, PD-L1, or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In one embodiment, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (e.g., a BCMACAR+ cell population) compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population (e.g., a BCMACAR+ cell population).

In some embodiments of any of the methods disclosed herein, a non-responder has, or is identified as having, an exhausted phenotype of PD1/PD-L1+CAR+ and co-expression of LAG3 in the CAR-expressing cell population (e.g., a BCMACAR+ cell population).

In some embodiments of any of the methods disclosed herein, a non-responder has, or is identified as having, a greater percentage of PD-1/PD-L1+/TIM-3+ cells in the CAR-expressing cell population (e.g., a BCMACAR+ cell population) compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population (e.g., a BCMACAR+ cell population).

In some embodiments of any of the methods disclosed herein, the presence of CD8+CD27+CD45RO− T cells in an apheresis sample is a positive predictor of the subject response to a CAR-expressing cell therapy (e.g., a BCMACAR therapy).

In some embodiments of any of the methods disclosed herein, a high percentage of PD1+CAR+ and LAG3+ or TIM3+ T cells in an apheresis sample is a poor prognostic predictor of the subject response to a CAR-expressing cell therapy (e.g., a BCMACAR therapy).

In some embodiments of any of the methods disclosed herein, the responder (e.g., the complete or partial responder) has one, two, three or more (or all) of the following profile: (i) has a greater number of CD27+ immune effector cells compared to a reference value, e.g., a non-responder number of CD27+ immune effector cells; (ii) (i) has a greater number of CD8+ T cells compared to a reference value, e.g., a non-responder number of CD8+ T cells; (iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting TEFF cells, resting TREG cells, naïve CD4 cells, unstimulated memory cells or early memory T cells, or a combination thereof, compared to a reference value, e.g., a non-responder number of resting TEFF cells, resting TREG cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFα. In one embodiment, an increased level or activity of a cytokine is chosen from one or both of IL-17a and CCL20, is indicative of increased responsiveness or decreased relapse.

In some embodiments of any of the methods disclosed herein, a transduction efficiency of 15% or higher in (vii) is indicative of increased responsiveness or decreased relapse.

In some embodiments of any of the methods disclosed herein, a transduction efficiency of less than 15% in (vii) is indicative of decreased responsiveness or increased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, or Cheson criteria as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

Alternatively, or in combination with the methods disclosed herein, responsive to said value, performing one, two, three four or more of: administering e.g., to a responder or a non-relapser, a CAR-expressing cell therapy; administered an altered dosing of a CAR-expressing cell therapy; altering the schedule or time course of a CAR-expressing cell therapy; administering, e.g., to a non-responder or a partial responder, an additional agent in combination with a CAR-expressing cell therapy, e.g., a checkpoint inhibitor, e.g., a checkpoint inhibitor described herein; administering to a non-responder or partial responder a therapy that increases the number of younger T cells in the subject prior to treatment with a CAR-expressing cell therapy; modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder; administering an alternative therapy, e.g., for a non-responder or partial responder or relapser; or if the subject is, or is identified as, a non-responder or a relapser, decreasing the TREG cell population and/or TREG gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

Biopolymer Delivery Methods

In some embodiments, one or more CAR-expressing cells as disclosed herein can be administered or delivered to the subject via a biopolymer scaffold, e.g., a biopolymer implant.

Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxyhexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., Nature Biotechnology, 2015, 33:97-101; and WO2014/110591.

I. Methods of Detecting

Disclosed are methods of detecting CD229 on a cell comprising administering a composition comprising one or more of the disclosed antibodies or fragments thereof to a sample and detecting the binding of the antibody or fragment thereof to CD229. For example, the antibody or fragment thereof can comprise a variable heavy chain comprising a sequence having at least 90% identity to a sequence set forth in SEQ ID NOs:16, 17, 18, 19, 20, 21, 22, 23, 24, 25, 26, 27, 28, 29, or 30; a variable light chain comprising a sequence having at least 90% identity to a sequence set forth in SEQ ID NOs:31, 32, 33, 34, 35, 36, 37, 38, 39, 40, 41, 42, 43, 44, or 45; or both.

In some instances, detecting the binding of the antibody or fragment thereof to CD229 comprises immunostaining.

J. Methods of Killing CD229 Cells

Disclosed are methods of killing CD229 positive cells comprising administering an effective amount of a cell genetically modified to express one or more of the disclosed CAR polypeptides to a sample comprising CD229 positive cells. Cells genetically modified to express one or more of the disclosed CAR polypeptides can be, but are not limited to, T cells or NK cells. In some instances, the T cell can be a γδ T cell or an αβ T cell.

Disclosed are methods of killing CD229 positive cells comprising administering an effective amount of a T cell genetically modified to express one or more of the disclosed CAR polypeptides to a sample comprising CD229 positive cells. For example, disclosed are methods of killing CD229 positive cells comprising administering an effective amount of a T cell genetically modified to express a CAR polypeptide comprising a CD229 antigen binding domain, a transmembrane domain, and an intracellular signaling domain.

K. Methods of Making Cells

Disclosed are methods of making a cell comprising transducing a cell with one or more of the disclosed vectors. In some instances, the cell can be, but is not limited to, T cells or NK cells. In some instances, the T cell can be a γδ T cell or an αβ T cell.

Disclosed are methods of making a cell comprising transducing a T cell with one or more of the disclosed vectors. For example, disclosed are methods of making a cell comprising transducing a T cell with a vector comprising the nucleic acid sequence capable of encoding a disclosed CAR polypeptide to a subject in need thereof.

L. Methods of Activating T Cells

Disclosed are methods of activating a T cell expressing one of the CAR polypeptides disclosed herein comprising culturing the T cell with a cell expressing CD229 and detecting the presence or absence of IFN-γ after culturing, wherein the presence of IFN-γ indicates the activation of the T cell.

M. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more of the antibodies or fragments thereof disclosed herein.

Also disclosed are kits comprising one or more of the vectors disclosed herein.

EXAMPLES

A. Example 1

Multiple myeloma (MM) is the second most common hematologic malignancy causing approximately 12,500 deaths this year in the U.S. alone. While there have been considerable therapeutic advances in the past decade, this cancer is still considered incurable and despite initial responses, practically all patients will eventually experience a fatal relapse. Relapses are thought to be due to chemotherapy-resistant MM propagating cells that persist even after the destruction of the bulk of tumor cells by chemotherapy. This population needs to be targeted effectively in addition to the tumor bulk to achieve lasting remissions and cures in MM.

Chimeric antigen receptors (CARs) are engineered proteins containing domains for antigen binding, structure/scaffolding and effector cell signaling. In its most common form a single chain variable fragment (scFv) is used for antigen binding, parts of CD8 or the immunoglobulin hinge/transmembrane domains to provide essential structural elements, and signaling domains derived from CD3ζ and CD28 or 4-1BB for T cell activation. It has been shown that autologous T cells expressing CARs directed against CD19 have strong clinical activity against CD19+ lymphoid malignancies, particularly B-ALL and a number of trials have been initiated to treat various hematological and some solid cancers using CAR T cells. The advantage of using CAR T cells versus a monoclonal antibody with the same specificity is that such an approach combines the specificity of an antibody with the durability and efficacy of a memory T cell response targeting MM.

Antigens currently investigated as targets for CAR T cells in MM include CD138, immunoglobulin kappa light chain, CD19, and BCMA. For CD138 and kappa light chain-specific CAR T cells no results have been reported yet. For CD19 a single case has been reported, indicating clinical activity of CAR T cells despite the absence of CD19 expression from the bulk of MM cells. Encouraging results from an early-phase clinical trial have been reported for BCMA-specific CAR T cells, with a complete response and a very good partial response in the two patients treated at the highest dose level. Whether these responses will be durable remains to be seen, as BCMA is absent from naïve and memory B cells, which represent a reservoir for MM-precursor cells that are considered responsible for the frequent relapses in MM. CS-1 is a member of the SLAM family of lymphocyte receptors and the target of elotuzumab, a monoclonal antibody with some clinical activity in MM. A study of CAR T cells targeting CS-1 in MM is underway, but no clinical results have been reported yet.

1. Tissue Distribution and Antibody Targeting of CD229.

Figure 1A:
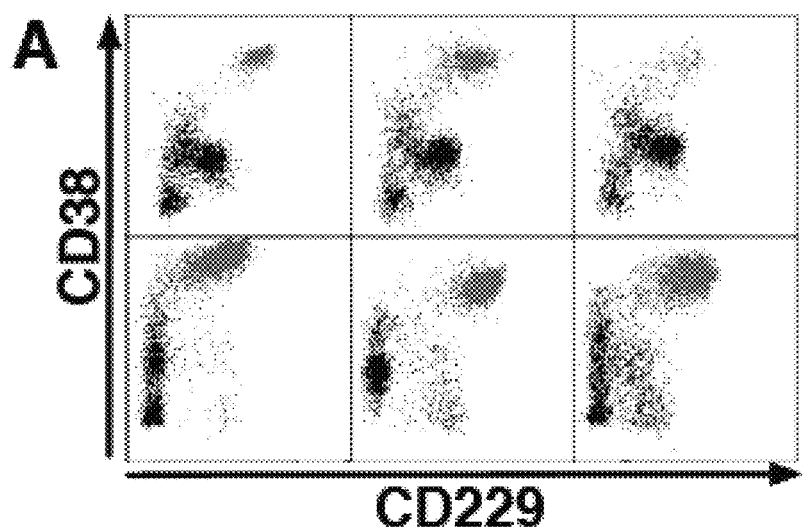
FIGS. 1A, 1B, 1C, 1D, 1E, 1F, and 1G show the expression of CD229 in MM. (A) Dot blots of 6 patients showing CD229 expression levels gated on all lymphocytes after doublet exclusion. Highlighted in red the "classical" PC population (CD138+CD38+). (B) In a clonogenic growth assay, clonal MM clusters were counted 7-10 days after culture initiation using MM cell line MOLP-8 (left) or KMS-12-BM (right). Bars indicate standard error of mean values derived from three separate experiments. Numbers of colonies produced by MM cells transfected with CD229 siRNA or scrambled control siRNA were compared to those of cultures with untreated cells. Asterisks indicate statistically significant differences (*P<0.05). (C) NK cell mediated cytotoxicity against MM cell line U266 in the presence of increasing concentrations of monoclonal anti-CD229 antibody or and isotype control antibody. (D) CD229 mRNA expression was analyzed in healthy tissues by qRT-PCR and normalized to the tissue's respective expression of housekeeping gene GAPDH. (E). Flow cytometry analysis of CD229 expression in subsets of bone-marrow mononuclear cells (BMMC), peripheral blood mononuclear cells (PBMC), and tonsil from healthy control. (F) Schematic representation of clonotypic hierarchy and interconversion of myeloma plasma cells (PC), CD138low PC, and chemotherapyresistant Pre-PC (adapted from (3)). (G) (Top panel) Gating scheme to identify chemotherapy resistant CD19-138-plasma cells. Initial gates include CD19-2-3-14-16-235a-(left), followed by gating for CD200+319+(middle) and then differentiated into CD38+ plasma cells that are CD138-positive and -negative, respectively. (Bottom panel) Expression of CD229 in four patients with MM. Blue histogram represents CD38+CD138high, green histogram CD38+CD138low and grey histogram FMO control.
Figure 1B:
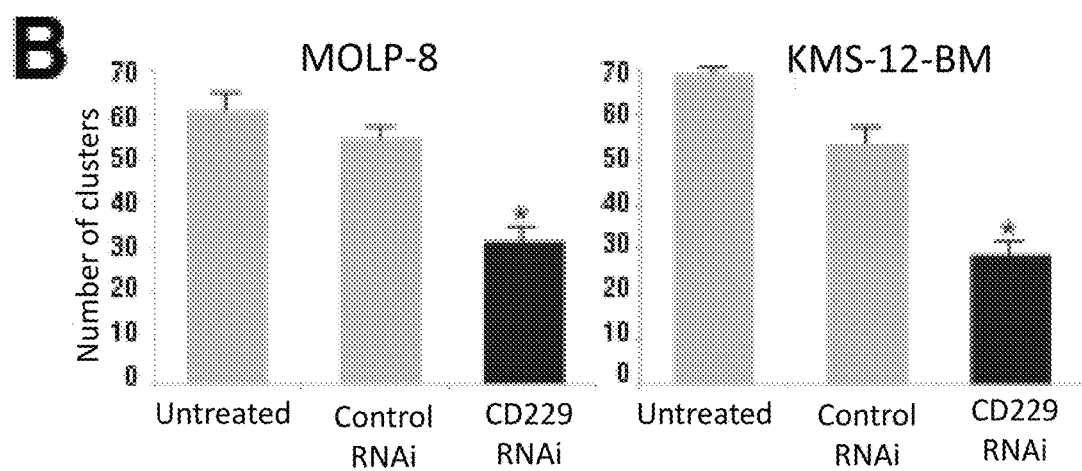
Figure 1C:
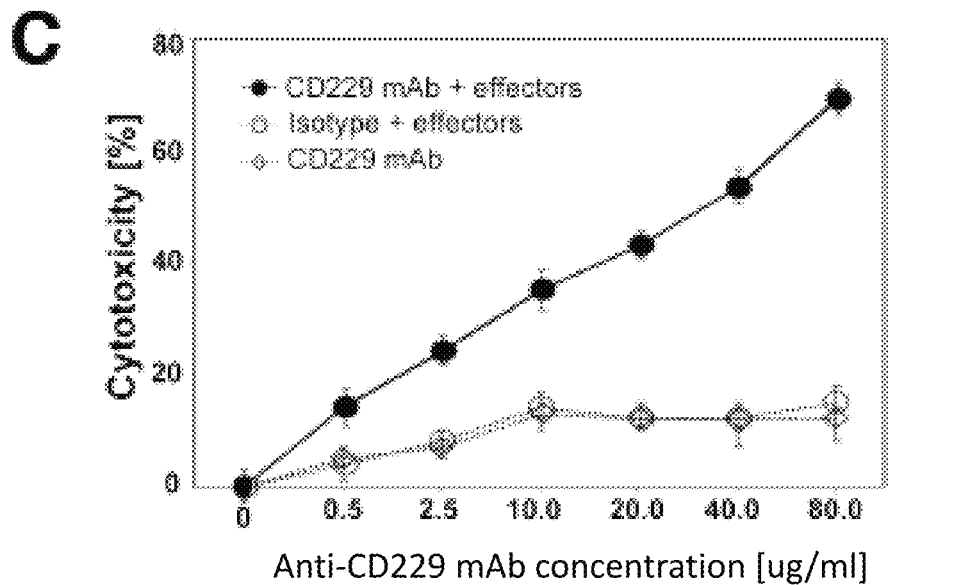
Figure 1D:
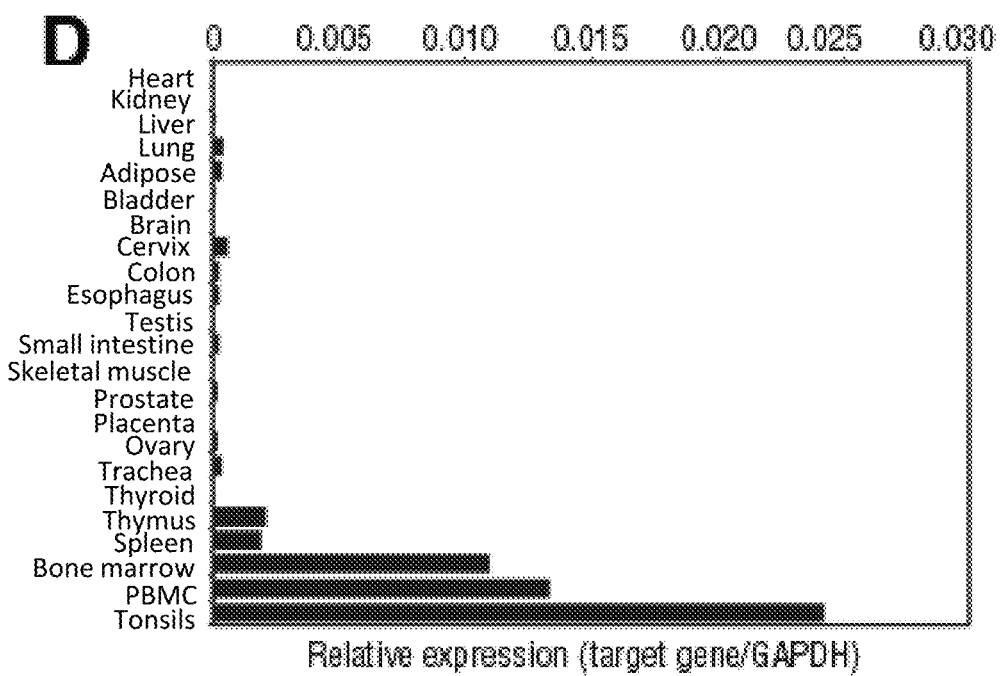
Figures 1E, 1F, 1G:
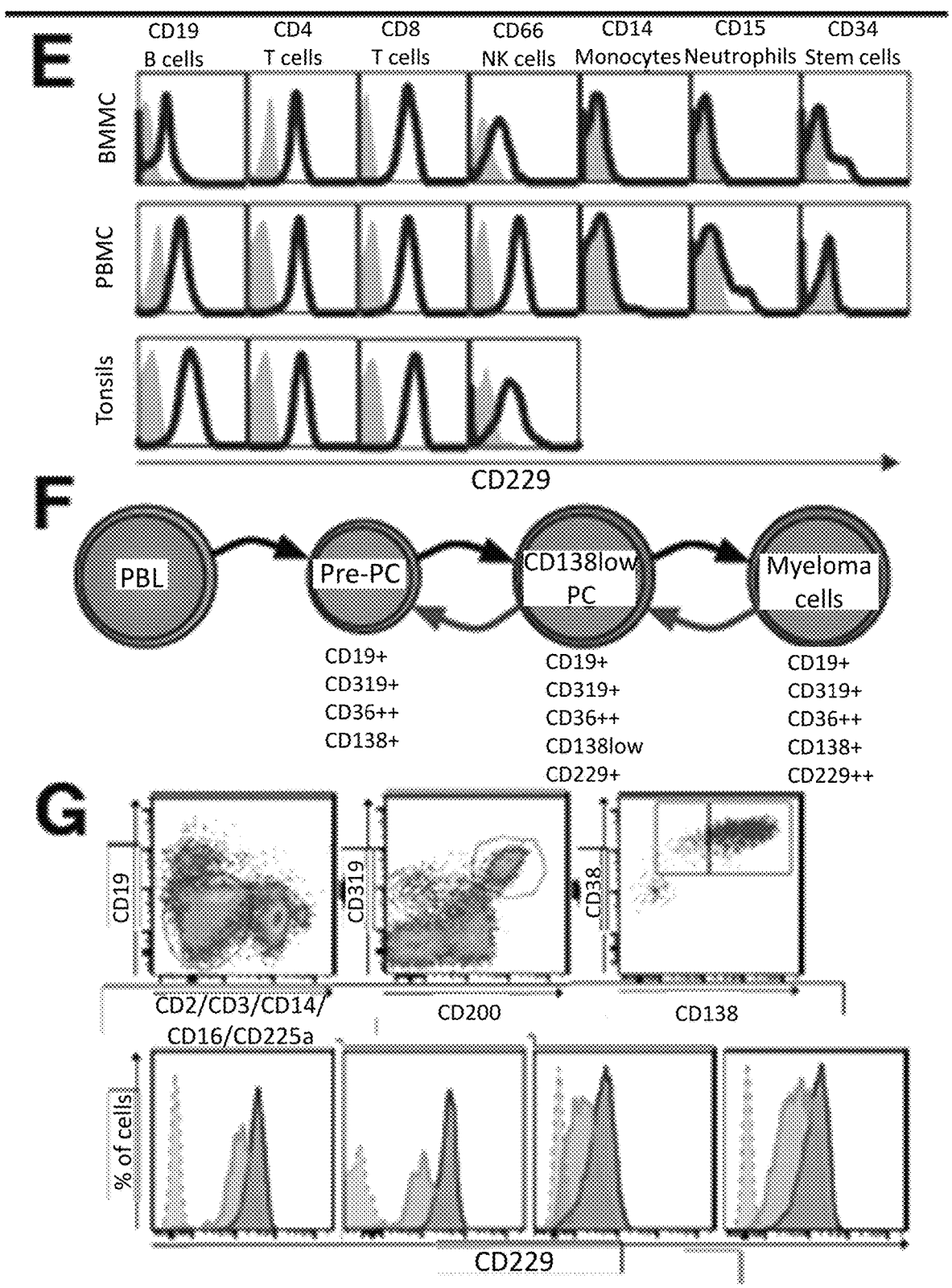

CD229, a SLAM family member, is strongly expressed on the surface of MM cell lines and primary MM cells (FIG. 1A). Importantly knockdown of CD229 significantly reduces the clonogenicity of MM cell lines, indicating a significant barrier toward immune escape through down-regulation of CD229 (FIG. 1B). Studies also show that CD229 plays an anti-apoptotic role in MM, indicating another barrier toward immune escape. Using a murine monoclonal antibody against human CD229 it was also found that this antigen can be targeted efficiently via complement-derived cytotoxicity (CDC) and antibody dependent cellular cytotoxicity (ADCC, FIG. 1C). CD229 is absent from the vast majority of tissues (FIG. 1D) including CD34+ hematopoietic stem/progenitor cells, with expression limited to lymphatic tissues (FIG. 1E). As interconversion of myeloma plasma cell populations with different antigen expression patterns and resistance to current treatment regimens has been reported (FIG. 1F), CD229 expression on MM cellular subsets was analyzed. CD229 is homogeneously and strongly expressed not only on the bulk of MM cells but also myeloma precursors (FIG. 1G). These data strongly indicate that CD229 represents a promising target for CAR T cell therapy in MM due to its expression on all relevant malignant cell populations, which should result in deeper remissions or even cures.

2. Identification of Anti-CD229 scFv Domains.

Figure 2A:
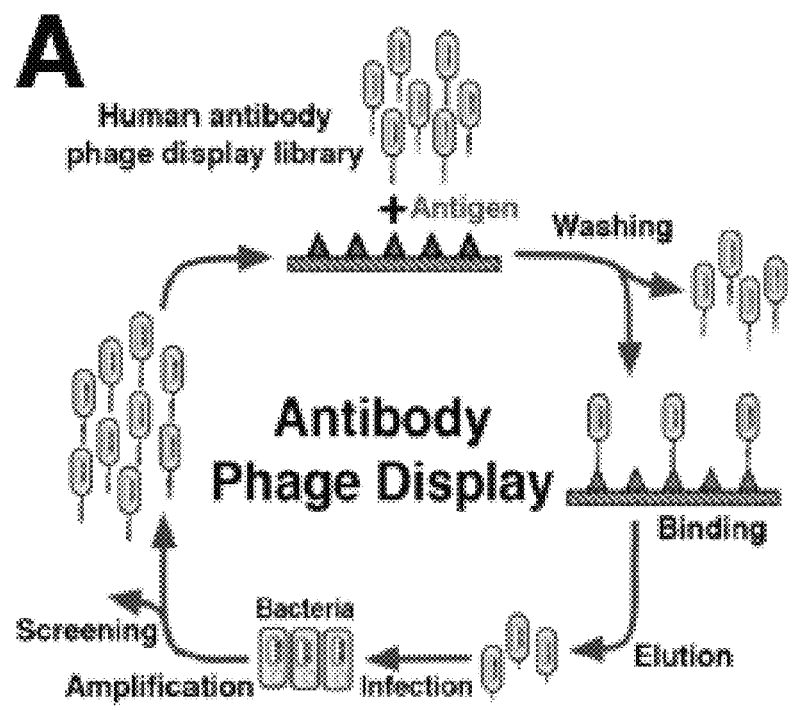
Figure 2B:
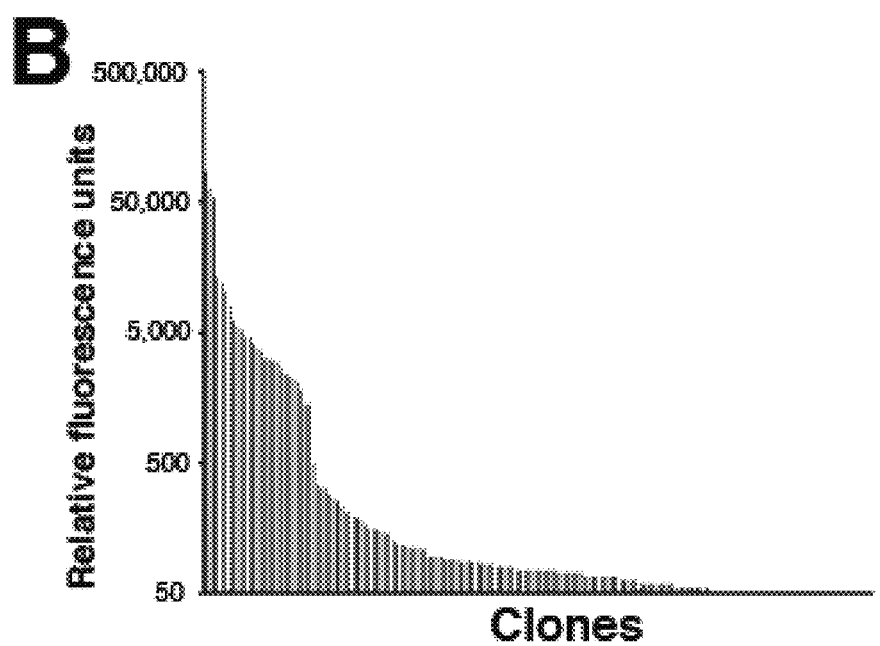
Figure 2C:
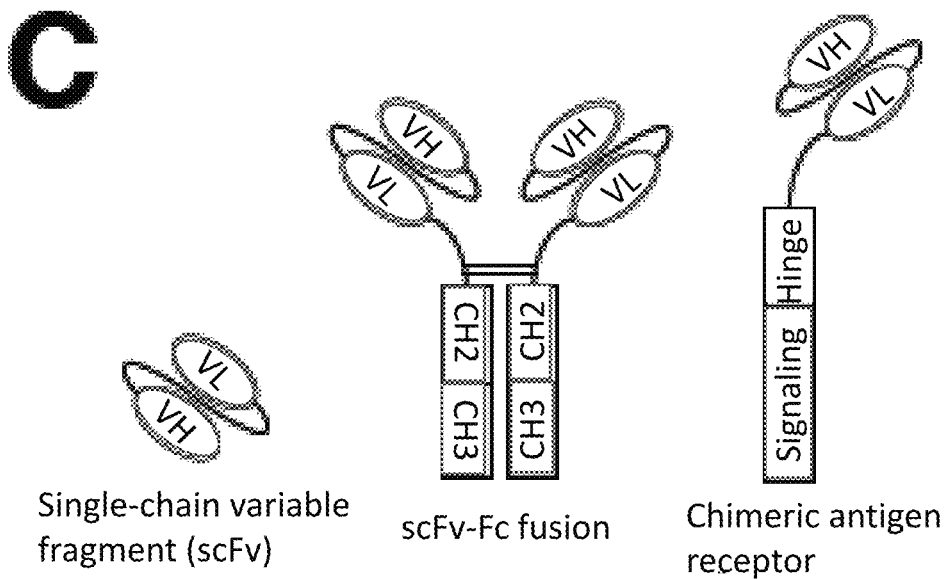

As no monoclonal anti-CD229 antibodies were available for conversion to CAR format, novel high-affinity scFv domains were generated for use in anti-CD229 CAR constructs and mined a human antibody phage display library with a diversity of >1010 clones (FIG. 2A). As this library is derived from human immunoglobulin genes, the immunogenicity of the resulting CAR constructs in humans is expected to be low compared to CARs using murine or partially humanized antibody domains. Antibodies in the library are displayed as scFv domains and contain both heavy and light chain variable regions connected by a linker, enabling rapid conversion from phage to CARs once binders are identified. After two rounds of specific enrichment of phage binders by panning, 1,323 clones specific for the extracellular domain (ECD) of human CD229 were obtained. After further selection and bacterial expression of 168 clones, 32 CD229 binders were chosen for additional studies based on time-resolved fluorescence (TRF) signal intensity ≥5-fold over background (FIG. 2B); 23 of these clones were identified to have unique heavy and light chain combinations by Sanger sequencing.

3. Generation of Anti-CD229 CAR T Cells.

Figure 2D:
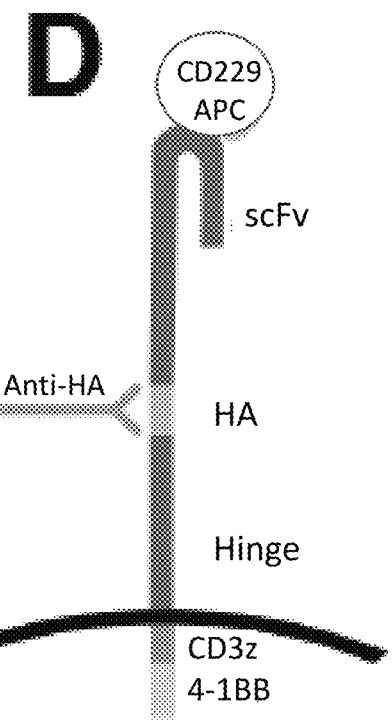
Figure 2E:
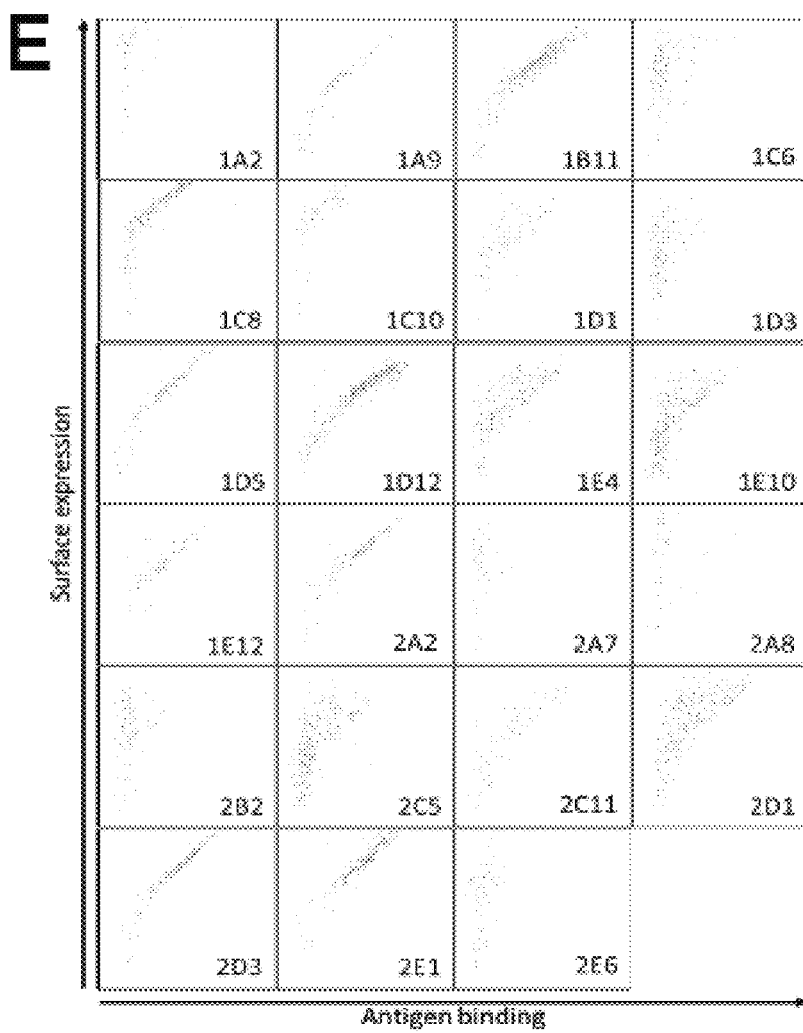
Figure 2F:
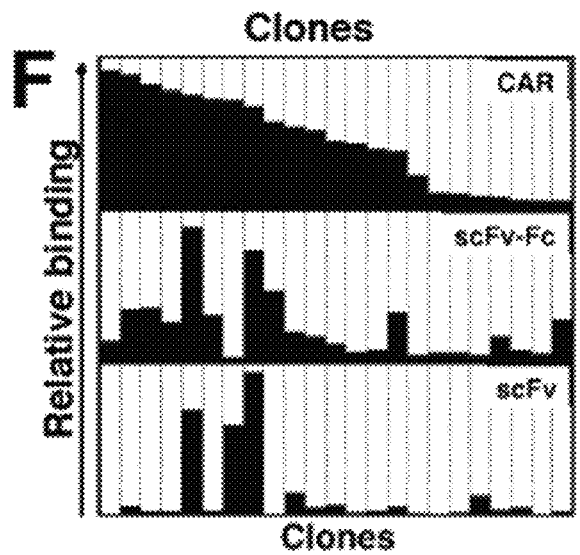

In the final CAR construct, the scFv can be joined directly to a 45 amino acid hinge domain, which can alter binding properties of the antibodies. In order to identify clones likely to be amenable to CAR conversion, the scFv was fused to an immunoglobulin Fc domain (scFv-Fc fusion, FIG. 2C) and the constructs were expressed in human 293T cells. 20 of the 23 unique scFv binders still recognized CD229 with the new C-terminal fusion partner. All 23 unique binders were then cloned into the CAR vector (FIG. 2D). The second-generation CAR construct uses a CD8α hinge and transmembrane domain with a CD3ζ signaling and a 4-1BB co-stimulatory domain. In addition a hemagglutinin (HA) tag was added between the scFv and hinge domains to allow the simultaneous assessment of antigen binding and surface expression (FIG. 2D). Individual CAR constructs were expressed in 293T cells, and analyzed by flow cytometry after staining with allophycocyanin (APC)-labeled recombinant CD229 and a phycoerythrin (PE)-labeled anti-HA antibody. 15 of the 23 constructs showed high surface expression and CD229 binding (FIG. 2E). Interestingly, results from the two soluble antibody-screening assays did not correlate with the cell-based screening assay indicating unique binding behavior of CARs (FIG. 2F).

CD3/CD28 bead-activated primary human T cells were transduced with lentiviral particles generated from these 15 CAR constructs and GFP control plasmids. The ability of immobilized recombinant CD229 to activate the CAR T cells was compared. Twelve of the 15 constructs showed T cell activation as determined by increased IFNγ production measured by intracellular cytokine staining and flow cytometry analysis (FIG. 3A).

The 15 constructs comprise sequences shown in Table 11.

TABLE 11

15 CAR construct clones

| | Clone 1A9 |
|---|---|
| V-GENE and allele | Homsap IGKV1-5*01 F |
| J-GENE and allele | Homsap IGKJ4*01 F |
| V-J-Region | DIQMTQSPSSLSASVGDRVTITCRASQSIGSSLHWYQQKPGKAPKFLIYDAS SLESGVPSRFSGSGSGTEFTLTISSLQPDDFATYYCQQYNSYPLTFGGGTKL EIK (SEQ ID NO: 239) |
| V-Region | DIQMTQSPSSLSASVGDRVTITCRASQSIGSSLHWYQQKPGKAPKFLIYDAS SLESGVPSRFSGSGSGTEFTLTISSLQPDDFATYYCQQYNS (SEQ ID NO: 240) |
| FR1-IMGT | DIQMTQSPSSLSASVGDRVTITCRAS (SEQ ID NO: 241) |
| CDR1-IMGT | QSIGSS (SEQ ID NO: 89) |
| FR2-IMGT | LHWYQQKPGKAPKFLIY (SEQ ID NO: 242) |
| CDR2-IMGT | DAS |
| FR3-IMGT | SLESGVPSRFSGSGSGTEFTLTISSLQPDDFATYYC (SEQ ID NO: 243) |
| CDR3-IMGT | QQYNSYPLT (SEQ ID NO: 90) |
| J-Region | LTFGGGTKLEIK (SEQ ID NO: 244) |
| FR4-IMGT | FGGGTKLEIK (SEQ ID NO: 245) |
| Junction | CQQYNSYPLTF (SEQ ID NO: 246) |
| | Clone 1B11 |
| V-GENE and allele | Homsap IGLV2-11*01 F |
| J-GENE and allele | Homsap IGLJ1*01 F |
| V-J-Region | QSGLTQPRSVSGSPGQSVTISCTGTSSDVGGYNYVSWYQQHPGKAPKLMI YDVSKRPSGVPDRFSGSKSGNTASLTVSGLQAEDEADYYCSSYAGSNTFV FGSGTKLTVL (SEQ ID NO: 247) |
| V-Region | QSGLTQPRS.VSGSPGQSVTISCTGTSSDVGGYNYVSWYQQHPGKAPKLMI YDVSKRPSGVP.DRFSGSKSGNTASLTVSGLQAEDEADYYCSSYAGSNT (SEQ ID NO: 248) |
| FR1-IMGT | QSGLTQPRSVSGSPGQSVTISCTGT (SEQ ID NO: 249) |
| CDR1-IMGT | SSDVGGYNY (SEQ ID NO: 91) |
| FR2-IMGT | VSWYQQHPGKAPKLMIY (SEQ ID NO: 250) |
| CDR2-IMGT | DVS |

TABLE 11-continued

15 CAR construct clones

| | |
|---|---|
| FR3-IMGT | KRPSGVPDRFSGSKSGNTASLTVSGLQAEDEADYYC (SEQ ID NO: 251) |
| CDR3-IMGT | SSYAGSNTFV (SEQ ID NO: 92) |
| J-Region | VFGSGTKLTVL (SEQ ID NO: 252) |
| FR4-IMGT | FGSGTKLTVL (SEQ ID NO: 253) |
| Junction | CSSYAGSNTFVF (SEQ ID NO: 254) |

Clone 1C8

| | |
|---|---|
| V-GENE and allele | Homsap IGKV3-15*01 F |
| J-GENE and allele | Homsap IGKJ4*01 F |
| V-J-Region | DIVMTQSPATLSVSPGERATLSCRASQSVGSSLAWYQQKPGQAPRLLIYGGSVRATGIP.ARFSGSGSGTEFTLTISSLQSEDFAAYYCQQYNSYPLTFGGGTKLEIK (SEQ ID NO: 255) |
| V-Region | DIVMTQSPATLSVSPGERATLSCRASQSVGSSLAWYQQKPGQAPRLLIYGGSVRATGIPARFSGSGSGTEFTLTISSLQSEDFAAYYCQQYNSY (SEQ ID NO: 256) |
| FR1-IMGT | DIVMTQSPATLSVSPGERATLSCRAS (SEQ ID NO: 257) |
| CDR1-IMGT | QSVGSS (SEQ ID NO: 93) |
| FR2-IMGT | LAWYQQKPGQAPRLLIY (SEQ ID NO: 258) |
| CDR2-IMGT | GGS |
| FR3-IMGT | VRATGIPARFSGSGSGTEFTLTISSLQSEDFAAYYC (SEQ ID NO: 259) |
| CDR3-IMGT | QQYNSYPLT (SEQ ID NO: 94) |
| J-Region | LTFGGGTKLEIK (SEQ ID NO: 260) |
| FR4-IMGT | FGGGTKLEIK (SEQ ID NO: 261) |
| Junction | CQQYNSYPLTF (SEQ ID NO: 262) |

Clone 1D1

| | |
|---|---|
| V-GENE and allele | Homsap IGLV6-57*01 F |
| J-GENE and allele | Homsap IGLJ2*01 F |
| V-J-Region | NFMLTQPHSVSESPGKTVTISCTGSSGSIASNYVQWYQQRPGSSPTTVIYEDNQRPSGVPDRFSGSIDSSSNSASLTISGLKTEDEADYYCQSYDGSNPVVFGGGTQLTVL (SEQ ID NO: 263) |
| V-Region | NFMLTQPHSVSESPGKTVTISCTGSSGSIASNYVQWYQQRPGSSPTTVIYEDNQRPSGVPDRFSGSIDSSSNSASLTISGLKTEDEADYYCQSYDGS (SEQ ID NO: 264) |
| FR1-IMGT | NFMLTQPHSVSESPGKTVTISCTGS (SEQ ID NO: 265) |
| CDR1-IMGT | SGSIASNY (SEQ ID NO: 95) |
| FR2-IMGT | VQWYQQRPGSSPTTVIY (SEQ ID NO: 266) |
| CDR2-IMGT | EDN |
| FR3-IMGT | QRPSGVPDRFSGSIDSSSNSASLTISGLKTEDEADYYC (SEQ ID NO: 267) |
| CDR3-IMGT | QSYDGSNPVV (SEQ ID NO: 96) |

TABLE 11-continued

15 CAR construct clones

| | |
|---|---|
| J-Region | VVFGGGTQLTVL (SEQ ID NO: 268) |
| FR4-IMGT | FGGGTQLTVL (SEQ ID NO: 269) |
| Junction | CQSYDGSNPVVF (SEQ ID NO: 270) |

Clone 1D5

| | |
|---|---|
| V-GENE and allele | Homsap IGKV1-39*01 F |
| J-GENE and allele | Homsap IGKJ2*01 F |
| V-J-Region | DIQMTQSPSSLSASVGDRVTITCRASQSISSYLNWYQQKPGKAPKLLIYAASSLQSGVPSRFSGSGSGTDFTLTISSLQPEDFATYYCQQSYSTLYTFGQGTKLEIK (SEQ ID NO: 271) |
| V-Region | DIQMTQSPSSLSASVGDRVTITCRASQSISSYLNWYQQKPGKAPKLLIYAASSLQSGVPSRFSGSGSGTDFTLTISSLQPEDFATYYCQQSYST (SEQ ID NO: 272) |
| FR1-IMGT | DIQMTQSPSSLSASVGDRVTITCRAS (SEQ ID NO: 273) |
| CDR1-IMGT | QSISSY (SEQ ID NO: 97) |
| FR2-IMGT | LNWYQQKPGKAPKLLIY (SEQ ID NO: 274) |
| CDR2-IMGT | AAS |
| FR3-IMGT | SLQSGVP.SRFSGSGSGTDFTLTISSLQPEDFATYYC (SEQ ID NO: 275) |
| CDR3-IMGT | QQSYSTLYT (SEQ ID NO: 98) |
| J-Region | YTFGQGTKLEIK (SEQ ID NO: 276) |
| FR4-IMGT | FGQGTKLEIK (SEQ ID NO: 277) |
| Junction | CQQSYSTLYTF (SEQ ID NO: 278) |

Clone 1D12

| | |
|---|---|
| V-GENE and allele | Homsap IGKV1-33*01 F |
| J-GENE and allele | Homsap IGKJ3*01 F |
| V-J-Region | DIQMTQSPSSLSASVGDRVTITCQASQDISNYLNWYQQKPGKAPKLLIYDASNLETGVPSRFSGSGSGTDFTFTISSLQPEDIATYYCQQYDNLPITFGPGTKVDIK (SEQ ID NO: 279) |
| V-Region | DIQMTQSPSSLSASVGDRVTITCQASQDISNYLNWYQQKPGKAPKLLIYDASNLETGVPSRFSGSGSGTDFTFTISSLQPEDIATYYCQQYDNL (SEQ ID NO: 280) |
| FR1-IMGT | DIQMTQSPSSLSASVGDRVTITCQAS (SEQ ID NO: 281) |
| CDR1-IMGT | QDISNY (SEQ ID NO: 99) |
| FR2-IMGT | LNWYQQKPGKAPKLLIY (SEQ ID NO: 282) |
| CDR2-IMGT | DAS |
| FR3-IMGT | NLETGVPSRFSGSGSGTDFTFTISSLQPEDIATYYC (SEQ ID NO: 283) |
| CDR3-IMGT | QQYDNLPIT (SEQ ID NO: 100) |
| J-Region | TFGPGTKVDIK (SEQ ID NO: 284) |

TABLE 11-continued

15 CAR construct clones

| | |
|---|---|
| FR4-IMGT | FGPGTKVDIK (SEQ ID NO: 285) |
| Junction | CQQYDNLPITF (SEQ ID NO: 286) |

Clone 1E4

| | |
|---|---|
| V-GENE and allele | Homsap IGLV6-57*01 F |
| J-GENE and allele | Homsap IGLJ3*02 F |
| V-J-Region | NFMLTQPHS.VSGSPGKTVTISCTRSSGYIASNYVQWYQQRPGSAPTTVIYE DNQRPSGVP.DRFSGSIDSSSNSASLTISGLKTEDEADYYCQSYDSSNQGVF GGGTKLTVL (SEQ ID NO: 287) |
| V-Region | NFMLTQPHS.VSGSPGKTVTISCTRSSGYIASNYVQWYQQRPGSAPTTVIYE DNQRPSGVPDRFSGSIDSSSNSASLTISGLKTEDEADYYCQSYDSSN (SEQ ID NO: 288) |
| FR1-IMGT | NFMLTQPHSVSGSPGKTVTISCTRS (SEQ ID NO: 289) |
| CDR1-IMGT | SGYIASNY (SEQ ID NO: 101) |
| FR2-IMGT | VQWYQQRPGSAPTTVIY (SEQ ID NO: 290) |
| CDR2-IMGT | EDN |
| FR3-IMGT | QRPSGVPDRFSGSIDSSSNSASLTISGLKTEDEADYYC (SEQ ID NO: 291) |
| CDR3-IMGT | QSYDSSNQGV (SEQ ID NO: 102) |
| J-Region | VFGGGTKLTVL (SEQ ID NO: 292) |
| FR4-IMGT | FGGGTKLTVL (SEQ ID NO: 293) |
| Junction | CQSYDSSNQGVF (SEQ ID NO: 294) |

Clone 1E10

| | |
|---|---|
| V-GENE and allele | Homsap IGLV6-57*01 F |
| J-GENE and allele | Homsap IGLJ2*01 F |
| V-J-Region | NFMLTQPHSVSGSPGKTVTISCTRSSGYIASNYVQWYQQRPGSSPTTLIYD DDQRPSGVPDRFSGSIDRSSNSASLTISGLKTEDEGDYYCQSYDSSLVIFGG GTKVTVL (SEQ ID NO: 295) |
| V-Region | NFMLTQPHS.VSGSPGKTVTISCTRSSGYIASNYVQWYQQRPGSSPTTLIYD DDQRPSGVPDRFSGSIDRSSNSASLTISGLKTEDEGDYYCQSYDSS (SEQ ID NO: 296) |
| FR1-IMGT | NFMLTQPHSVSGSPGKTVTISCTRS (SEQ ID NO: 297) |
| CDR1-IMGT | SGYIASNY (SEQ ID NO: 103) |
| FR2-IMGT | VQWYQQRPGSSPTTLIY (SEQ ID NO: 298) |
| CDR2-IMGT | DDD |
| FR3-IMGT | QRPSGVPDRFSGSIDRSSNSASLTISGLKTEDEGDYYC (SEQ ID NO: 299) |
| CDR3-IMGT | QSYDSSLVI (SEQ ID NO: 104) |
| J-Region | VIFGGGTKVTVL (SEQ ID NO: 300) |
| FR4-IMGT | FGGGTKVTVL (SEQ ID NO: 301) |
| Junction | CQSYDSSLVIF (SEQ ID NO: 302) |

TABLE 11-continued

15 CAR construct clones

Clone 1E12

| | |
|---|---|
| V-GENE and allele | Homsap IGKV1-5*01 F |
| J-GENE and allele | Homsap IGKJ4*01 F |
| V-J-Region | DIQMTQSPSSLSASVGDRVTITCRASQSIGSSLHWYQQKPGKAPKFLIYDAS SLESGVPSRFSGSGSGTEFTLTISSLQPDDCATYYCQQYNSYPLTFGGGTKL EIK (SEQ ID NO: 303) |
| V-Region | DIQMTQSPSSLSASVGDRVTITCRASQSIGSSLHWYQQKPGKAPKFLIYDAS SLESGVPSRFSGSGSGTEFTLTISSLQPDDCATYYCQQYNS (SEQ ID NO: 304) |
| FR1-IMGT | DIQMTQSPSSLSASVGDRVTITCRAS (SEQ ID NO: 305) |
| CDR1-IMGT | QSIGSS (SEQ ID NO: 105) |
| FR2-IMGT | LHWYQQKPGKAPKFLIY (SEQ ID NO: 306) |
| CDR2-IMGT | DAS |
| FR3-IMGT | SLESGVPSRFSGSGSGTEFTLTISSLQPDDCATYYC (SEQ ID NO: 307) |
| CDR3-IMGT | QQYNSYPLT (SEQ ID NO: 106) |
| J-Region | LTFGGGTKLEIK (SEQ ID NO: 308) |
| FR4-IMGT | FGGGTKLEIK (SEQ ID NO: 309) |
| Junction | CQQYNSYPLTF (SEQ ID NO: 310) |

Clone 2A2

| | |
|---|---|
| V-GENE and allele | Homsap IGLV2-11*01 F |
| J-GENE and allele | Homsap IGLJ2*01 F |
| V-J-Region | QSALTQPRS.VSGSPGQSVTISCTGTSSDVGSYNYVSWYQQSPGKAPKLMI YDVSNRPSGVS.NRFSGSKSGNTASLTISGLQSEDEADYYCTSYGSYDIPVIF GGGTKLTVL (SEQ ID NO: 311) |
| V-Region | QSALTQPRS.VSGSPGQSVTISCTGTSSDVGSYNYVSWYQQSPGKAPKLMI YDVSNRPSGVS.NRFSGSKSGNTASLTISGLQSEDEADYYCTSYGSYD (SEQ ID NO: 312) |
| FR1-IMGT | QSALTQPRSVSGSPGQSVTISCTGT (SEQ ID NO: 313) |
| CDR1-IMGT | SSDVGSYNY (SEQ ID NO: 107) |
| FR2-IMGT | VSWYQQSPGKAPKLMIY (SEQ ID NO: 314) |
| CDR2-IMGT | DVS |
| FR3-IMGT | NRPSGVSNRFSGSKSGNTASLTISGLQSEDEADYYC (SEQ ID NO: 315) |
| CDR3-IMGT | TSYGSYDIPVI (SEQ ID NO: 108) |
| J-Region | VIFGGGTKLTVL (SEQ ID NO: 316) |
| FR4-IMGT | FGGGTKLTVL (SEQ ID NO: 317) |
| Junction | CTSYGSYDIPVIF (SEQ ID NO: 318) |

TABLE 11-continued

15 CAR construct clones

Clone 2C5

| | |
|---|---|
| V-GENE and allele | Homsap IGLV6-57*01 F |
| J-GENE and allele | Homsap IGLJ2*01 F |
| V-J-Region | NFMLTQPHSVSGSPGKAVTISCTRSSGNIARSFVQWYQQRPGSAPTAVIYE DNRRPSGVPDRFSGSFDSSSNSASLTISGLKTEDEADYYCQSYDSSNHVVF GGGTKVTVL (SEQ ID NO: 319) |
| V-Region | NFMLTQPHSVSGSPGKAVTISCTRSSGNIARSFVQWYQQRPGSAPTAVIYE DNRRPSGVPDRFSGSFDSSSNSASLTISGLKTEDEADYYCQSYDSSN (SEQ ID NO: 320) |
| FR1-IMGT | NFMLTQPHSVSGSPGKAVTISCTRS (SEQ ID NO: 321) |
| CDR1-IMGT | SGNIARSF (SEQ ID NO: 109) |
| FR2-IMGT | VQWYQQRPGSAPTAVIY (SEQ ID NO: 322) |
| CDR2-IMGT | EDN |
| FR3-IMGT | RRPSGVPDRFSGSFDSSSNSASLTISGLKTEDEADYYC (SEQ ID NO: 323) |
| CDR3-IMGT | QSYDSSNHVV (SEQ ID NO: 110) |
| J-Region | VVFGGGTKVTVL (SEQ ID NO: 324) |
| FR4-IMGT | FGGGTKVTVL (SEQ ID NO: 325) |
| Junction | CQSYDSSNHVVF (SEQ ID NO: 326) |

Clone 2C11

| | |
|---|---|
| V-GENE and allele | Homsap IGLV6-57*01 F |
| J-GENE and allele | Homsap IGLJ1*01 F |
| V-J-Region | NFMLTQPHSVSGSPGKTVTISCTRSSGYIASNYVQWYQQRPGSSPTTLIYD DDQRPSGVPDRFSGSIDRSSNSASLTISGLKTEDEGDYYCQSYDSTTEVFGT GTKLTVL (SEQ ID NO: 327) |
| V-Region | NFMLTQPHSVSGSPGKTVTISCTRSSGYIASNYVQWYQQRPGSSPTTLIYD DDQRPSGVPDRFSGSIDRSSNSASLTISGLKTEDEGDYYCQSYDST (SEQ ID NO: 328) |
| FR1-IMGT | NFMLTQPHSVSGSPGKTVTISCTRS (SEQ ID NO: 329) |
| CDR1-IMGT | SGYIASNY (SEQ ID NO: 111) |
| FR2-IMGT | VQWYQQRPGSSPTTLIY (SEQ ID NO: 330) |
| CDR2-IMGT | DDD |
| FR3-IMGT | QRPSGVPDRFSGSIDRSSNSASLTISGLKTEDEGDYYC (SEQ ID NO: 331) |
| CDR3-IMGT | QSYDSTTEV (SEQ ID NO: 112) |
| J-Region | VFGTGTKLTVL (SEQ ID NO: 332) |
| FR4-IMGT | FGTGTKLTVL (SEQ ID NO: 333) |
| Junction | CQSYDSTTEVF (SEQ ID NO: 334) |

Clone 2D1

| | |
|---|---|
| V-GENE and allele | Homsap IGLV6-57*01 F |

TABLE 11-continued

15 CAR construct clones

| | |
|---|---|
| J-GENE and allele | Homsap IGLJ2*01 F |
| V-J-Region | NFMLTQPHSVSESPGKTVTISCTGSSGSIASNYVQWYQQRPGSSPTTVIYED NQRPSGVPDRFSGSIDSSSNSASLTISGLKTEDEADYYCQSYDSSNQGVFGG GTQLTVL (SEQ ID NO: 335) |
| V-Region | NFMLTQPHSVSESPGKTVTISCTGSSGSIASNYVQWYQQRPGSSPTTVIYED NQRPSGVPDRFSGSIDSSSNSASLTISGLKTEDEADYYCQSYDSSN (SEQ ID NO: 336) |
| FR1-IMGT | NFMLTQPHSVSESPGKTVTISCTGS (SEQ ID NO: 337) |
| CDR1-IMGT | SGSIASNY (SEQ ID NO: 113) |
| FR2-IMGT | VQWYQQRPGSSPTTVIY (SEQ ID NO: 338) |
| CDR2-IMGT | EDN |
| FR3-IMGT | QRPSGVPDRFSGSIDSSSNSASLTISGLKTEDEADYYC (SEQ ID NO: 339) |
| CDR3-IMGT | QSYDSSNQGV (SEQ ID NO: 114) |
| J-Region | VFGGGTQLTVL (SEQ ID NO: 340) |
| FR4-IMGT | FGGGTQLTVL (SEQ ID NO: 341) |
| Junction | CQSYDSSNQGVF (SEQ ID NO: 342) |

Clone 2D3

| | |
|---|---|
| V-GENE and allele | Homsap IGKV1-39*01 F |
| J-GENE and allele | Homsap IGKE*01 F |
| V-J-Region | DIQMTQSPSSVSASVGDRVTITCRASQSISSYLNWYQQKPGKAPKLLIYAA SSLQSGVPSRFSGSGSGTDFTLTISSLQPEDFATYYCQQSYSTPWTFGQGTK LEIK (SEQ ID NO: 343) |
| V-Region | DIQMTQSPSSVSASVGDRVTITCRASQSISSYLNWYQQKPGKAPKLLIYAA SSLQSGVPSRFSGSGSGTDFTLTISSLQPEDFATYYCQQSYST (SEQ ID NO: 344) |
| FR1-IMGT | DIQMTQSPSSVSASVGDRVTITCRAS (SEQ ID NO: 345) |
| CDR1-IMGT | QSISSY (SEQ ID NO: 115) |
| FR2-IMGT | LNWYQQKPGKAPKLLIY (SEQ ID NO: 346) |
| CDR2-IMGT | AAS |
| FR3-IMGT | SLQSGVPSRFSGSGSGTDFTLTISSLQPEDFATYYC (SEQ ID NO: 347) |
| CDR3-IMGT | QQSYSTPWT (SEQ ID NO: 116) |
| J-Region | WTFGQGTKLEIK (SEQ ID NO: 348) |
| FR4-IMGT | FGQGTKLEIK (SEQ ID NO: 349) |
| Junction | CQQSYSTPWTF (SEQ ID NO: 350) |

Clone 2E1

| | |
|---|---|
| V-GENE and allele | Homsap IGKV1-39*01 F |
| J-GENE and allele | Homsap IGKE*01 F |

TABLE 11-continued

15 CAR construct clones

| | |
|---|---|
| V-J-Region | DIQMTQSPSSLSASVGDRVTISCQASQDISNYLNWYQQKPGKAPKLLIYAASSLQSGVPSRFSGSGSGTDFTLTISSLQPEDFATYYCLQDYNYPWTFGQGTKVEIK (SEQ ID NO: 351) |
| V-Region | DIQMTQSPSSLSASVGDRVTISCQASQDISNYLNWYQQKPGKAPKLLIYAASSLQSGVPSRFSGSGSGTDFTLTISSLQPEDFATYYCLQDYNY (SEQ ID NO: 352) |
| FR1-IMGT | DIQMTQSPSSLSASVGDRVTISCQAS (SEQ ID NO: 353) |
| CDR1-IMGT | QDISNY (SEQ ID NO: 117) |
| FR2-IMGT | LNWYQQKPGKAPKLLIY (SEQ ID NO: 354) |
| CDR2-IMGT | AAS |
| FR3-IMGT | SLQSGVPSRFSGSGSGTDFTLTISSLQPEDFATYYC (SEQ ID NO: 355) |
| CDR3-IMGT | LQDYNYPWT (SEQ ID NO: 118) |
| J-Region | WTFGQGTKVEIK (SEQ ID NO: 356) |
| FR4-IMGT | FGQGTKVEIK (SEQ ID NO: 357) |
| Junction | CLQDYNYPWTF (SEQ ID NO: 358) |

4. Initial Analyses Regarding SLAM Cross-Reactivity.

Using scFv-Fc variants of the CAR binders, which were expressed in mammalian 293F cells, an initial analysis of cross-reactivity of four randomly chosen constructs was performed against a smaller panel of SLAM family receptors. None of these clones were cross-reactive to SLAM/CD150, SLAMF2/CD48, SLAMF8/BLAME, or murine CD229 (FIG. 3B).

5. Autotargeting of T Cells by Anti-CD229 CAR T Cells.

The fact that CD229 is expressed on normal T and NK cells indicates a potential for autotargeting. Growth kinetics of primary human T cells transduced with anti-CD229 CAR constructs and enriched >90% by FACS™, fluorescent activated cell sorting, for CAR expression were analyzed, but no significant differences compared to T cells transduced with GFP as a control were observed (FIG. 3C). In addition, a cytotoxicity assay was performed using two of the activating CAR constructs and no significant cytotoxicity towards healthy autologous T cells was observed (FIG. 4B). These results indicate that CD229 targeting CARs have no significant killing activity against themselves or autologous T cells. This is consistent with recent studies demonstrating that normal T and NK cells are resistant to CAR effector cells despite potent tumor cell lysis. It is thought that this reflects the ability of healthy T cells, but not tumor cells, to rapidly downregulate target antigens and upregulate protective pathways that prevent their lysis.

6. Cytotoxic Activity Against K562 Cells Expressing CD229 and Autologous T Cells.

A truncated variant of CD229 lacking its intracellular signalling domains was expressed in human K562 cells (K562-CD229), which do not express HLA class I molecules and are therefore not subject to killing by potentially alloreactive T cells. In addition, autologous untransduced T cells were cultured in parallel to transduced T cell populations and also used as target cells. K562-CD229 cells and autologous untransduced T cells were labelled with calcein AM and incubated for 4 h with effector T cell populations. Purified anti-CD229 CAR T cells expressing clone 2D3 or clone 2A2, which had shown substantial surface expression, antigen binding, and increased IFNγ expression after CD229-crosslinking, or T cells transduced with GFP only were used as effector populations and co-cultures were analyzed by flow cytometry (FIG. 4A). T cells expressing anti-CD229 CARs showed significant dose-dependent lysis of CD229 expressing K562-CD229 cells but no or limited cytotoxicity towards healthy T cells (FIG. 4B) These results provide proof of principle that specifically targeting cancer cells expressing CD229 using the CAR T cells is feasible.

B. Example 2

T cells engineered to express CARs (CAR T cells) targeting CD19 are highly effective in refractory B-cell acute lymphoblastic leukemia (B-ALL). For instance, a pediatric B-ALL study reported a complete remission (CR) rate of 92%, with 76% of responses sustained at 6 months. In MM, however, the efficacy of CD19-specific CAR T cell therapy remains uncertain. While one successful case was reported last year, the vast majority of MM cells do not express CD19. CAR T cells targeting B-cell maturation antigen (BCMA), the immunoglobulin kappa light chain, CD138, and CS1 have specifically been developed for MM therapy. No responses were observed for CAR T cells targeting immunoglobulin kappa or CD138, and there are no clinical trials investigating CS-1 CAR T cells, presumably due to its wide off-tissue expression on many normal immune cells. CAR T cells targeting B-cell maturation antigen (BCMA), an antigen expressed with exquisite specificity on terminally differentiated plasma and MM cells, have resulted in promising overall response rates in multiple clinical trials. While these findings are very encouraging and demonstrate the potential utility of CAR T cells as a treatment for MM, these are early results. Long-term outcomes remain uncertain, as the only published report on the clinical efficacy of BCMA CAR T cells described elapses in all treated patients. This observation would be in line with the absence of BCMA from MM precursor cells, which are considered responsible for the frequent relapses in this disease. In addition, to the best of our knowledge, eligibility criteria for all ongoing clinical trials using BCMA CAR T cells include confirmation of substantial surface expression of BCMA. While there is a surprising lack of information regarding BCMA expression in larger cohorts of patients with MM and no such information is yet available from the ongoing clinical trials, data indicates that only a minority of patients would be eligible due to high heterogeneity of BCMA expression in patients with MM. Hence, there is a need for novel CAR T cell approaches targeting antigens that are frequently expressed at high levels on MM cells and that are present not only on terminally differentiated MM plasma cells but also on their more therapy-resistant precursors.

CD229, a member of the SLAM (signaling lymphocyte activation molecule) family of proteins, is strongly expressed on terminally differentiated MM plasma cells, but absent from any non-lymphoid tissues and CD34+ hematopoietic stem cells. Importantly, CD229 is also expressed on CD19-138-MM pre-plasma cells, and memory B cells, another potential reservoir of MM precursor cells. In MM cells, CD229 confers resistance to spontaneous apoptosis and it can be targeted efficiently using a murine monoclonal antibody. However, a potential issue with CD229 as a therapeutic target is its relatively strong expression on healthy T and NK cells. CAR T cells targeting a variant of CD229 have been developed, termed $CD229^{CT2}$, wherein the variant of CD229 is specifically expressed on all populations harboring MM cells. Importantly, on healthy cells $CD229^{CT2}$ is not expressed on activated T cells and NK cells and is only found at low levels on a subpopulation of resting T cells and B cells, potentially allowing the exclusive targeting of MM cells by modulating CAR T cell avidity. A CAR T cell approach targeting this antigen in MM can result in sustained remissions or even cures. 1. Validation of $CD229^{CT2}$ as a target for CAR T cell therapy for human MM.

CD229 located on chromosome arm 1q, which is frequently amplified in MM, is expressed on MM precursor cells and terminally differentiated MM plasma cells. Eradicating both populations simultaneously using $CD229^{CT2}$ CAR T cells may lead to more durable responses or even cures.

i. Tissue Distribution and Antibody Targeting of CD229.

Figures 6A, 6B:
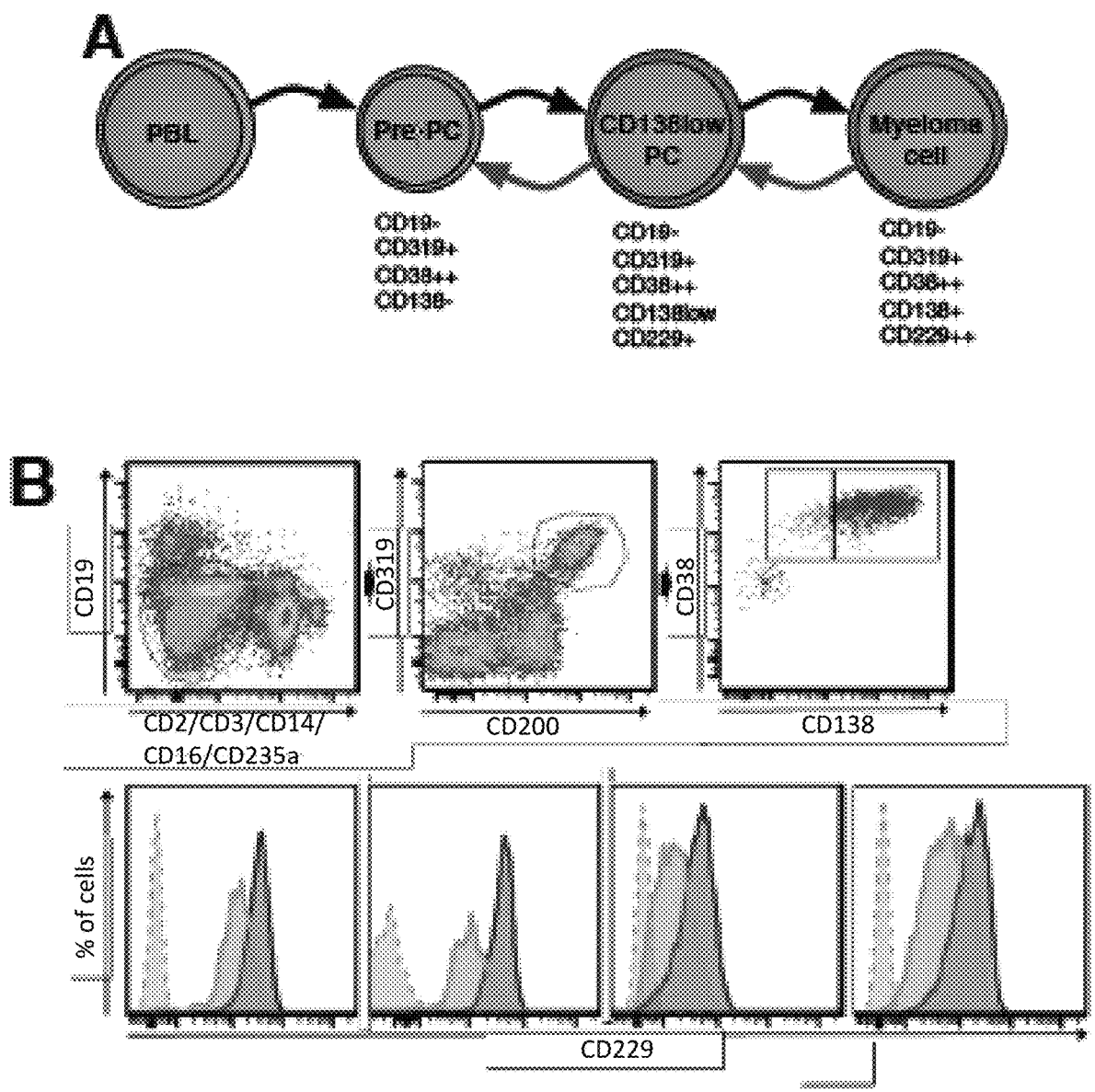
Figures 6C, 6D:
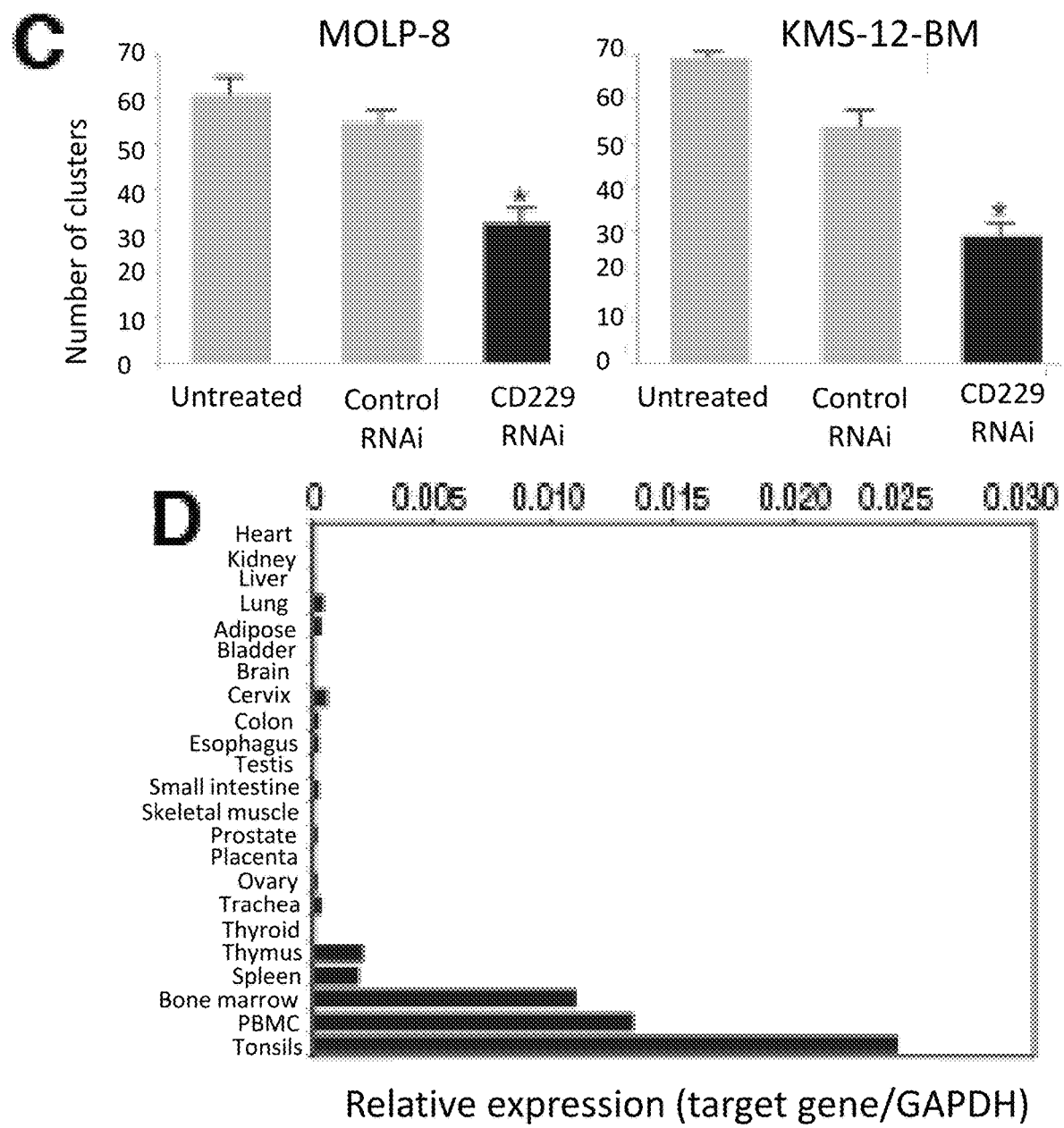

It was previously reported that CD229 is strongly expressed on the surface of MM cell lines and primary MM cells. As interconversion of myeloma plasma cell populations with different antigen expression patterns and resistance to current treatment regimens has been reported (FIG. 6A), CD229 expression was analyzed on various cellular subsets of MM. It was demonstrated that CD229 is homogeneously and strongly expressed not only on the bulk of MM cells but also on myeloma precursors (FIG. 6B). Knockdown of CD229 significantly reduces the clonogenicity of MM cell lines, indicating a significant barrier toward immune escape through downregulation of CD229 (FIG. 6C). Using a murine monoclonal antibody against human CD229 it was also found that this antigen can be targeted efficiently via complement derived cytotoxicity (CDC) and antibody dependent cellular cytotoxicity. CD229 is absent from tissues other than lymphatic tissues (FIG. 6D).

ii. Expression of Common CAR Targets on Healthy Blood Cell Subsets and Bone Marrow B Cell Precursors.

Figures 6E, 6F, 6G:
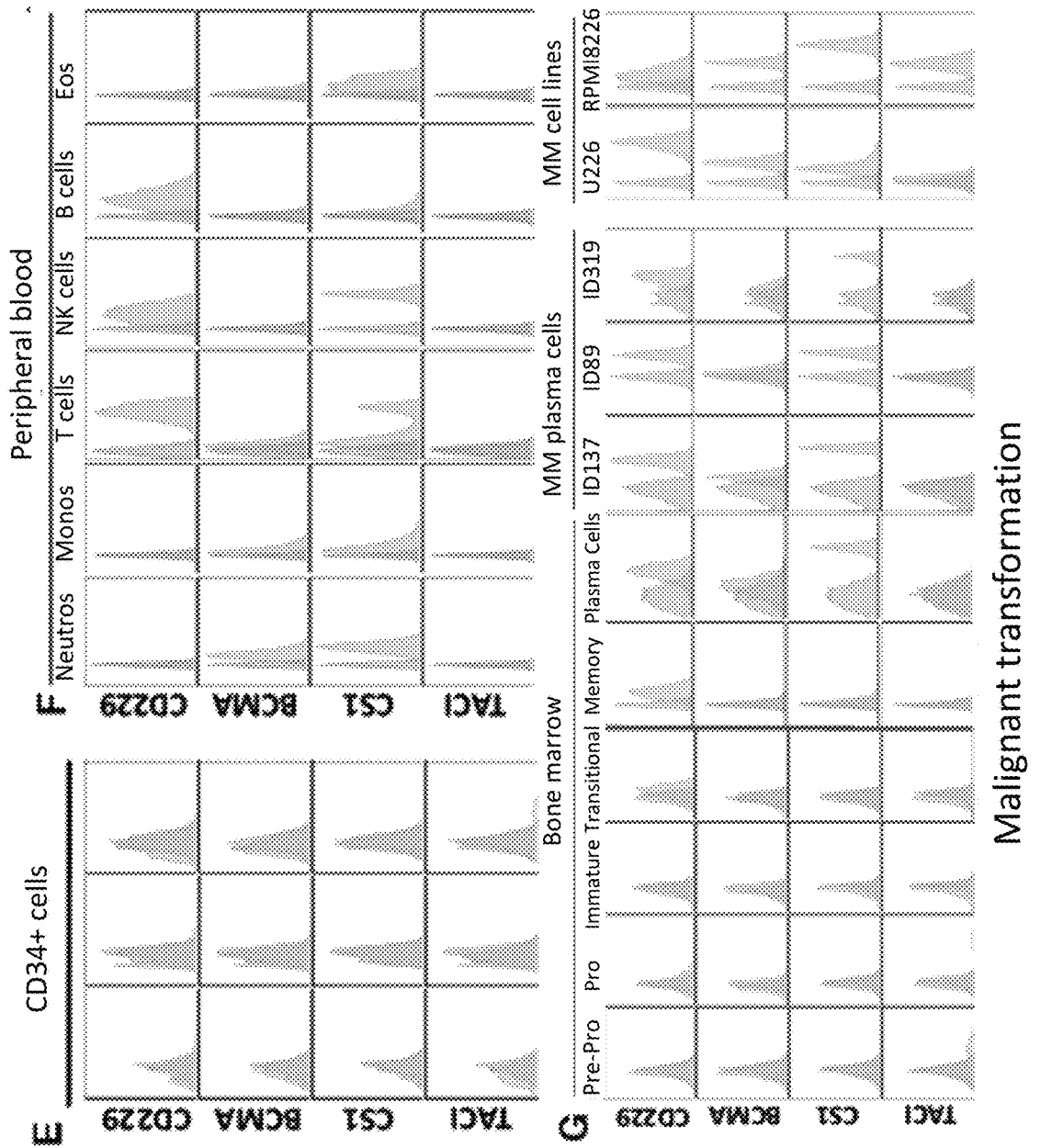

BCMA is currently being evaluated as a target of CAR T cell therapies for the treatment of MM. BCMA is a receptor for the TNF superfamily ligand APRIL. Another receptor for APRIL is transmembrane activator and CAML interactor (TACI). A CAR using APRIL as its binding domain targeting cells expressing either BCMA or TACI has been developed and can counteract selection of variants that are single-negative for either BCMA or TACI. Another antigen against which CAR T cells have been developed for the treatment of MM is CS-1. Like CD229, CS-1 belongs to the SLAM family of receptors. The monoclonal antibody elotuzumab, which targets CS-1, has been approved for the treatment of MM. The expression of CD229 was compared to these three targets on healthy peripheral blood cell subsets, CD34+ hematopoietic stem cells, bone-marrow B lineage cells, as well as MM cell lines, and primary human MM cells. Using flow cytometry, it was found that all four targets are absent from CD34+ hematopoietic stem cells (FIG. 6E). It was further confirmed that CD229 is expressed on T, B, and NK cells, while BCMA and TACI appeared to be absent from all analyzed peripheral blood cell subsets, with the possible exception of low-level BCMA expression on neutrophils and monocytes (FIG. 6F). Importantly, it was found that CS-1 was broadly expressed on almost all healthy cell subsets, though only showing low expression on B cells (FIG. 6F). Analyzing B lineage cells in bone-marrow samples from patients with MM, all targets were absent from the earliest stages of B cell development and, in the case of CS-1 and BCMA, any B lineage cells except for plasma cells (FIG. 6G). In contrast, CD229 expression is apparent at the transitional B cell stage and continues through the plasma cell stage. This finding is important, since malignant transformation of MM cells is known to occur at the memory B cell stage. In contrast, targeting BCMA and CS-1 would only eradicate terminally differentiated MM plasma cells. Finally, analyzing MM cells, strong expression of both CD229 and CS-1 were observed, and comparably low levels of BCMA expression (FIG. 6G). Previous reports have shown more variable BCMA expression including relatively high expression but also the absence of detectable BCMA expression in some cases. Surprisingly, TACI expression was only observed on MM cell line RPMI-8226 but not on any primary MM cells. From these preliminary analyses it was concluded that CD229 can be superior to others targets, capturing MM cells at all stages of the disease and showing homogeneous and high expression on the malignant cells of all analyzed patients.

iii. Identification of Anti-CD229 scFv Domains.

Figure 7A:
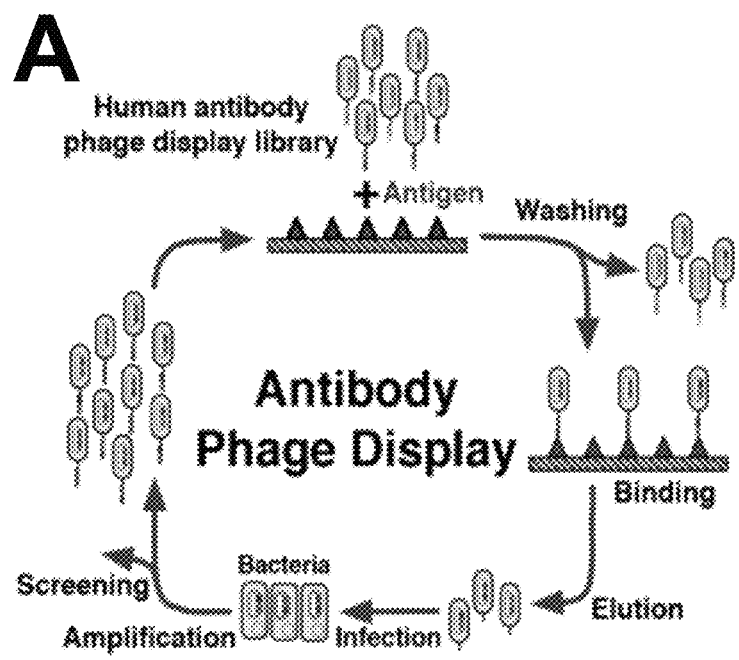
Figure 7B:
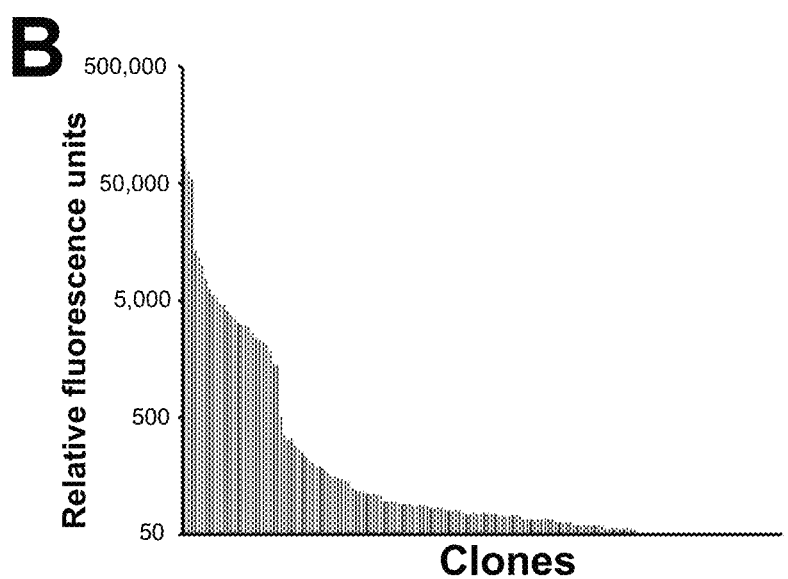
Figure 7C:
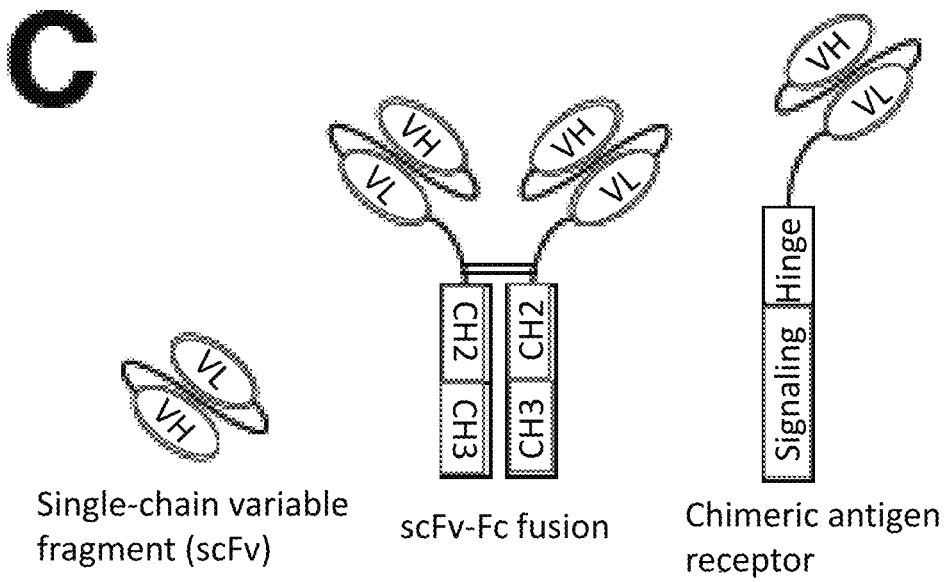

As no human monoclonal anti-CD229 antibodies were available for conversion to CAR format, novel high-affinity scFv domains were generated for use in the anti-CD229 CAR constructs. A human antibody phage display library with a diversity of >$10^{10}$ clones was mined (FIG. 7A). As the library is derived from human immunoglobulin genes, the immunogenicity of the resulting CAR constructs in humans is expected to be low compared to CARs using murine or partially humanized antibody domains. Antibodies in the library are displayed as scFv domains and contain both heavy and light chain variable regions connected by a linker, enabling rapid conversion from phage to CARs once binders are identified. After two rounds of specific enrichment of phage binders by panning, 1,323 clones specific for the extracellular domain (ECD) of human CD229 were obtained. After further selection and bacterial expression of 168 clones, 32 CD229 binders were chosen for additional studies based on time-resolved florescence (TRF) signal intensity ≥5-fold over background (FIG. 7B); 23 of these clones were identified to have unique heavy and light chain combinations by Sanger sequencing.

iv. Generation of CD229-Specific Antibodies and CAR Constructs.

Figure 7D:
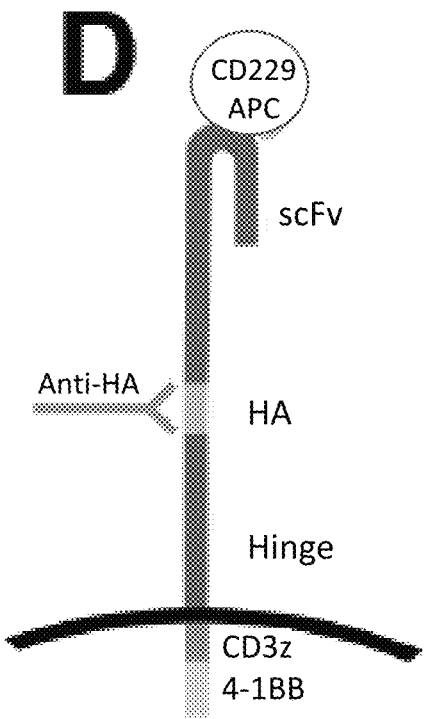
Figure 7E:
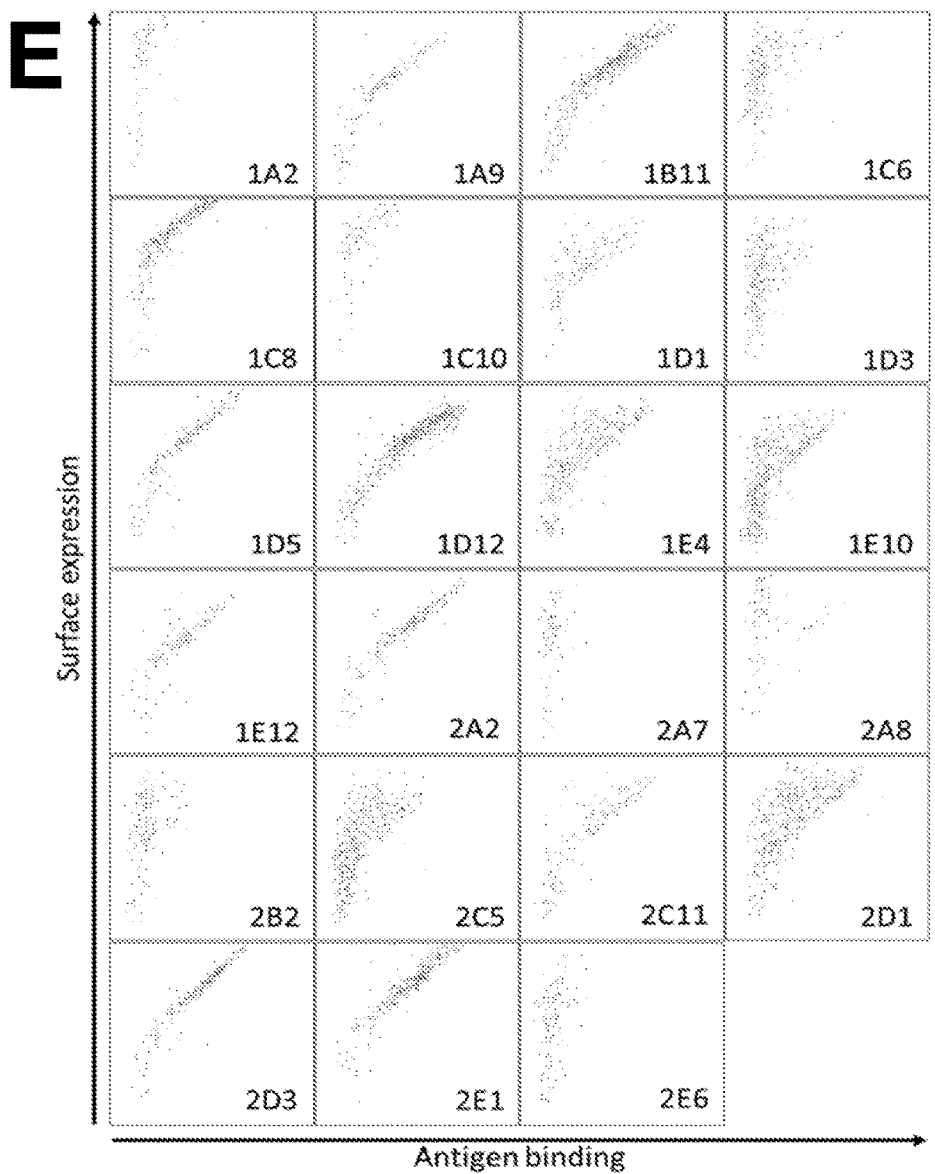
Figure 7F:
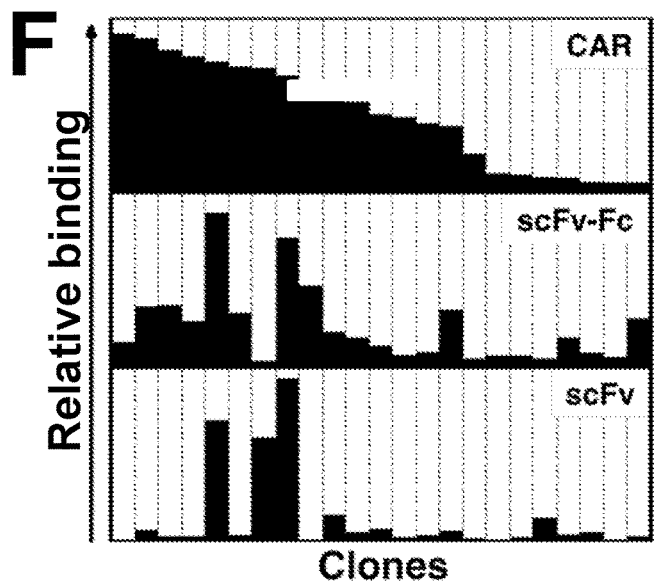
Figure 7G:
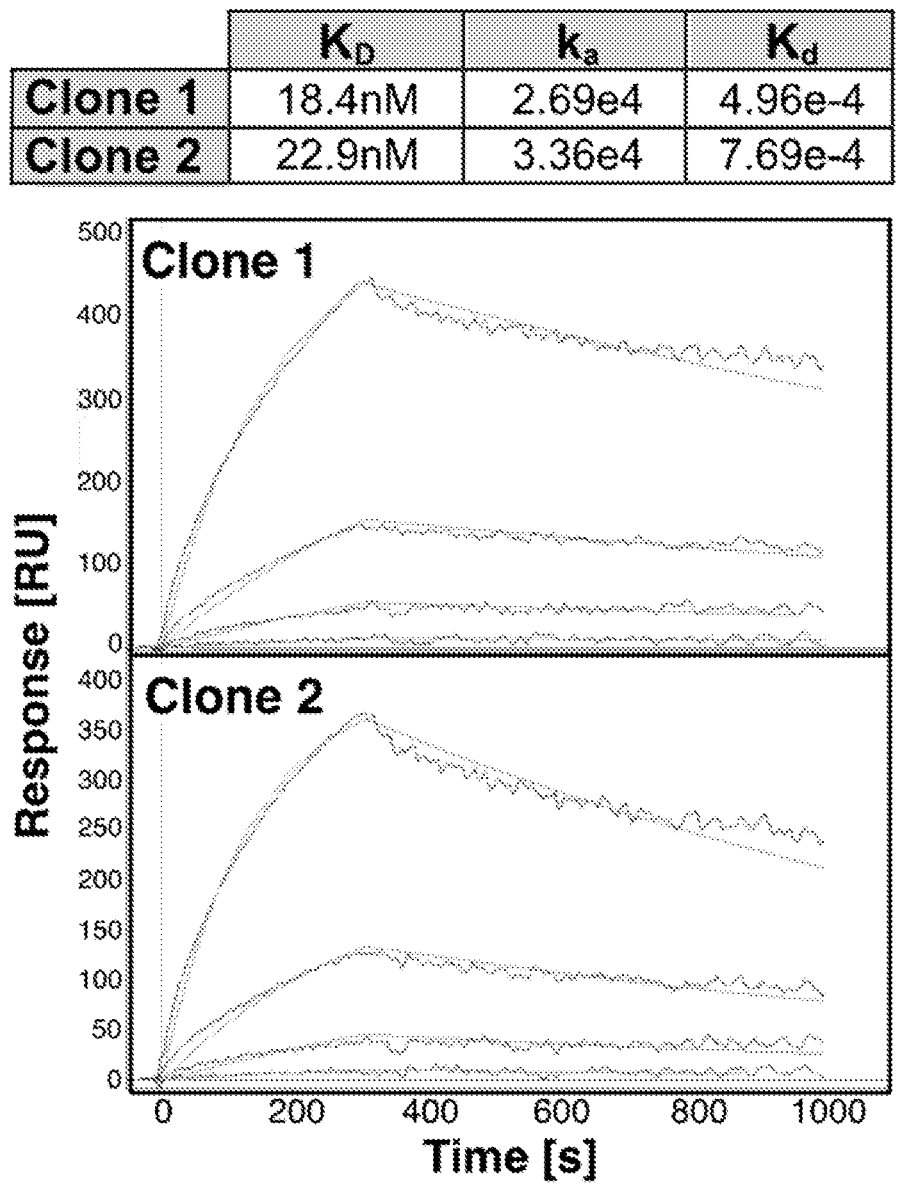

In the final CAR construct, the scFv can be joined directly to a 45 amino acid hinge domain, which can alter binding properties of the antibodies. In order to identify clones likely to be amenable to CAR conversion, the scFv was fused to an immunoglobulin Fc domain (scFv-Fc fusion, FIG. 7C) and the constructs were expressed in human 293T cells. 20 of the 23 unique scFv binders still recognized CD229 with the new C-terminal fusion partner. All 23 unique binders were cloned into the CAR vector (FIG. 7D). The second-generation CAR construct uses a CD8α hinge and transmembrane domain with a CD3ζ signaling and a 4-1BB costimulatory domain. In addition, a hemagglutinin (HA) tag was added between the scFv and hinge domains to allow the simultaneous assessment of antigen binding and surface expression (FIG. 7D). Individual CAR constructs were expressed in 293T cells, and analyzed by flow cytometry after staining with allophycocyanin (APC)-labeled recombinant CD229 and a phycoerythrin (PE)-labeled anti-HA antibody. The majority, 15 of the 23 constructs, showed high surface expression and CD229 binding (FIG. 7E). In line with the previously described importance of the 45 amino acid hinge domain for CAR activity, results from the two soluble antibody-screening assays showed limited correlation with the cell-based screening assay confirming the unique binding behavior of CARs (FIG. 7F).

Figure 7H:
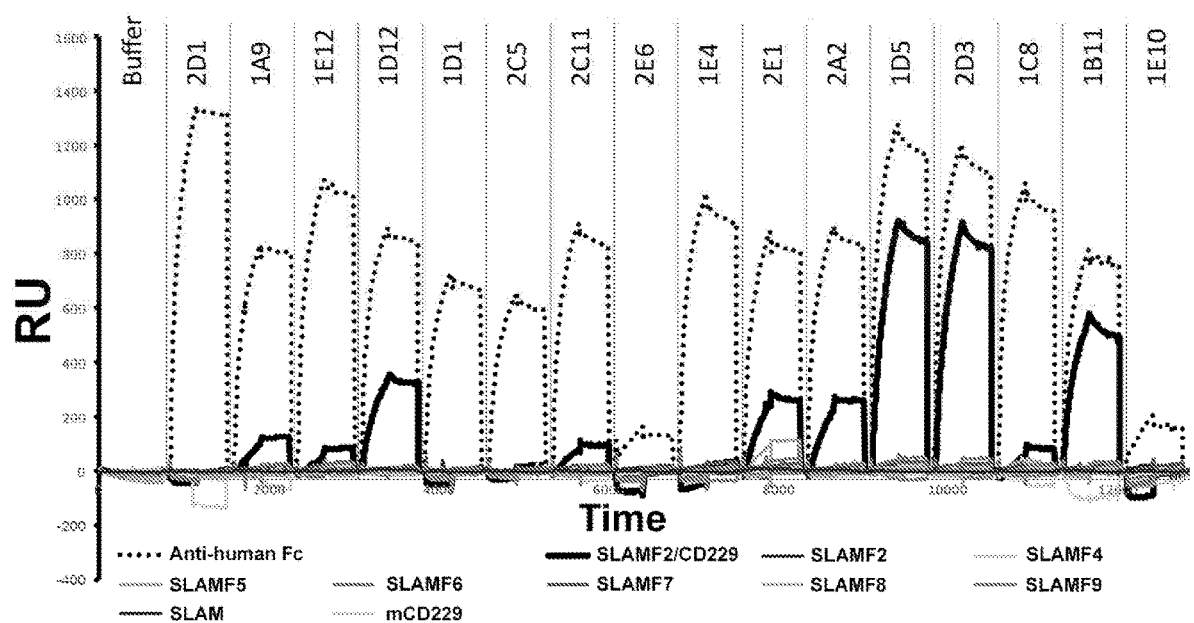
Figure 7I:
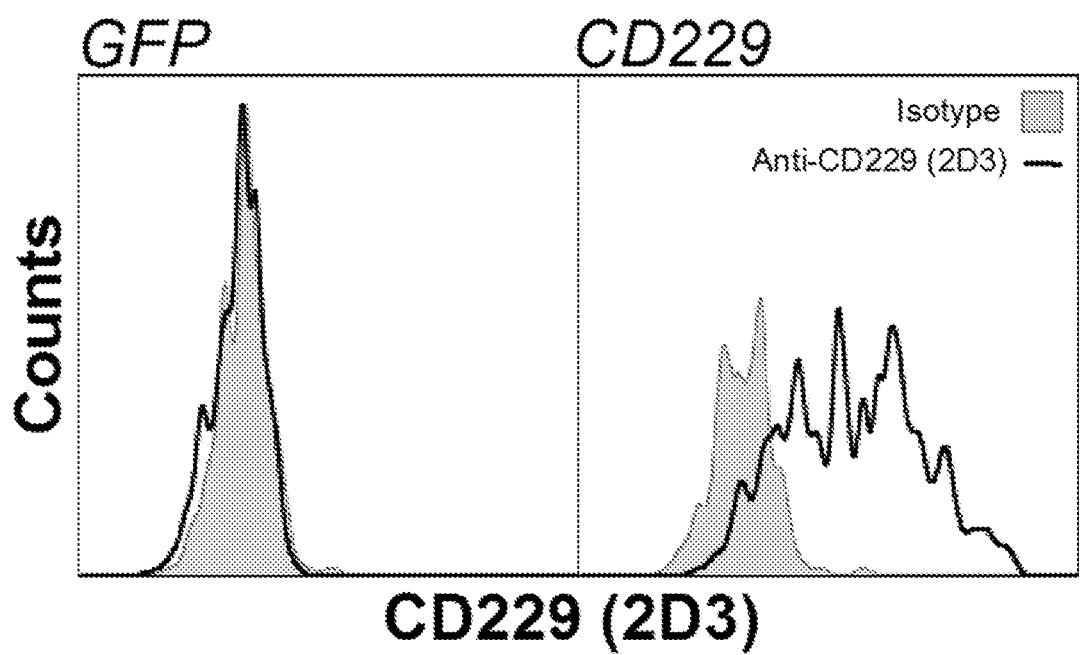
Figures 7J, 7K, 7L:
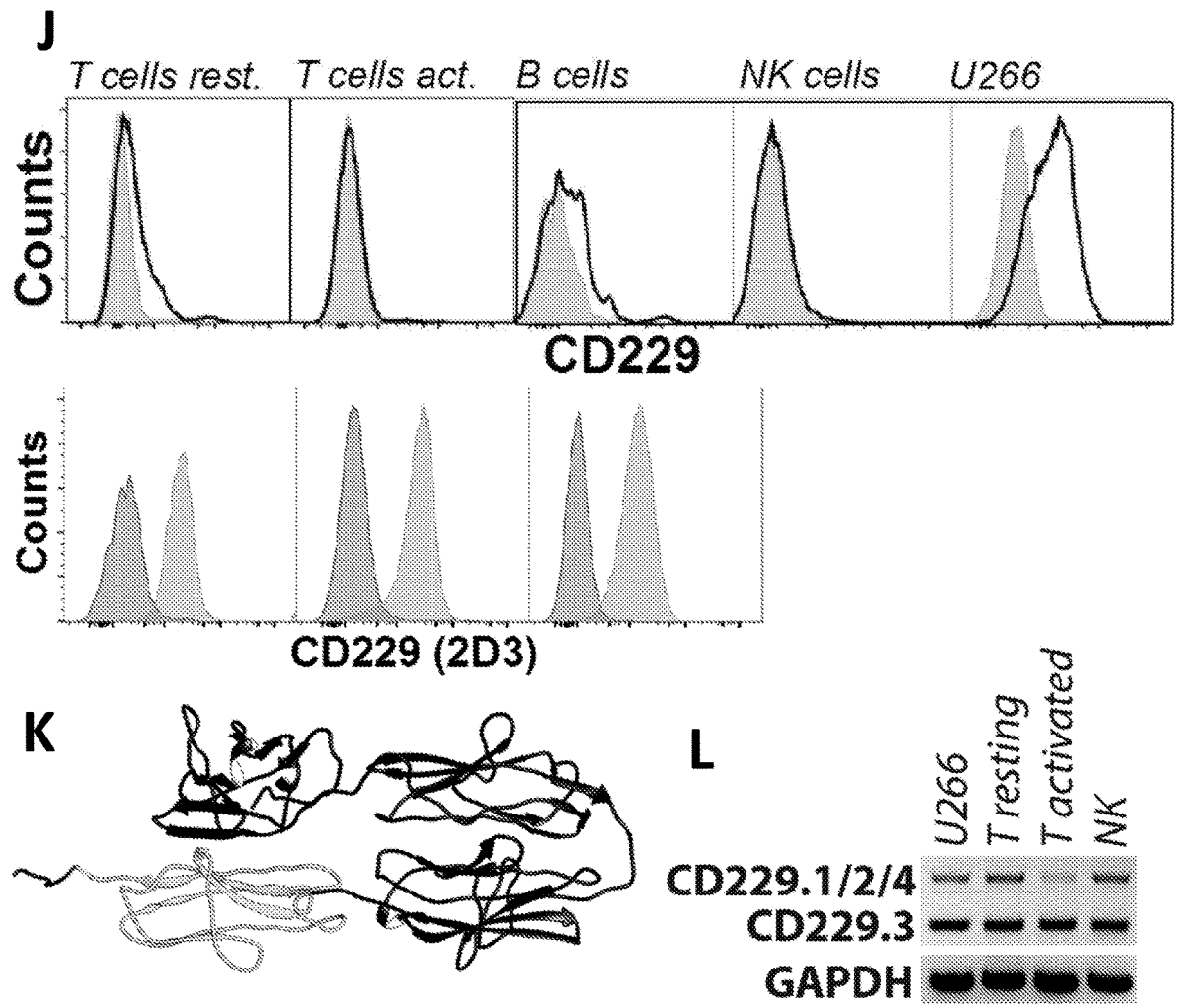

Using a high-throughput surface plasmon resonance (SPR) assay, the crossreactivity and binding kinetics of the antibodies to all SLAM family members were determined. It was found that our antibodies had low nanomolar affinities to CD229 (FIG. 7G) and that the antibodies did not bind to any other SLAM receptors with any measurable affinity (FIG. 7H). For all downstream analyses clone 2D3 was selected, which was found to perform well in all assays. The specificity of 2D3 was confirmed. CD229 was overexpressed in 293T cells and these cells were stained with 2D3. It was found that the antibody did not stain parental 293T cells but that it bound strongly to transfected 293T cells (FIG. 7I) further confirming its specificity for CD229. Healthy lymphocyte subsets as well as primary MM cells and MM cell lines were stained, and binding was analyzed by flow cytometry. In contrast to previous findings using the commercially available CD229 antibody HLy9.1.25 (FIG. 7F) only minor staining by 2D3 was observed on resting T cells and B cells, and no staining of NK cells or activated T cells (FIG. 7J). Importantly, strong staining of MM cell line U266 and even stronger staining of primary CD19-CD38+ CD138+MM plasma cells was still observed (FIG. 7J). In order to investigate the differential binding of 2D3 to healthy lymphocytes, expression of CD229 isoforms was determined by qualitative RT-PCR. CD229 isoform 3 lacks a large extracellular domain proximal to the transmembrane domain corresponding to the C2-type 2 domain of CD229, while isoforms 1, 2, and 4 contain this region (FIG. 7K). Lower expression of isoforms 1, 2, and 4 were observed in activated T cells (FIG. 7L). 2D3 recognizes a variant of CD229 by binding to an epitope within the extracellular C2-type 2 domain of CD229, which is absent or inaccessible in the majority of healthy lymphocyte subsets. This variant, or group of variants, was termed $CD229^{CT2}$.

v. $CD229^{CT2}$ CAR Manufacturing and Anti-MM Efficacy.

Figures 8A, 8B, 8C:
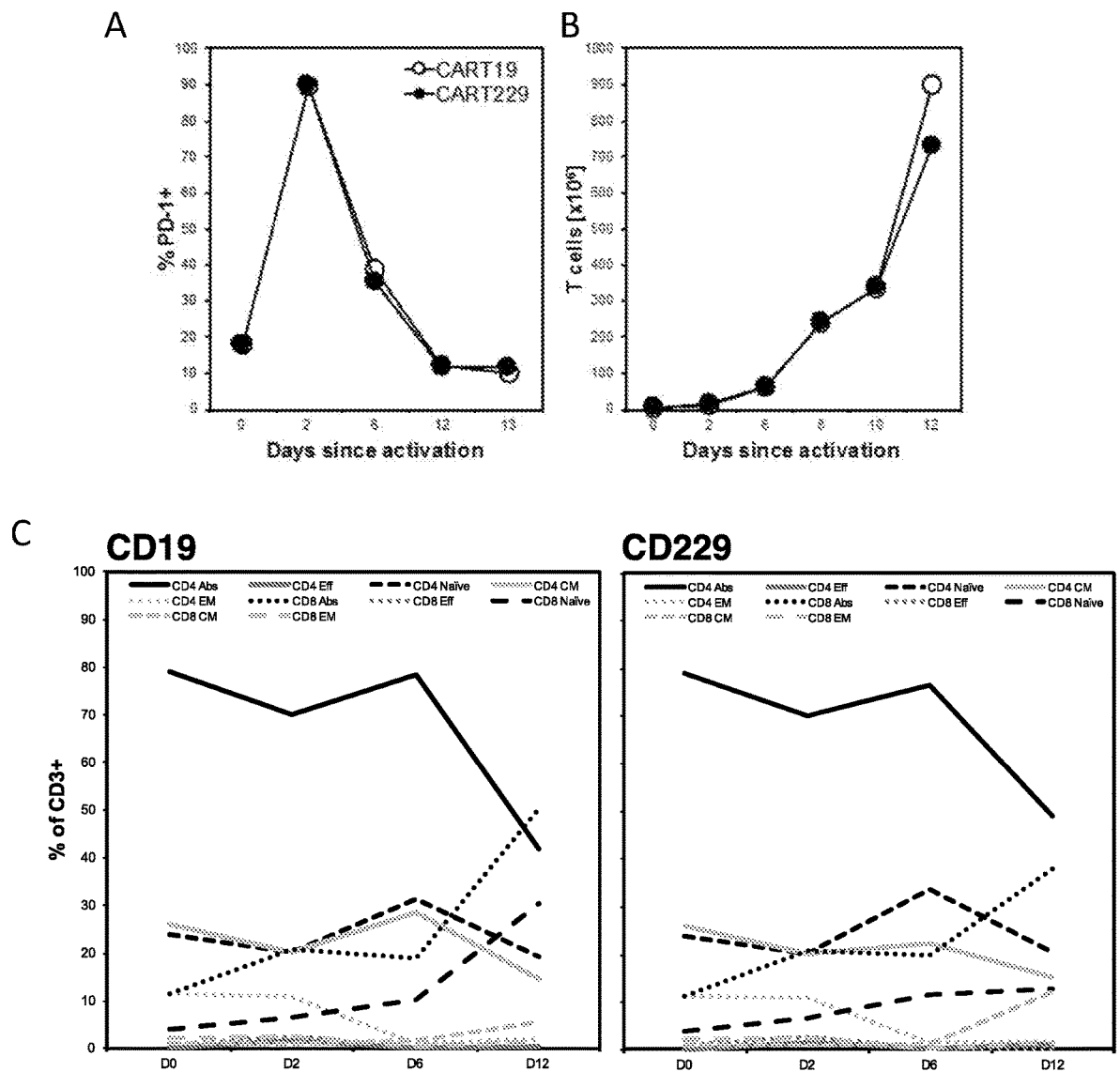
Figure 8D:
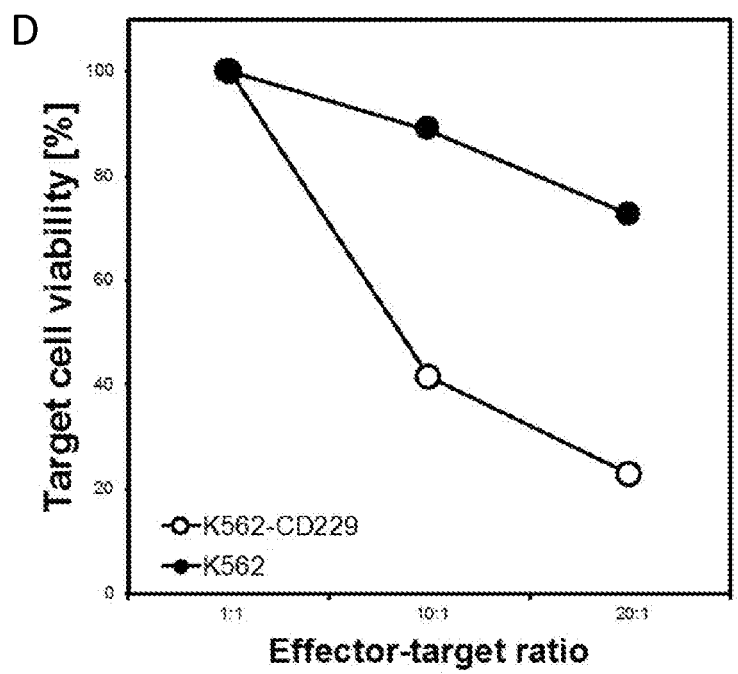

A second generation $CD229^{CT2}$- and, for comparative purposes, CD19-specific CAR T cells using the 4-1BB costimulatory and CD8α hinge and transmembrane domains was generated. In order to generate the CD19-specific CAR the $CD229^{CT2}$-specific scFv domain was replaced with the previously described CD19-specific scFv clone FMC63. Using lentiviral gene transfer primary human T cells expressing each CAR was engineered. In order to address the possibility of undesired spontaneous T cell activation in the absence of antigen, called tonic signaling, by the construct PD-1 expression (FIG. 8A) and expansion (FIG. 8B) of the $CD229^{CT2}$ CAR T cells was determined. Importantly, the CAR T cells did not show any signs of early exhaustion, a hallmark of tonic signaling. Analyzing the T cell phenotype during CAR T cell production, $CD229^{CT2}$ CAR T cell phenotypes mirrored those of CD19 CAR T cells (FIG. 8C). The cytotoxic activity of the CAR T cells was determined using various target cells. CD229 CAR T cells showed strong cytotoxic activity against K562 cells transduced with a CD229 expression construct, but only limited cytotoxicity against parental K562 cells (FIG. 8D).

Figure 8E:
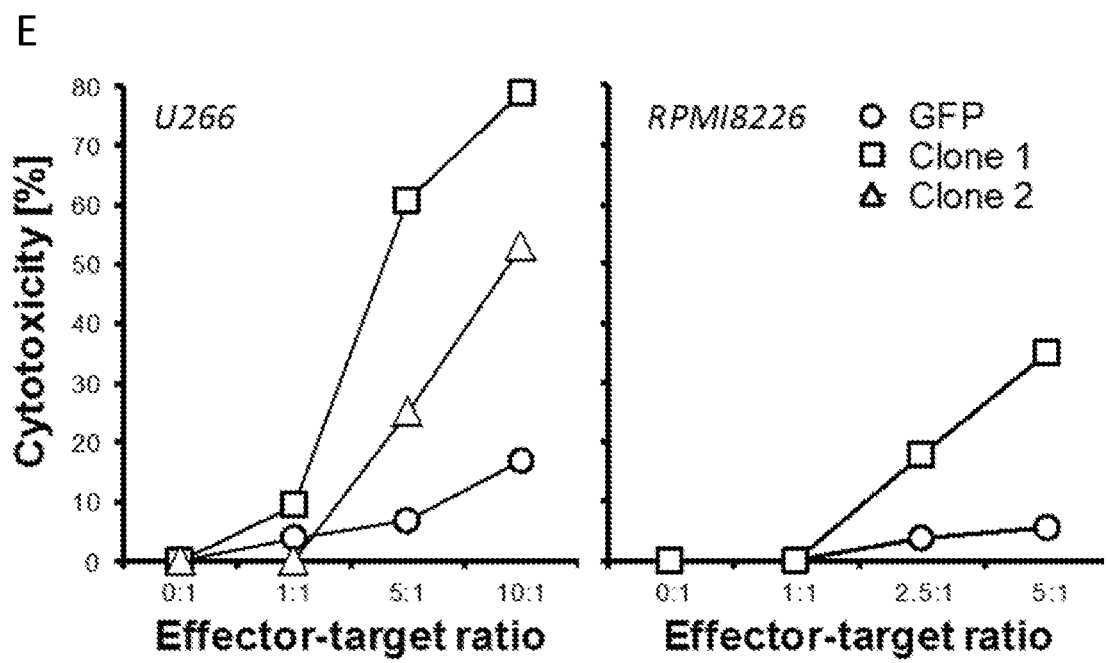
Figure 8F:
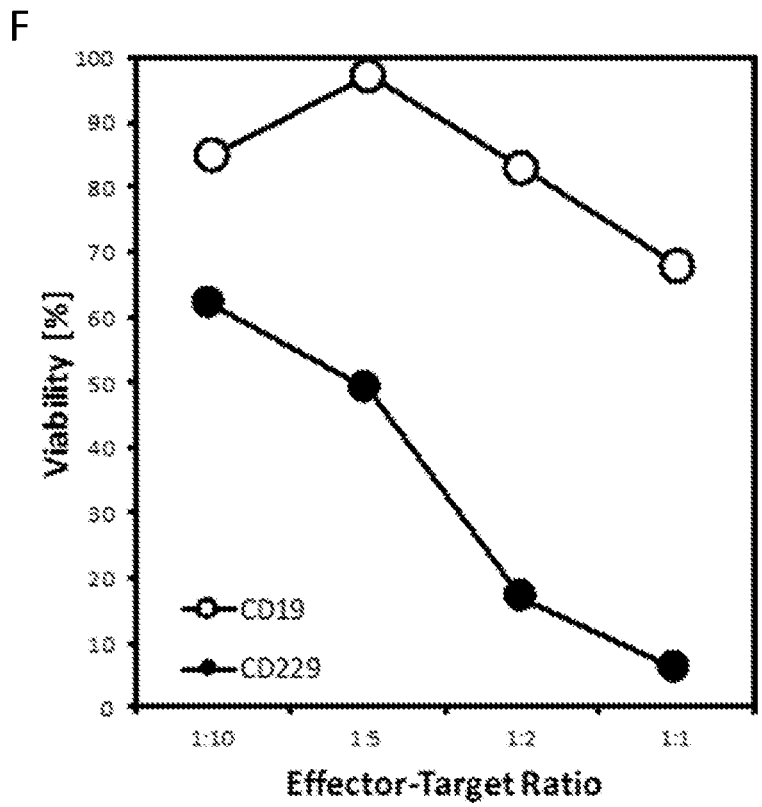
Figure 8G:
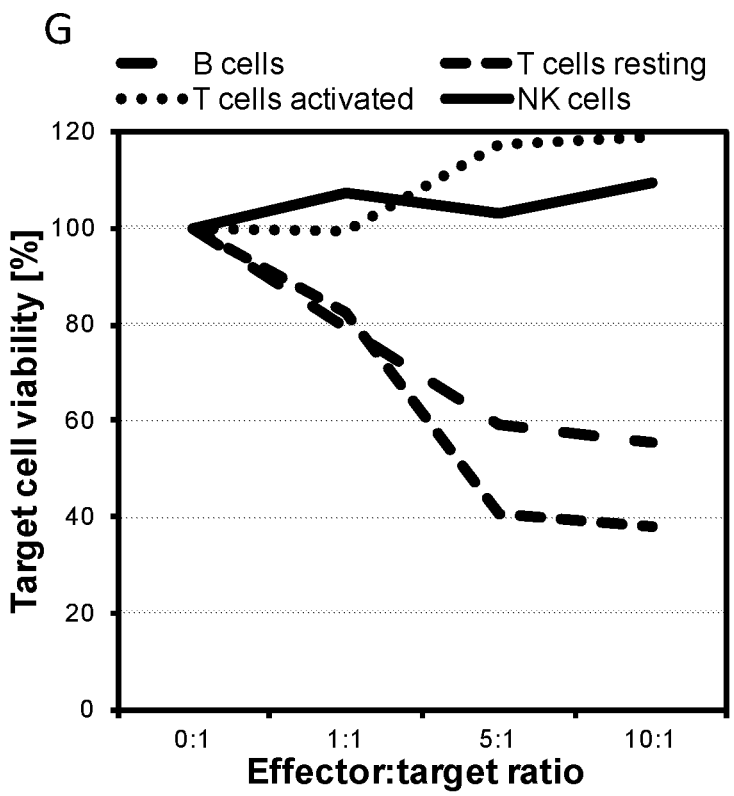
Figure 8H:
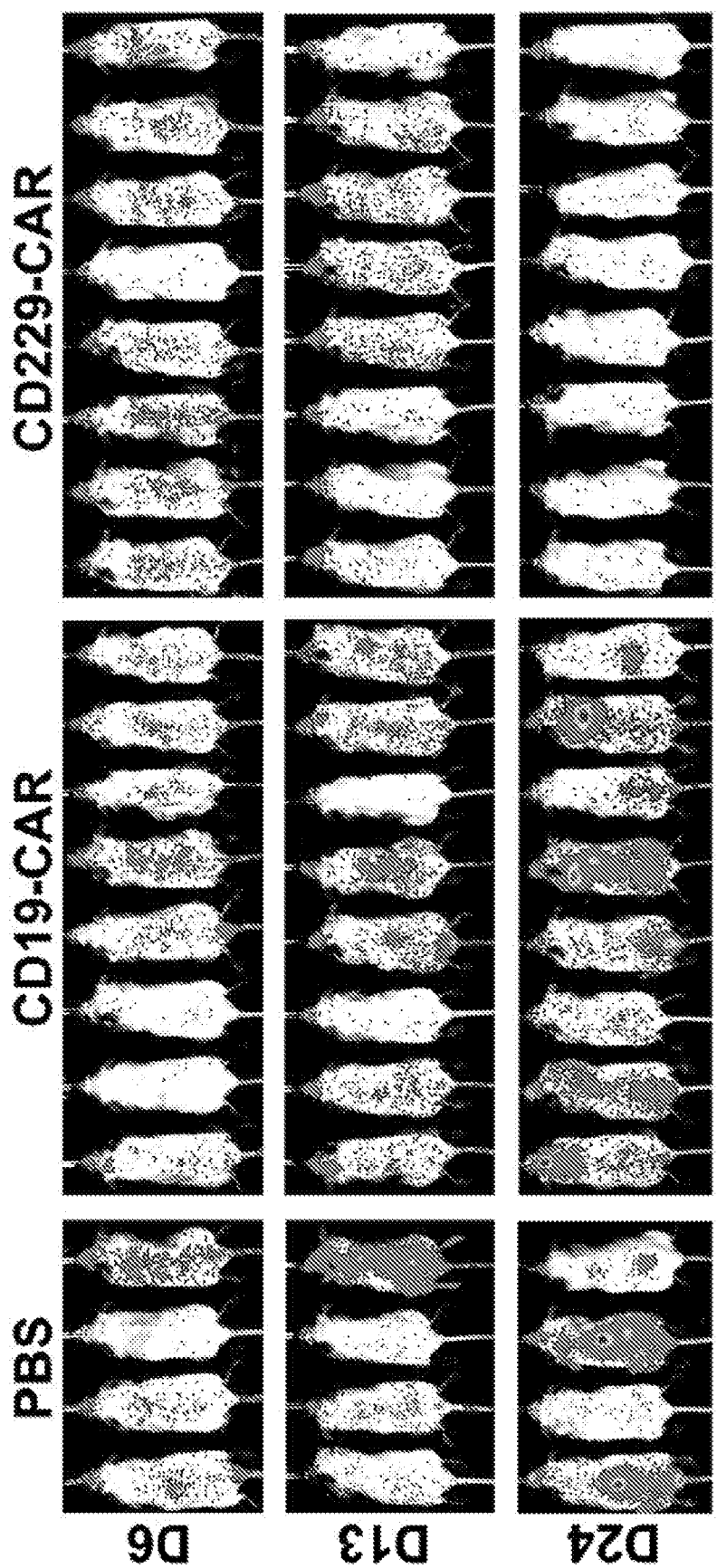

Strong cytotoxic activity against the CD229-positive MM cell lines U266 and RPMI-8226 at low effector-target ratios was observed, in contrast to minimal killing by T cells transduced with a GFP control construct (FIG. 8E). Using cells manufactured according to the most recent protocol even at effector-target ratios of 1:10 and 1:5 strong killing of the MM cell line U266 was observed (FIG. 8F). The cytotoxic activity against healthy lymphocyte subsets, which we had previously found to express CD229 using HLy9.1.25 but which showed little or no binding by 2D3 was determined. Importantly, only killing of B cells and resting T cells was observed, while no cytotoxic activity was observed against T cells activated with CD3/CD28 beads or NK cells (FIG. 8G). Lack of killing of activated T cells also explains the undisturbed expansion of the CD229 CAR T cells during manufacturing (FIG. 8A) and correlates with the binding data (FIG. 7I). Cytotoxicity against purified CD34+ hematopoietic stem cells was also not observed (data not shown). Finally, the in vivo efficacy of CD229 and CD19 CAR T cells was determined using immunocompromised NOD.Cg-PrkdcSCidI12rgtmlwji/SzJ (NSG) mice after engraftment with U266 cells. We found that $CD229^{CT2}$ CAR T cells had completely eradicated MM cells expressing luciferase after only 18 days, while mice treated with CD19 CAR T cells or PBS still showed strong bioluminescence signal (FIG. 8H). In addition to demonstrating strong anti-MM efficacy, this result further confirms the absence of tonic signaling, as this phenomenon is accompanied by poor in vivo activity.

The binding of clone 2D3 to Burkitt's lymphoma cell lines Daudi and Raji was demonstrated (FIG. 9). This result is in line with the finding that CD229 is widely expressed on B lineage cells and demonstrates that the CD229 CAR T cells are able to target not only multiple myeloma but also other malignancies, such as lymphoma.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Surveillance E, and End Results Program. seer.cancer.gov/statfacts/html/mulmy.html2014.
2. Mahindra A, Laubach J, Raje N, Munshi N, Richardson PG, Anderson K. Latest advances and current challenges in the treatment of multiple myeloma. Nature reviews Clinical oncology. 2012; 9(3):135-43. Epub 2012/02/22. doi: 10.1038/nrclinonc.2012.15. PubMed PMID: 22349016.

3. Chaidos A, Barnes C P, Cowan G, May P C, Melo V, Hatjiharissi E, Papaioannou M, Harrington H, Doolittle H, Terpos E, Dimopoulos M, Abdalla S, Yarranton H, Naresh K, Foroni L, Reid A, Rahemtulla A, Stumpf M, Roberts I, Karadimitris A. Clinical drug resistance linked to interconvertible phenotypic and functional states of tumor-propagating cells in multiple myeloma. Blood. 2013; 121(2):318-28. Epub 2012/11/22. doi: 10.1182/blood-2012-06-436220. PubMed PMID: 23169779.
4. Sadelain M, Brentjens R, Riviere I. The basic principles of chimeric antigen receptor design. Cancer discovery. 2013; 3(4):388-98. Epub 2013/04/04. doi: 10.1158/2159-8290.CD-12-0548. PubMed PMID: 23550147; PubMed Central PMCID: PMC3667586.
5. Porter D L, Levine B L, Kalos M, Bagg A, June C H. Chimeric antigen receptor-modified T cells in chronic lymphoid leukemia. N Engl J Med. 2011; 365(8):725-33. Epub 2011/08/13. doi: 10.1056/NEJMoa1 103849. PubMed PMID: 21830940; PubMed Central PMCID: PMC3387277.
6. Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med. 2013; 368(16):1509-18. Epub 2013/03/27. doi: 10.1056/NEJMoa1215134. PubMed PMID: 23527958; PubMed Central PMCID: PMC4058440.
7. clinicaltrials.gov/2014.
8. Garfall A L, Maus M V, Hwang W T, Lacey S F, Mahnke Y D, Melenhorst J J, Zheng Z, Vogl D T, Cohen A D, Weiss B M, Dengel K, Kerr N D, Bagg A, Levine B L, June C H, Stadtmauer E A. Chimeric Antigen Receptor T Cells against CD19 for Multiple Myeloma. The New England journal of medicine. 2015; 373(11):1040-7. Epub 2015/09/10. doi: 10.1056/NEJMoa1504542. PubMed PMID: 26352815; PubMed Central PMCID: PMC4646711.
9. Novak A J, Darce J R, Arendt B K, Harder B, Henderson K, Kindsvogel W, Gross J A, Greipp P R, Jelinek D F. Expression of BCMA, TACI, and BAFF-R in multiple myeloma: a mechanism for growth and survival. Blood. 2004; 103(2):689-94. doi: 10.1182/blood-2003-06-2043. PubMed PMID: 14512299.
10. Engel P, Eck M J, Terhorst C. The SAP and SLAM families in immune responses and X-linked lymphoproliferative disease. Nature reviews Immunology. 2003; 3(10):813-21. Epub 2003/10/03. doi: 10.1038/nri1202. PubMed PMID: 14523387.
11. Lonial S, Dimopoulos M, Palumbo A, White D, Grosicki S, Spicka I, Walter-Croneck A, Moreau P, Mateos M V, Magen H, Belch A, Reece D, Beksac M, Spencer A, Oakervee H, Orlowski R Z, Taniwaki M, Rollig C, Einsele H, Wu K L, Singhal A, San-Miguel J, Matsumoto M, Katz J, Bleickardt E, Poulart V, Anderson K C, Richardson P, Investigators E-. Elotuzumab Therapy for Relapsed or Refractory Multiple Myeloma. The New England journal of medicine. 2015; 373(7):621-31. Epub 2015/06/03. doi: 10.1056/NEJMoa1505654. PubMed PMID: 26035255.
12. Atanackovic D, Panse J, Hildebrandt Y, Jadczak A, Kobold S, Cao Y, Templin J, Meyer S, Reinhard H, Bartels K, Lajmi N, Zander A R, Marx A H, Bokemeyer C, Kroger N. Surface molecule CD229 as a novel target for the diagnosis and treatment of multiple myeloma. Haematologica. 2011; 96(10):1512-20. Epub 2011/05/25. doi: 10.3324/haematol.2010.036814. PubMed PMID: 21606160; PubMed Central PMCID: PMC3186313.
13. Yousef S, Kovacsovics-Bankowski M, Salama M E, Bhardwaj N, Steinbach M, Langemo A, Kovacsovics T, Marvin J, Binder M, Panse J, Kroger N, Luetkens T, Atanackovic D. CD229 is expressed on the surface of plasma cells carrying an aberrant phenotype and chemotherapy-resistant precursor cells in multiple myeloma. Hum Vaccin Immunother. 2015; 11(7):1606-11. Epub 2015/05/23. doi: 10.1080/21645515.2015.1046658. PubMed PMID: 26001047.
14. Schofield D J, Pope A R, Clementel V, Buckell J, Chapple S, Clarke K F, Conquer J S, Crofts A M, Crowther S R, Dyson M R, Flack G, Griffin G J, Hooks Y, Howat W J, Kolb-Kokocinski A, Kunze S, Martin C D, Maslen G L, Mitchell J N, O'Sullivan M, Perera R L, Roake W, Shadbolt S P, Vincent K J, Warford A, Wilson W E, Xie J, Young J L, McCafferty J. Application of phage display to high throughput antibody generation and characterization. Genome biology. 2007; 8(11):R254. Epub 2007/12/01. doi: 10.1186/gb-2007-8-11-r254. PubMed PMID: 18047641; PubMed Central PMCID: PMC2258204.
15. Chu J, Deng Y, Benson D M, He S, Hughes T, Zhang J, Peng Y, Mao H, Yi L, Ghoshal K, He X, Devine S M, Zhang X, Caligiuri M A, Hofmeister C C, Yu J. CS1-specific chimeric antigen receptor (CAR)-engineered natural killer cells enhance in vitro and in vivo antitumor activity against human multiple myeloma. Leukemia. 2014; 28(4):917-27. Epub 2013/09/27. doi: 10.1038/leu.2013.279. PubMed PMID: 24067492; PubMed Central PMCID: PMC3967004.
16. Mamonkin M, Rouce R H, Tashiro H, Brenner M K. A T-cell-directed chimeric antigen receptor for the selective treatment of T-cell malignancies. Blood. 2015; 126(8):983-92. Epub 2015/06/10. doi: 10.1182/blood-2015-02-629527. PubMed PMID: 26056165; PubMed Central PMCID: PMC4543231.
17. Chu J, He S, Deng Y, Zhang J, Peng Y, Hughes T, Yi L, Kwon C H, Wang Q E, Devine S M, He X, Bai X F, Hofmeister C C, Yu J. Genetic modification of T cells redirected toward CS1 enhances eradication of myeloma cells. Clinical cancer research: an official journal of the American Association for Cancer Research. 2014; 20(15):3989-4000. Epub 2014/03/29. doi: 10.1158/1078-0432.CCR-13-2510. PubMed PMID: 24677374; PubMed Central PMCID: PMC4119545.

We claim:

1. A chimeric antigen receptor (CAR) polypeptide, comprising a CD229 antigen binding domain, a transmembrane domain, and an intracellular signaling domain, wherein the CD229 antigen binding domain comprises an amino acid sequence set forth in SEQ ID NO:14.

2. The CAR polypeptide of claim 1, wherein the intracellular signaling domain comprises a co-stimulatory signaling region.

3. The CAR polypeptide of claim 2, wherein the co-stimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

4. The CAR polypeptide of claim 1, wherein the intracellular signaling domain is a T cell signaling domain.

5. The CAR polypeptide of claim 1, wherein the intracellular signaling domain comprises a CD3 zeta (CD3) signaling domain.

6. The CAR polypeptide of claim 1, wherein the intracellular signaling domain comprises a CD3t signaling domain and a co-stimulatory signaling region, wherein the co-stimulatory signaling region comprises the cytoplasmic domain of CD28 or 4-1BB.

7. The CAR polypeptide of claim 1, wherein the CD229 antigen binding domain comprises a heavy chain immunoglobulin variable region comprising:

a. a complementarity determining region 1 (CDR1) comprising the sequence of SEQ ID NO:83;
b. a CDR2 comprising the sequence of SEQ ID NO:84; and
c. a CDR3 comprising the sequence of SEQ ID NO:85.

8. The CAR polypeptide of claim 1, wherein the CD229 antigen binding domain comprises a light chain immunoglobulin variable region comprising:

a. a complementarity determining region 1 (CDR1) comprising the sequence of SEQ ID NO:115;
b. a CDR2 comprising the sequence of AAS; and
c. a CDR3 comprising the sequence of SEQ ID NO:116.

9. The CAR polypeptide of claim 1, wherein the transmembrane domain comprises an immunoglobulin Fc domain.

10. The CAR polypeptide of claim 9, wherein the immunoglobulin Fc domain is an immunoglobulin G Fc domain.

11. The CAR polypeptide of claim 1, wherein the transmembrane domain comprises a CD8α domain, CD3ζ, FcεR1γ, CD4, CD7, CD28, OX40, or H2-Kb.

12. The CAR polypeptide of claim 1 further comprising a tag sequence.

13. The CAR polypeptide of claim 12, wherein the tag sequence is located between the CD229 antigen binding domain and the transmembrane domain.

14. The CAR polypeptide of claim 12, wherein the tag sequence is a hemagglutinin tag.

15. The CAR polypeptide of claim 1 further comprising a hinge region.

16. The CAR polypeptide of claim 1, further comprising a tag sequence and a hinge region, wherein the hinge region is located between the tag sequence and the transmembrane domain.

17. A kit comprising the CAR polypeptide of claim 1.

18. A method of killing CD229 positive cells comprising administering an effective amount of a T cell genetically modified to express the CAR polypeptide of claim 1 to a sample comprising CD229 positive cells.

19. A method of making a cell comprising transducing a T cell with a vector comprising a nucleic acid sequence encoding the CAR polypeptide of claim 1.

20. A method of activating a T cell of claim expressing the CAR polypeptide of claim 1 comprising culturing the T cell with a cell expressing CD229 and detecting the presence or absence of IFN-γ after culturing, wherein the presence of IFN-γ indicates the activation of the T cell.

\* \* \* \* \*

SEQUENCE LISTING

```
<160> NUMBER OF SEQ ID NOS: 358

<210> SEQ ID NO 1
<211> LENGTH: 246
<212> TYPE: PRT
<213> ORGANISM: Artificial Sequence
<220> FEATURE:
```

-continued

<223> OTHER INFORMATION: Synthetic construct; CD229 antigen binding
      domains

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Ala Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Trp Asn Asp Pro His Met Val Asp Tyr Trp Gly
            100                 105                 110

Gln Gly Thr Leu Val Thr Val Ser Ser Leu Glu Gly Gly Gly Gly Ser
        115                 120                 125

Gly Gly Gly Gly Ser Gly Gly Ala Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Ser Ile Gly Ser Ser Leu His Trp Tyr Gln Gln
                165                 170                 175

Lys Pro Gly Lys Ala Pro Lys Phe Leu Ile Tyr Asp Ala Ser Ser Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Tyr Asn Ser Tyr Pro Leu Thr Phe Gly Gly Gly Thr
225                 230                 235                 240

Lys Leu Glu Ile Lys Arg
                245

<210> SEQ ID NO 2
<211> LENGTH: 250
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 2

Gln Met Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Ala Asp Met Glu Leu Arg Asp Tyr Tyr Gly Met Asp Val Trp
            100                 105                 110

Gly Gln Gly Thr Leu Val Thr Val Ser Ser Leu Glu Gly Gly Gly
            115                 120                 125

Ser Gly Gly Gly Gly Ser Gly Gly Ala Ser Gln Ser Gly Leu Thr
            130                 135             140

Gln Pro Arg Ser Val Ser Gly Ser Pro Gly Gln Ser Val Thr Ile Ser
145                 150                 155                 160

Cys Thr Gly Thr Ser Ser Asp Val Gly Gly Tyr Asn Tyr Val Ser Trp
                165                 170                 175

Tyr Gln Gln His Pro Gly Lys Ala Pro Lys Leu Met Ile Tyr Asp Val
                180                 185                 190

Ser Lys Arg Pro Ser Gly Val Pro Asp Arg Phe Ser Gly Ser Lys Ser
                195                 200                 205

Gly Asn Thr Ala Ser Leu Thr Val Ser Gly Leu Gln Ala Glu Asp Glu
            210                 215                 220

Ala Asp Tyr Tyr Cys Ser Ser Tyr Ala Gly Ser Asn Thr Phe Val Phe
225                 230                 235                 240

Gly Ser Gly Thr Lys Leu Thr Val Leu Gly
                245                 250

<210> SEQ ID NO 3
<211> LENGTH: 246
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 3

Gln Val Gln Leu Leu Glu Ser Gly Gly Gly Val Ala Gln Pro Gly Arg
1               5                   10                  15

Ser Leu Lys Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Cys Thr Asn Gly Val Cys Tyr Pro Asp Tyr Trp Gly
            100                 105                 110

Gln Gly Thr Leu Val Thr Val Ser Ser Leu Glu Gly Gly Gly Gly Ser
            115                 120                 125

Gly Gly Gly Gly Ser Gly Gly Ala Ser Asp Ile Val Met Thr Gln
            130                 135             140

Ser Pro Ala Thr Leu Ser Val Pro Gly Glu Arg Ala Thr Leu Ser
145                 150                 155                 160

Cys Arg Ala Ser Gln Ser Val Gly Ser Ser Leu Ala Trp Tyr Gln Gln
                165                 170                 175

Lys Pro Gly Gln Ala Pro Arg Leu Leu Ile Tyr Gly Gly Ser Val Arg
                180                 185                 190
```

Ala Thr Gly Ile Pro Ala Arg Phe Ser Gly Ser Gly Ser Gly Thr Glu
            195                 200                 205

Phe Thr Leu Thr Ile Ser Ser Leu Gln Ser Glu Asp Phe Ala Ala Tyr
        210                 215                 220

Tyr Cys Gln Gln Tyr Asn Ser Tyr Pro Leu Thr Phe Gly Gly Gly Thr
225                 230                 235                 240

Lys Leu Glu Ile Lys Arg
                245

<210> SEQ ID NO 4
<211> LENGTH: 250
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Thr Val Tyr Tyr Cys
                85                  90                  95

Ala Arg Ser Pro Ser Thr Val Val Thr Pro Phe Ser Asp Tyr Trp Gly
            100                 105                 110

Gln Gly Thr Leu Val Thr Val Ser Ser Leu Glu Gly Gly Gly Gly Ser
        115                 120                 125

Gly Gly Gly Gly Ser Gly Gly Ala Ser Asn Phe Met Leu Thr Gln
    130                 135                 140

Pro His Ser Val Ser Glu Ser Pro Gly Lys Thr Val Thr Ile Ser Cys
145                 150                 155                 160

Thr Gly Ser Ser Gly Ser Ile Ala Ser Asn Tyr Val Gln Trp Tyr Gln
                165                 170                 175

Gln Arg Pro Gly Ser Ser Pro Thr Thr Val Ile Tyr Glu Asp Asn Gln
            180                 185                 190

Arg Pro Ser Gly Val Pro Asp Arg Phe Ser Gly Ser Ile Asp Ser Ser
        195                 200                 205

Ser Asn Ser Ala Ser Leu Thr Ile Ser Gly Leu Lys Thr Glu Asp Glu
    210                 215                 220

Ala Asp Tyr Tyr Cys Gln Ser Tyr Asp Gly Ser Asn Pro Val Val Phe
225                 230                 235                 240

Gly Gly Gly Thr Gln Leu Thr Val Leu Gly
                245                 250

<210> SEQ ID NO 5
<211> LENGTH: 244
<212> TYPE: PRT
<213> ORGANISM: Artificial Sequence
<220> FEATURE:

<223> OTHER INFORMATION: Synthetic construct; CD229 antigen binding
       domains

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Arg His Gly Gly Thr Asn Ala Phe Asp Ile Trp Gly Gln Gly
            100                 105                 110

Thr Met Val Thr Val Ser Ser Leu Glu Gly Gly Gly Ser Gly Gly
        115                 120                 125

Gly Gly Ser Gly Gly Gly Ala Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
210                 215                 220

Gln Gln Ser Tyr Ser Thr Leu Tyr Thr Phe Gly Gln Gly Thr Lys Leu
225                 230                 235                 240

Glu Ile Lys Arg

<210> SEQ ID NO 6
<211> LENGTH: 242
<212> TYPE: PRT
<213> ORGANISM: Artificial Sequence
<220> FEATURE:
<223> OTHER INFORMATION: Synthetic construct; CD229 antigen binding
       domains

<400> SEQUENCE: 6

Gln Ile Thr Leu Lys Glu Ser Gly Pro Thr Leu Val Lys Pro Thr Glu
1               5                   10                  15

Thr Leu Thr Leu Thr Cys Thr Phe Ser Gly Phe Ser Leu Asn Thr Gly
            20                  25                  30

Gly Val Ser Val Gly Trp Val Arg Gln Thr Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

```
Val Leu Thr Met Thr Asn Met Asp Thr Val Asp Thr Ala Thr Tyr Tyr
                85                  90                  95

Cys Ala His Ser Ala Ala Gly Val Asp Tyr Trp Gly Gln Gly Thr Leu
           100                 105                 110

Val Thr Val Ser Ser Leu Glu Gly Gly Gly Ser Gly Gly Gly Gly
       115                 120                 125

Ser Gly Gly Gly Ala Ser Asp Ile Gln Met Thr Gln Ser Pro Ser Ser
130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
               165                 170                 175

Ala Pro Lys Leu Leu Ile Tyr Asp Ala Ser Asn Leu Glu Thr Gly Val
           180                 185                 190

Pro Ser Arg Phe Ser Gly Ser Gly Ser Gly Thr Asp Phe Thr Phe Thr
           195                 200                 205

Ile Ser Ser Leu Gln Pro Glu Asp Ile Ala Thr Tyr Tyr Cys Gln Gln
       210                 215                 220

Tyr Asp Asn Leu Pro Ile Thr Phe Gly Pro Gly Thr Lys Val Asp Ile
225                 230                 235                 240

Lys Arg

<210> SEQ ID NO 7
<211> LENGTH: 246
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 7

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Leu Arg Gln Ala Pro Gly Gln Asp Leu Glu Trp Met
        35                  40                  45

Gly Trp Ile Asp Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Trp Asn Tyr Glu Leu Asp Tyr Trp Gly Gln Gly Thr Leu
            100                 105                 110

Val Thr Val Ser Ser Leu Glu Gly Gly Gly Ser Gly Gly Gly Gly
        115                 120                 125

Ser Gly Gly Gly Ala Ser Asn Phe Met Leu Thr Gln Pro His Ser Val
130                 135                 140

Ser Gly Ser Pro Gly Lys Thr Val Thr Ile Ser Cys Thr Arg Ser Ser
145                 150                 155                 160

Gly Tyr Ile Ala Ser Asn Tyr Val Gln Trp Tyr Gln Gln Arg Pro Gly
                165                 170                 175

Ser Ala Pro Thr Thr Val Ile Tyr Glu Asp Asn Gln Arg Pro Ser Gly
            180                 185                 190
```

Val Pro Asp Arg Phe Ser Gly Ser Ile Asp Ser Ser Asn Ser Ala
            195                 200                 205

Ser Leu Thr Ile Ser Gly Leu Lys Thr Glu Asp Glu Ala Asp Tyr Tyr
            210                 215                 220

Cys Gln Ser Tyr Asp Ser Ser Asn Gln Gly Val Phe Gly Gly Gly Thr
225                 230                 235                 240

Lys Leu Thr Val Leu Val
                245

<210> SEQ ID NO 8
<211> LENGTH: 245
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 8

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Leu Arg Gln Ala Pro Gly Gln Asp Leu Glu Trp Met
            35                  40                  45

Gly Trp Ile Asp Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Asn Tyr Glu Leu Asp Tyr Trp Gly Gln Gly Thr Leu
            100                 105                 110

Val Thr Val Ser Ser Leu Glu Gly Gly Gly Ser Gly Gly Gly Gly
            115                 120                 125

Ser Gly Gly Gly Ala Ser Asn Phe Met Leu Thr Gln Pro His Ser Val
        130                 135                 140

Ser Gly Ser Pro Gly Lys Thr Val Thr Ile Ser Cys Thr Arg Ser Ser
145                 150                 155                 160

Gly Tyr Ile Ala Ser Asn Tyr Val Gln Trp Tyr Gln Gln Arg Pro Gly
                165                 170                 175

Ser Ser Pro Thr Thr Leu Ile Tyr Asp Asp Asp Gln Arg Pro Ser Gly
            180                 185                 190

Val Pro Asp Arg Phe Ser Gly Ser Ile Asp Arg Ser Asn Ser Ala
            195                 200                 205

Ser Leu Thr Ile Ser Gly Leu Lys Thr Glu Asp Glu Gly Asp Tyr Tyr
            210                 215                 220

Cys Gln Ser Tyr Asp Ser Ser Leu Val Ile Phe Gly Gly Gly Thr Lys
225                 230                 235                 240

Val Thr Val Leu Gly
                245

<210> SEQ ID NO 9
<211> LENGTH: 247
<212> TYPE: PRT
<213> ORGANISM: Artificial Sequence
<220> FEATURE:

<223> OTHER INFORMATION: Synthetic construct; CD229 antigen binding
      domains

<400> SEQUENCE: 9

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ile Ser Ser Gly Gly Thr Glu Val Gln Asp Tyr Trp
            100                 105                 110

Gly Gln Gly Thr Leu Val Thr Val Ser Ser Leu Glu Gly Gly Gly Gly
        115                 120                 125

Ser Gly Gly Gly Gly Ser Gly Gly Ala Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Gly Ser Ser Leu His Trp Tyr Gln
            165                 170                 175

Gln Lys Pro Gly Lys Ala Pro Lys Phe Leu Ile Tyr Asp Ala Ser Ser
        180                 185                 190

Leu Glu Ser Gly Val Pro Ser Arg Phe Ser Gly Ser Gly Ser Gly Thr
    195                 200                 205

Glu Phe Thr Leu Thr Ile Ser Ser Leu Gln Pro Asp Asp Cys Ala Thr
    210                 215                 220

Tyr Tyr Cys Gln Gln Tyr Asn Ser Tyr Pro Leu Thr Phe Gly Gly Gly
225                 230                 235                 240

Thr Lys Leu Glu Ile Lys Arg
                245

<210> SEQ ID NO 10
<211> LENGTH: 251
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 10

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

```
Met Glu Leu Ser Ser Leu Arg Ser Asp Asp Thr Ala Val Tyr Tyr Cys
            85                  90                  95

Ala Arg Asp Glu Leu Trp Ala Thr Asn Tyr Tyr Met Asp Val Trp
        100                 105                 110

Gly Lys Gly Thr Leu Val Thr Val Ser Ser Leu Glu Gly Gly Gly
        115                 120                 125

Ser Gly Gly Gly Gly Ser Gly Gly Ala Ser Gln Ser Ala Leu Thr
        130                 135                 140

Gln Pro Arg Ser Val Ser Gly Ser Pro Gly Gln Ser Val Thr Ile Ser
145                 150                 155                 160

Cys Thr Gly Thr Ser Ser Asp Val Gly Ser Tyr Asn Tyr Val Ser Trp
                    165                 170                 175

Tyr Gln Gln Ser Pro Gly Lys Ala Pro Lys Leu Met Ile Tyr Asp Val
                    180                 185                 190

Ser Asn Arg Pro Ser Gly Val Ser Asn Arg Phe Ser Gly Ser Lys Ser
                    195                 200                 205

Gly Asn Thr Ala Ser Leu Thr Ile Ser Gly Leu Gln Ser Glu Asp Glu
                    210                 215                 220

Ala Asp Tyr Tyr Cys Thr Ser Tyr Gly Ser Tyr Asp Ile Pro Val Ile
225                 230                 235                 240

Phe Gly Gly Gly Thr Lys Leu Thr Val Leu Gly
                    245                 250

<210> SEQ ID NO 11
<211> LENGTH: 246
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 11

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Tyr Ile His Trp Leu Arg Gln Ala Pro Gly Gln Asp Leu Glu Trp Met
            35                  40                  45

Gly Trp Ile Asp Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Asn Tyr Glu Leu Asp Tyr Trp Gly Arg Gly Thr Leu
            100                 105                 110

Val Thr Val Ser Pro Leu Glu Gly Gly Gly Ser Gly Gly Gly Gly
        115                 120                 125

Ser Gly Gly Gly Ala Ser Asn Phe Met Leu Thr Gln Pro His Ser Val
        130                 135                 140

Ser Gly Ser Pro Gly Lys Ala Val Thr Ile Ser Cys Thr Arg Ser Ser
145                 150                 155                 160

Gly Asn Ile Ala Arg Ser Phe Val Gln Trp Tyr Gln Gln Arg Pro Gly
                    165                 170                 175

Ser Ala Pro Thr Ala Val Ile Tyr Glu Asp Asn Arg Arg Pro Ser Gly
                    180                 185                 190
```

Val Pro Asp Arg Phe Ser Gly Ser Phe Asp Ser Ser Ser Asn Ser Ala
        195                 200                 205

Ser Leu Thr Ile Ser Gly Leu Lys Thr Glu Asp Glu Ala Asp Tyr Tyr
        210                 215                 220

Cys Gln Ser Tyr Asp Ser Ser Asn His Val Val Phe Gly Gly Gly Thr
225             230                 235                 240

Lys Val Thr Val Leu Gly
            245

<210> SEQ ID NO 12
<211> LENGTH: 245
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 12

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Leu Arg Gln Ala Pro Gly Gln Asp Leu Glu Trp Met
        35                  40                  45

Gly Trp Ile Asp Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Asn Tyr Glu Leu Asp Tyr Trp Gly Gln Gly Thr Leu
            100                 105                 110

Val Thr Val Ser Ser Leu Glu Gly Gly Gly Ser Gly Gly Gly Gly
        115                 120                 125

Ser Gly Gly Gly Ala Ser Asn Phe Met Leu Thr Gln Pro His Ser Val
    130                 135                 140

Ser Gly Ser Pro Gly Lys Thr Val Thr Ile Ser Cys Thr Arg Ser Ser
145                 150                 155                 160

Gly Tyr Ile Ala Ser Asn Tyr Val Gln Trp Tyr Gln Gln Arg Pro Gly
            165                 170                 175

Ser Ser Pro Thr Thr Leu Ile Tyr Asp Asp Asp Gln Arg Pro Ser Gly
        180                 185                 190

Val Pro Asp Arg Phe Ser Gly Ser Ile Asp Arg Ser Asn Ser Ala
        195                 200                 205

Ser Leu Thr Ile Ser Gly Leu Lys Thr Glu Asp Glu Gly Asp Tyr Tyr
        210                 215                 220

Cys Gln Ser Tyr Asp Ser Thr Thr Glu Val Phe Gly Thr Gly Thr Lys
225             230                 235                 240

Leu Thr Val Leu Gly
            245

<210> SEQ ID NO 13
<211> LENGTH: 249
<212> TYPE: PRT
<213> ORGANISM: Artificial Sequence
<220> FEATURE:

<223> OTHER INFORMATION: Synthetic construct; CD229 antigen binding
      domains

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ala Lys Pro Tyr Ser Ser Asp Phe Asp Ile Trp Gly Gln
            100                 105                 110

Gly Thr Met Val Thr Val Ser Ser Leu Glu Gly Gly Gly Ser Gly
        115                 120                 125

Gly Gly Gly Ser Gly Gly Ala Ser Asn Phe Met Leu Thr Gln Pro
    130                 135                 140

His Ser Val Ser Glu Ser Pro Gly Lys Thr Val Thr Ile Ser Cys Thr
145                 150                 155                 160

Gly Ser Ser Gly Ser Ile Ala Ser Asn Tyr Val Gln Trp Tyr Gln Gln
                165                 170                 175

Arg Pro Gly Ser Ser Pro Thr Thr Val Ile Tyr Glu Asp Asn Gln Arg
            180                 185                 190

Pro Ser Gly Val Pro Asp Arg Phe Ser Gly Ser Ile Asp Ser Ser Ser
        195                 200                 205

Asn Ser Ala Ser Leu Thr Ile Ser Gly Leu Lys Thr Glu Asp Glu Ala
    210                 215                 220

Asp Tyr Tyr Cys Gln Ser Tyr Asp Ser Ser Asn Gln Gly Val Phe Gly
225                 230                 235                 240

Gly Gly Thr Gln Leu Thr Val Leu Gly
                245

<210> SEQ ID NO 14
<211> LENGTH: 243
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 14

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Ala
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Arg Gly Asn Ser Asn Ser Phe Asp Tyr Trp Gly Gln Gly Thr
            100                 105                 110

Leu Val Thr Val Ser Ser Leu Glu Gly Gly Gly Ser Gly Gly Gly
            115                 120                 125

Gly Ser Gly Gly Gly Ala Ser Asp Ile Gln Met Thr Gln Ser Pro Ser
        130                 135                 140

Ser Val Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys Arg

<210> SEQ ID NO 15
<211> LENGTH: 245
<212> TYPE: PRT
<213> ORGANISM: Artificial Sequence
<220> FEATURE:
<223> OTHER INFORMATION: Synthetic construct; CD229 antigen binding
      domains

<400> SEQUENCE: 15

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ala Lys Pro Tyr Ser Ser Asp Phe Asp Ile Trp Gly Gln
            100                 105                 110

Gly Thr Met Val Thr Val Ser Ser Leu Glu Gly Gly Gly Ser Gly
        115                 120                 125

Gly Gly Gly Ser Gly Gly Gly Ala Ser Asp Ile Gln Met Thr Gln Ser
    130                 135                 140

Pro Ser Ser Leu Ser Ala Ser Val Gly Asp Arg Val Thr Ile Ser Cys
145                 150                 155                 160

Gln Ala Ser Gln Asp Ile Ser Asn Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190
```

-continued

```
Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Leu Gln Asp Tyr Asn Tyr Pro Trp Thr Phe Gly Gln Gly Thr Lys
225                 230                 235                 240

Val Glu Ile Lys Arg
                245

<210> SEQ ID NO 16
<211> LENGTH: 121
<212> TYPE: PRT
<213> ORGANISM: Artificial Sequence
<220> FEATURE:
<223> OTHER INFORMATION: Synthetic construct; Variable Heavy Chain

<400> SEQUENCE: 16

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Ala Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Trp Asn Asp Pro His Met Val Asp Tyr Trp Gly
            100                 105                 110

Gln Gly Thr Leu Val Thr Val Ser Ser
        115                 120

<210> SEQ ID NO 17
<211> LENGTH: 122
<212> TYPE: PRT
<213> ORGANISM: Artificial Sequence
<220> FEATURE:
<223> OTHER INFORMATION: Synthetic construct; Variable Heavy Chain

<400> SEQUENCE: 17

Gln Met Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Asp Met Glu Leu Arg Asp Tyr Tyr Tyr Gly Met Asp Val Trp
            100                 105                 110

Gly Gln Gly Thr Leu Val Thr Val Ser Ser
        115                 120
```

<210> SEQ ID NO 18
<211> LENGTH: 121
<212> TYPE: PRT
<213> ORGANISM: Artificial Sequence
<220> FEATURE:
<223> OTHER INFORMATION: Synthetic construct; Variable Heavy Chain

<400> SEQUENCE: 18

Gln Val Gln Leu Leu Glu Ser Gly Gly Val Ala Gln Pro Gly Arg
1               5                   10                  15

Ser Leu Lys Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Cys Thr Asn Gly Val Cys Tyr Pro Asp Tyr Trp Gly
            100                 105                 110

Gln Gly Thr Leu Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic construct; Variable Heavy Chain

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Val Tyr Tyr Cys
                85                  90                  95

Ala Arg Ser Pro Ser Thr Val Val Thr Pro Phe Ser Asp Tyr Trp Gly
            100                 105                 110

Gln Gly Thr Leu Val Thr Val Ser Ser
        115                 120

<210> SEQ ID NO 20
<211> LENGTH: 119
<212> TYPE: PRT
<213> ORGANISM: Artificial Sequence
<220> FEATURE:
<223> OTHER INFORMATION: Synthetic construct; Variable Heavy Chain

<400> SEQUENCE: 20

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Arg His Gly Gly Thr Asn Ala Phe Asp Ile Trp Gly Gln Gly
            100                 105                 110

Thr Met Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: Synthetic construct; Variable Heavy Chain

<400> SEQUENCE: 21

Gln Ile Thr Leu Lys Glu Ser Gly Pro Thr Leu Val Lys Pro Thr Glu
1               5                   10                  15

Thr Leu Thr Leu Thr Cys Thr Phe Ser Gly Phe Ser Leu Asn Thr Gly
            20                  25                  30

Gly Val Ser Val Gly Trp Val Arg Gln Thr Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Thr Val Asp Thr Ala Thr Tyr Tyr
                85                  90                  95

Cys Ala His Ser Ala Ala Gly Val Asp Tyr Trp Gly Gln Gly Thr Leu
            100                 105                 110

Val Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: Synthetic construct; Variable Heavy Chain

<400> SEQUENCE: 22

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Leu Arg Gln Ala Pro Gly Gln Asp Leu Glu Trp Met
        35                  40                  45

Gly Trp Ile Asp Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Trp Asn Tyr Glu Leu Asp Tyr Trp Gly Gln Gly Thr Leu
                100                 105                 110

Val Thr Val Ser Ser
        115

<210> SEQ ID NO 23
<211> LENGTH: 117
<212> TYPE: PRT
<213> ORGANISM: Artificial Sequence
<220> FEATURE:
<223> OTHER INFORMATION: Synthetic construct; Variable Heavy Chain

<400> SEQUENCE: 23

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Tyr Ile His Trp Leu Arg Gln Ala Pro Gly Gln Asp Leu Glu Trp Met
        35                  40                  45

Gly Trp Ile Asp Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Asn Tyr Glu Leu Asp Tyr Trp Gly Gln Gly Thr Leu
                100                 105                 110

Val Thr Val Ser Ser
        115

<210> SEQ ID NO 24
<211> LENGTH: 122
<212> TYPE: PRT
<213> ORGANISM: Artificial Sequence
<220> FEATURE:
<223> OTHER INFORMATION: Synthetic construct; Variable Heavy Chain

<400> SEQUENCE: 24

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

```
Cys Ala His Ile Ser Ser Gly Gly Thr Glu Val Gln Asp Tyr Trp
            100                 105                 110
Gly Gln Gly Thr Leu Val Thr Val Ser Ser
        115                 120
```

<210> SEQ ID NO 25
<211> LENGTH: 122
<212> TYPE: PRT
<213> ORGANISM: Artificial Sequence
<220> FEATURE:
<223> OTHER INFORMATION: Synthetic construct; Variable Heavy Chain

<400> SEQUENCE: 25

```
Gln Met Gln Leu Val Gln Ser Gly Ala Glu Val Lys Lys Pro Gly Ser
1               5                   10                  15
Ser Val Lys Val Ser Cys Lys Ala Ser Gly Thr Phe Ser Ser Tyr
            20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Asp Asp Thr Ala Val Tyr Tyr Cys
                85                  90                  95
Ala Arg Asp Glu Leu Trp Ala Thr Asn Tyr Tyr Tyr Met Asp Val Trp
            100                 105                 110
Gly Lys Gly Thr Leu Val Thr Val Ser Ser
        115                 120
```

<210> SEQ ID NO 26
<211> LENGTH: 117
<212> TYPE: PRT
<213> ORGANISM: Artificial Sequence
<220> FEATURE:
<223> OTHER INFORMATION: Synthetic construct; Variable Heavy Chain

<400> SEQUENCE: 26

```
Gln Val Gln Leu Val Glu Ser Gly Ala Glu Val Lys Lys Pro Gly Ala
1               5                   10                  15
Ser Val Lys Val Ser Cys Lys Ala Ser Gly Tyr Thr Phe Thr Ala Tyr
            20                  25                  30
Tyr Ile His Trp Leu Arg Gln Ala Pro Gly Gln Asp Leu Glu Trp Met
            35                  40                  45
Gly Trp Ile Asp Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp Trp Asn Tyr Glu Leu Asp Tyr Trp Gly Arg Gly Thr Leu
            100                 105                 110
Val Thr Val Ser Pro
        115
```

<210> SEQ ID NO 27
<211> LENGTH: 117
<212> TYPE: PRT

<213> ORGANISM: Artificial Sequence
<220> FEATURE:
<223> OTHER INFORMATION: Synthetic construct; Variable Heavy Chain

<400> SEQUENCE: 27

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Tyr Ile His Trp Leu Arg Gln Ala Pro Gly Gln Asp Leu Glu Trp Met
            35                  40                  45

Gly Trp Ile Asp Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Trp Asn Tyr Glu Leu Asp Tyr Trp Gly Gln Gly Thr Leu
            100                 105                 110

Val Thr Val Ser Ser
        115

<210> SEQ ID NO 28
<211> LENGTH: 120
<212> TYPE: PRT
<213> ORGANISM: Artificial Sequence
<220> FEATURE:
<223> OTHER INFORMATION: Synthetic construct; Variable Heavy Chain

<400> SEQUENCE: 28

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ala Lys Pro Tyr Ser Ser Asp Phe Asp Ile Trp Gly Gln
            100                 105                 110

Gly Thr Met Val Thr Val Ser Ser
        115                 120

<210> SEQ ID NO 29
<211> LENGTH: 118
<212> TYPE: PRT
<213> ORGANISM: Artificial Sequence
<220> FEATURE:
<223> OTHER INFORMATION: Synthetic construct; Variable Heavy Chain

<400> SEQUENCE: 29

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Asn Ser Asn Ser Phe Asp Tyr Trp Gly Gln Gly Thr
            100                 105                 110

Leu Val Thr Val Ser Ser
            115

<210> SEQ ID NO 30
<211> LENGTH: 120
<212> TYPE: PRT
<213> ORGANISM: Artificial Sequence
<220> FEATURE:
<223> OTHER INFORMATION: Synthetic construct; Variable Heavy Chain

<400> SEQUENCE: 30

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ala Lys Pro Tyr Ser Ser Asp Phe Asp Ile Trp Gly Gln
            100                 105                 110

Gly Thr Met Val Thr Val Ser Ser
            115                 120

<210> SEQ ID NO 31
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Leu Glu Ile Lys Arg
            100                 105

<210> SEQ ID NO 32
<211> LENGTH: 111
<212> TYPE: PRT
<213> ORGANISM: Artificial Sequence
<220> FEATURE:
<223> OTHER INFORMATION: Synthetic construct; Variable Light Chain

<400> SEQUENCE: 32

Gln Ser Gly Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Phe Val Phe Gly Ser Gly Thr Lys Leu Thr Val Leu Gly
                100                 105                 110

<210> SEQ ID NO 33
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 33

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Ser
                20                  25                  30

Leu Ala Trp Tyr Gln Gln Lys Pro Gly Gln Ala Pro Arg Leu Leu Ile
                35                  40                  45

Tyr Gly Gly Ser Val Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Ala Tyr Tyr Cys Gln Gln Tyr Asn Ser Tyr Pro Leu
                85                  90                  95

Thr Phe Gly Gly Gly Thr Lys Leu Glu Ile Lys Arg
            100                 105

<210> SEQ ID NO 34
<211> LENGTH: 112
<212> TYPE: PRT
<213> ORGANISM: Artificial Sequence
<220> FEATURE:
<223> OTHER INFORMATION: Synthetic construct; Variable Light Chain

<400> SEQUENCE: 34

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Ser Asn Pro Val Val Phe Gly Gly Gly Thr Gln Leu Thr Val Leu Gly
            100                 105                 110

<210> SEQ ID NO 35
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Tyr
                85                  90                  95

Thr Phe Gly Gln Gly Thr Lys Leu Glu Ile Lys Arg
            100                 105

<210> SEQ ID NO 36
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
            85                  90                  95

Thr Phe Gly Pro Gly Thr Lys Val Asp Ile Lys Arg
        100                 105

<210> SEQ ID NO 37
<211> LENGTH: 112
<212> TYPE: PRT
<213> ORGANISM: Artificial Sequence
<220> FEATURE:
<223> OTHER INFORMATION: Synthetic construct; Variable Light Chain

<400> SEQUENCE: 37

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Gly Val Phe Gly Gly Gly Thr Lys Leu Thr Val Leu Val
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Synthetic construct; Variable Light Chain

<400> SEQUENCE: 38

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ser Pro Thr Thr Leu
        35                  40                  45

Ile Tyr Asp Asp Asp Gln Arg Pro Ser Gly Val Pro Asp Arg Phe Ser
50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Ser Leu Val Ile Phe Gly Gly Gly Thr Lys Val Thr Val Leu Gly
            100                 105                 110

<210> SEQ ID NO 39
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Cys Ala Thr Tyr Tyr Cys Gln Gln Tyr Asn Ser Tyr Pro Leu
                85                  90                  95

Thr Phe Gly Gly Gly Thr Lys Leu Glu Ile Lys Arg
            100                 105

<210> SEQ ID NO 40
<211> LENGTH: 112
<212> TYPE: PRT
<213> ORGANISM: Artificial Sequence
<220> FEATURE:
<223> OTHER INFORMATION: Synthetic construct; Variable Light Chain

<400> SEQUENCE: 40

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Tyr Val Ser Trp Tyr Gln Gln Ser Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Thr Ser Tyr Gly Ser Tyr
                85                  90                  95

Asp Ile Pro Val Ile Phe Gly Gly Gly Thr Lys Leu Thr Val Leu Gly
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Synthetic construct; Variable Light Chain

<400> SEQUENCE: 41

Asn Phe Met Leu Thr Gln Pro His Ser Val Ser Gly Ser Pro Gly Lys
1               5                   10                  15

Ala Val Thr Ile Ser Cys Thr Arg Ser Ser Gly Asn Ile Ala Arg Ser
            20                  25                  30

Phe Val Gln Trp Tyr Gln Gln Arg Pro Gly Ser Ala Pro Thr Ala Val
        35                  40                  45

Ile Tyr Glu Asp Asn Arg Arg Pro Ser Gly Val Pro Asp Arg Phe Ser
    50                  55                  60

Gly Ser Phe Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Val Phe Gly Gly Gly Thr Lys Val Thr Val Leu Gly
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Synthetic construct; Variable Light Chain

<400> SEQUENCE: 42

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
                20                  25                  30

Tyr Val Gln Trp Tyr Gln Gln Arg Pro Gly Ser Ser Pro Thr Thr Leu
            35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Thr Thr Glu Val Phe Gly Thr Gly Thr Lys Leu Thr Val Leu Gly
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Synthetic construct; Variable Light Chain

<400> SEQUENCE: 43

Asn Phe Met Leu Thr Gln Pro His Ser Val Glu Ser Pro Gly Lys
1               5                   10                  15

Thr Val Thr Ile Ser Cys Thr Gly Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Gly Val Phe Gly Gly Gly Thr Gln Leu Thr Val Leu Gly
            100                 105                 110

<210> SEQ ID NO 44
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 44

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg
            100                 105

<210> SEQ ID NO 45
<211> LENGTH: 108
<212> TYPE: PRT
<213> ORGANISM: Artificial Sequence
<220> FEATURE:
<223> OTHER INFORMATION: Synthetic construct; Variable Light Chain

<400> SEQUENCE: 45

Asp Ile Gln Met Thr Gln Ser Pro Ser Ser Leu Ser Ala Ser Val Gly
1               5                   10                  15

Asp Arg Val Thr Ile Ser Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg
            100                 105

<210> SEQ ID NO 46
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 46

Gly Phe Ser Leu Ser Thr Ser Gly Val Gly
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic construct; CDRs in heavy chain

<400> SEQUENCE: 47

Ile Tyr Trp Asn Asp Asp Lys
1               5

<210> SEQ ID NO 48
<211> LENGTH: 13
<212> TYPE: PRT
<213> ORGANISM: Artificial Sequence
<220> FEATURE:
<223> OTHER INFORMATION: Synthetic construct; CDRs in heavy chain

<400> SEQUENCE: 48

Ala Arg Met Gly Trp Asn Asp Pro His Met Val Asp Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 49

Gly Gly Thr Phe Ser Ser Tyr Ala
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 50

Ile Ile Pro Ile Phe Gly Thr Ala
1               5

<210> SEQ ID NO 51
<211> LENGTH: 15
<212> TYPE: PRT
<213> ORGANISM: Artificial Sequence
<220> FEATURE:
<223> OTHER INFORMATION: Synthetic construct; CDRs in heavy chain

<400> SEQUENCE: 51

Ala Ala Asp Met Glu Leu Arg Asp Tyr Tyr Tyr Gly Met Asp Val
1               5                   10                  15

<210> SEQ ID NO 52
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 52

Gly Phe Thr Phe Ser Ser Tyr Gly
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic construct; CDRs in heavy chain

```
<400> SEQUENCE: 53

Ile Ser Tyr Asp Gly Ser Asn Lys
1               5

<210> SEQ ID NO 54
<211> LENGTH: 14
<212> TYPE: PRT
<213> ORGANISM: Artificial Sequence
<220> FEATURE:
<223> OTHER INFORMATION: Synthetic construct; CDRs in heavy chain

<400> SEQUENCE: 54

Ala Lys Asp Thr Cys Thr Asn Gly Val Cys Tyr Pro Asp Tyr
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 55

Ile Ser Ala Tyr Asn Gly Asn Thr
1               5

<210> SEQ ID NO 56
<211> LENGTH: 14
<212> TYPE: PRT
<213> ORGANISM: Artificial Sequence
<220> FEATURE:
<223> OTHER INFORMATION: Synthetic construct; CDRs in heavy chain

<400> SEQUENCE: 56

Ala Arg Ser Pro Ser Thr Val Val Thr Pro Phe Ser Asp Tyr
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 57

Gly Phe Thr Phe Asp Asp Tyr Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 58

Ile Ser Trp Asn Ser Gly Ser Ile
1               5

<210> SEQ ID NO 59
<211> LENGTH: 12
<212> TYPE: PRT
<213> ORGANISM: Artificial Sequence
<220> FEATURE:
<223> OTHER INFORMATION: Synthetic construct; CDRs in heavy chain
```

<400> SEQUENCE: 59

Ala Lys Arg His Gly Gly Thr Asn Ala Phe Asp Ile
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 60

Gly Phe Ser Leu Asn Thr Gly Gly Val Ser
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic construct; CDRs in heavy chain

<400> SEQUENCE: 61

Ile Tyr Trp Asn Asp Asp Lys
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic construct; CDRs in heavy chain

<400> SEQUENCE: 62

Ala His Ser Ala Ala Gly Val Asp Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 63

Gly Tyr Thr Phe Thr Ala Tyr Tyr
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 64

Ile Asp Pro Asn Ser Gly Gly Thr
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic construct; CDRs in heavy chain

```
<400> SEQUENCE: 65

Ala Arg Gly Trp Asn Tyr Glu Leu Asp Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 66

Gly Tyr Thr Phe Thr Ala Tyr Tyr
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 67

Ile Asp Pro Asn Ser Gly Gly Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 68

Ala Arg Asp Trp Asn Tyr Glu Leu Asp Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 69

Gly Phe Ser Leu Ser Thr Ser Gly Val Gly
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic construct; CDRs in heavy chain

<400> SEQUENCE: 70

Ile Tyr Trp Asn Asp Asp Lys
1               5

<210> SEQ ID NO 71
<211> LENGTH: 14
<212> TYPE: PRT
<213> ORGANISM: Artificial Sequence
<220> FEATURE:
<223> OTHER INFORMATION: Synthetic construct; CDRs in heavy chain
```

<400> SEQUENCE: 71

Ala His Ile Ser Ser Gly Gly Thr Glu Val Gln Asp Tyr
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 72

Ile Ile Pro Ile Phe Gly Thr Ala
1               5

<210> SEQ ID NO 73
<211> LENGTH: 15
<212> TYPE: PRT
<213> ORGANISM: Artificial Sequence
<220> FEATURE:
<223> OTHER INFORMATION: Synthetic construct; CDRs in heavy chain

<400> SEQUENCE: 73

Ala Arg Asp Glu Leu Trp Ala Thr Asn Tyr Tyr Tyr Met Asp Val
1               5                   10                  15

<210> SEQ ID NO 74
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 74

Gly Tyr Thr Phe Thr Ala Tyr Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 75

Ile Asp Pro Asn Ser Gly Gly Thr
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 76

Ala Arg Asp Trp Asn Tyr Glu Leu Asp Tyr
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic construct; CDRs in heavy chain

```
<400> SEQUENCE: 77

Gly Tyr Thr Phe Thr Ala Tyr Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 78

Ile Asp Pro Asn Ser Gly Gly Thr
1               5

<210> SEQ ID NO 79
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 79

Ala Arg Asp Trp Asn Tyr Glu Leu Asp Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 80

Gly Phe Ser Leu Ser Thr Ser Gly Val Gly
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic construct; CDRs in heavy chain

<400> SEQUENCE: 81

Ile Tyr Trp Asn Asp Asp Lys
1               5

<210> SEQ ID NO 82
<211> LENGTH: 12
<212> TYPE: PRT
<213> ORGANISM: Artificial Sequence
<220> FEATURE:
<223> OTHER INFORMATION: Synthetic construct; CDRs in heavy chain

<400> SEQUENCE: 82

Ala Gln Ala Lys Pro Tyr Ser Ser Asp Phe Asp Ile
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Synthetic construct; CDRs in heavy chain
```

```
<400> SEQUENCE: 83

Gly Phe Thr Phe Asp Asp Tyr Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic construct; CDRs in heavy chain

<400> SEQUENCE: 84

Ile Ser Trp Asn Ser Gly Ser Ile
1               5

<210> SEQ ID NO 85
<211> LENGTH: 11
<212> TYPE: PRT
<213> ORGANISM: Artificial Sequence
<220> FEATURE:
<223> OTHER INFORMATION: Synthetic construct; CDRs in heavy chain

<400> SEQUENCE: 85

Ala Lys Arg Gly Asn Ser Asn Ser Phe Asp Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic construct; CDRs in heavy chain

<400> SEQUENCE: 86

Gly Phe Ser Leu Ser Thr Ser Gly Val Gly
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic construct; CDRs in heavy chain

<400> SEQUENCE: 87

Ile Tyr Trp Asn Asp Asp Lys
1               5

<210> SEQ ID NO 88
<211> LENGTH: 12
<212> TYPE: PRT
<213> ORGANISM: Artificial Sequence
<220> FEATURE:
<223> OTHER INFORMATION: Synthetic construct; CDRs in heavy chain

<400> SEQUENCE: 88

Ala Gln Ala Lys Pro Tyr Ser Ser Asp Phe Asp Ile
1               5                   10

<210> SEQ ID NO 89
<211> LENGTH: 6
<212> TYPE: PRT
<213> ORGANISM: Artificial Sequence
<220> FEATURE:
<223> OTHER INFORMATION: Synthetic construct; CDRs in light chain
```

```
<400> SEQUENCE: 89

Gln Ser Ile Gly Ser Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 90

Gln Gln Tyr Asn Ser Tyr Pro Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 91

Ser Ser Asp Val Gly Gly Tyr Asn Tyr
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic construct; CDRs in light chain

<400> SEQUENCE: 92

Ser Ser Tyr Ala Gly Ser Asn Thr Phe Val
1               5                   10

<210> SEQ ID NO 93
<211> LENGTH: 6
<212> TYPE: PRT
<213> ORGANISM: Artificial Sequence
<220> FEATURE:
<223> OTHER INFORMATION: Synthetic construct; CDRs in light chain

<400> SEQUENCE: 93

Gln Ser Val Gly Ser Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 94

Gln Gln Tyr Asn Ser Tyr Pro Leu Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct; CDRs in light chain
```

```
<400> SEQUENCE: 95

Ser Gly Ser Ile Ala Ser Asn Tyr
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic construct; CDRs in light chain

<400> SEQUENCE: 96

Gln Ser Tyr Asp Gly Ser Asn Pro Val Val
1               5                   10

<210> SEQ ID NO 97
<211> LENGTH: 5
<212> TYPE: PRT
<213> ORGANISM: Artificial Sequence
<220> FEATURE:
<223> OTHER INFORMATION: Synthetic construct; CDRs in light chain

<400> SEQUENCE: 97

Gln Ser Ile Ser Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 98

Gln Gln Ser Tyr Ser Thr Leu Tyr Thr
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic construct; CDRs in light chain

<400> SEQUENCE: 99

Gln Asp Ile Ser Asn Tyr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 100

Gln Gln Tyr Asp Asn Leu Pro Ile Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct; CDRs in light chain
```

```
<400> SEQUENCE: 101

Ser Gly Tyr Ile Ala Ser Asn Tyr
1               5

<210> SEQ ID NO 102
<211> LENGTH: 10
<212> TYPE: PRT
<213> ORGANISM: Artificial Sequence
<220> FEATURE:
<223> OTHER INFORMATION: Synthetic construct; CDRs in light chain

<400> SEQUENCE: 102

Gln Ser Tyr Asp Ser Ser Asn Gln Gly Val
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Synthetic construct; CDRs in light chain

<400> SEQUENCE: 103

Ser Gly Tyr Ile Ala Ser Asn Tyr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 104

Gln Ser Tyr Asp Ser Ser Leu Val Ile
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic construct; CDRs in light chain

<400> SEQUENCE: 105

Gln Ser Ile Gly Ser Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 106

Gln Gln Tyr Asn Ser Tyr Pro Leu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic construct; CDRs in light chain
```

```
<400> SEQUENCE: 107

Ser Ser Asp Val Gly Ser Tyr Asn Tyr
1               5

<210> SEQ ID NO 108
<211> LENGTH: 11
<212> TYPE: PRT
<213> ORGANISM: Artificial Sequence
<220> FEATURE:
<223> OTHER INFORMATION: Synthetic construct; CDRs in light chain

<400> SEQUENCE: 108

Thr Ser Tyr Gly Ser Tyr Asp Ile Pro Val Ile
1               5                   10

<210> SEQ ID NO 109
<211> LENGTH: 8
<212> TYPE: PRT
<213> ORGANISM: Artificial Sequence
<220> FEATURE:
<223> OTHER INFORMATION: Synthetic construct; CDRs in light chain

<400> SEQUENCE: 109

Ser Gly Asn Ile Ala Arg Ser Phe
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic construct; CDRs in light chain

<400> SEQUENCE: 110

Gln Ser Tyr Asp Ser Ser Asn His Val Val
1               5                   10

<210> SEQ ID NO 111
<211> LENGTH: 8
<212> TYPE: PRT
<213> ORGANISM: Artificial Sequence
<220> FEATURE:
<223> OTHER INFORMATION: Synthetic construct; CDRs in light chain

<400> SEQUENCE: 111

Ser Gly Tyr Ile Ala Ser Asn Tyr
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 112

Gln Ser Tyr Asp Ser Thr Thr Glu Val
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic construct; CDRs in light chain
```

```
<400> SEQUENCE: 113

Ser Gly Ser Ile Ala Ser Asn Tyr
1               5

<210> SEQ ID NO 114
<211> LENGTH: 10
<212> TYPE: PRT
<213> ORGANISM: Artificial Sequence
<220> FEATURE:
<223> OTHER INFORMATION: Synthetic construct; CDRs in light chain

<400> SEQUENCE: 114

Gln Ser Tyr Asp Ser Ser Asn Gln Gly Val
1               5                   10

<210> SEQ ID NO 115
<211> LENGTH: 6
<212> TYPE: PRT
<213> ORGANISM: Artificial Sequence
<220> FEATURE:
<223> OTHER INFORMATION: Synthetic construct; CDRs in light chain

<400> SEQUENCE: 115

Gln Ser Ile Ser Ser Tyr
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 116

Gln Gln Ser Tyr Ser Thr Pro Trp Thr
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic construct; CDRs in light chain

<400> SEQUENCE: 117

Gln Asp Ile Ser Asn Tyr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic construct; CDRs in light chain

<400> SEQUENCE: 118

Leu Gln Asp Tyr Asn Tyr Pro Trp Thr
1               5

<210> SEQ ID NO 119
<211> LENGTH: 738
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains
```

<400> SEQUENCE: 119

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attggaatga tgataagcgc     180
tacagcccat ctctgaagag caggctcacc atcgccaagg acacctccaa aaaccaggtg     240
gtccttacaa tgaccaacat ggaccctgtg gacacagcca cgtattactg tgcacggatg     300
ggctggaacg atcctcatat ggttgactac tggggccagg gcaccctggt caccgtctcc     360
tcactcgagg gtggaggcgg ttcaggcgga ggtggctctg gcggtggcgc tagcgacatc     420
cagatgaccc agtctccatc ctccctgtct gcgtctgtag gagacagagt caccatcact     480
tgccgggcaa gtcagagcat tggcagctct ttacattggt atcagcagaa accagggaaa     540
gcccctaagt tcctgatcta tgatgcctcc agtttggaaa gtggggtccc atcaaggttc     600
agcggcagtg gatctgggac agaattcact ctcaccatca gcagcctgca gcctgatgat     660
tttgcaactt attactgcca acagtataat agttacccgc tcactttcgg cggagggacc     720
aagctggaga tcaaacgt                                                    738
```

<210> SEQ ID NO 120
<211> LENGTH: 750
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 120

```
cagatgcagc tggtggagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca atccacgag cacagcctac     240
atggagctga gcagcctgag atctgaggac acggccgtgt attactgtgc ggccgatatg     300
gaactacggg actactacta cggtatggac gtctggggcc aaggaaccct ggtcaccgtc     360
tcctcactcg agggtggagg cggttcaggc ggaggtggct ctgcggtgg cgctagccag     420
tctgggctga ctcagcctcg ctcagtgtcc gggtctcctg gacagtcagt caccatctcc     480
tgcactggaa ccagcagtga tgttggtggt tataactatg tctcctggta ccaacagcac     540
ccaggcaaag cccccaaact catgatttat gatgtcagta gcggccctc aggggtccct     600
gatcgcttct ctggctccaa gtctggcaac acggcctccc tgaccgtctc tgggctccag     660
gctgaggatg aggctgatta ttactgcagc tcctatgcag cagcaatac ttttgtcttc     720
ggatctggga ccaagctgac cgtcctaggt                                       750
```

<210> SEQ ID NO 121
<211> LENGTH: 738
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 121

```
caggtgcagc tgttggagtc tgggggaggc gtggcccagc ctgggaggtc cctgaaactc      60
tcctgtgcag cctctggatt caccttcagt agctatggca tgcactgggt ccgccaggct     120
```

```
ccaggcgagg ggctggagtg ggtggcagtt atatcatatg atggaagtaa taaatactat    180
gcagactccg tgaagggccg attcaccatc tccagagaca attccaagaa cacgctgtat    240
ctgcaaatga acagtctgag agccgaggac acggctgtat attactgtgc aaaagatact    300
tgtactaatg gtgtatgcta ccctgactac tggggccagg gcaccctggt caccgtctcc    360
tcactcgagg gtggaggcgg ttcaggcgga ggtggctctg gcggtggcgc tagcgatatt    420
gtgatgacgc agtctccagc caccctgtct gtgtctccag gggaaagagc caccctctcc    480
tgcagggcca gccagagtgt tggcagcagc ttagcctggt accagcagaa acctggccag    540
gctcccaggc tcctcatcta tggtggatcc gtcaggccca ctggtatccc agccaggttc    600
agtggcagtg ggtctgggac agagttcact ctcaccatca gcagcctgca gtctgaagat    660
tttgcagctt attactgtca gcagtataat agttacccgc tcactttcgg cggagggacc    720
aagctggaga tcaaacgt                                                  738

<210> SEQ ID NO 122
<211> LENGTH: 750
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 122
gaagtgcagc tggtgcagtc tggagctgag gtgaagaagc ctggggcctc agtgaaggtc     60
tcctgcaagg cttctggtta cacctttacc agctatggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagatcgcct    300
agtacggtgt aaccccatt cagcgactac tggggccagg gcaccctggt caccgtctcc    360
tcactcgagg gtggaggcgg ttcaggcgga ggtggctctg gcggtggcgc tagcaatttt    420
atgctgactc agccccactc tgtgtcggag tctccgggga gacggtaac catctcctgc    480 accggcagca gtggcagcat tgccagcaac tatgtgcagt ggtaccagca gcgcccgggc    540 agttcccccca ccactgtgat ctatgaggat aaccaaagac cctctggggt ccctgatcgg    600
ttctctggct ccatcgacag ctcctccaac tctgcctccc tcaccatctc tggactgaag    660
actgaggacg aggctgacta ctactgtcag tcttatgatg cagcaaccc tgtggttttc    720 ggcggaggga cccagctcac cgttttaggt                                    750

<210> SEQ ID NO 123
<211> LENGTH: 732
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 123
gaggtgcagc tggtggagtc tgggggaggc ttggtacagc ctggcaggtc cctgagactc     60
tcctgtgcag cctctggatt cacctttgat gattatgcca tgcactgggt ccggcaagct    120
ccagggaagg gcctgagtg ggtctcaggt attagttgga atagtggtag cataggctat    180
gcggactctg tgaagggccg attcaccatc tccagagaca cgccaagaa ctccctgtat    240
```

| | |
|---|---|
| ctgcaaatga acagtctgag agctgaggac acggccttgt attactgtgc aaaacggcat | 300 |
| ggagggacca atgctttttga tatctggggc caagggacaa tggtcaccgt ctcttcactc | 360 |
| gagggtggag gcggttcagg cggaggtggc tctggcggtg gcgctagcga catccagatg | 420 |
| acccagtctc catcctccct gtctgcatct gtaggagaca gagtcaccat cacttgccgg | 480 |
| gcaagtcaga gcattagcag ctatttaaat tggtatcagc agaaaccagg aaagcccct | 540 |
| aagctcctga tctatgctgc atccagtttg caaagtgggg tcccatcaag gttcagtggc | 600 |
| agtggatctg ggacagattt cactctcacc atcagcagtc tgcaacctga agattttgca | 660 |
| acttactact gtcaacagag ttacagtacc ctttacactt ttggccaggg gaccaagctg | 720 |
| gagatcaaac gt | 732 |

<210> SEQ ID NO 124
<211> LENGTH: 726
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 124

| | |
|---|---|
| cagatcaccct tgaaggagtc tggacctacg ctggtgaaac ccacagaaac cctcacgctg | 60 |
| acctgcaccct tctctgggtt ctcactcaac actggtggag tgagtgtggg ctgggtccgt | 120 |
| cagccccag gaaaggccct ggagtggctt gcactcattt attggaatga tgataagcgc | 180 |
| tacagcccat ctctgaagag caggctcacc atcaccaagg acacctccaa aaaccaggtg | 240 |
| gtccttacaa tgaccaacat ggacactgtg gacacggcca catattactg tgcacacagc | 300 |
| gcggctggag ttgactactg gggccaggga accctggtca ccgtctcttc actcgagggt | 360 |
| ggaggcggtt caggcggagg tggctctggc ggtggcgcta gcgacatcca gatgacccag | 420 |
| tctccatcct ccctgtctgc atctgtagga gacagagtca ccatcacttg ccaggcgagt | 480 |
| caggacatta gcaactattt aaattggtat cagcagaaac agggaaagc ccctaagctc | 540 |
| ctgatctacg atgcatccaa tttggaaaca ggggtcccat caaggttcag tggaagtgga | 600 |
| tctgggacag attttacttt caccatcagc agcctgcagc ctgaagatat tgcaacatat | 660 |
| tactgtcaac agtatgataa tctcccccatc actttcggcc ctgggaccaa agtggatatc | 720 |
| aaacgt | 726 |

<210> SEQ ID NO 125
<211> LENGTH: 738
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 125

| | |
|---|---|
| caggtgcagc tggtggagtc tggggctgag gtgaagaagc ctggggcctc agtgaaggtc | 60 |
| tcctgcaagg cttctggata cactttttacc gcctactata tacactggct gcgacaggcc | 120 |
| cctggacaag accttgagtg gatgggatgg atcgacccta cagtggtgg cacaaactat | 180 |
| gcacagaaat ttcagggcag ggtcaccatg accagggaca cgtccatcag cacagcctac | 240 |
| atggagctga gcaggctgag atctgacgac acggccgtgt attactgtgc gagaggctgg | 300 |
| aattacgaac ttgactactg gggccaggga accctggtca ccgtctcctc actcgagggt | 360 |
| ggaggcggtt caggcggagg tggctctggc ggtggcgcta gcaatttttat gctgactcag | 420 |

```
ccccactctg tgtcggggtc tccggggaag acggtgacca tctcctgcac ccgcagcagt    480
ggctacattg ccagcaacta tgtacagtgg taccagcagc gcccgggcag tgcccccacc    540
actgtgatct atgaggataa ccaaagaccc tctggggtcc ctgatcggtt ctctggctcc    600
atcgacagct cctccaactc tgcctccctc accatctctg gactgaagac tgaggacgag    660
gctgactact actgtcagtc ttatgatagc agcaatcaag gggtgttcgg cggagggacc    720
aagctgaccg tcctagtg                                                  738
```

<210> SEQ ID NO 126
<211> LENGTH: 735
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 126

```
caggtgcagc tggtggagtc tggggctgag gtgaagaagc ctggggcctc agtgaaggtc    60
tcctgcaagg cttctggata cacttttacc gcctactata tacactggct gcgacaggcc   120
cctggacaag accttgagtg gatgggatgg atcgacccta cagtggtgg cacaaactat    180 gcacagaaat ttcagggcag ggtcaccatg accagggaca cgtccatcag cacagcctac    240
atggagctga gcaggctgag atctgacgac acagccgtgt attactgtgc gagagactgg    300
aattacgaac ttgactactg gggccagggc accctggtca ccgtctcctc actcgagggt    360
ggaggcggtt caggcggagg tggctctggc ggtggcgcta gcaatttttat gctgactcag    420 ccccactctg tgtcggggtc tccggggaag acggtgacca tctcctgcac ccgcagcagt    480
ggctacattg ccagcaacta tgtacagtgg taccagcagc gcccgggcag ttccccacc     540 actctgatat atgacgatga ccaaagaccc tctggggtcc ctgatcggtt ctctggctcc    600
atcgacagat cctccaattc tgcctccctc accatctctg gctgaagac tgaggacgag     660 ggtgactact actgtcagtc ttatgatagc agccttgtga tattcggcgg ggggaccaag    720
gtcaccgtcc taggt                                                    735
```

<210> SEQ ID NO 127
<211> LENGTH: 741
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 127

```
cagatcacct tgaaggagtc gggtcctacg ctggtgaaac ccacacagac cctcacgctg    60
acctgcacct tctctgggtt ctcactcagc actagtggag tgggtgtggg ctggatccgt    120
cagcccccag gaaaggccct ggagtggctt gcactcattt attggaatga tgataagcgc    180
tacagcccat ctctgaagag caggctcacc atcaccaagg acacctccaa aaaccaggtg    240
gtccttacaa tgaccaacat ggaccctgtg gacacagcca catattactg tgcacacatt    300
tccagtagtg gtggtaccga agtacaagac tactggggcc agggaacccct ggtcaccgtc    360 tcctcactcg agggtggagg cggttcaggc ggaggtggct ctggcggtgg cgctagcgac    420
atccagatga cccagtctcc atcctccctg tctgcgtctg taggagacag agtcaccatc    480
acttgccggg caagtcagag cattggcagc tctttacatt ggtatcagca gaaaccaggg    540
```

-continued

```
aaagccccta agttcctgat ctatgatgcc tccagtttgg aaagtggggt cccatcaagg    600
ttcagcggca gtggatctgg gacagaattc actctcacca tcagcagcct gcagcctgat    660
gattgtgcaa cttattactg ccaacagtat aatagttacc cgctcacttt cggcggaggg    720
accaagctgg agatcaaacg t                                              741
```

<210> SEQ ID NO 128
<211> LENGTH: 753
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 128

```
caaatgcagc tggtgcagtc tggggctgag gtgaagaagc ctgggtcctc ggtgaaggtc     60
tcctgtaagg cttctggagg caccttcagc agctatgcta tcagctgggt gcgacaggcc    120
cctggacaag gcttgagtg gatgggaggg atcatcccta tctttggtac agcaaactac     180
gcacagaagt tccagggcag agtcacgatt accgcggaca aatccacgag cacagcctac    240
atggagctga gcagcctgag atctgacgac acggccgtgt attactgtgc gagagatgaa    300
ctctgggcta caaactacta ctacatggac gtctgggca aaggaaccct ggtcaccgtc     360
tcctcactcg agggtggagg cggttcaggc ggaggtggct ctggcggtgg cgctagccag    420
tctgcgctga ctcagcctcg ctcagtgtcc gggtctcctg gacagtcagt caccatctcc    480
tgcactggaa ccagcagtga tgttggtagt tataactatg tctcctggta ccaacagagc    540
ccaggcaaag cccccaaact catgatttat gatgtcagta atcggccctc aggggtttct    600
aatcgcttct ctggctccaa gtctggcaac acggcctccc tgaccatctc tgggctccag    660
tctgaggacg aggctgatta ttattgcacc tcatatggaa gctacgacat acctgtgatt    720
ttcggcggag ggaccaagct gaccgtccta ggt                                 753
```

<210> SEQ ID NO 129
<211> LENGTH: 738
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 129

```
caggtgcagc tggtggagtc tggggctgag gtgaagaagc ctggggcctc agtgaaggtc     60
tcctgcaagg cttctggata cacttttacc gcctactata tacactggct gcgacaggcc    120
cctggacaag accttgagtg gatgggatgg atcgaccta acagtggtgg cacaaactat     180
gcacagaaat tcagggcag ggtcaccatg accaggaca cgtccatcag cacagcctac       240
atggagctga gcaggctgag atctgacgac acggccgtgt attactgtgc gagagactgg    300
aattacgaac ttgactactg gggccggggc accctggtca ccgtctcccc actcgagggt    360
ggaggcggtt caggcggagg tggctctggc ggtggcgcta gcaatttat gctgactcag     420 ccccactctg tgtcggggtc tccggggaag gcggtgacca tctcctgcac ccgcagcagt    480
ggcaacattg ccaggagttt tgtgcagtgg taccaacagc gcccgggcag tgcccccacc    540
gctgtgatct atgaggataa ccgaagaccc tctggggtcc ctgatcgctt ctctggctcc    600
ttcgacagct cctccaattc tgcctccctc accatctctg gcctgaagac tgaggacgag    660
```

```
gctgactact actgtcagtc ttatgatagc agcaatcatg tggtattcgg cggagggacc      720
aaggtcaccg tcctaggt                                                    738

<210> SEQ ID NO 130
<211> LENGTH: 735
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 130
caggtgcagc tggtggagtc tggggctgag gtgaagaagc ctggggcctc agtgaaggtc       60
tcctgcaagg cttctggata cactttttacc gcctactata tacactggct gcgacaggcc    120
cctggacaag accttgagtg gatgggatgg atcgacccta acagtggtgg cacaaactat    180
gcacagaaat ttcagggcag ggtcaccatg accagggaca cgtccatcag cacagcctac    240
atggagctga gcaggctgag atctgacgac acggccgtgt attactgtgc gagagactgg    300
aattacgagc ttgactactg gggccagggc accctggtca ccgtctcctc actcgagggt    360
ggaggcggtt caggcggagg tggctctggc ggtggcgcta gcaattttat gctgactcag    420
ccccactctg tgtcggggtc tccggggaag acggtgacca tctcctgcac ccgcagcagt    480
ggctacattg ccagcaacta tgtacagtgg taccagcagc gcccgggcag ttcccccacc    540
actctgatat atgacgatga ccaaagaccc tctggggtcc ctgatcggtt ctctggctcc    600
atcgacagat cctccaattc tgcctccctc accatctctg gctgaagac tgaggacgag    660 ggtgactact actgtcagtc ttatgatagc accacggaag tcttcggaac tgggaccaag    720
ctgaccgtcc taggt                                                     735

<210> SEQ ID NO 131
<211> LENGTH: 747
<212> TYPE: DNA
<213> ORGANISM: Artificial Sequence
<220> FEATURE:
<223> OTHER INFORMATION: Synthetic construct; Nucleic acid sequences
      encoding CD229 antigen binding domains

<400> SEQUENCE: 131
cagatcacct tgaaggagtc tggtcctacg ctggtgaaac ccacacagac cctcacgctg       60
acctgcacct ctctgggtt ctcactcagc actagtggag tgggtgtggg ctggatccgt      120
cagcccccag gaaaggccct ggagtggctt gcactcattt attggaatga tgataagcgc    180
tacagcccat ctctgaagag caggctcacc atcaccaagg acacctccaa aaaccaggtg    240
gtccttacaa tgaccaacat ggaccctgtg gacacagcca catattactg tgcccaggca    300
aaaccgtata gcagcgattt tgatatctgg ggccaaggga caatggtcac cgtctcttca    360
ctcgagggtg aggcggttc aggcggaggt ggctctggcg gtggcgctag caattttatg    420
ctgactcagc cccactctgt gtcggagtct ccggggaaga cggtaaccat ctcctgcacc    480
ggcagcagtg gcagcattgc cagcaactat gtgcagtggt accagcagcg cccgggcagt    540
tcccccacca ctgtgatcta tgaggataac caaagaccct ctggggtccc tgatcggttc    600
tctggctcca tcgacagctc tctaactct gcctccctca ccatctctgg actgaagact    660
gaggacgagg ctgactacta ctgtcagtct tatgatagca gcaatcaggg ggtattcggc    720
ggcgggaccc agctcaccgt cctaggt                                        747
```

<210> SEQ ID NO 132
<211> LENGTH: 729
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 132

```
caggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat      180
gcggactccg cgaagggccg gttcaccatc tccagagaca attccaagaa cacgctgtat     240
ctgcaaatga acagcctgag agccgaggac acggccgtct attactgtgc gaaaggggg      300
aactccaact cttttgacta ctggggccag ggaaccctgg tcaccgtctc ctcactcgag     360
ggtggaggcg gttcaggcgg aggtggctct ggcggtggcg ctagcgacat ccagatgacc     420
cagtctccat cttccgtgtc tgcatctgta ggagacagag tcaccatcac ttgccgggca     480
agtcagagca ttagcagcta tttaaattgg tatcagcaga accagggaa agcccctaag      540
ctcctgatct atgctgcatc cagtttgcaa agtggggtcc catcaaggtt cagtggcagt     600
ggatctggga cagatttcac tctcaccatc agcagtctgc aacctgaaga ttttgcaact     660
tactactgtc aacagagtta cagtaccccc tggacgttcg gccaagggac caagctggag     720
atcaaacgt                                                             729
```

<210> SEQ ID NO 133
<211> LENGTH: 735
<212> TYPE: DNA
<213> ORGANISM: Artificial Sequence
<220> FEATURE:
<223> OTHER INFORMATION: Synthetic construct; Nucleic acid sequences encoding CD229 antigen binding domains

<400> SEQUENCE: 133

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt actggaatga tgataagcgc     180
tacagcccat ctctgaagag caggctcacc atcaccaagg acacctccaa aaaccaggtg     240
gtccttacaa tgaccaacat ggaccctgtg acacagcca catattactg tgcccaggca      300
aaaccgtata gcagcgattt tgatatctgg ggccaaggga caatggtcac cgtctcttca     360
ctcgaggggtg gaggcggttc aggcggaggt ggctctggcg gtggcgctag cgacatccag    420
atgacccagt ctccatcctc cctgtctgca tctgtaggag acagagtcac catctcttgc     480
caggcgagtc aggacattag taactattta aattggtatc agcagaaacc agggaaagcc     540
cctaagctcc tgatctatgc tgcatccagt ttgcaaagtg gggtcccatc aaggttcagt     600
ggcagtggat ctgggacaga tttcactctc accatcagca gtctgcaacc tgaagatttt     660
gcaacttatt actgtctaca agattacaat tacccgtgga cgttcggcca ggggaccaag     720
gtggaaatca aacgt                                                      735
```

<210> SEQ ID NO 134
<211> LENGTH: 363
<212> TYPE: DNA
<213> ORGANISM: Artificial Sequence

```
<220> FEATURE:
<223> OTHER INFORMATION: Synthetic construct; Nucleic acid sequences
      encoding Variable Heavy Chains

<400> SEQUENCE: 134
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attggaatga tgataagcgc     180
tacagcccat ctctgaagag caggctcacc atcgccaagg acacctccaa aaaccaggtg     240
gtccttacaa tgaccaacat ggaccctgtg gacacagcca cgtattactg tgcacggatg     300
ggctggaacg atcctcatat ggttgactac tggggccagg caccctggt caccgtctcc      360 tca                                                                   363

<210> SEQ ID NO 135
<211> LENGTH: 366
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 135
cagatgcagc tggtggagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggaca atccacgag cacagcctac       240 atggagctga gcagcctgag atctgaggac acggccgtgt attactgtgc ggccgatatg     300
gaactacggg actactacta cggtatggac gtctggggcc aaggaaccct ggtcaccgtc     360
tcctca                                                               366

<210> SEQ ID NO 136
<211> LENGTH: 363
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 136
caggtgcagc tgttggagtc tgggggaggc gtggcccagc ctggggaggtc cctgaaactc      60 tcctgtgcag cctctggatt caccttcagt agctatggca tgcactgggt ccgccaggct     120
ccaggcgagg ggctggagtg ggtggcagtt atatcatatg atggaagtaa taaatactat     180
gcagactccg tgaagggccg attcaccatc tccagagaca attccaagaa cacgctgtat     240
ctgcaaatga acagtctgag agccgaggac acggctgtat attactgtgc aaaagatact     300
tgtactaatg gtgtatgcta ccctgactac tggggccagg caccctggt caccgtctcc      360 tca                                                                   363

<210> SEQ ID NO 137
<211> LENGTH: 363
<212> TYPE: DNA
<213> ORGANISM: Artificial Sequence
<220> FEATURE:
<223> OTHER INFORMATION: Synthetic construct; Nucleic acid sequences
      encoding Variable Heavy Chains
```

<400> SEQUENCE: 137

```
gaagtgcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acgaccgtgt attactgtgc gagatcgcct   300
agtacggtgg taaccccatt cagcgactac tggggccagg gcaccctggt caccgtctcc   360
tca                                                                 363
```

<210> SEQ ID NO 138
<211> LENGTH: 357
<212> TYPE: DNA
<213> ORGANISM: Artificial Sequence
<220> FEATURE:
<223> OTHER INFORMATION: Synthetic construct; Nucleic acid sequences encoding Variable Heavy Chains

<400> SEQUENCE: 138

```
gaggtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag cataggctat   180
gcggactctg tgaagggccg attcaccatc tccagagaca acgccaagaa ctccctgtat   240
ctgcaaatga acagtctgag agctgaggac acggccttgt attactgtgc aaaacggcat   300
ggagggacca atgcttttga tatctgggc caagggacaa tggtcaccgt ctcttca       357
```

<210> SEQ ID NO 139
<211> LENGTH: 351
<212> TYPE: DNA
<213> ORGANISM: Artificial Sequence
<220> FEATURE:
<223> OTHER INFORMATION: Synthetic construct; Nucleic acid sequences encoding Variable Heavy Chains

<400> SEQUENCE: 139

```
cagatcacct tgaaggagtc tggacctacg ctggtgaaac ccacagaaac cctcacgctg    60
acctgcacct ctctgggtt ctcactcaac actggtggag tgagtgtggg ctgggtccgt   120
cagaccccag gaaaggccct ggagtggctt gcactcattt attggaatga tgataagcgc   180
tacagcccat ctctgaagag caggctcacc atcaccaagg acacctccaa aaaccaggtg   240
gtccttacaa tgaccaacat ggacactgtg gacacggcca catattactg tgcacacagc   300
gcggctggag ttgactactg gggccaggga accctggtca ccgtctcttc a           351
```

<210> SEQ ID NO 140
<211> LENGTH: 351
<212> TYPE: DNA
<213> ORGANISM: Artificial Sequence
<220> FEATURE:
<223> OTHER INFORMATION: Synthetic construct; Nucleic acid sequences encoding Variable Heavy Chains

<400> SEQUENCE: 140

```
caggtgcagc tggtggagtc tggggctgag gtgaagaagc ctggggcctc agtgaaggtc    60
tcctgcaagg cttctggata cacttttacc gcctactata tacactggct gcgacaggcc   120
cctggacaag accttgagtg gatgggatgg atcgaccta acagtggtgg cacaaactat   180
```

| | |
|---|---|
| gcacagaaat tcagggcag gtcaccatg accagggaca cgtccatcag cacagcctac | 240 |
| atggagctga gcaggctgag atctgacgac acggccgtgt attactgtgc gagaggctgg | 300 |
| aattacgaac ttgactactg gggccagggc accctggtca ccgtctcctc a | 351 |

<210> SEQ ID NO 141
<211> LENGTH: 351
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 141

| | |
|---|---|
| caggtgcagc tggtggagtc tggggctgag gtgaagaagc ctggggcctc agtgaaggtc | 60 |
| tcctgcaagg cttctggata cacttttacc gcctactata tacactggct gcgacaggcc | 120 |
| cctggacaag accttgagtg gatgggatgg atcgacccta acagtggtgg cacaaactat | 180 |
| gcacagaaat tcagggcag gtcaccatg accagggaca cgtccatcag cacagcctac | 240 |
| atggagctga gcaggctgag atctgacgac acagccgtgt attactgtgc gagagactgg | 300 |
| aattacgaac ttgactactg gggccagggc accctggtca ccgtctcctc a | 351 |

<210> SEQ ID NO 142
<211> LENGTH: 366
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 142

| | |
|---|---|
| cagatcacct tgaaggagtc gggtcctacg ctggtgaaac ccacacagac cctcacgctg | 60 |
| acctgcacct tctctgggtt ctcactcagc actagtggag tgggtgtggg ctggatccgt | 120 |
| cagcccccag gaaaggccct ggagtggctt gcactcattt attggaatga tgataagcgc | 180 |
| tacagcccat ctctgaagag caggctcacc atcaccaagg acacctccaa aaaccaggtg | 240 |
| gtccttacaa tgaccaacat ggaccctgtg gacacagcca catattactg tgcacacatt | 300 |
| tccagtagtg gtggtaccga agtacaagac tactggggcc agggaaccct ggtcaccgtc | 360 |
| tcctca | 366 |

<210> SEQ ID NO 143
<211> LENGTH: 366
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 143

| | |
|---|---|
| caaatgcagc tggtgcagtc tggggctgag gtgaagaagc ctgggtcctc ggtgaaggtc | 60 |
| tcctgtaagg cttctggagg caccttcagc agctatgcta tcagctgggt gcgacaggcc | 120 |
| cctggacaag gcttgagtg gatgggaggg atcatcccta tctttggtac agcaaactac | 180 |
| gcacagaagt tccagggcag agtcacgatt accgcggaca aatccacgag cacagcctac | 240 |
| atggagctga gcagcctgag atctgacgac acggccgtgt attactgtgc gagagatgaa | 300 |
| ctctgggcta caaactacta ctacatggac gtctggggca aaggaaccct ggtcaccgtc | 360 |
| tcctca | 366 |

<210> SEQ ID NO 144
<211> LENGTH: 351
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 144
caggtgcagc tggtggagtc tggggctgag gtgaagaagc ctggggcctc agtgaaggtc      60
tcctgcaagg cttctggata cacttttacc gcctactata tacactggct gcgacaggcc     120
cctggacaag accttgagtg gatgggatgg atcgaccctc acagtggtgg cacaaactat     180
gcacagaaat tcagggcag ggtcaccatg accagggaca cgtccatcag cacagcctac     240
atggagctga gcaggctgag atctgacgac acggccgtgt attactgtgc gagagactgg     300
aattacgaac ttgactactg gggccggggc accctggtca ccgtctcccc a             351

<210> SEQ ID NO 145
<211> LENGTH: 351
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 145
caggtgcagc tggtggagtc tggggctgag gtgaagaagc ctggggcctc agtgaaggtc      60
tcctgcaagg cttctggata cacttttacc gcctactata tacactggct gcgacaggcc     120
cctggacaag accttgagtg gatgggatgg atcgaccctc acagtggtgg cacaaactat     180
gcacagaaat tcagggcag ggtcaccatg accagggaca cgtccatcag cacagcctac     240
atggagctga gcaggctgag atctgacgac acggccgtgt attactgtgc gagagactgg     300
aattacgagc ttgactactg gggccagggc accctggtca ccgtctcctc a             351

<210> SEQ ID NO 146
<211> LENGTH: 360
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 146
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attggaatga tgataagcgc     180
tacagcccat ctctgaagag caggctcacc atcaccaagg acacctccaa aaaccaggtg     240
gtccttacaa tgaccaacat ggaccctgtg gacacagcca catattactg tgcccaggca     300
aaaccgtata gcagcgattt tgatatctgg ggccaaggga caatggtcac cgtctcttca     360

<210> SEQ ID NO 147
<211> LENGTH: 354
<212> TYPE: DNA
<213> ORGANISM: Artificial Sequence
<220> FEATURE:
<223> OTHER INFORMATION: Synthetic construct; Nucleic acid sequences
      encoding Variable Heavy Chains

<400> SEQUENCE: 147

```
caggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat      180
gcggactccg cgaagggccg gttcaccatc tccagagaca attccaagaa cacgctgtat     240
ctgcaaatga acagcctgag agccgaggac acggccgtct attactgtgc gaaaggggg      300 aactccaact cttttgacta ctggggccag ggaaccctgg tcaccgtctc ctca           354
```

<210> SEQ ID NO 148
<211> LENGTH: 360
<212> TYPE: DNA
<213> ORGANISM: Artificial Sequence
<220> FEATURE:
<223> OTHER INFORMATION: Synthetic construct; Nucleic acid sequences encoding Variable Heavy Chains

<400> SEQUENCE: 148

```
cagatcacct tgaaggagtc tggtcctacg ctggtgaaac ccacacagac cctcacgctg      60
acctgcacct tctctgggtt ctcactcagc actagtggaa tgggtgtggg ctggatccgt     120
cagcccccag gaaaggccct ggagtggctt gcactcattt actggaatga tgataagcgc     180
tacagcccat ctctgaagag caggctcacc atcaccaagg acacctccaa aaaccaggtg     240
gtccttacaa tgaccaacat ggaccctgtg acacagcca catattactg tgcccaggca       300
aaaccgtata gcagcgattt tgatatctgg ggccaaggga caatggtcac cgtctcttca     360
```

<210> SEQ ID NO 149
<211> LENGTH: 324
<212> TYPE: DNA
<213> ORGANISM: Artificial Sequence
<220> FEATURE:
<223> OTHER INFORMATION: Synthetic construct; Nucleic acid sequences encoding Variable Light Chains

<400> SEQUENCE: 149

```
gacatccaga tgacccagtc tccatcctcc ctgtctgcgt ctgtaggaga cagagtcacc      60
atcacttgcc gggcaagtca gagcattggc agctctttac attggtatca gcagaaacca     120
gggaaagccc ctaagttcct gatctatgat gcctccagtt tggaaagtgg ggtcccatca     180
aggttcagcg gcagtggatc tgggacagaa ttcactctca ccatcagcag cctgcagcct     240
gatgattttg caacttatta ctgccaacag tataatagtt acccgctcac tttcggcgga     300
gggaccaagc tggagatcaa acgt                                             324
```

<210> SEQ ID NO 150
<211> LENGTH: 333
<212> TYPE: DNA
<213> ORGANISM: Artificial Sequence
<220> FEATURE:
<223> OTHER INFORMATION: Synthetic construct; Nucleic acid sequences encoding Variable Light Chains

<400> SEQUENCE: 150

```
cagtctgggc tgactcagcc tcgctcagtg tccgggtctc ctggacagtc agtcaccatc      60
tcctgcactg gaaccagcag tgatgttggt ggttataact atgtctcctg gtaccaacag     120
cacccaggca aagccccaa actcatgatt tatgatgtca gtaagcggcc ctcagggtc        180 cctgatcgct tctctggctc caagtctggc aacacggcct ccctgaccgt ctctgggctc     240
```
caggctgagg atgaggctga ttattactgc agctcctatg caggcagcaa tactttttgtc    300 ttcggatctg ggaccaagct gaccgtccta ggt    333

<210> SEQ ID NO 151
<211> LENGTH: 324
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 151
gatattgtga tgacgcagtc tccagccacc ctgtctgtgt ctccagggga aagagccacc    60
ctctcctgca gggccagcca gagtgttggc agcagcttag cctggtacca gcagaaacct    120
ggccaggctc ccaggctcct catctatggt ggatccgtca gggccactgg tatcccagcc    180
aggttcagtg gcagtgggtc tgggacagag ttcactctca ccatcagcag cctgcagtct    240
gaagattttg cagcttatta ctgtcagcag tataatagtt acccgctcac tttcggcgga    300
gggaccaagc tggagatcaa acgt    324

<210> SEQ ID NO 152
<211> LENGTH: 336
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 152
aattttatgc tgactcagcc ccactctgtg tcggagtctc cggggaagac ggtaaccatc    60
tcctgcaccg gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatggcag caaccctgtg    300
gttttcggcg gagggaccca gctcaccgtt ttaggt    336

<210> SEQ ID NO 153
<211> LENGTH: 324
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 153
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccttttacac ttttggccag    300 gggaccaagc tggagatcaa acgt    324

<210> SEQ ID NO 154
<211> LENGTH: 324
<212> TYPE: PRT
<213> ORGANISM: Artificial Sequence
<220> FEATURE:
<223> OTHER INFORMATION: Synthetic construct; Nucleic acid sequences
    encoding Variable Light Chains

<400> SEQUENCE: 154

Gly Ala Cys Ala Thr Cys Cys Ala Gly Ala Thr Gly Ala Cys Cys
1               5                   10                  15

Ala Gly Thr Cys Thr Cys Cys Ala Thr Cys Cys Thr Cys Cys Thr
                20                  25                  30

Gly Thr Cys Thr Gly Cys Ala Thr Cys Thr Gly Thr Ala Gly Gly Ala
            35                  40                  45

Gly Ala Cys Ala Gly Ala Gly Thr Cys Ala Cys Ala Thr Cys Ala
        50                  55                  60

Cys Thr Thr Gly Cys Cys Ala Gly Gly Cys Gly Ala Gly Thr Cys Ala
65                  70                  75                  80

Gly Gly Ala Cys Ala Thr Thr Ala Gly Cys Ala Ala Cys Thr Ala Thr
                85                  90                  95

Thr Thr Ala

<400> SEQUENCE: 155

```
aattttatgc tgactcagcc ccactctgtg tcggggtctc cggggaagac ggtgaccatc      60
tcctgcaccc gcagcagtgg ctacattgcc agcaactatg tacagtggta ccagcagcgc     120
ccgggcagtg cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatcaaggg     300
gtgttcggcg agggaccaa gctgaccgtc ctagtg                                336
```

<210> SEQ ID NO 156
<211> LENGTH: 333
<212> TYPE: DNA
<213> ORGANISM: Artificial Sequence
<220> FEATURE:
<223> OTHER INFORMATION: Synthetic construct; Nucleic acid sequences encoding Variable Light Chains

<400> SEQUENCE: 156

```
aattttatgc tgactcagcc ccactctgtg tcggggtctc cggggaagac ggtgaccatc      60
tcctgcaccc gcagcagtgg ctacattgcc agcaactatg tacagtggta ccagcagcgc     120
ccgggcagtt cccccaccac tctgatatat gacgatgacc aaagaccctc tggggtccct     180
gatcggttct ctggctccat cgacagatcc tccaattctg cctccctcac catctctggg     240
ctgaagactg aggacgaggg tgactactac tgtcagtctt atgatagcag ccttgtgata     300
ttcggcgggg ggaccaaggt caccgtccta ggt                                  333
```

<210> SEQ ID NO 157
<211> LENGTH: 324
<212> TYPE: DNA
<213> ORGANISM: Artificial Sequence
<220> FEATURE:
<223> OTHER INFORMATION: Synthetic construct; Nucleic acid sequences encoding Variable Light Chains

<400> SEQUENCE: 157

```
gacatccaga tgacccagtc tccatcctcc ctgtctgcgt ctgtaggaga cagagtcacc      60
atcacttgcc gggcaagtca gagcattggc agctctttac attggtatca gcagaaacca     120
gggaaagccc ctaagttcct gatctatgat gcctccagtt tggaaagtgg ggtcccatca     180
aggttcagcg gcagtggatc tgggacagaa ttcactctca ccatcagcag cctgcagcct     240
gatgattgtg caacttatta ctgccaacag tataatagtt acccgctcac tttcggcgga     300
gggaccaagc tggagatcaa acgt                                            324
```

<210> SEQ ID NO 158
<211> LENGTH: 336
<212> TYPE: DNA
<213> ORGANISM: Artificial Sequence
<220> FEATURE:
<223> OTHER INFORMATION: Synthetic construct; Nucleic acid sequences encoding Variable Light Chains

<400> SEQUENCE: 158

```
cagtctgcgc tgactcagcc tcgctcagtg tccgggtctc ctggacagtc agtcaccatc      60
tcctgcactg gaaccagcag tgatgttggt agttataact atgtctcctg gtaccaacag     120
agcccaggca agcccccaa actcatgatt tatgatgtca gtaatcggcc ctcagggggtt     180 tctaatcgct tctctggctc caagtctggc aacacggcct ccctgaccat ctctgggctc     240
```

```
cagtctgagg acgaggctga ttattattgc acctcatatg gaagctacga catacctgtg    300
attttcggcg gagggaccaa gctgaccgtc ctaggt                              336
```

<210> SEQ ID NO 159
<211> LENGTH: 336
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 159

```
aattttatgc tgactcagcc ccactctgtg tcggggtctc cggggaaggc ggtgaccatc    60
tcctgcaccc gcagcagtgg caacattgcc aggagttttg tgcagtggta ccaacagcgc   120
ccgggcagtg cccccaccgc tgtgatctat gaggataacc gaagaccctc tggggtccct   180
gatcgcttct ctggctcctt cgacagctcc tccaattctg cctccctcac catctctggc   240
ctgaagactg aggacgaggc tgactactac tgtcagtctt atgatagcag caatcatgtg   300
gtattcggcg gagggaccaa ggtcaccgtc ctaggt                              336
```

<210> SEQ ID NO 160
<211> LENGTH: 333
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 160

```
aattttatgc tgactcagcc ccactctgtg tcggggtctc cggggaagac ggtgaccatc    60
tcctgcaccc gcagcagtgg ctacattgcc agcaactatg tacagtggta ccagcagcgc   120
ccgggcagtt cccccaccac tctgatatat gacgatgacc aaagaccctc tggggtccct   180
gatcggttct ctggctccat cgacagatcc tccaattctg cctccctcac catctctggg   240
ctgaagactg aggacgaggg tgactactac tgtcagtctt atgatagcac cacggaagtc   300
ttcggaactg ggaccaagct gaccgtccta ggt                                 333
```

<210> SEQ ID NO 161
<211> LENGTH: 336
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 161

```
aattttatgc tgactcagcc ccactctgtg tcggagtctc cggggaagac ggtaaccatc    60
tcctgcaccg gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tctaactctg cctccctcac catctctgga   240
ctgaagactg aggacgaggc tgactactac tgtcagtctt atgatagcag caatcagggg   300
gtattcggcg gcgggaccca gctcaccgtc ctaggt                              336
```

<210> SEQ ID NO 162
<211> LENGTH: 324
<212> TYPE: DNA
<213> ORGANISM: Artificial Sequence

```
<220> FEATURE:
<223> OTHER INFORMATION: Synthetic construct; Nucleic acid sequences
      encoding Variable Light Chains

<400> SEQUENCE: 162
gacatccaga tgacccagtc tccatcttcc gtgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctggac gttcggccaa     300 gggaccaagc tggagatcaa acgt                                            324

<210> SEQ ID NO 163
<211> LENGTH: 324
<212> TYPE: DNA
<213> ORGANISM: Artificial Sequence
<220> FEATURE:
<223> OTHER INFORMATION: Synthetic construct; Nucleic acid sequences
      encoding Variable Light Chains

<400> SEQUENCE: 163
gacatccaga tgacccagtc tccatcctcc ctgtctgcat ctgtaggaga cagagtcacc     60
atctcttgcc aggcgagtca ggacattagt aactatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttatta ctgtctacaa gattacaatt acccgtggac gttcggccag    300
gggaccaagg tggaaatcaa acgt                                            324

<210> SEQ ID NO 164
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 164
gggttctcac tcagcactag tggagtgggt                                       30

<210> SEQ ID NO 165
<211> LENGTH: 21
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 165
atttattgga atgatgataa g                                                21

<210> SEQ ID NO 166
<211> LENGTH: 39
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 166
gcacggatgg gctggaacga tcctcatatg gttgactac                             39
```

<210> SEQ ID NO 167
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 167
ggaggcacct tcagcagcta tgct                                              24

<210> SEQ ID NO 168
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 168
atcatcccta tctttggtac agca                                              24

<210> SEQ ID NO 169
<211> LENGTH: 45
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 169
gcggccgata tggaactacg ggactactac tacggtatgg acgtc                       45

<210> SEQ ID NO 170
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 170
ggattcacct tcagtagcta tggc                                              24

<210> SEQ ID NO 171
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 171
atatcatatg atggaagtaa taaa                                              24

<210> SEQ ID NO 172
<211> LENGTH: 42
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 172
gcaaaagata cttgtactaa tggtgtatgc taccctgact ac                          42

<210> SEQ ID NO 173
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 173
ggttacacct ttaccagcta tggt                                        24

<210> SEQ ID NO 174
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 174
atcagcgctt acaatggtaa caca                                        24

<210> SEQ ID NO 175
<211> LENGTH: 42
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 175
gcgagatcgc ctagtacggt ggtaacccca ttcagcgact ac                    42

<210> SEQ ID NO 176
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 176
ggattcacct ttgatgatta tgcc                                        24

<210> SEQ ID NO 177
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 177
attagttgga atagtggtag cata                                        24

<210> SEQ ID NO 178
<211> LENGTH: 36
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 178
gcaaaacggc atggagggac caatgctttt gatatc                           36

<210> SEQ ID NO 179
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 179
gggttctcac tcaacactgg tggagtgagt                                      30

<210> SEQ ID NO 180
<211> LENGTH: 21
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 180
atttattgga atgatgataa g                                               21

<210> SEQ ID NO 181
<211> LENGTH: 27
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 181
gcacacagcg cggctggagt tgactac                                         27

<210> SEQ ID NO 182
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 182
ggatacactt ttaccgccta ctat                                            24

<210> SEQ ID NO 183
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 183
atcgacccta acagtggtgg caca                                            24

<210> SEQ ID NO 184
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 184
gcgagaggct ggaattacga acttgactac                                      30

<210> SEQ ID NO 185

<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 185
ggatacactt ttaccgccta ctat                                          24

<210> SEQ ID NO 186
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 186
atcgacccta acagtggtgg caca                                          24

<210> SEQ ID NO 187
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 187
gcgagagact ggaattacga acttgactac                                    30

<210> SEQ ID NO 188
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 188
gggttctcac tcagcactag tggagtgggt                                    30

<210> SEQ ID NO 189
<211> LENGTH: 21
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 189
atttattgga atgatgataa g                                             21

<210> SEQ ID NO 190
<211> LENGTH: 42
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 190
gcacacattt ccagtagtgg tggtaccgaa gtacaagact ac                      42

<210> SEQ ID NO 191
<211> LENGTH: 24

<212> TYPE: DNA
<213> ORGANISM: Artificial Sequence
<220> FEATURE:
<223> OTHER INFORMATION: Synthetic construct; CDR present in the heavy
      chain

<400> SEQUENCE: 191
ggaggcacct tcagcagcta tgct                                             24

<210> SEQ ID NO 192
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 192
atcatcccta tctttggtac agca                                             24

<210> SEQ ID NO 193
<211> LENGTH: 45
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 193
gcgagagatg aactctgggc tacaaactac tactacatgg acgtc                      45

<210> SEQ ID NO 194
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 194
ggatacactt ttaccgccta ctat                                             24

<210> SEQ ID NO 195
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 195
atcgacccta acagtggtgg caca                                             24

<210> SEQ ID NO 196
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 196
gcgagagact ggaattacga acttgactac                                       30

<210> SEQ ID NO 197
<211> LENGTH: 24
<212> TYPE: DNA

<213> ORGANISM: Artificial Sequence
<220> FEATURE:
<223> OTHER INFORMATION: Synthetic construct; CDR present in the heavy chain

<400> SEQUENCE: 197
ggatacactt ttaccgccta ctat                                          24

<210> SEQ ID NO 198
<211> LENGTH: 24
<212> TYPE: DNA
<213> ORGANISM: Artificial Sequence
<220> FEATURE:
<223> OTHER INFORMATION: Synthetic construct; CDR present in the heavy chain

<400> SEQUENCE: 198 atcgaccta acagtggtgg caca                                           24

<210> SEQ ID NO 199
<211> LENGTH: 30
<212> TYPE: DNA
<213> ORGANISM: Artificial Sequence
<220> FEATURE:
<223> OTHER INFORMATION: Synthetic construct; CDR present in the heavy chain

<400> SEQUENCE: 199
gcgagagact ggaattacga gcttgactac                                    30

<210> SEQ ID NO 200
<211> LENGTH: 30
<212> TYPE: DNA
<213> ORGANISM: Artificial Sequence
<220> FEATURE:
<223> OTHER INFORMATION: Synthetic construct; CDR present in the heavy chain

<400> SEQUENCE: 200
gggttctcac tcagcactag tggagtgggt                                    30

<210> SEQ ID NO 201
<211> LENGTH: 21
<212> TYPE: DNA
<213> ORGANISM: Artificial Sequence
<220> FEATURE:
<223> OTHER INFORMATION: Synthetic construct; CDR present in the heavy chain

<400> SEQUENCE: 201
atttattgga atgatgataa g                                             21

<210> SEQ ID NO 202
<211> LENGTH: 36
<212> TYPE: DNA
<213> ORGANISM: Artificial Sequence
<220> FEATURE:
<223> OTHER INFORMATION: Synthetic construct; CDR present in the heavy chain

<400> SEQUENCE: 202
gcccaggcaa aaccgtatag cagcgatttt gatatc                             36

<210> SEQ ID NO 203
<211> LENGTH: 24
<212> TYPE: DNA
<213> ORGANISM: Artificial Sequence

```
<220> FEATURE:
<223> OTHER INFORMATION: Synthetic construct; CDR present in the heavy
      chain

<400> SEQUENCE: 203
ggattcacct ttgatgatta tgcc                                          24

<210> SEQ ID NO 204
<211> LENGTH: 24
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 204
attagttgga atagtggtag cata                                          24

<210> SEQ ID NO 205
<211> LENGTH: 33
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 205
gcgaaaaggg ggaactccaa ctcttttgac tac                                33

<210> SEQ ID NO 206
<211> LENGTH: 30
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 206
gggttctcac tcagcactag tggagtgggt                                    30

<210> SEQ ID NO 207
<211> LENGTH: 21
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 207
atttactgga atgatgataa g                                             21

<210> SEQ ID NO 208
<211> LENGTH: 36
<212> TYPE: DNA
<213> ORGANISM: Artificial Sequence
<220> FEATURE:
<223> OTHER INFORMATION: Synthetic construct; CDR present in the heavy
      chain

<400> SEQUENCE: 208
gcccaggcaa aaccgtatag cagcgatttt gatatc                             36

<210> SEQ ID NO 209
<211> LENGTH: 18
<212> TYPE: DNA
<213> ORGANISM: Artificial Sequence
<220> FEATURE:
```

```
<223> OTHER INFORMATION: Synthetic construct; CDR present in the light
      chain

<400> SEQUENCE: 209
cagagcattg gcagctct                                                       18

<210> SEQ ID NO 210
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 210
caacagtata atagttaccc gctcact                                             27

<210> SEQ ID NO 211
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 211
agcagtgatg ttggtggtta taactat                                             27

<210> SEQ ID NO 212
<211> LENGTH: 30
<212> TYPE: DNA
<213> ORGANISM: Artificial Sequence
<220> FEATURE:
<223> OTHER INFORMATION: Synthetic construct; CDR present in the light
      chain

<400> SEQUENCE: 212
agctcctatg caggcagcaa tacttttgtc                                          30

<210> SEQ ID NO 213
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 213
cagagtgttg gcagcagc                                                       18

<210> SEQ ID NO 214
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 214
cagcagtata atagttaccc gctcact                                             27

<210> SEQ ID NO 215
<211> LENGTH: 24
<212> TYPE: DNA
<213> ORGANISM: Artificial Sequence
<220> FEATURE:
```

```
<223> OTHER INFORMATION: Synthetic construct; CDR present in the light
      chain

<400> SEQUENCE: 215
agtggcagca ttgccagcaa ctat                                          24

<210> SEQ ID NO 216
<211> LENGTH: 30
<212> TYPE: DNA
<213> ORGANISM: Artificial Sequence
<220> FEATURE:
<223> OTHER INFORMATION: Synthetic construct; CDR present in the light
      chain

<400> SEQUENCE: 216
cagtcttatg atggcagcaa ccctgtggtt                                    30

<210> SEQ ID NO 217
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 217
cagagcatta gcagctat                                                 18

<210> SEQ ID NO 218
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 218
caacagagtt acagtaccct ttacact                                       27

<210> SEQ ID NO 219
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 219
caggacatta gcaactat                                                 18

<210> SEQ ID NO 220
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 220
caacagtatg ataatctccc catcact                                       27

<210> SEQ ID NO 221
<211> LENGTH: 24
<212> TYPE: DNA
<213> ORGANISM: Artificial Sequence
<220> FEATURE:
```

<223> OTHER INFORMATION: Synthetic construct; CDR present in the light
      chain

<400> SEQUENCE: 221
agtggctaca ttgccagcaa ctat                                            24

<210> SEQ ID NO 222
<211> LENGTH: 30
<212> TYPE: DNA
<213> ORGANISM: Artificial Sequence
<220> FEATURE:
<223> OTHER INFORMATION: Synthetic construct; CDR present in the light
      chain

<400> SEQUENCE: 222
cagtcttatg atagcagcaa tcaagggtg                                       30

<210> SEQ ID NO 223
<211> LENGTH: 24
<212> TYPE: DNA
<213> ORGANISM: Artificial Sequence
<220> FEATURE:
<223> OTHER INFORMATION: Synthetic construct; CDR present in the light
      chain

<400> SEQUENCE: 223
agtggctaca ttgccagcaa ctat                                            24

<210> SEQ ID NO 224
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 224
cagtcttatg atagcagcct tgtgata                                         27

<210> SEQ ID NO 225
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 225
cagagcattg gcagctct                                                   18

<210> SEQ ID NO 226
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 226
caacagtata atagttaccc gctcact                                         27

<210> SEQ ID NO 227
<211> LENGTH: 27
<212> TYPE: DNA
<213> ORGANISM: Artificial Sequence

```
<220> FEATURE:
<223> OTHER INFORMATION: Synthetic construct; CDR present in the light
      chain

<400> SEQUENCE: 227
agcagtgatg ttggtagtta taactat                                            27

<210> SEQ ID NO 228
<211> LENGTH: 33
<212> TYPE: DNA
<213> ORGANISM: Artificial Sequence
<220> FEATURE:
<223> OTHER INFORMATION: Synthetic construct; CDR present in the light
      chain

<400> SEQUENCE: 228
acctcatatg gaagctacga catacctgtg att                                     33

<210> SEQ ID NO 229
<211> LENGTH: 24
<212> TYPE: DNA
<213> ORGANISM: Artificial Sequence
<220> FEATURE:
<223> OTHER INFORMATION: Synthetic construct; CDR present in the light
      chain

<400> SEQUENCE: 229
agtggcaaca ttgccaggag tttt                                               24

<210> SEQ ID NO 230
<211> LENGTH: 30
<212> TYPE: DNA
<213> ORGANISM: Artificial Sequence
<220> FEATURE:
<223> OTHER INFORMATION: Synthetic construct; CDR present in the light
      chain

<400> SEQUENCE: 230
cagtcttatg atagcagcaa tcatgtggta                                         30

<210> SEQ ID NO 231
<211> LENGTH: 24
<212> TYPE: DNA
<213> ORGANISM: Artificial Sequence
<220> FEATURE:
<223> OTHER INFORMATION: Synthetic construct; CDR present in the light
      chain

<400> SEQUENCE: 231
agtggctaca ttgccagcaa ctat                                               24

<210> SEQ ID NO 232
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 232
cagtcttatg atagcaccac ggaagtc                                            27

<210> SEQ ID NO 233
<211> LENGTH: 24
<212> TYPE: DNA
<213> ORGANISM: Artificial Sequence
<220> FEATURE:
```

<223> OTHER INFORMATION: Synthetic construct; CDR present in the light
      chain

<400> SEQUENCE: 233
agtggcagca ttgccagcaa ctat                                          24

<210> SEQ ID NO 234
<211> LENGTH: 30
<212> TYPE: DNA
<213> ORGANISM: Artificial Sequence
<220> FEATURE:
<223> OTHER INFORMATION: Synthetic construct; CDR present in the light
      chain

<400> SEQUENCE: 234
cagtcttatg atagcagcaa tcaggggta                                     30

<210> SEQ ID NO 235
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 235
cagagcatta gcagctat                                                 18

<210> SEQ ID NO 236
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 236
caacagagtt acagtaccccc ctggacg                                      27

<210> SEQ ID NO 237
<211> LENGTH: 18
<212> TYPE: DNA
<213> ORGANISM: Artificial Sequence
<220> FEATURE:
<223> OTHER INFORMATION: Synthetic construct; CDR present in the light
      chain

<400> SEQUENCE: 237
caggacatta gtaactat                                                 18

<210> SEQ ID NO 238
<211> LENGTH: 27
<212> TYPE: DNA
<213> ORGANISM: Artificial Sequence
<220> FEATURE:
<223> OTHER INFORMATION: Synthetic construct; CDR present in the light
      chain

<400> SEQUENCE: 238
ctacaagatt acaattaccc gtggacg                                       27

<210> SEQ ID NO 239
<211> LENGTH: 107
<212> TYPE: PRT
<213> ORGANISM: Artificial Sequence
<220> FEATURE:

<223> OTHER INFORMATION: Synthetic construct; CAR construct

<400> SEQUENCE: 239

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Leu Glu Ile Lys
            100                 105
```

<210> SEQ ID NO 240
<211> LENGTH: 93
<212> TYPE: PRT
<213> ORGANISM: Artificial Sequence
<220> FEATURE:
<223> OTHER INFORMATION: Synthetic construct; CAR construct

<400> SEQUENCE: 240

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser
                85                  90
```

<210> SEQ ID NO 241
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 241

```
Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25
```

<210> SEQ ID NO 242
<211> LENGTH: 17
<212> TYPE: PRT
<213> ORGANISM: Artificial Sequence
<220> FEATURE:
<223> OTHER INFORMATION: Synthetic construct; CAR construct -continued

<400> SEQUENCE: 242

Leu His Trp Tyr Gln Gln Lys Pro Gly Lys Ala Pro Lys Phe Leu Ile
1               5                   10                  15

Tyr

<210> SEQ ID NO 243
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 243

Ser Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35

<210> SEQ ID NO 244
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 244

Leu Thr Phe Gly Gly Gly Thr Lys Leu Glu Ile Lys
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 245

Phe Gly Gly Gly Thr Lys Leu Glu Ile Lys
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 246

Cys Gln Gln Tyr Asn Ser Tyr Pro Leu Thr Phe
1               5                   10

<210> SEQ ID NO 247
<211> LENGTH: 110
<212> TYPE: PRT
<213> ORGANISM: Artificial Sequence
<220> FEATURE:
<223> OTHER INFORMATION: Synthetic construct; CAR construct

<400> SEQUENCE: 247

Gln Ser Gly Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Phe Val Phe Gly Ser Gly Thr Lys Leu Thr Val Leu
            100                 105                 110

<210> SEQ ID NO 248
<211> LENGTH: 98
<212> TYPE: PRT
<213> ORGANISM: Artificial Sequence
<220> FEATURE:
<223> OTHER INFORMATION: Synthetic construct; CAR construct

<400> SEQUENCE: 248

Gln Ser Gly Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr

<210> SEQ ID NO 249
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 249

Gln Ser Gly Leu Thr Gln Pro Arg Ser Val Ser Gly Ser Pro Gly Gln
1               5                   10                  15

Ser Val Thr Ile Ser Cys Thr Gly Thr
            20                  25

<210> SEQ ID NO 250
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 250

Val Ser Trp Tyr Gln Gln His Pro Gly Lys Ala Pro Lys Leu Met Ile
1               5                   10                  15

Tyr

<210> SEQ ID NO 251
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 251

Lys Arg Pro Ser Gly Val Pro Asp Arg Phe Ser Gly Ser Lys Ser Gly
1               5                   10                  15

Asn Thr Ala Ser Leu Thr Val Ser Gly Leu Gln Ala Glu Asp Glu Ala
            20                  25                  30

Asp Tyr Tyr Cys
        35

<210> SEQ ID NO 252
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 252

Val Phe Gly Ser Gly Thr Lys Leu Thr Val Leu
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 253

Phe Gly Ser Gly Thr Lys Leu Thr Val Leu
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 254

Cys Ser Ser Tyr Ala Gly Ser Asn Thr Phe Val Phe
1               5                   10

<210> SEQ ID NO 255
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 255

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Ser
            20                  25                  30

Leu Ala Trp Tyr Gln Gln Lys Pro Gly Gln Ala Pro Arg Leu Leu Ile
        35                  40                  45

Tyr Gly Gly Ser Val Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ala Tyr Tyr Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 256
<211> LENGTH: 94
<212> TYPE: PRT
<213> ORGANISM: Artificial Sequence
<220> FEATURE:
<223> OTHER INFORMATION: Synthetic construct; CAR construct

<400> SEQUENCE: 256

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Ser
            20                  25                  30

Leu Ala Trp Tyr Gln Gln Lys Pro Gly Gln Ala Pro Arg Leu Leu Ile
        35                  40                  45

Tyr Gly Gly Ser Val Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ala Tyr Tyr Cys Gln Gln Tyr Asn Ser Tyr
                85                  90

<210> SEQ ID NO 257
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 257

Asp Ile Val Met Thr Gln Ser Pro Ala Thr Leu Ser Val Ser Pro Gly
1               5                   10                  15

Glu Arg Ala Thr Leu Ser Cys Arg Ala Ser
            20                  25

<210> SEQ ID NO 258
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 258

Leu Ala Trp Tyr Gln Gln Lys Pro Gly Gln Ala Pro Arg Leu Leu Ile
1               5                   10                  15

Tyr

<210> SEQ ID NO 259
<211> LENGTH: 36
<212> TYPE: PRT
<213> ORGANISM: Artificial Sequence
<220> FEATURE:
<223> OTHER INFORMATION: Synthetic construct; CAR construct

```
<400> SEQUENCE: 259

Val Arg Ala Thr Gly Ile Pro Ala Arg Phe Ser Gly Ser Gly Ser Gly
1               5                   10                  15

Thr Glu Phe Thr Leu Thr Ile Ser Ser Leu Gln Ser Glu Asp Phe Ala
            20                  25                  30

Ala Tyr Tyr Cys
        35

<210> SEQ ID NO 260
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 260

Leu Thr Phe Gly Gly Gly Thr Lys Leu Glu Ile Lys
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 261

Phe Gly Gly Gly Thr Lys Leu Glu Ile Lys
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 262

Cys Gln Gln Tyr Asn Ser Tyr Pro Leu Thr Phe
1               5                   10

<210> SEQ ID NO 263
<211> LENGTH: 111
<212> TYPE: PRT
<213> ORGANISM: Artificial Sequence
<220> FEATURE:
<223> OTHER INFORMATION: Synthetic construct; CAR construct

<400> SEQUENCE: 263

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95
```

```
Ser Asn Pro Val Val Phe Gly Gly Gly Thr Gln Leu Thr Val Leu
            100                 105                 110

<210> SEQ ID NO 264
<211> LENGTH: 97
<212> TYPE: PRT
<213> ORGANISM: Artificial Sequence
<220> FEATURE:
<223> OTHER INFORMATION: Synthetic construct; CAR construct

<400> SEQUENCE: 264

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Ser

<210> SEQ ID NO 265
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 265

Asn Phe Met Leu Thr Gln Pro His Ser Val Ser Glu Ser Pro Gly Lys
1               5                   10                  15

Thr Val Thr Ile Ser Cys Thr Gly Ser
            20                  25

<210> SEQ ID NO 266
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 266

Val Gln Trp Tyr Gln Gln Arg Pro Gly Ser Ser Pro Thr Thr Val Ile
1               5                   10                  15

Tyr

<210> SEQ ID NO 267
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 267

Gln Arg Pro Ser Gly Val Pro Asp Arg Phe Ser Gly Ser Ile Asp Ser
1               5                   10                  15

Ser Ser Asn Ser Ala Ser Leu Thr Ile Ser Gly Leu Lys Thr Glu Asp
            20                  25                  30
```

Glu Ala Asp Tyr Tyr Cys
        35

<210> SEQ ID NO 268
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 268

Val Val Phe Gly Gly Gly Thr Gln Leu Thr Val Leu
1               5                   10

<210> SEQ ID NO 269
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 269

Phe Gly Gly Gly Thr Gln Leu Thr Val Leu
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 270

Cys Gln Ser Tyr Asp Gly Ser Asn Pro Val Val Phe
1               5                   10

<210> SEQ ID NO 271
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Tyr
                85                  90                  95

Thr Phe Gly Gln Gly Thr Lys Leu Glu Ile Lys
            100                 105

<210> SEQ ID NO 272
<211> LENGTH: 94
<212> TYPE: PRT
<213> ORGANISM: Artificial Sequence
<220> FEATURE:
<223> OTHER INFORMATION: Synthetic construct; CAR construct

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr
                85                  90

<210> SEQ ID NO 273
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 274
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 274

Leu Asn Trp Tyr Gln Gln Lys Pro Gly Lys Ala Pro Lys Leu Leu Ile
1               5                   10                  15

Tyr

<210> SEQ ID NO 275
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 275

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 276
<211> LENGTH: 12
<212> TYPE: PRT
<213> ORGANISM: Artificial Sequence
<220> FEATURE:

<223> OTHER INFORMATION: Synthetic construct; CAR construct

<400> SEQUENCE: 276

Tyr Thr Phe Gly Gln Gly Thr Lys Leu Glu Ile Lys
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 277

Phe Gly Gln Gly Thr Lys Leu Glu Ile Lys
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 278

Cys Gln Gln Ser Tyr Ser Thr Leu Tyr Thr Phe
1               5                   10

<210> SEQ ID NO 279
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 279

Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Pro Gly Thr Lys Val Asp Ile Lys
            100                 105

<210> SEQ ID NO 280
<211> LENGTH: 94
<212> TYPE: PRT
<213> ORGANISM: Artificial Sequence
<220> FEATURE:
<223> OTHER INFORMATION: Synthetic construct; CAR construct

<400> SEQUENCE: 280

Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
            20                  25                  30

-continued

```
Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu
                 85                  90

<210> SEQ ID NO 281
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 281

Asp Ile Gln Met Thr Gln Ser Pro Ser Ser Leu Ser Ala Ser Val Gly
 1               5                  10                  15

Asp Arg Val Thr Ile Thr Cys Gln Ala Ser
            20                  25

<210> SEQ ID NO 282
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 282

Leu Asn Trp Tyr Gln Gln Lys Pro Gly Lys Ala Pro Lys Leu Leu Ile
 1               5                  10                  15

Tyr

<210> SEQ ID NO 283
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 283

Asn Leu Glu Thr Gly Val Pro Ser Arg Phe Ser Gly Ser Gly Ser Gly
 1               5                  10                  15

Thr Asp Phe Thr Phe Thr Ile Ser Ser Leu Gln Pro Glu Asp Ile Ala
            20                  25                  30

Thr Tyr Tyr Cys
        35

<210> SEQ ID NO 284
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 284

Thr Phe Gly Pro Gly Thr Lys Val Asp Ile Lys
 1               5                  10

<210> SEQ ID NO 285
<211> LENGTH: 10
```

```
<212> TYPE: PRT
<213> ORGANISM: Artificial Sequence
<220> FEATURE:
<223> OTHER INFORMATION: Synthetic construct; CAR construct

<400> SEQUENCE: 285

Phe Gly Pro Gly Thr Lys Val Asp Ile Lys
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 286

Cys Gln Gln Tyr Asp Asn Leu Pro Ile Thr Phe
1               5                   10

<210> SEQ ID NO 287
<211> LENGTH: 111
<212> TYPE: PRT
<213> ORGANISM: Artificial Sequence
<220> FEATURE:
<223> OTHER INFORMATION: Synthetic construct; CAR construct

<400> SEQUENCE: 287

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Gly Val Phe Gly Gly Gly Thr Lys Leu Thr Val Leu
            100                 105                 110

<210> SEQ ID NO 288
<211> LENGTH: 98
<212> TYPE: PRT
<213> ORGANISM: Artificial Sequence
<220> FEATURE:
<223> OTHER INFORMATION: Synthetic construct; CAR construct

<400> SEQUENCE: 288

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80
```

Leu Lys Thr Glu Asp Glu Ala Asp Tyr Tyr Cys Gln Ser Tyr Asp Ser
            85                  90                  95

Ser Asn

<210> SEQ ID NO 289
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 289

Asn Phe Met Leu Thr Gln Pro His Ser Val Ser Gly Ser Pro Gly Lys
1               5                   10                  15

Thr Val Thr Ile Ser Cys Thr Arg Ser
            20                  25

<210> SEQ ID NO 290
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 290

Val Gln Trp Tyr Gln Gln Arg Pro Gly Ser Ala Pro Thr Thr Val Ile
1               5                   10                  15

Tyr

<210> SEQ ID NO 291
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 291

Gln Arg Pro Ser Gly Val Pro Asp Arg Phe Ser Gly Ser Ile Asp Ser
1               5                   10                  15

Ser Ser Asn Ser Ala Ser Leu Thr Ile Ser Gly Leu Lys Thr Glu Asp
            20                  25                  30

Glu Ala Asp Tyr Tyr Cys
                35

<210> SEQ ID NO 292
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 292

Val Phe Gly Gly Gly Thr Lys Leu Thr Val Leu
1               5                   10

<210> SEQ ID NO 293
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 293

Phe Gly Gly Gly Thr Lys Leu Thr Val Leu
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 294

Cys Gln Ser Tyr Asp Ser Ser Asn Gln Gly Val Phe
1               5                   10

<210> SEQ ID NO 295
<211> LENGTH: 110
<212> TYPE: PRT
<213> ORGANISM: Artificial Sequence
<220> FEATURE:
<223> OTHER INFORMATION: Synthetic construct; CAR construct

<400> SEQUENCE: 295

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ser Pro Thr Thr Leu
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Ser Leu Val Ile Phe Gly Gly Gly Thr Lys Val Thr Val Leu
            100                 105                 110

<210> SEQ ID NO 296
<211> LENGTH: 97
<212> TYPE: PRT
<213> ORGANISM: Artificial Sequence
<220> FEATURE:
<223> OTHER INFORMATION: Synthetic construct; CAR construct

<400> SEQUENCE: 296

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ser Pro Thr Thr Leu
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Ser

<210> SEQ ID NO 297
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 297

Asn Phe Met Leu Thr Gln Pro His Ser Val Ser Gly Ser Pro Gly Lys
1               5                   10                  15

Thr Val Thr Ile Ser Cys Thr Arg Ser
            20                  25

<210> SEQ ID NO 298
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 298

Val Gln Trp Tyr Gln Gln Arg Pro Gly Ser Ser Pro Thr Thr Leu Ile
1               5                   10                  15

Tyr

<210> SEQ ID NO 299
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 299

Gln Arg Pro Ser Gly Val Pro Asp Arg Phe Ser Gly Ser Ile Asp Arg
1               5                   10                  15

Ser Ser Asn Ser Ala Ser Leu Thr Ile Ser Gly Leu Lys Thr Glu Asp
            20                  25                  30

Glu Gly Asp Tyr Tyr Cys
        35

<210> SEQ ID NO 300
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 300

Val Ile Phe Gly Gly Gly Thr Lys Val Thr Val Leu
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 301

Phe Gly Gly Gly Thr Lys Val Thr Val Leu
1               5                   10

<210> SEQ ID NO 302

```
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 302

Cys Gln Ser Tyr Asp Ser Ser Leu Val Ile Phe
1               5                   10

<210> SEQ ID NO 303
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Cys Ala Thr Tyr Tyr Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 304
<211> LENGTH: 93
<212> TYPE: PRT
<213> ORGANISM: Artificial Sequence
<220> FEATURE:
<223> OTHER INFORMATION: Synthetic construct; CAR construct

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Ser
            20                  25                  30

Leu His Trp Tyr Gln Gln Lys Pro Gly Lys Ala Pro Lys Phe Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Cys Ala Thr Tyr Tyr Cys Gln Gln Tyr Asn Ser
                85                  90

<210> SEQ ID NO 305
<211> LENGTH: 26
<212> TYPE: PRT
<213> ORGANISM: Artificial Sequence
<220> FEATURE:
<223> OTHER INFORMATION: Synthetic construct; CAR construct
```

```
<400> SEQUENCE: 305

Asp Ile Gln Met Thr Gln Ser Pro Ser Ser Leu Ser Ala Ser Val Gly
1               5                   10                  15
Asp Arg Val Thr Ile Thr Cys Arg Ala Ser
            20                  25

<210> SEQ ID NO 306
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 306

Leu His Trp Tyr Gln Gln Lys Pro Gly Lys Ala Pro Lys Phe Leu Ile
1               5                   10                  15
Tyr

<210> SEQ ID NO 307
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 307

Ser Leu Glu Ser Gly Val Pro Ser Arg Phe Ser Gly Ser Gly Ser Gly
1               5                   10                  15
Thr Glu Phe Thr Leu Thr Ile Ser Ser Leu Gln Pro Asp Asp Cys Ala
            20                  25                  30
Thr Tyr Tyr Cys
        35

<210> SEQ ID NO 308
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 308

Leu Thr Phe Gly Gly Gly Thr Lys Leu Glu Ile Lys
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 309

Phe Gly Gly Gly Thr Lys Leu Glu Ile Lys
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic construct; CAR construct
```

```
<400> SEQUENCE: 310

Cys Gln Gln Tyr Asn Ser Tyr Pro Leu Thr Phe
1               5                   10

<210> SEQ ID NO 311
<211> LENGTH: 111
<212> TYPE: PRT
<213> ORGANISM: Artificial Sequence
<220> FEATURE:
<223> OTHER INFORMATION: Synthetic construct; CAR construct

<400> SEQUENCE: 311

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Tyr Val Ser Trp Tyr Gln Gln Ser Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Thr Ser Tyr Gly Ser Tyr
                85                  90                  95

Asp Ile Pro Val Ile Phe Gly Gly Gly Thr Lys Leu Thr Val Leu
            100                 105                 110

<210> SEQ ID NO 312
<211> LENGTH: 97
<212> TYPE: PRT
<213> ORGANISM: Artificial Sequence
<220> FEATURE:
<223> OTHER INFORMATION: Synthetic construct; CAR construct

<400> SEQUENCE: 312

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Tyr Val Ser Trp Tyr Gln Gln Ser Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Thr Ser Tyr Gly Ser Tyr
                85                  90                  95

Asp

<210> SEQ ID NO 313
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 313

Gln Ser Ala Leu Thr Gln Pro Arg Ser Val Ser Gly Ser Pro Gly Gln
1               5                   10                  15
```

```
Ser Val Thr Ile Ser Cys Thr Gly Thr
            20                  25
```

<210> SEQ ID NO 314
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 314

```
Val Ser Trp Tyr Gln Gln Ser Pro Gly Lys Ala Pro Lys Leu Met Ile
1               5                   10                  15

Tyr
```

<210> SEQ ID NO 315
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 315

```
Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ser Glu Asp Glu Ala
            20                  25                  30

Asp Tyr Tyr Cys
        35
```

<210> SEQ ID NO 316
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 316

```
Val Ile Phe Gly Gly Gly Thr Lys Leu Thr Val Leu
1               5                   10
```

<210> SEQ ID NO 317
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 317

```
Phe Gly Gly Gly Thr Lys Leu Thr Val Leu
1               5                   10
```

<210> SEQ ID NO 318
<211> LENGTH: 13
<212> TYPE: PRT
<213> ORGANISM: Artificial Sequence
<220> FEATURE:
<223> OTHER INFORMATION: Synthetic construct; CAR construct

<400> SEQUENCE: 318

```
Cys Thr Ser Tyr Gly Ser Tyr Asp Ile Pro Val Ile Phe
1               5                   10
```

<210> SEQ ID NO 319

```
<211> LENGTH: 111
<212> TYPE: PRT
<213> ORGANISM: Artificial Sequence
<220> FEATURE:
<223> OTHER INFORMATION: Synthetic construct; CAR construct

<400> SEQUENCE: 319

Asn Phe Met Leu Thr Gln Pro His Ser Val Ser Gly Ser Pro Gly Lys
1               5                   10                  15

Ala Val Thr Ile Ser Cys Thr Arg Ser Ser Gly Asn Ile Ala Arg Ser
            20                  25                  30

Phe Val Gln Trp Tyr Gln Gln Arg Pro Gly Ser Ala Pro Thr Ala Val
        35                  40                  45

Ile Tyr Glu Asp Asn Arg Arg Pro Ser Gly Val Pro Asp Arg Phe Ser
    50                  55                  60

Gly Ser Phe Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Val Phe Gly Gly Gly Thr Lys Val Thr Val Leu
            100                 105                 110

<210> SEQ ID NO 320
<211> LENGTH: 98
<212> TYPE: PRT
<213> ORGANISM: Artificial Sequence
<220> FEATURE:
<223> OTHER INFORMATION: Synthetic construct; CAR construct

<400> SEQUENCE: 320

Asn Phe Met Leu Thr Gln Pro His Ser Val Ser Gly Ser Pro Gly Lys
1               5                   10                  15

Ala Val Thr Ile Ser Cys Thr Arg Ser Ser Gly Asn Ile Ala Arg Ser
            20                  25                  30

Phe Val Gln Trp Tyr Gln Gln Arg Pro Gly Ser Ala Pro Thr Ala Val
        35                  40                  45

Ile Tyr Glu Asp Asn Arg Arg Pro Ser Gly Val Pro Asp Arg Phe Ser
    50                  55                  60

Gly Ser Phe Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 321
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 321

Asn Phe Met Leu Thr Gln Pro His Ser Val Ser Gly Ser Pro Gly Lys
1               5                   10                  15

Ala Val Thr Ile Ser Cys Thr Arg Ser
            20                  25

<210> SEQ ID NO 322
<211> LENGTH: 17
<212> TYPE: PRT
```

```
<213> ORGANISM: Artificial Sequence
<220> FEATURE:
<223> OTHER INFORMATION: Synthetic construct; CAR construct

<400> SEQUENCE: 322

Val Gln Trp Tyr Gln Gln Arg Pro Gly Ser Ala Pro Thr Ala Val Ile
1               5                   10                  15

Tyr

<210> SEQ ID NO 323
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 323

Arg Arg Pro Ser Gly Val Pro Asp Arg Phe Ser Gly Ser Phe Asp Ser
1               5                   10                  15

Ser Ser Asn Ser Ala Ser Leu Thr Ile Ser Gly Leu Lys Thr Glu Asp
            20                  25                  30

Glu Ala Asp Tyr Tyr Cys
        35

<210> SEQ ID NO 324
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 324

Val Val Phe Gly Gly Gly Thr Lys Val Thr Val Leu
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 325

Phe Gly Gly Gly Thr Lys Val Thr Val Leu
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 326

Cys Gln Ser Tyr Asp Ser Ser Asn His Val Val Phe
1               5                   10

<210> SEQ ID NO 327
<211> LENGTH: 110
<212> TYPE: PRT
<213> ORGANISM: Artificial Sequence
<220> FEATURE:
<223> OTHER INFORMATION: Synthetic construct; CAR construct
```

<400> SEQUENCE: 327

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ser Pro Thr Thr Leu
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Thr Thr Glu Val Phe Gly Thr Gly Thr Lys Leu Thr Val Leu
            100                 105                 110

<210> SEQ ID NO 328
<211> LENGTH: 97
<212> TYPE: PRT
<213> ORGANISM: Artificial Sequence
<220> FEATURE:
<223> OTHER INFORMATION: Synthetic construct; CAR construct

<400> SEQUENCE: 328

Asn Phe Met Leu Thr Gln Pro His Ser Val Ser Gly Ser Pro Gly Lys
1               5                   10                  15

Thr Val Thr Ile Ser Cys Thr Arg Ser Ser Gly Tyr Ile Ala Ser Asn
            20                  25                  30

Tyr Val Gln Trp Tyr Gln Gln Arg Pro Gly Ser Ser Pro Thr Thr Leu
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Gly Asp Tyr Tyr Cys Gln Ser Tyr Asp Ser
                85                  90                  95

Thr

<210> SEQ ID NO 329
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 329

Asn Phe Met Leu Thr Gln Pro His Ser Val Ser Gly Ser Pro Gly Lys
1               5                   10                  15

Thr Val Thr Ile Ser Cys Thr Arg Ser
            20                  25

<210> SEQ ID NO 330
<211> LENGTH: 17
<212> TYPE: PRT
<213> ORGANISM: Artificial Sequence
<220> FEATURE:
<223> OTHER INFORMATION: Synthetic construct; CAR construct

```
<400> SEQUENCE: 330

Val Gln Trp Tyr Gln Gln Arg Pro Gly Ser Ser Pro Thr Thr Leu Ile
1               5                   10                  15

Tyr

<210> SEQ ID NO 331
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 331

Gln Arg Pro Ser Gly Val Pro Asp Arg Phe Ser Gly Ser Ile Asp Arg
1               5                   10                  15

Ser Ser Asn Ser Ala Ser Leu Thr Ile Ser Gly Leu Lys Thr Glu Asp
            20                  25                  30

Glu Gly Asp Tyr Tyr Cys
        35

<210> SEQ ID NO 332
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 332

Val Phe Gly Thr Gly Thr Lys Leu Thr Val Leu
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 333

Phe Gly Thr Gly Thr Lys Leu Thr Val Leu
1               5                   10

<210> SEQ ID NO 334
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 334

Cys Gln Ser Tyr Asp Ser Thr Thr Glu Val
1               5                   10

<210> SEQ ID NO 335
<211> LENGTH: 111
<212> TYPE: PRT
<213> ORGANISM: Artificial Sequence
<220> FEATURE:
<223> OTHER INFORMATION: Synthetic construct; CAR construct

<400> SEQUENCE: 335

Asn Phe Met Leu Thr Gln Pro His Ser Val Ser Glu Ser Pro Gly Lys
1               5                   10                  15
```

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Ser Asn Gln Gly Val Phe Gly Gly Gly Thr Gln Leu Thr Val Leu
            100                 105                 110

<210> SEQ ID NO 336
<211> LENGTH: 98
<212> TYPE: PRT
<213> ORGANISM: Artificial Sequence
<220> FEATURE:
<223> OTHER INFORMATION: Synthetic construct; CAR construct

<400> SEQUENCE: 336

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 337
<211> LENGTH: 25
<212> TYPE: PRT
<213> ORGANISM: Artificial Sequence
<220> FEATURE:
<223> OTHER INFORMATION: Synthetic construct; CAR construct

<400> SEQUENCE: 337

Asn Phe Met Leu Thr Gln Pro His Ser Val Ser Glu Ser Pro Gly Lys
1               5                   10                  15

Thr Val Thr Ile Ser Cys Thr Gly Ser
            20                  25

<210> SEQ ID NO 338
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 338

Val Gln Trp Tyr Gln Gln Arg Pro Gly Ser Ser Pro Thr Thr Val Ile
1               5                   10                  15

Tyr

<210> SEQ ID NO 339
<211> LENGTH: 38
<212> TYPE: PRT
<213> ORGANISM: Artificial Sequence
<220> FEATURE:
<223> OTHER INFORMATION: Synthetic construct; CAR construct

<400> SEQUENCE: 339

```
Gln Arg Pro Ser Gly Val Pro Asp Arg Phe Ser Gly Ser Ile Asp Ser
1               5                   10                  15

Ser Ser Asn Ser Ala Ser Leu Thr Ile Ser Gly Leu Lys Thr Glu Asp
            20                  25                  30

Glu Ala Asp Tyr Tyr Cys
        35
```

<210> SEQ ID NO 340
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 340

```
Val Phe Gly Gly Gly Thr Gln Leu Thr Val Leu
1               5                   10
```

<210> SEQ ID NO 341
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 341

```
Phe Gly Gly Gly Thr Gln Leu Thr Val Leu
1               5                   10
```

<210> SEQ ID NO 342
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 342

```
Cys Gln Ser Tyr Asp Ser Ser Asn Gln Gly Val Phe
1               5                   10
```

<210> SEQ ID NO 343
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 343

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gln Gly Thr Lys Leu Glu Ile Lys
            100                 105

<210> SEQ ID NO 344
<211> LENGTH: 94
<212> TYPE: PRT
<213> ORGANISM: Artificial Sequence
<220> FEATURE:
<223> OTHER INFORMATION: Synthetic construct; CAR construct

<400> SEQUENCE: 344

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr
                 85                  90

<210> SEQ ID NO 345
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 345

Asp Ile Gln Met Thr Gln Ser Pro Ser Ser Val Ser Ala Ser Val Gly
  1               5                  10                  15

Asp Arg Val Thr Ile Thr Cys Arg Ala Ser
                 20                  25

<210> SEQ ID NO 346
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 346

Leu Asn Trp Tyr Gln Gln Lys Pro Gly Lys Ala Pro Lys Leu Leu Ile
  1               5                  10                  15

Tyr

<210> SEQ ID NO 347
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 347

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 348
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 348

Trp Thr Phe Gly Gln Gly Thr Lys Leu Glu Ile Lys
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 349

Phe Gly Gln Gly Thr Lys Leu Glu Ile Lys
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 350

Cys Gln Gln Ser Tyr Ser Thr Pro Trp Thr Phe
1               5                   10

<210> SEQ ID NO 351
<211> LENGTH: 107
<212> TYPE: PRT
<213> ORGANISM: Artificial Sequence
<220> FEATURE:
<223> OTHER INFORMATION: Synthetic construct; CAR construct

<400> SEQUENCE: 351

Asp Ile Gln Met Thr Gln Ser Pro Ser Ser Leu Ser Ala Ser Val Gly
1               5                   10                  15

Asp Arg Val Thr Ile Ser Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

```
Thr Phe Gly Gln Gly Thr Lys Val Glu Ile Lys
            100                 105

<210> SEQ ID NO 352
<211> LENGTH: 94
<212> TYPE: PRT
<213> ORGANISM: Artificial Sequence
<220> FEATURE:
<223> OTHER INFORMATION: Synthetic construct; CAR construct

<400> SEQUENCE: 352

Asp Ile Gln Met Thr Gln Ser Pro Ser Ser Leu Ser Ala Ser Val Gly
1               5                   10                  15

Asp Arg Val Thr Ile Ser Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr
            85                  90

<210> SEQ ID NO 353
<211> LENGTH: 26
<212> TYPE: PRT
<213> ORGANISM: Artificial Sequence
<220> FEATURE:
<223> OTHER INFORMATION: Synthetic construct; CAR construct

<400> SEQUENCE: 353

Asp Ile Gln Met Thr Gln Ser Pro Ser Ser Leu Ser Ala Ser Val Gly
1               5                   10                  15

Asp Arg Val Thr Ile Ser Cys Gln Ala Ser
            20                  25

<210> SEQ ID NO 354
<211> LENGTH: 17
<212> TYPE: PRT
<213> ORGANISM: Artificial Sequence
<220> FEATURE:
<223> OTHER INFORMATION: Synthetic construct; CAR construct

<400> SEQUENCE: 354

Leu Asn Trp Tyr Gln Gln Lys Pro Gly Lys Ala Pro Lys Leu Leu Ile
1               5                   10                  15

Tyr

<210> SEQ ID NO 355
<211> LENGTH: 36
<212> TYPE: PRT
<213> ORGANISM: Artificial Sequence
<220> FEATURE:
<223> OTHER INFORMATION: Synthetic construct; CAR construct

<400> SEQUENCE: 355

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30
```

```
Thr Tyr Tyr Cys
        35

<210> SEQ ID NO 356
<211> LENGTH: 12
<212> TYPE: PRT
<213> ORGANISM: Artificial Sequence
<220> FEATURE:
<223> OTHER INFORMATION: Synthetic construct; CAR construct

<400> SEQUENCE: 356

Trp Thr Phe Gly Gln Gly Thr Lys Val Glu Ile Lys
1               5                   10

<210> SEQ ID NO 357
<211> LENGTH: 10
<212> TYPE: PRT
<213> ORGANISM: Artificial Sequence
<220> FEATURE:
<223> OTHER INFORMATION: Synthetic construct; CAR construct

<400> SEQUENCE: 357

Phe Gly Gln Gly Thr Lys Val Glu Ile Lys
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Synthetic construct; CAR construct

<400> SEQUENCE: 358

Cys Leu Gln Asp Tyr Asn Tyr Pro Trp Thr Phe
1               5                   10
```